United States Patent
Kaspar et al.

(10) Patent No.: US 12,228,571 B2
(45) Date of Patent: Feb. 18, 2025

(54) CELL-BASED ASSAY FOR MEASURING DRUG PRODUCT POTENCY

(71) Applicant: Novartis AG, Basel (CH)

(72) Inventors: Brian Kaspar, New Albany, OH (US); Allan Kaspar, Carlsbad, CA (US); Kevin Foust, Poway, CA (US); Martin Fugere, San Diego, CA (US); Eunhye Park, San Diego, CA (US); Gretchen Thomsen, San Diego, CA (US); Fengrong Zuo, San Diego, CA (US)

(73) Assignee: Novartis AG, Basel (CH)

(*) Notice: Subject to any disclaimer, the term of this patent is extended or adjusted under 35 U.S.C. 154(b) by 1083 days.

(21) Appl. No.: 16/972,956

(22) PCT Filed: Jun. 7, 2019

(86) PCT No.: PCT/US2019/035963
§ 371 (c)(1),
(2) Date: Dec. 7, 2020

(87) PCT Pub. No.: WO2019/236949
PCT Pub. Date: Dec. 12, 2019

(65) Prior Publication Data
US 2021/0255185 A1    Aug. 19, 2021

Related U.S. Application Data

(60) Provisional application No. 62/682,263, filed on Jun. 8, 2018.

(51) Int. Cl.
| | | |
|---|---|---|
| *G01N 33/569* | (2006.01) | |
| *A61K 48/00* | (2006.01) | |
| *C12N 5/0793* | (2010.01) | |
| *C12N 15/52* | (2006.01) | |
| *C12N 15/63* | (2006.01) | |
| *C12N 15/86* | (2006.01) | |
| *C12N 15/87* | (2006.01) | |
| *G01N 1/30* | (2006.01) | |

(52) U.S. Cl.
CPC ..... *G01N 33/56966* (2013.01); *A61K 48/005* (2013.01); *C12N 5/0619* (2013.01); *C12N 15/52* (2013.01); *C12N 15/63* (2013.01); *C12N 15/86* (2013.01); *C12N 15/87* (2013.01); *G01N 1/30* (2013.01); *A61K 48/00* (2013.01); *C12N 2501/11* (2013.01); *C12N 2501/115* (2013.01); *C12N 2750/14143* (2013.01)

(58) Field of Classification Search
CPC ...... A61K 48/00; A61K 48/005; C12N 15/52; C12N 15/63; C12N 15/86; C12N 15/87; C12N 2501/11; C12N 2501/115; C12N 2750/14143; C12N 5/0619; C12Q 1/701; G01N 1/30; G01N 33/56966
See application file for complete search history.

(56) References Cited

U.S. PATENT DOCUMENTS

| | | |
|---|---|---|
| 5,139,941 A | 8/1992 | Muzyczka et al. |
| 5,173,414 A | 12/1992 | Lebkowski et al. |
| 5,173,418 A | 12/1992 | Molin et al. |
| 5,786,211 A | 7/1998 | Johnson |
| 5,871,982 A | 2/1999 | Wilson et al. |
| 6,258,595 B1 | 7/2001 | Gao et al. |
| 6,376,237 B1 | 4/2002 | Colosi |
| 6,756,207 B1 | 6/2004 | Giuliano et al. |
| 7,198,951 B2 | 4/2007 | Gao et al. |
| 7,704,721 B2 | 4/2010 | Wright et al. |
| 8,361,977 B2 | 1/2013 | Baker et al. |
| 8,980,853 B2 | 3/2015 | Bennett et al. |
| 9,415,121 B2 | 8/2016 | Kaspar et al. |
| 10,793,861 B2 | 10/2020 | Kaspar et al. |
| 2002/0045591 A1* | 4/2002 | Geiger ........... C07K 14/705 514/44 R |
| 2005/0053922 A1 | 3/2005 | Schaffer et al. |
| 2005/0153446 A1* | 7/2005 | Steindler ............ A61P 25/16 435/368 |
| 2009/0202490 A1 | 8/2009 | Schaffer et al. |
| 2012/0177605 A1 | 7/2012 | Kaspar et al. |
| 2013/0072548 A1 | 3/2013 | Wright et al. |
| 2015/0252384 A1 | 9/2015 | Kaspar et al. |
| 2016/0038613 A1 | 2/2016 | Kaspar et al. |
| 2016/0152955 A1 | 6/2016 | Sakamoto et al. |
| 2016/0272976 A1 | 9/2016 | Kaspar et al. |
| 2017/0216458 A1 | 8/2017 | Kaspar et al. |

(Continued)

FOREIGN PATENT DOCUMENTS

| | | |
|---|---|---|
| CN | 105087650 A | 11/2015 |
| EP | 2933335 A1 | 10/2015 |

(Continued)

OTHER PUBLICATIONS

Fawaz et al., "A potency assay for a replication incompetent adenovirus type 5 carrying a human fgf-4 gene," Anal. Biochem., 2005, vol. 342, No. 1, pp. 34-44.*
Klement et al., "Ataxin-1 Nuclear Localization and Aggregation: Role in Polyglutamine-Induced Disease in SCA1 Transgenic Mice," Cell, 1998, vol. 95, issue 1, pp. 41-53.*
Miller et al., "460. A quantitative method for determining adenovirus gene transfer efficiency with established and primary human tumor cell cultures," Mol. Therapy, 2001, vol. 3, No. 5, p. S165.*
Qu, W. et al., "Calcium-ion-modulated ceramic hydroxyapatite resin for the scalable purification of recombinant Adeno-Associated Virus serotype 9," Journal of Chromatography B, 2015, vol. 990, pp. 15-22.
Amir et al., "Rett syndrome is caused by mutations in X-linked MECP2, encoding methyl-CpG-binding protein 2," Nature Genetics, Oct. 1999, 23:185-188.

(Continued)

*Primary Examiner* — Galina M. Yakovleva
(74) *Attorney, Agent, or Firm* — Joshua J. Buchman

(57) ABSTRACT

The invention relates to an in vitro quantative cell-based assay that uses a primary mouse cell model system permissive to viral vector infection and a quantitative high content image-based system for determining potency of a transgene-expressing viral vector drug product for lot disposition.

24 Claims, 58 Drawing Sheets

Specification includes a Sequence Listing.

(56) References Cited

U.S. PATENT DOCUMENTS

| | | | |
|---|---|---|---|
| 2018/0036431 | A1 | 2/2018 | Kaspar et al. |
| 2019/0336618 | A1 | 11/2019 | Kaspar |
| 2020/0179467 | A1 | 6/2020 | Kaspar et al. |
| 2021/0317474 | A1 | 10/2021 | Kaspar et al. |

FOREIGN PATENT DOCUMENTS

| | | | | |
|---|---|---|---|---|
| EP | 3054006 | A1 | 8/2016 | |
| WO | WO 95/13365 | A1 | 5/1995 | |
| WO | WO 95/13392 | A1 | 5/1995 | |
| WO | WO 96/17947 | A1 | 6/1996 | |
| WO | WO 97/06243 | A1 | 2/1997 | |
| WO | WO 97/08298 | A1 | 3/1997 | |
| WO | WO 97/09441 | A2 | 3/1997 | |
| WO | WO 97/21825 | A1 | 6/1997 | |
| WO | WO-9809657 | A2 | 3/1998 | |
| WO | WO 99/11764 | A2 | 3/1999 | |
| WO | WO 01/83692 | A2 | 11/2001 | |
| WO | WO-2004113494 | A2 | 12/2004 | |
| WO | WO-2005046598 | A2 | 5/2005 | |
| WO | WO-2010002846 | A1 | 1/2010 | |
| WO | WO 2010/129021 | A1 | 11/2010 | |
| WO | WO-2011079018 | A2 | 6/2011 | |
| WO | WO 2011/094198 | A1 | 8/2011 | |
| WO | WO-2013190059 | A1 | 12/2013 | |
| WO | WO-2013192005 | A2 | 12/2013 | |
| WO | WO-2014022582 | A1 * | 2/2014 | ......... A61K 38/1709 |
| WO | WO 2014/178863 | A1 | 11/2014 | |
| WO | WO-2015013148 | A2 | 1/2015 | |
| WO | WO 2015/031392 | A9 | 3/2015 | |
| WO | WO 2016/004319 | A1 | 1/2016 | |
| WO | WO-2016100575 | A1 | 6/2016 | |
| WO | WO-2016128407 | A1 | 8/2016 | |
| WO | WO-2016128408 | A1 | 8/2016 | |
| WO | WO 2017/160360 | A2 | 9/2017 | |
| WO | WO 2017/173283 | A1 | 10/2017 | |
| WO | WO 2017/181113 | A1 | 10/2017 | |
| WO | WO-2018055206 | A1 | 3/2018 | |
| WO | WO 2019/011817 | A1 | 1/2019 | |
| WO | WO 2019/094253 | A1 | 5/2019 | |
| WO | WO 2019/236949 | A1 | 12/2019 | |

OTHER PUBLICATIONS

Baker, M., "Digital PCR hits its stride," Nature Methods, Jun. 2012, 9(6):541-544.

Boutin et al., "Prevalence of Serum IgG and Neutralizing Factors Against Adeno-Associated Virus (AAV) Types 1, 2, 5, 6, 8, and 9 in the Healthy Population: Implications for Gene Therapy Using AAV Vectors," Human Gene Therapy, 2010, vol. 21, No. 6, 704-712.

Carter, B.J., "Adeno-associated virus vectors," Current Opinion in Biotechnology, 1992, 3(5): 533-539.

Chu et al., "SV40 DNA transfection of cells in suspension: analysis of efficiency of transcription and translation of T-antigen," Gene (1981) 13:197-202.

Clark et al., "A stable cell line carrying adenovirus-inducible rep and cap genes allows for infectivity titration of adeno-associated virus vectors," Gene Therapy (1996) 3:1124-1132.

Crowther et al., "An Adeno-Associated Virus-Based Toolkit for Preferential Targeting and Manipulating Quiescent Neural Stem Cells in the Adult Hippocampus," Stem Cell Reports, Mar. 13, 2018, vol. 10, pp. 1146-1159.

De et al., "High Levels of Persistent Expression of α1-Antitrypsin Mediated by the Nonhuman Primate Serotype rh. 10 Adeno-associated Virus Despite Preexisting Immunity to Common Human Adeno-associated Viruses," Mol. Ther, Jan. 2006, 13(1): 67-76.

Duque et al., "A Large Animal Model of Spinal Muscular Atrophy and Correction of Phenotype," Ann Neurol 2015, 77:399-414.

Eaves et al., "Isolation and Properties of an Exocellular Nuclease of Serratia Marcescens," J. Bact. 1963, 85, 273-278.

Encinas et al., "Gene regulation in adult neural stem cells. Current challenges and possible applications," Advanced Drug Delivery Reviews, 2017, 120: 118-132.

Ebinger et al., "Headache and Backache After Lumbar Puncture in Children and Adolescents: A Prospective Study," Pediatrics, Jun. 2004, 113(6):1588-1592.

Farkas et al., "Multimode light microscopy and the dynamics of molecules, cells, and tissues," Ann. Rev. Physiol. (1993) 55:785-817.

Farrar et al., "Emerging Therapies and Challenges in Spinal Muscular Atrophy," Ann Neurol., 2017, 81: 355-368.

Foust et al., "Rescue of the spinal muscular atrophy phenotype in a mouse model by early postnatal delivery of SMN," Nature Biotechnol., Mar. 2010, 28(3): 271-274, 11 pages provided.

Foust et al., "Therapeutic AAV9-mediated Suppression of Mutant SOD1 Slows Disease Progression and Extends Survival in Models of Inherited ALS," Molecular Therapy, Dec. 2013, vol. 21, No. 12, 2148-2159.

Gao et al., "Clades of Adeno-associated viruses are widely disseminated in human tissues," J. Virol (2004) 78(12): 6381-6388.

GenBank NCBI Reference Sequence AF085716.1, Adeno-associated virus 5 DNA binding trs helicase (Rep22) and capsid protein (VP1) genes, complete cds, Feb. 9, 1999, 3 pages.

GenBank NCBI Reference Sequence AX753246.1, Sequence 1 from Patent EP1310571, Jun. 23, 2003, 2 pages.

GenBank NCBI Reference Sequence AX753249.1, Sequence 4 from Patent EP1310571, Jun. 23, 2003, 2 pages.

GenBank NCBI Reference Sequence NC_001401.2, Adeno-associated virus-2, complete genome, Aug. 13, 2018, 6 pages.

GenBank NCBI Reference Sequence NC_001829.1, Adeno-associated virus-4, complete genome, Aug. 13, 2018, 3 pages.

GenBank NCBI Reference Sequence NC_001862.1, Adeno-associated virus 6, complete genome, Jan. 12, 2004, 3 pages.

GenBank NCBI Reference Sequence NC_002077.1, Adeno-associated virus-1, complete genome, Aug. 13, 2018, 3 pages.

GenBank NCBI Reference Sequence: NM_000344.2, *Homo sapiens* survival of motor neuron 1, telomeric (SMN1), transcript variant d, mRNA, Aug. 10, 2008, 4 pages.

GenBank NCBI Reference Sequence NM_017411.4, *Homo sapiens* survival of motor neuron 2, centromeric (SMN2), transcript variant d, mRNA, Apr. 20, 2021, 5 pages.

Giuliano and Taylor, "Measurement and manipulation of cytoskeletal dynamics in living cells," Curr. Op. Cell Biol., 1995, 7:4-12.

Giuliano et al., "Fluorescent protein biosensors: measurement of molecular dynamics in living cells," Annu. Rev. Biophys. Biomol. Struct. (1995) 24:405-434.

Glanzman et al., "The Children's Hospital of Philadelphia Infant Test of Neuromuscular Disorders (Chop Intend): test development and reliability." Neuromuscular Disorders, Mar. 2010, 20(3):155-161, 11 pages provided.

Graham et al., "A new technique for the assay of infectivity of human adenovirus 5 DNA, " Virology, (1973) 52:456-467.

Gurney et al., "Motor neuron degeneration in mice that express a human Cu,Zn superoxide dismutase mutation," Science, Jun. 1994, vol. 264, pp. 1772-1775.

Guy et al., "Reversal of Neurological Defects in a Mouse Model of Rett Syndrome," Science, Feb. 2007, 315(5815): 1143-1147.

Hahn et al., "Patterns of elevated free calcium and calmodulin activation in living cells," Nature (1992) 359:736-738.

Hermens et al., "Purification of Recombinant Adeno-Associated Virus by Iodixanol Gradient Ultracentrifugation Allows Rapid and Reproducible Preparation of Vector Stocks for Gene Transfer in the Nervous System," Human Gene Therapy, Jul. 1999, 10:1885-1891.

Hermonat et al., "Use of adeno-associated virus as a mammalian DNA cloning vector: Transduction of neomycin resistance into mammalian tissue culture cells," PNAS USA, Oct. 1984, 81:6466-6470.

Hildebrandt et al., "Targeting of neural stem cells in the hippocampus of adult rats by custom-made Ad vectors," Brain Struct Funct (2010) 215:105-113.

Jeune et al., "Pre-existing Anti-Adeno-Associated Virus Antibodies as a Challenge in AAV Gene Therapy," Human Gene Therapy Methods, Apr. 2013, 24(2):59-67.

Kaplitt et al., "Safety and tolerability of gene therapy with an adeno-associated virus (AAV) borne GAD gene for Parkinson's disease: an open label, phase I trial" Lancet (2007) 369:2097-2105.

(56) References Cited

OTHER PUBLICATIONS

Kiechl-Kohlendorfor et al., "Cerebrospinal Fluid Leakage After Lumbar Puncture in Neonates: Incidence and Sonographic Appearance," American Journal of Roentgenology, 2003, 181: 231-234.
Kotterman et al., "Enhanced selective gene delivery to neural stem cells in vivo by an adeno-associated viral variant," Development (2015) 142: 1885-1892.
Laughlin et al., "Cloning of infectious adeno-associated virus genomes in bacterial plasmids," Gene, 1983, 23:65-73.
Lebkowski et al., "Adeno-Associated Virus: a Vector System for Efficient Introduction and Integration of DNA into a Variety of Mammalian Cell Types," Mol Cell Biol, Oct. 1988, 8(10): 3988-3996.
Lefebvre et al., "Correlation between severity and SMN protein level in spinal muscular atrophy," Nature Genetics, (1997) 16:265-269.
Lefebvre et al., "Identification and Characterization of a Spinal Muscular Atrophy-Determining Gene," Cell, Jan. 1995, 80:155-65.
Levitt et al., "Definition of an efficient synthetic poly(A) site," Genes & Development, 1989, 3:1019-1025.
Lock et al., "Absolute Determination of Single-Stranded and Self-Complementary Adeno-Associated Viral Vector Genome Titers by Droplet Digital PCR," Human Gene Therapy Methods (Apr. 2014) 25(2):115-125.
Lorson et al., "A single nucleotide in the SMN gene regulates splicing and is responsible for spinal muscular atrophy," PNAS, May 1999, 96: 6307-6311.
Lowes et al., "Impact of Age and Motor Function in a Phase 1/2A Study of Infants With SMA Type 1 Receiving Single-Dose Gene Replacement Therapy," Pediatric Neurology (2019) 98: 39-45.
Marks, Jr., W.J. et al., "Gene delivery of AAV2-neurturin for Parkinson's disease: a double-blind, randomised, controlled trial," Lancet Neurol. (2010) 9:1164-1172.
Matagne et al., "A codon-optimized Mecp2 transgene corrects breathing deficits and improves survival in a mouse model of Rett syndrome," Neurobiology of Disease, 2017, vol. 99, pp. 1-11.
McCarty et al., "Sequences Required for Coordinate Induction of Adeno-Associated Virus p19 and p40 Promoters by Rep Protein," J Virol., Jun. 1991, 65(6):2936-2945.
McLaughlin et al., "Adeno-Associated Virus General Transduction Vectors: Analysis of Proviral Structures," J Virol, Jun. 1988, 62(6):1963-1973.
Mendell et al., "Phase I Gene Transfer Clinical Trial for Spinal Muscular Atrophy Type 1 Delivering avxs-101," Protocol No. AVXS-101-CL-101 (formerly AVXS-101), IND No. 15699, Version 14.0, Apr. 21, 2016, 63 pages.
Mendell et al., "Phase I Gene Transfer clinical trial for spinal muscular atrophy type 1 delivering the survival motor neuron gene by self-complementary AAV9," The Research Institute at Nationwide Children's Hospital Center for Gene Therapy, Protocol Version 1.0, Oct. 5, 2012, 33 pages.
Mendell, J.R., "Phase I Gene Transfer clinical trial for spinal muscular atrophy type 1 delivering the survival motor neuron gene by self-complementary AAV9," The Research Institute at Nationwide Children's Hospital Center for Gene Therapy, IND# 15699, Version 6.2, Apr. 4, 2014, 34 pages.
Mendell et al., "Single-Dose Gene-Replacement Therapy for Spinal Muscular Atrophy," N Engl J Med 2017, 337(18): 1713-1722.
Mendell et al., Supplementary Appendix to Single-Dose Gene-Replacement Therapy for Spinal Muscular Atrophy, N Engl J Med 2017, 337(18): 1713-1722, 4 pages.
Mingozzi et al., "Pharmacological Modulation of Humoral Immunity in a Nonhuman Primate Model of AAV Gene Transfer for Hemophilia B," Mol Ther, Jul. 2012, 20(7):1410-1416.
Monani et al., "A Single Nucleotide Difference That Alters Splicing Patterns Distinguishes the SMA Gene SMN1 From the Copy Gene SMN2," Human Molecular Genetics, 1999, vol. 8, No. 7, 1177-1183.

Monani, U.R., "Spinal Muscular Atrophy: A Deficiency in a Ubiquitous Protein; a Motor Neuron-Specific Disease," Neuron, Dec. 2005, 48: 885-896.
Monteilhet et al., "A 10 Patient Case Report on the Impact of Plasmapheresis Upon Neutralizing Factors Against Adeno-associated Virus (AAV) Types 1, 2, 6, and 8," Mol. Therapy, Nov. 2011, 19(11): 2084-2091.
Mori et al., "Two novel adeno-associated viruses from cynomolgus monkey: pseudotyping characterization of capsid protein," Virology, (2004) 330: 375-383.
Muzyczka, N., "Use of adeno-associated virus as a general transduction vector for mammalian cells," Curr. Top. Microbiol. Immunol (1992) 158:97-129.
Myslinski et al., "An unusually compact external promoter for RNA polymerase III transcription of the human H1RNA gene," Nucleic Acids Research, 2001, 29(12): 2502-2509.
Nestle et al., "An extracellular nuclease from Serratia marcescens. II. Specificity of the enzyme," J. Biol. Chem., Oct. 1969, 244(19), 5219-5225.
Oertle et al., "Nogo-A Inhibits Neurite Outgrowth and Cell Spreading with Three Discrete Regions," The Journal of Neuroscience, Jul. 2003, 23(13): 5393-5406.
Oprea et al., "Plastin 3 Is a Protective Modifier of Autosomal Recessive Spinal Muscular Atrophy," Science, Apr. 2008, 320(5875): 524-527, 11 pages provided.
Pacak et al., "Recombinant Adeno-Associated Virus Serotype 9 Leads to Preferential Cardiac Transduction In Vivo," Circ. Res, (2006) 99(4): e3-e9.
Park et al., "Spinal Muscular Atrophy: New and Emerging Insights from Model Mice," Curr Neurol Neurosci Rep., Mar. 2010, 10(2): 108-117, 14 pages provided.
Paul et al., "Increased Viral Titer Through Concentration of Viral Harvests from Retroviral Packaging Lines," Human Gene Therapy, 1993, vol. 4, No. 5, pp. 609-615.
Perrin et al., "An experimental rabies vaccine produced with a new BHK-21 suspension cell culture process: use of serum-free medium and perfusion-reactor system," Vaccine (1995) 13:1244-1250.
Potter et al., "A simplified purification protocol for recombinant adeno-associated virus vectors," Molecular Therapy—Methods & Clinical Development, vol. 1, Jan. 2014, pp. 14034, 8 pages.
Prior et al., "A Positive Modifier of Spinal Muscular Atrophy in the SMN2 Gene," The American Journal of Human Genetics, Sep. 2009, 85, 408-413.
Proll et al., "Potential of label-free detection in high-content-screening applications," Journal of Chromatography, Aug. 2007, 1161(1-2): 2-8.
Qu et al., "Scalable Downstream Strategies for Purification of Recombinant Adeno-Associated Virus Vectors in Light of the Properties," Current Pharmaceutical Biotechnology, 2015, 16(8), 684-695.
Rao et al., "Gene Therapy for Spinal Muscular Atrophy: An Emerging Treatment Option for a Devastating Disease", J Manag Care Spec Pharm, Dec. 2018, 24(12-a Suppl): S3-S16.
Rashnonejad et al., "Large-Scale Production of Adeno-Associated Viral Vector Serotype-9 Carrying the Human Survival Motor Neuron Gene," Mol Biotechnol (2016) 58: 30-36.
Ruffing et al., "Mutations in the carboxy terminus of adeno-associated virus 2 capsid proteins affect viral infectivity: lack of an RGD integrin-binding motif," Journal of General Virology (1994), 75, 3385-3392.
Samulski et al., "Helper-free stocks of recombinant adeno-associated viruses: normal integration does not require viral gene expression," J. Virol, Sep. 1989, 63(9): 3822-3828.
Samulski et al., "Cloning of adeno-associated virus into pBR322: rescue of intact virus from the recombinant plasmid in human cells," Proc. Natl. Acad. Sci. USA (1982), 79(6): 2077-281.
Schmidt et al., "Selective Targeting of Adenoviral Vectors to Neural Precursor Cells in the Hippocampus of Adult Mice: New Prospects for In Situ Gene Therapy," Stem Cells, 2007, 25: 2910-2918.
Senapathy and Carter, "Molecular Cloning of Adeno-associated Virus Variant Genomes and Generation of Infectious Virus by Recombination in Mammalian Cells," J. Biol. Chem., Apr. 1984, 259(7):4661-4666.

(56) References Cited

OTHER PUBLICATIONS

Singh et al., "A Multi-Exon-Skipping Detection Assay Reveals Surprising Diversity of Splice Isoforms of Spinal Muscular Atrophy Genes," PLoS One, 7(11):e49595, 17 pages, 2012.

Srivastava et al., "Nucleotide Sequence and Organization of the Adeno-Associated Virus 2 Genome," J Virol., Feb. 1983, 45(2): 555-564.

Strobel et al., "Comparative Analysis of Cesium Chloride- and Iodixanol-Based Purification of Recombinant Adeno-Associated Viral Vectors for Preclinical Applications," Human Gene Therapy Methods, 26(4): 147-157, 2015.

Sun et al., "Engineered viral vectors for functional interrogation, deconvolution, and manipulation of neural circuits," Curr. Opin. Neurobiol. 2018, 50: 163-170.

Sykes et al., "Quantitation of targets for PCR by use of limiting dilution," Biotechniques, 1992, 13(3): 444-449.

Tomono et al., "Ultracentrifugation-free chromatography-mediated large-scale purification of recombinant adeno-associated virus serotype 1 (rAAV1)," Molecular Therapy—Methods & Clinical Development, (2016) 3:15058, 8 pages.

Tratschin et al., "A Human Parvovirus, Adeno-Associated Virus, as a Eucaryotic Vector: Transient Expression and Encapsidation of the Procaryotic Gene for Chloramphenicol Acetyltransferase," Mol Cell Biol., 1984, 4(10): 2072-2081.

Tratschin et al., "Adeno-Associated Virus Vector for High-Frequency Integration, Expression, and Rescue of Genes in Mammalian Cells," Mol Cell Biol., Nov. 1985, 5(11): 3251-3260.

UniProt Accession No. Q16637 (SMN_Human), Nov. 1, 1996, 23 pages.

United States Pharmacopeia <787>, Subvisible Particulate Matter In Therapeutic Protein Injections, May 2021, 3 pages.

United States Pharmacopeia <785>, Osmolality and Osmolarity, USP32-NF27 p. 305, Pharmacopeial Forum: vol. No. 34(5) p. 1251, http://www.uspbpep.com/usp32/pub/data/v32270/usp32nf27s0_c785.html, 4 pages, May 11, 2021.

United States Pharmacopeia <791>, pH, USP29-NF24 p. 2730, Pharmacopeial Forum: vol. No. 29(6) p. 2037, http://www.uspbpep.com/usp29/v29240/usp29nf24s0_c791.html, May 11, 2021.

Waggoner et al., "Multiparameter fluorescence imaging microscopy: reagents and instruments," Hum. Pathol. (1996) 27:494-502.

Wang et al., "Adeno-associated virus serotype 8 efficiently delivers genes to muscle and heart," Nature Biotech (2005) 23(3): 321-328.

Worgall et al., "Treatment of Late Infantile Neuronal Ceroid Lipofuscinosis by CNS Administration of a Serotype 2 Adeno-Associated Virus Expressing CLN2 cDNA, " Human Gene Therapy, May 2008, 19(5):463-474.

Wright et al., "Manufacturing and Regulatory Strategies for Clinical AAV2-hRPE65," Current Gene Therapy, 2010, 10: 341-349.

Wright et al., "Product-Related Impurities in Clinical-Grade Recombinant AAV Vectors: Characterization and Risk Assessment," Biomedicines 2014, 2, 80-97.

Miyake and Shimada, "3.Gene Delivery and Expression Series Viral Vector Mediated Gene Delivery and Expression(4)", Nihon Ika Daigaku Igakkai Zasshi, 2012, vol. 8, pp. 150-156 (with English abstract).

Mizutani, Ken'ichi, "Neural Progenitor Cells", Brain Science Dictionary, [Online] Apr. 17, 2017, Internet, retrieved from: https://bsd.neuroinf.jp/w/index.php?title=%E7%A5%9E%E7%B5%8C%E5%89%8D%E9%A7%86%E7%B4%B0%E8%83%9E&oldid=37640 (with English machine translation), 15 pages.

Novartis, "Novartis data again demonstrate age-appropriate development when Zolgensma is used presymptomatically, and post-hoc data reveal SMA Type 1 patients could speak, swallow, and maintain airway protection," Mar. 14, 2022, 5 pages.

U.S. Department of Health and Human Services et al., "Q4B Evaluation and Recommendation of Pharmacopoeial Texts for Use in the ICH Regions. Annex 3(R1) Test for Particulate Contamination: Subvisible Particles General Chapter Guidance for Industry," Sep. 2017, 10 pages, retrieved from https://www.fda.gov/media/71231/download.

Clark, K.R., et al., "Highly Purified Recombinant Adeno-Associated Virus Vectors Are Biologically Active and Free of Detectable Helper and Wild-Type Viruses," Hum Gene Ther., Apr. 1999, 10(6): 1031-1039.

Embury, C.M., et al., "Cathepsin B Improves β-Amyloidosis and Learning and Memory in Models of Alzheimer's Disease" Journal of Neuroimmune Pharmacology, 2017, vol. 12, pp. 340-352.

Kiyota, T., et al., "AAV2/1 CD74 Gene Transfer Reduces β-amyloidosis and Improves Learning and Memory in a Mouse Model of Alzheimer's Disease," Molecular Therapy, 2015, vol. 23(11), pp. 1712-1721 (10 pages provided).

Robert, M-A. et al., "Manufacturing of recombinant adeno-associated viruses using mammalian expression platforms," Biotechnology Journal, 2017, vol. 12, 1600193, 16 pages.

Schnepp, B. and Clark, K.R., "Highly Purified Recombinant Adeno-Associated Virus Vectors. Preparation and Quantitation," Methods Mol Med., 2002, 69: 427-443.

AveXis, Inc., AveXis, Inc.'s Initial Response to the Form FDA 483 Issued on Aug. 2, 2019 to the San Diego, CA Quality Control Laboratory, FEI: 3014617030, Investigators: Scott T. Ballard and Mibaly S. Ligmond, dated Aug. 23, 2019, 59 pages Department of Health and Human Services, Food and Drug Administration, Form FDA 483, dated Aug. 2, 2019, to the San Diego, CA Quality Control Laboratory, FEI No. 3014617030, 5 pages.

Keown, A., "Kaspar Brothers Impeded Internal Investigation into Data Manipulation, Novartis Claims," BioSpace, Sep. 25, 2019, 6 pages, retrieved from https://www.biospace.com/article/novartis-continues-to-point-its-finger-at-the-kaspar-brothers-over-avexis-data-manipulation/.

\* cited by examiner

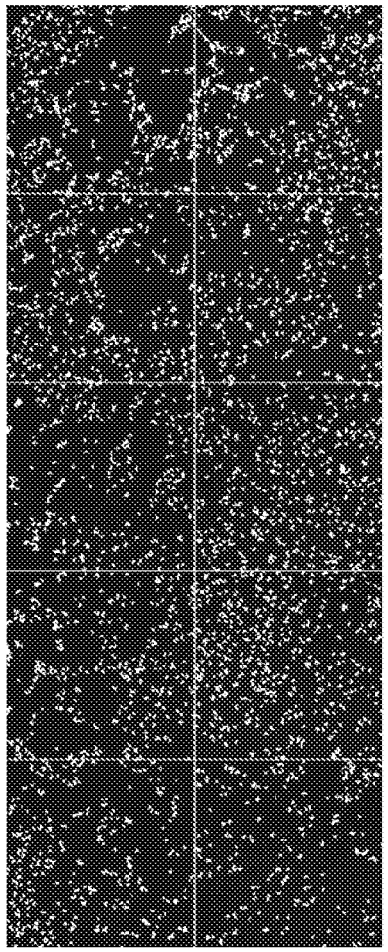
FIG. 5A (images obtained with a 10x objective)
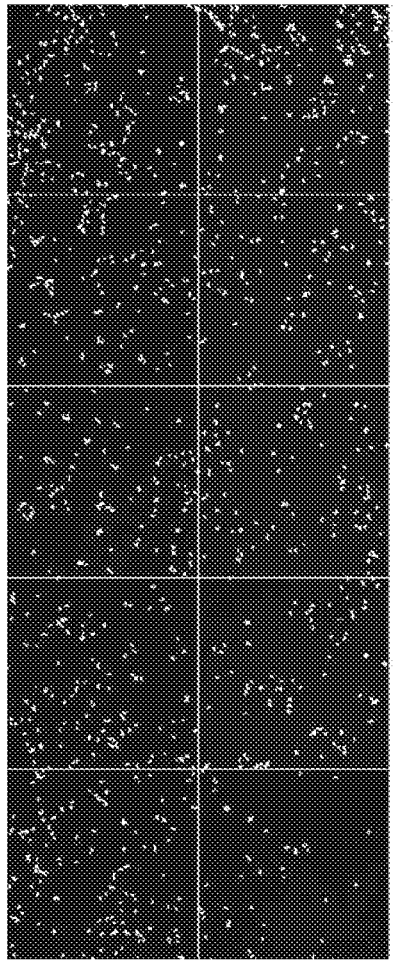
FIG. 5B (images obtained with a 10x objective)

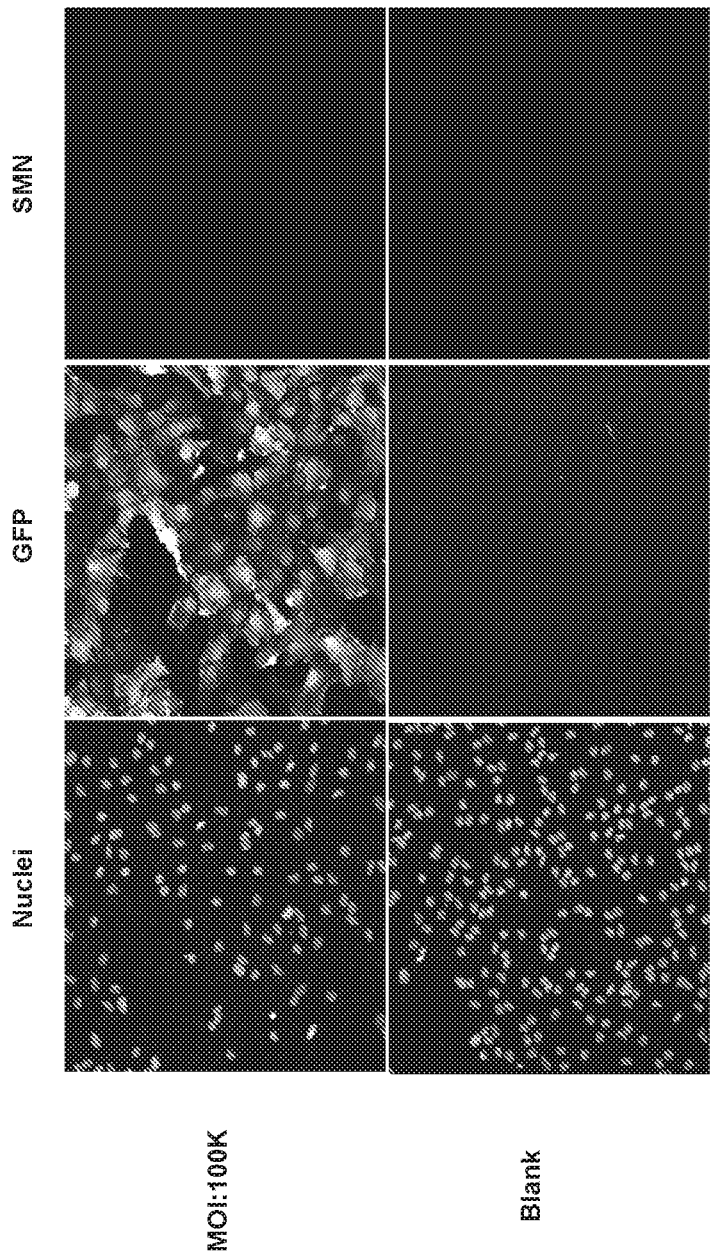
FIG. 7 (images obtained with a 20x objective)

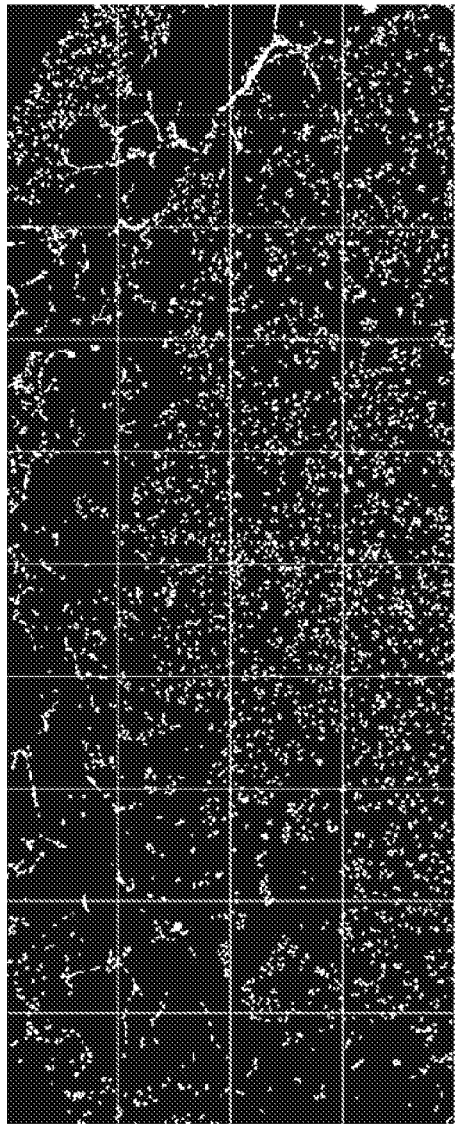
FIG. 8A (images obtained with a 20x objective)
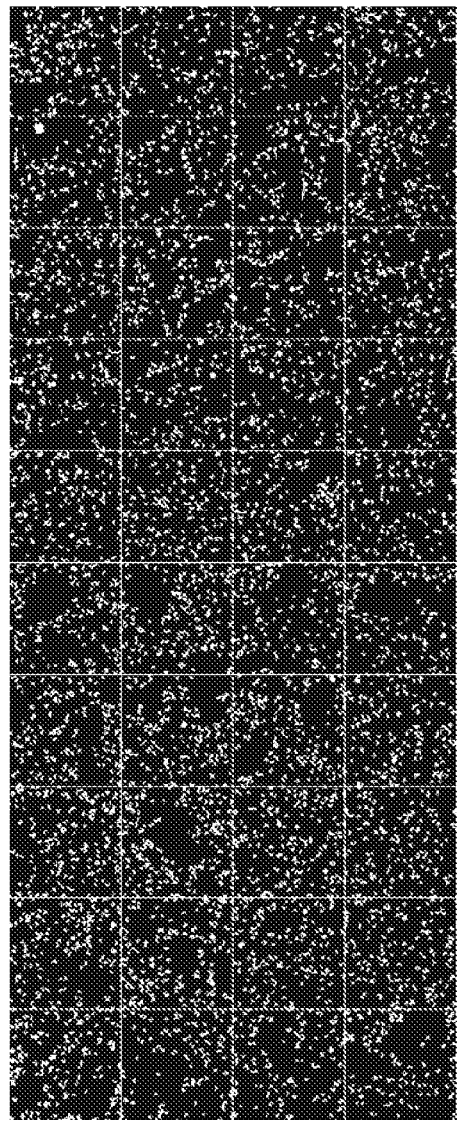
FIG. 8B (images obtained with a 20x objective)

(images obtained with a 20x objective)

(images obtained with a 20x objective)

(images obtained with a 20x objective)

(error bars indicate standard deviation)

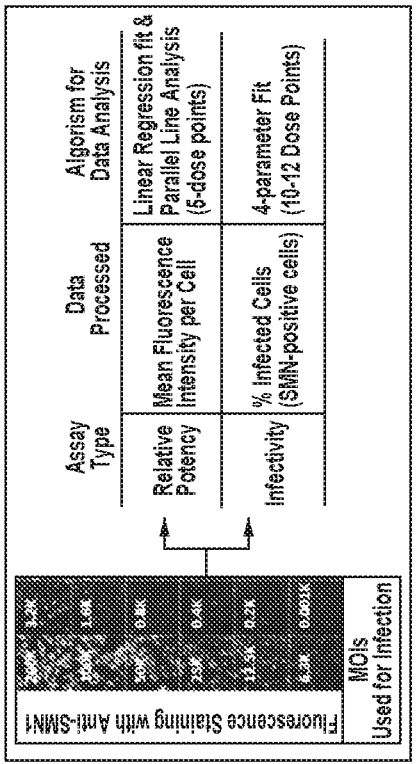
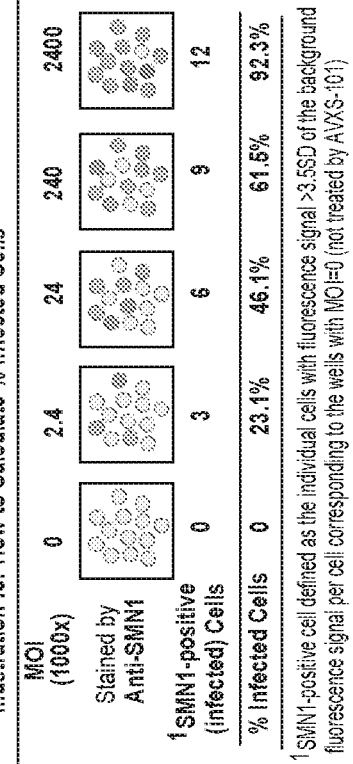
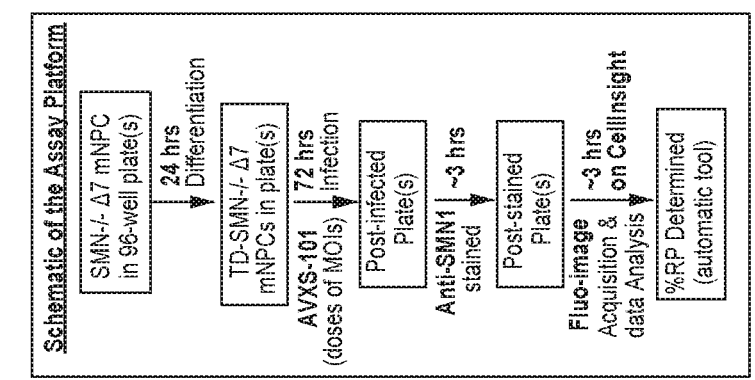
FIG. 15B
FIG. 15C
FIG. 15A pSMN map pHELP map pAAV2/9 map

| Step / Notebook Page | Date | Details | | | | Notes |
|---|---|---|---|---|---|---|
| Thaw Page 3 | 7/22/2015 | Flasks seeded | 25 | Old Passage | 0 | Cells were not counted, but full vial from ATCC ($1\times10^6$ cells) were plated. Four media changes between this step and the next. |
| | | Seeding Density | $1\times10^6$ cells | New Passage | 1* | |
| Passage Page 5 | 7/27/2015 | Flasks seeded | 75 | Old Passage | 1 | Cells before splitting were 95% confluent. Adherence selection step after seeding lead to significant portion of non-adherent cells lost: ~35% cell loss by visual inspection. |
| | | Seeding Density | 1:1 | New Passage | 2 | |
| Passage Page 7 | 7/29/2015 | Flasks seeded | 75 | Old Passage | 2 | Adherence selection step included after seeding. |
| | | Seeding Density | 1:1 | New Passage | 3 | |
| Passage Page 8 | 7/31/2015 | Flasks seeded | 2 x 175 | Old Passage | 3 | Adherence selection step included after seeding, with much less pronounced loss of cells by visual inspection. |
| | | Seeding Density | 1:4.7 | New Passage | 4 | |
| Passage Page 9 | 8/3/2015 | Flasks seeded | 8 x 175 | Old Passage | 4 | One media change between this step and the next. |
| | | Seeding Density | 1:4 | New Passage | 5 | |
| Passage Page 10 | 8/6/2015 | Flasks seeded | 20 x 175 | Old Passage | 5 | One media change between this step and the next. |
| | | Seeding Density | 1:3 or 1:2 | New Passage | 6 | |
| Harvest/ Cryo-preservation Pages 11-15 | 8/9/2015 | Cell Concentration | $1\times10^7$ cells/mL | Vials Filled | 22 | Pooled 2 cell suspensions to yield $1\times10^8$ cells and $1.2\times10^8$ cells. |

Note: All Total Cells reported above have the unit of "cells" and indicate total cells recovered.
All Seeding Densities reported above have the unit of "cells/$cm^2$"
All flask sizes reported above have the unit of "$cm^2$".
All Cell Concentrations reported above have the unit of "cells/mL".
* Thawing was considered a passage, thus thawed cells were labeled as "passage 1".

FIG. 28

8,000 cells/cm², D5 Trans, D9 Harvest

| | Volume | Titer | Total vg | Step Recovery | Total Recovery |
|---|---|---|---|---|---|
| Lysate Pool | 3200 | 4.06E+10 | 1.30E+14 | | |
| post COHC + 0.45 | 4000 | 3.68E+10 | 1.47E+14 | 113% | 113% |
| TFF1 UF Retentate | 400 | 2.96E+11 | 1.18E+14 | 80% | 91% |
| TFF1 DF Retentate | 580 | 2.14E+11 | 1.24E+14 | 105% | 96% |
| TFF1 UF Permeate | 3600 | <4E8 | 1.44E+12 | 1% | |

12,000 cells/cm², D4 Trans, D8 Harvest

| | Volume | Titer | Total vg | Step Recovery | Total Recovery |
|---|---|---|---|---|---|
| Lysate Pool | 3200 | 6.25E+10 | 2.00E+14 | | |
| post COHC + 0.45 | 4000 | 4.73E+10 | 1.89E+14 | 95% | 95% |
| TFF1 UF Retentate | 400 | 4.30E+11 | 1.72E+14 | 91% | 86% |
| TFF1 DF Retentate | 502 | 3.64E+11 | 1.83E+14 | 106% | 91% |
| TFF1 UF Permeate | 3600 | <4.0E8 | 1.44E+12 | 1% | |

FIG. 37A

8,000 cells/cm², D5 Transfect, D9 Harvest

| | Volume | ug/mL | Total HCP ug | HCP Step Clearance | Total HCP Clearance |
|---|---|---|---|---|---|
| Lysate Pool | 3200 | 67.52 | 216065 | | |
| post COHC + 0.45 | 4000 | 49.47 | 197862 | 8.4% | 8.42% |
| TFF1 UF Retentate | 400 | 170.90 | 68358 | 65.5% | 68.36% |
| TFF1 DF Retentate | 580 | 52.17 | 30261 | 55.7% | 86% |
| TFF1 UF Permeate | 3600 | 29.50 | 106186 | 54% | |

12,000 cells/cm², D4 Transfect, D8 Harvest

| | Volume | ug/mL | Total HCP ug | HCP Step Clearance | Total HCP Clearance |
|---|---|---|---|---|---|
| Lysate Pool | 3200 | 58.38 | 186813 | | |
| post COHC + 0.45 | 4000 | 35.25 | 140988 | 24.5% | 24.53% |
| TFF1 UF Retentate | 400 | 120.09 | 48036 | 65.9% | 74.29% |
| TFF1 DF Retentate | 502 | 17.48 | 8775 | 81.7% | 95% |
| TFF1 UF Permeate | 3600 | 26.69 | 96080.4 | 68% | |

FIG. 37B

| Test Description | Test Method | Proposed Test Limit | NCH Phase 1 Lot NCHAAV9SMN0613 Date Manufactured: 18-Dec-2013 Test Date: 13-Feb-2017 to 08-Aug-2017 [1] | AVXS-101 Lot 600156 Date Manufactured: 07-Nov-2017 Test Date: 08-Nov-2017 to 26-Dec-2017 | AVXS-101 Lot 600307 Date Manufactured: 04-Dec-2017 Test Date: 05-Dec-2017 to 30-Jan-2017 |
|---|---|---|---|---|---|
| Genomic Titer by ddPCR | SOP-137 | $2.0 \times 10^{13} - 6.0 \times 10^{13}$ vg/mL | $1.1 \times 10^{13}$ vg/mL (n=9) [1] | $3.7 \times 10^{13}$ vg/mL (n=9) [2] | $4.0 \times 10^{13}$ vg/mL (n=14) [2] |
| Infectious Titer | SOP-192 | Report Results | $5.9 \times 10^{9}$ IU/mL [3] | $1.3 \times 10^{10}$ IU/mL [3] | $6.7 \times 10^{9}$ IU/mL [3] |
| Subvisible Particles | SOP-262 | ≤6000 particles/cont ≥ 10 μm; ≤600 particles/cont ≥ 25 μm | 22 particles/cont ≥ 10 μm; 4 particles/cont ≥ 25 μm | 119 particles/cont ≥ 10 μm; 4 particles/cont ≥ 25 μm | 9 particles/cont ≥ 10 μm; 2 particles/cont ≥ 25 μm |
| pH | SOP-057 | 7.5 – 8.5 | 7.9 | 7.9 | 8.0 |
| Osmolality | SOP-128 | 384 – 448 mOsm/kg | 410 mOsm/kg | 415 mOsm/kg | 410 mOsm/kg |
| Appearance by Visual Inspection | SOP-164 | Clear to slightly opaque, colorless to faint white solution, free of visible particulates | Clear and colorless solution, free of visible particles | Faint white, slightly opaque, free of visible particles [4] | Colorless, slightly opaque, free of visible particles |
| Total Protein by BCA | SOP-184 | 128 – 320 μg/mL per $1.0 \times 10^{13}$ vg/mL | 167 μg/mL [3] (177 μg/mL) [5] | 179 μg/mL [3] (661 μg/mL) [5] | 176 μg/mL [3] (702 μg/mL) [5] |
| Residual hcDNA by qPCR | SOP-190 | ≤ $1.2 \times 10^{6}$ pg/mL per $1.0 \times 10^{13}$ vg/mL | $3.7 \times 10^{5}$ pg/mL [3] ($3.9 \times 10^{5}$ pg/mL) [5] | $0.76 \times 10^{5}$ pg/mL [3] ($2.8 \times 10^{5}$ pg/mL) [5] | $0.68 \times 10^{5}$ pg/mL [3] ($2.72 \times 10^{5}$ pg/mL) [5] |
| % Empty Capsid by AUC | SOP-263 | ≤ 7% | 7% | 2% | 4% |
| Vector ID by SDS PAGE | SOP-180 | Main Bands of VP1, VP2, VP3 co-migrate with AVXS-101 control | Main Bands of VP1, VP2, VP3 co-migrate with AVXS-101 control<br><br>Main Band MWs:<br>VP1: 84.9-89.5 kDa<br>VP2: 65.9-69.1 kDa<br>VP3: 57.1-59.0 kDa | Main Bands of VP1, VP2, VP3 co-migrate with AVXS-101 control<br><br>Main Band MWs:<br>VP1: 83.6-84.4<br>VP2: 64.6-65.5<br>VP3: 56.2-57.2 | Main Bands of VP1, VP2, VP3 co-migrate with AVXS-101 control<br><br>Main Band MWs:<br>VP1: 82.9-84.9<br>VP2: 64.3-65.2<br>VP3: 56.0-56.7 |
| Purity by SDS-PAGE | SOP-180 | % Total Purity (VP1, VP2, VP3): ≥ 95% | % Total Purity: 98% (Avg n=4 gels) | % Total Purity: 99% (Avg, n=4 gels) | % Total Purity: 99% (Avg, n=4 gels) |

FIG. 42A

| Test Description | Test Method | Proposed Test Limit | NCH Phase 1 Lot NCHAAV9SMN0613 Date Manufactured: 18-Dec-2013 Test Date: 13-Feb-2017 to 08-Aug-2017 [1] | AVXS-101 Lot 600156 Date Manufactured: 07-Nov-2017 Test Date: 08-Nov-2017 to 26-Dec-2017 | AVXS-101 Lot 600307 Date Manufactured: 04-Dec-2017 Test Date: 05-Dec-2017 to 30-Jan-2017 |
|---|---|---|---|---|---|
| Total Impurities by SDS-PAGE | SOP-180 | % Total Impurities ≤5%<br><br>No single un-named impurity >2%<br><br>Named Impurities:<br>Report value<br><br>– Imp 1A (~71-73kDa)<br>– Imp 1 (~61-67 kDa)<br>– Imp 2 (~56-64 kDa)<br>– Imp 3 (~48-58 kDa)<br>– Imp 4 (~33-38 kDa)<br>– Imp 5 (~30-34 kDa) | % Total Impurities: 2% (Avg n=4 gels)<br><br>Individual Impurities (Avg n=4 gels)<br>– Imp 1: 1.5%<br>– Imp 3: <LOQ (1.0%) | % Total Impurities: 1% (Avg n=4 gels)<br><br>Individual Impurities (Avg n=4 gels)<br>– Imp 1: <LOQ (1.0%)<br>– Imp 3: <LOQ (1.0%)<br>– Imp 4: <LOQ (1.0%) | % Total Impurities: 1% (Avg n=4 gels)<br><br>Individual Impurities (Avg n=4 gels)<br>– Imp 1: 1.0%<br>– Imp 4: <LOQ (1.0%) |
| Vector Identity by Western | SOP-179 | Positive for AAV Capsid Protein | Positive for AAV Capsid Protein<br><br>Main Band MW<br>VP1: 79.7 kDa<br>VP2: 64.1 kDa<br>VP3: 55.7 kDa | Positive for AAV Capsid Protein<br><br>Main Band MW<br>VP1: 80.2 kDa<br>VP2: 66.2 kDa<br>VP3: 58.2 kDa | Positive for AAV Capsid Protein<br><br>Main Band MW<br>VP1: 79.1 kDa<br>VP2: 64.8 kDa<br>VP3: 57.5 kDa |
| Residual HCP by ELISA | SOP-183 | ≤40 ng/mL per $1.0 \times 10^{13}$ vg/mL | <LOQ (8 ng/mL) [5] | <LOQ (8 ng/mL) [5] | <LOQ (8 ng/mL) [5] |
| Vector Genome Identity by ddPCR | SOP-137 | Confirms | Confirms | Confirms | Confirms |
| Residual BSA by ELISA | SOP-181 | ≤3.0 ng/mL per $1.0 \times 10^{13}$ vg/mL | <LOQ (0.50 ng/mL) [5] | <LOQ (0.50 ng/mL) [5] | <LOQ (0.50 ng/mL) [5] |
| Residual Benzonase by ELISA | SOP-182 | ≤1.0 ng/mL per $1.0 \times 10^{13}$ vg/mL | <LOQ (0.20 ng/mL) [5] | <LOQ (0.20 ng/mL) [5] | <LOQ (0.20 ng/mL) [5] |
| In-vivo Relative Potency | SOP-285 | 80 – 120% | 100% [6] | | |

FIG. 42B

| Test Description | Proposed Test Limits | Pair Wise Comparison | | |
|---|---|---|---|---|
| | | Process A (Phase 1) | Process B (Phase 3) | Relative %Difference |
| Genomic Titer by ddPCR | $2.0 \times 10^{13} - 6.0 \times 10^{13}$ vg/mL | $1.1 \times 10^{13}$ vg/mL | $3.7 \times 10^{13}$ vg/mL | NA [1] |
| Infectious Titer | Report Results | $0.59 \times 10^{10}$ IU/mL | $1.3 \times 10^{10}$ IU/mL | 120% [2] |
| Subvisible Particles ≥ 10 μm | ≤ 6000 particles/cont ≥ 10 μm | 22 | 119 | 441% [3] |
| Subvisible Particles ≥ 25 μm | ≤ 600 particles/cont ≥ 25 μm | 4 | 4 | 0% |
| pH | 7.5 – 8.5 | 7.9 | 7.9 | 0% |
| Osmolality | 384 – 448 mOsm/kg | 410 mOsm/kg | 415 mOsm/kg | 1% |
| Appearance | Clear to slightly opaque, colorless to faint white solution, free of visible particulates | Clear and colorless solution, free of visible particles | Faint white, slightly opaque, free of visible particles | NA |
| Total Protein by BCA | 128 – 320 μg/mL per $1.0 \times 10^{13}$ vg/mL | 167 μg/mL | 179 μg/mL | 7% |
| Residual hcDNA by qPCR | ≤ $1.2 \times 10^{6}$ pg/mL per $1.0 \times 10^{13}$ vg/mL | $3.7 \times 10^{5}$ pg/mL | $0.76 \times 10^{5}$ pg/mL | 80% |
| % Empty Capsid by AUC | ≤ 7% | 7% | 2% | 71% [4] |
| Purity by SDS-PAGE | ≥ 95% | 98% | 99% | 1% |
| Total Impurities by SDS-PAGE | ≤ 5% | 2% | 1% | 50% |
| Residual HCP by ELISA | ≤ 40 ng/mL per $1.0 \times 10^{13}$ vg/mL | < LOQ (8 ng/mL) | < LOQ (8 ng/mL) | 0% |
| Residual BSA by ELISA | ≤ 3.0 ng/mL per $1.0 \times 10^{13}$ vg/mL | < LOQ (0.50 ng/mL) | < LOQ (0.50 ng/mL) | 0% |
| Residual Benzonase by ELISA | ≤ 1.0 ng/mL per $1.0 \times 10^{13}$ vg/mL | < LOQ (0.20 ng/mL) | < LOQ (0.20 ng/mL) | 0% |
| In-vivo Relative Potency | 80 – 120% | 100% | | |

[1] Relative % difference not applicable as the manufacturing target for genomic titer was changed between Process A and Process B.

[2] This value should be viewed in the context of expected variability for a biological assay which can often vary between 50% to 200% of the true value. That being said, AveXis recognized the need for improvement and has recently performed additional development and qualification work to improve this assay (SOP-328 and RPT-471). It should also be noted that infectivity efficiency of the HeLa RC32 cell line by AAV9-based viral vectors remains challenging.

[3] Considerable relative % difference for subvisible particles between Process A and Process B is noted; however, the absolute value for Process B is well below the proposed testing limits.

[4] Process B using CsCl gradient is more effective in removing empty capsids when compared to Process A which used iodixanol.

FIG. 43

| Test Description | Proposed Test Limits | Pair Wise Comparison | | |
| --- | --- | --- | --- | --- |
| | | Process B (600156) | Process B (600307) | Relative %Difference |
| Genomic Titer by ddPCR | $2.0 \times 10^{13} - 6.0 \times 10^{13}$ vg/mL | $3.7 \times 10^{13}$ vg/mL | $4.0 \times 10^{13}$ vg/mL | 8% |
| Infectious Titer | Report Results | $1.3 \times 10^{10}$ IU/mL | $0.67 \times 10^{10}$ IU/mL | 48% |
| Subvisible Particles $\geq 10$ μm | $\leq 6000$ particles/cont $\geq 10$ μm | 119 | 9 | 92% [1] |
| Subvisible Particles $\geq 25$ μm | $\leq 600$ particles/cont $\geq 25$ μm | 4 | 2 | 50% |
| pH | 7.5 – 8.5 | 7.9 | 8.0 | 1% |
| Osmolality | 384 – 448 mOsm/kg | 415 mOsm/kg | 410 mOsm/kg | 1% |
| Appearance | Clear to slightly opaque, colorless to faint white solution, free of visible particulates | Faint white, slightly opaque, free of visible particles | Colorless, slightly opaque, free of visible particles | NA |
| Total Protein by BCA | 128 – 320 μg/mL per $1.0 \times 10^{13}$ vg/mL | 179 μg/mL | 176 μg/mL | 2% |
| Residual hcDNA by qPCR | $\leq 1.2 \times 10^{6}$ pg/mL per $1.0 \times 10^{13}$ vg/mL | $0.76 \times 10^{5}$ pg/mL | $0.68 \times 10^{5}$ pg/mL | 11% |
| % Empty Capsid by AUC | $\leq 7\%$ | 2% | 4% | 100% [1] |
| Purity by SDS-PAGE | $\geq 95\%$ | 99% | 99% | 0% |
| Total Impurities by SDS-PAGE | $\leq 5\%$ | 1% | 1% | 0% |
| Residual HCP by ELISA | $\leq 40$ ng/mL per $1.0 \times 10^{13}$ vg/mL | < LOQ (8 ng/mL) | < LOQ (8 ng/mL) | 0% |
| Residual BSA by ELISA | $\leq 3.0$ ng/mL per $1.0 \times 10^{13}$ vg/mL | < LOQ (0.50 ng/mL) | < LOQ (0.50 ng/mL) | 0% |
| Residual Benzonase by ELISA | $\leq 1.0$ ng/mL per $1.0 \times 10^{13}$ vg/mL | < LOQ (0.20 ng/mL) | < LOQ (0.20 ng/mL) | 0% |
| In-vivo Relative Potency | 80 – 120% | | | |

[1] Relative % difference for subvisible particles and % Empty Capsid is ~100% between the two Process B lots; however, all values are well below the proposed testing limits and the Process B lots are considered to be consistent with regards to these test results.

FIG. 44

| Attribute | Method | Stability Time-point (mos) | | | | |
|---|---|---|---|---|---|---|
| | | 0 | 3 | 6 | 9 | 12 |
| | | February 2017 | May 2017 | August 2017 | November 2017 | February 2018 |
| Genomic Titer by ddPCR | SOP-137 v1.0 | $6.6 \times 10^{12}$ vg/mL | $6.1 \times 10^{12}$ vg/mL | $6.5 \times 10^{12}$ vg/mL | NA | NA |
| | SOP-137 v3.0 | N/A | N/A | $1.1 \times 10^{13}$ vg/mL [1] | $8.7 \times 10^{12}$ vg/mL | Target 26Feb18 |
| In vivo Relative Potency [2] | SOP-285 | 100% | | | | Pending |
| Infectious Titer | SOP-192 | $6.3 \times 10^{9}$ IU/mL | $8.4 \times 10^{9}$ IU/mL [3] | $1.1 \times 10^{10}$ IU/mL | $6.3 \times 10^{9}$ IU/mL | Pending |
| Purity by SDS-PAGE | SOP-180 | %Total Purity: 98% (n=4 gels)<br><br>%Total Impurities: 2% (n=4 gels)<br><br>Individual Impurities:<br>Imp 1: 1.7%<br>Imp 3: <LOQ (1.0%) | % Total Purity: 98% (n=4 gels)<br><br>%Total Impurities: 2% (n=4 gels)<br><br>Individual Impurities:<br>Imp 1: 1.7% | % Total Purity: 99% (n=4 gels)<br><br>%Total Impurities: 1% (n=4 gels)<br><br>Individual Impurities:<br>Imp 1: 1.2% | %Total Purity: 99% (Avg n=4 gels)<br><br>%Total Impurities: 1% (Avg n=4 gels)<br><br>Individual Impurities:<br>Imp 1: 1.3% | Pending |

[1] Lot was re-tested using an improved method, SOP-137 v3.0, per CAPA-19 around the 6-mo timepoint. As a result, a new titer value of $1.1 \times 10^{13}$ vg/mL was re-assigned for NCH Lot NCHAAV9SMN0613. All subsequent stability time-points were analyzed using SOP-137 v3.0.

[2] Lot NCHAAV9SMN0613 was manufactured in December 2013 and was tested on February 2017 as T0. A 100% potency was assigned at T0 and the potencies for all subsequent time points were calculated relative to the T0 value.

[3] Infectious Titer testing was performed approximately 4 months from $T_0$ as it was added to the respective stability protocol on June 2017.

FIG. 45

| NCHAAV SMN0613 | Empty Peak | | | Full Peak 1 | | | Full Peak 2 | | |
|---|---|---|---|---|---|---|---|---|---|
| | s-value | %area | MW (MDa) | s-value | %area | MW (MDa) | s-value | %area | MW (MDa) |
| Rep 1 (red) | 62.58 | 8.53 | 1.97 | 85.23 | 47.76 | 3.11 | 101.76 | 37.20 | 4.01 |
| Rep 2 (blue) | 62.50 | 8.39 | 2.36 | 85.33 | 49.14 | 3.77 | 101.94 | 39.36 | 4.85 |
| Avg | 62.54 | 8.46 | 2.17 | 85.28 | 48.45 | 3.44 | 101.85 | 38.28 | 4.43 |

| 600307 | Empty Peak | | | Full Peak 1 | | | Full Peak 2 | | |
|---|---|---|---|---|---|---|---|---|---|
| | s-value | %area | MW (MDa) | s-value | %area | MW (MDa) | s-value | %area | MW (MDa) |
| Rep 1 (red) | 62.12 | 3.68 | 3.32 | 85.51 | 52.18 | 5.30 | 101.91 | 38.46 | 7.11 |
| Rep 2 (blue) | 60.83 | 3.78 | 2.86 | 85.14 | 53.43 | 4.63 | 102.33 | 36.62 | 6.24 |
| Avg | 61.48 | 3.73 | 3.09 | 85.33 | 52.81 | 4.97 | 102.12 | 37.54 | 6.68 |

```
                              SEQUENCE LISTING

<160> NUMBER OF SEQ ID NOS: 4

<210> SEQ ID NO 1
<211> LENGTH: 2359
<212> TYPE: DNA
<213> ORGANISM: Artificial Sequence
<220> FEATURE:
<223> OTHER INFORMATION: SMN vector sequence

<400> SEQUENCE: 1
ctgcgcgctc gctcgctcac tgaggccgcc cgggcaaagc ccgggcgtcg gcgacctttt      60
ggtcgcccgg cctcagtgag cgagcgagcg cgcagagagg gagtggaatt cacgcgtgga    120
tctgaattca attcacgcgt ggtacctctg gtcgttacat aacttacggt aaatggcccg    180
cctggctgac cgcccaacga cccccgccca ttgacgtcaa taatgacgta tgttcccata    240
gtaacgccaa tagggacttt ccattgacgt caatgggtgg agtatttacg gtaaactgcc    300
cacttggcag tacatcaagt gtatcatatg ccaagtacgc cccctattga cgtcaatgac    360
ggtaaatggc ccgcctggca ttatgcccag tacatgacct tatgggactt tcctacttgg    420
cagtacatct actcgaggcc acgttctgct tcactctccc catctccccc cctccccac    480 ccccaatttt gtatttattt atttttttaat tattttgtgc agcgatgggg gcggggggg    540 ggggggggcg cgcgccaggc ggggcggggc ggggcgaggg gcgggcggg gcgaggcgga    600 gaggtgcggc ggcagccaat cagagcggcg cgctccgaaa gtttccttttt atggcgaggc    660 ggcggcggcg gcggccctat aaaaagcgaa gcgcgcggcg ggcgggagcg ggatcagcca    720
ccgcggtggc ggcctagagt cgacgaggaa ctgaaaaacc agaaagttaa ctggtaagtt    780
tagtcttttt gtcttttatt tcaggtcccg gatccggtgg tggtgcaaat caaagaactg    840
ctcctcagtg gatgttgcct ttacttctag gcctgtacgg aagtgttact tctgctctaa    900
aagctgcgga attgtacccg cggccgatcc accggtccgg aattcccggg atatcgtcga    960
cccacgcgtc cgggccccac gctgcgcacc cgcgggtttg ctatggcgat gagcagcggc   1020
ggcagtggtg gcggcgtccc ggagcaggag gattccgtgc tgttccggcg cggcacaggc   1080
cagagcgatg attctgacat ttgggatgat acagcactga taaagcata tgataaagct   1140 gtggcttcat ttaagcatgc tctaaagaat ggtgacattt gtgaaacttc gggtaaacca   1200 aaaccacac ctaaaagaaa acctgctaag aagaataaaa gccaaaagaa gaatactgca   1260
gcttccttac aacagtggaa agttggggac aaatgttctg ccatttggtc agaagacggt   1320
tgcatttacc cagctaccat tgcttcaatt gattttaaga gagaaacctg tgttgtggtt   1380
tacactggat atggaaatag agaggagcaa aatctgtccg atctactttc cccaatctgt   1440
gaagtagcta ataatataga acagaatgct caagagaatt aaaatgaaag ccaagtttca   1500
acagatgaaa gtgagaactc caggtctcct ggaaataaat cagataacat caagcccaaa   1560
tctgctccat ggaactcttt tctccctcca ccaccccca tgccagggcc aagactggga   1620
ccaggaaagc caggtctaaa attcaatggc ccaccaccgc caccgccacc accaccaccc   1680
cacttactat catgctggct gcctccattt ccttctggac caccaataat tcccccacca   1740
cctcccatat gtccagattc tcttgatgat gctgatgctt gggaagtat gttaatttca   1800 tggtacatga gtggctatca tactggctat tatatgggtt ttagacaaaa tcaaaaagaa   1860
```

| | |
|---|---|
| ggaaggtgct cacattcctt aaattaagga gaaatgctgg catagagcag cactaaatga | 1920 |
| caccactaaa gaaacgatca gacagatcta gaaagcttat cgataccgtc gactagagct | 1980 |
| cgctgatcag cctcgactgt gccttctagt tgccagccat ctgttgtttg cccctcccccc | 2040 |
| gtgccttcct tgaccctgga aggtgccact cccactgtcc tttcctaata aaatgaggaa | 2100 |
| attgcatcgc attgtctgag taggtgtcat tctattctgg ggggtggggt ggggcaggac | 2160 |
| agcaagggg aggattggga agacaatagc aggcatgctg gggagagatc gatctgagga | 2220 |
| accccctagtg atggagttgg ccactccctc tctgcgcgct cgctcgctca ctgaggccgg | 2280 |
| gcgaccaaag gtcgcccgac gcccgggctt tgcccgggcg gcctcagtga gcgagcgagc | 2340 |
| gcgcagagag ggagtggcc | 2359 |

```
<210> SEQ ID NO 2
<211> LENGTH: 1621
<212> TYPE: DNA
<213> ORGANISM: Homo sapiens

<400> SEQUENCE: 2
```

| | |
|---|---|
| ccacaaatgt gggagggcga taaccactcg tagaaagcgt gagaagttac tacaagcggt | 60 |
| cctcccggcc accgtactgt tccgctccca gaagccccgg gcggcggaag tcgtcactct | 120 |
| taagaaggga cggggcccca cgctgcgcac ccgcgggttt gctatggcga tgagcagcgg | 180 |
| cggcagtggt ggcggcgtcc cggagcagga ggattccgtg ctgttccggc gcggcacagg | 240 |
| ccagagcgat gattctgaca tttgggatga tacagcactg ataaaagcat atgataaagc | 300 |
| tgtggcttca tttaagcatg ctctaaagaa tggtgacatt tgtgaaactt cgggtaaacc | 360 |
| aaaaaccaca cctaaaagaa aacctgctaa gaagaataaa agccaaaaga agaatactgc | 420 |
| agcttcctta caacagtgga agttgggga caaatgttct gccatttggt cagaagacgg | 480 |
| ttgcatttac ccagctacca ttgcttcaat tgattttaag agagaaacct gtgttgtggt | 540 |
| ttacactgga tatggaaata gagaggagca aaatctgtcc gatctacttt ccccaatctg | 600 |
| tgaagtagct aataatatag aacagaatgc tcaagagaat gaaaatgaaa gccaagtttc | 660 |
| aacagatgaa agtgagaact ccaggtctcc tggaaataaa tcagataaca tcaagcccaa | 720 |
| atctgctcca tggaactctt ttctccctcc accaccccccc atgccagggc caagactggg | 780 |
| accaggaaag ccaggtctaa aattcaatgg cccaccaccg ccaccgccac caccaccacc | 840 |
| ccacttacta tcatgctggc tgcctccatt tccttctgga ccaccaataa ttccccccacc | 900 |
| acctcccata tgtccagatt ctcttgatga tgctgatgct tgggaagta tgttaatttc | 960 |
| atggtacatg agtggctatc atactggcta ttatatgggt ttcagacaaa atcaaaaaga | 1020 |
| aggaaggtgc tcacattcct taaattaagg agaaatgctg gcatagagca gcactaaatg | 1080 |
| acaccactaa agaaacgatc agacagatct ggaatgtgaa gcgttataga agataactgg | 1140 |
| cctcatttct tcaaaatatc aagtgttggg aaagaaaaaa ggaagtggaa tgggtaactc | 1200 |
| ttccttgatta aaagttatgt aataaccaaa tgcaatgtga atattttac tggactcttt | 1260 |
| tgaaaaacca tctgtaaaag actggggtgg gggtgggagg ccagcacggt ggtgaggcag | 1320 |
| ttgagaaaat ttgaatgtgg attagatttt gaatgatatt ggataattat tggtaatttt | 1380 |
| atggcctgtg agaagggtgt tgtagtttat aaaagactgt cttaatttgc atacttaagc | 1440 |
| atttaggaat gaagtgttag agtgtcttaa aatgtttcaa atggtttaac aaaatgtatg | 1500 |
| tgaggcgtat gtggcaaaat gttacagaat ctaactggtg gacatggctg ttcattgtac | 1560 |

```
tgttttttc tatcttctat atgtttaaaa gtatataata aaaatattta attttttttt    1620
a                                                                 1621
```

<210> SEQ ID NO 3
<211> LENGTH: 294
<212> TYPE: PRT
<213> ORGANISM: Homo sapiens

<400> SEQUENCE: 3

```
Met Ala Met Ser Ser Gly Gly Ser Gly Gly Val Pro Glu Gln Glu
1               5                   10                  15

Asp Ser Val Leu Phe Arg Arg Gly Thr Gly Gln Ser Asp Ser Asp
                20                  25                  30

Ile Trp Asp Asp Thr Ala Leu Ile Lys Ala Tyr Asp Lys Ala Val
                35                  40                  45

Ser Phe Lys His Ala Leu Lys Asn Gly Asp Ile Cys Glu Thr Ser Gly
    50                  55                  60

Lys Pro Lys Thr Thr Pro Lys Arg Lys Pro Ala Lys Lys Asn Lys Ser
65                  70                  75                  80

Gln Lys Lys Asn Thr Ala Ala Ser Leu Gln Gln Trp Lys Val Gly Asp
                85                  90                  95

Lys Cys Ser Ala Ile Trp Ser Glu Asp Gly Cys Ile Tyr Pro Ala Thr
                100                 105                 110

Ile Ala Ser Ile Asp Phe Lys Arg Glu Thr Cys Val Val Val Tyr Thr
                115                 120                 125

Gly Tyr Gly Asn Arg Glu Glu Gln Asn Leu Ser Asp Leu Leu Ser Pro
                130                 135                 140

Ile Cys Glu Val Ala Asn Asn Ile Glu Gln Asn Ala Gln Glu Asn Glu
145                 150                 155                 160

Asn Glu Ser Gln Val Ser Thr Asp Glu Ser Glu Asn Ser Arg Ser Pro
                165                 170                 175

Gly Asn Lys Ser Asp Asn Ile Lys Pro Lys Ser Ala Pro Trp Asn Ser
                180                 185                 190

Phe Leu Pro Pro Pro Pro Pro Met Pro Gly Pro Arg Leu Gly Pro Gly
                195                 200                 205

Lys Pro Gly Leu Lys Phe Asn Gly Pro Pro Pro Pro Pro Pro Pro Pro
                210                 215                 220

Pro Pro His Leu Leu Ser Cys Trp Leu Pro Pro Phe Pro Ser Gly Pro
225                 230                 235                 240

Pro Ile Ile Pro Pro Pro Pro Ile Cys Pro Asp Ser Leu Asp Asp
                245                 250                 255

Ala Asp Ala Leu Gly Ser Met Leu Ile Ser Trp Tyr Met Ser Gly Tyr
                260                 265                 270

His Thr Gly Tyr Tyr Met Gly Phe Arg Gln Asn Gln Lys Glu Gly Arg
                275                 280                 285

Cys Ser His Ser Leu Asn
                290
```

<210> SEQ ID NO 4
<211> LENGTH: 736
<212> TYPE: PRT
<213> ORGANISM: Adeno-associated virus

<400> SEQUENCE: 4

```
Met Ala Ala Asp Gly Tyr Leu Pro Asp Trp Leu Glu Asp Asn Leu Ser
1               5                   10                  15
```

-continued

```
Glu Gly Ile Arg Glu Trp Trp Ala Leu Lys Pro Gly Ala Pro Gln Pro
             20                  25                  30

Lys Ala Asn Gln Gln His Gln Asp Asn Ala Arg Gly Leu Val Leu Pro
         35                  40                  45

Gly Tyr Lys Tyr Leu Gly Pro Gly Asn Gly Leu Asp Lys Gly Glu Pro
 50                  55                  60

Val Asn Ala Ala Asp Ala Ala Ala Leu Glu His Asp Lys Ala Tyr Asp
 65                  70                  75                  80

Gln Gln Leu Lys Ala Gly Asp Asn Pro Tyr Leu Lys Tyr Asn His Ala
                 85                  90                  95

Asp Ala Glu Phe Gln Glu Arg Leu Lys Glu Asp Thr Ser Phe Gly Gly
             100                 105                 110

Asn Leu Gly Arg Ala Val Phe Gln Ala Lys Lys Arg Leu Leu Glu Pro
         115                 120                 125

Leu Gly Leu Val Glu Glu Ala Ala Lys Thr Ala Pro Gly Lys Lys Arg
 130                 135                 140

Pro Val Glu Gln Ser Pro Gln Glu Pro Asp Ser Ser Ala Gly Ile Gly
145                 150                 155                 160

Lys Ser Gly Ala Gln Pro Ala Lys Lys Arg Leu Asn Phe Gly Gln Thr
                 165                 170                 175

Gly Asp Thr Glu Ser Val Pro Asp Pro Gln Pro Ile Gly Glu Pro Pro
             180                 185                 190

Ala Ala Pro Ser Gly Val Gly Ser Leu Thr Met Ala Ser Gly Gly Gly
         195                 200                 205

Ala Pro Val Ala Asp Asn Asn Glu Gly Ala Asp Gly Val Gly Ser Ser
 210                 215                 220

Ser Gly Asn Trp His Cys Asp Ser Gln Trp Leu Gly Asp Arg Val Ile
225                 230                 235                 240

Thr Thr Ser Thr Arg Thr Trp Ala Leu Pro Thr Tyr Asn Asn His Leu
                 245                 250                 255

Tyr Lys Gln Ile Ser Asn Ser Thr Ser Gly Gly Ser Ser Asn Asp Asn
             260                 265                 270

Ala Tyr Phe Gly Tyr Ser Thr Pro Trp Gly Tyr Phe Asp Phe Asn Arg
         275                 280                 285

Phe His Cys His Phe Ser Pro Arg Asp Trp Gln Arg Leu Ile Asn Asn
 290                 295                 300

Asn Trp Gly Phe Arg Pro Lys Arg Leu Asn Phe Lys Leu Phe Asn Ile
305                 310                 315                 320

Gln Val Lys Glu Val Thr Asp Asn Asn Gly Val Lys Thr Ile Ala Asn
                 325                 330                 335

Asn Leu Thr Ser Thr Val Gln Val Phe Thr Asp Ser Asp Tyr Gln Leu
             340                 345                 350

Pro Tyr Val Leu Gly Ser Ala His Glu Gly Cys Leu Pro Pro Phe Pro
         355                 360                 365

Ala Asp Val Phe Met Ile Pro Gln Tyr Gly Tyr Leu Thr Leu Asn Asp
 370                 375                 380

Gly Ser Gln Ala Val Gly Arg Ser Ser Phe Tyr Cys Leu Glu Tyr Phe
385                 390                 395                 400

Pro Ser Gln Met Leu Arg Thr Gly Asn Asn Phe Gln Phe Ser Tyr Glu
                 405                 410                 415

Phe Glu Asn Val Pro Phe His Ser Ser Tyr Ala His Ser Gln Ser Leu
             420                 425                 430
```

```
Asp Arg Leu Met Asn Pro Leu Ile Asp Gln Tyr Leu Tyr Tyr Leu Ser
        435                 440                 445

Lys Thr Ile Asn Gly Ser Gly Gln Asn Gln Gln Thr Leu Lys Phe Ser
        450                 455                 460

Val Ala Gly Pro Ser Asn Met Ala Val Gln Gly Arg Asn Tyr Ile Pro
465                 470                 475                 480

Gly Pro Ser Tyr Arg Gln Gln Arg Val Ser Thr Thr Val Thr Gln Asn
                485                 490                 495

Asn Asn Ser Glu Phe Ala Trp Pro Gly Ala Ser Ser Trp Ala Leu Asn
            500                 505                 510

Gly Arg Asn Ser Leu Met Asn Pro Gly Pro Ala Met Ala Ser His Lys
        515                 520                 525

Glu Gly Glu Asp Arg Phe Phe Pro Leu Ser Gly Ser Leu Ile Phe Gly
        530                 535                 540

Lys Gln Gly Thr Gly Arg Asp Asn Val Asp Ala Asp Lys Val Met Ile
545                 550                 555                 560

Thr Asn Glu Glu Glu Ile Lys Thr Thr Asn Pro Val Ala Thr Glu Ser
                565                 570                 575

Tyr Gly Gln Val Ala Thr Asn His Gln Ser Ala Gln Ala Gln Ala Gln
            580                 585                 590

Thr Gly Trp Val Gln Asn Gln Gly Ile Leu Pro Gly Met Val Trp Gln
        595                 600                 605

Asp Arg Asp Val Tyr Leu Gln Gly Pro Ile Trp Ala Lys Ile Pro His
        610                 615                 620

Thr Asp Gly Asn Phe His Pro Ser Pro Leu Met Gly Gly Phe Gly Met
625                 630                 635                 640

Lys His Pro Pro Pro Gln Ile Leu Ile Lys Asn Thr Pro Val Pro Ala
                645                 650                 655

Asp Pro Pro Thr Ala Phe Asn Lys Asp Lys Leu Asn Ser Phe Ile Thr
            660                 665                 670

Gln Tyr Ser Thr Gly Gln Val Ser Val Glu Ile Glu Trp Glu Leu Gln
        675                 680                 685

Lys Glu Asn Ser Lys Arg Trp Asn Pro Glu Ile Gln Tyr Thr Ser Asn
        690                 695                 700

Tyr Tyr Lys Ser Asn Asn Val Glu Phe Ala Val Asn Thr Glu Gly Val
705                 710                 715                 720

Tyr Ser Glu Pro Arg Pro Ile Gly Thr Arg Tyr Leu Thr Arg Asn Leu
                725                 730                 735
```

CELL-BASED ASSAY FOR MEASURING DRUG PRODUCT POTENCY

CROSS REFERENCE TO RELATED APPLICATIONS

This application is a U.S. National Phase Application, filed under 35 U.S.C. § 371, of International Application No. PCT/US2019/035963, filed on Jun. 7, 2019, which claims priority to U.S. provisional patent application No. 62/682,263, filed Jun. 8, 2018, the contents of each of which are incorporated by reference herein in their entireties.

INCORPORATION BY REFERENCE OF SEQUENCE LISTING

The instant application contains a Sequence Listing which has been submitted in ASCII format via EFS-Web and is hereby incorporated by reference in its entirety. Said ASCII copy, created on Dec. 7, 2020 is named AVEX-004/N01US_SeqList.txt and is 15 kilobytes in size.

BACKGROUND

Adeno-associated virus (AAV) is a member of the parvoviridae family. The AAV genome is composed of a linear single-stranded DNA molecule which contains approximately 4.7 kilo bases (kb) and consists of two major open reading frames encoding the non-structural Rep (replication) and structural Cap (capsid) proteins. Flanking the AAV coding regions are two cis-acting nucleotide inverted terminal repeat (ITR) sequences, approximately 145 nucleotides in length, with interrupted palindromic sequences that can fold into hairpin structures that function as primers during initiation of DNA replication. In addition to their role in DNA replication, the ITR sequences have been shown to be necessary for viral integration, rescue from the host genome, and encapsidation of viral nucleic acid into mature virions.

Vectors derived from AAV are particularly attractive for delivering genetic material because (i) they are able to infect (transduce) a wide variety of non-dividing and dividing cell types including muscle fibers and neurons; (ii) they are devoid of the virus structural genes, thereby eliminating the natural host cell responses to virus infection, e.g., interferon-mediated responses; (iii) wild-type viruses have never been associated with any pathology in humans; (iv) in contrast to wild type AAVs, which are capable of integrating into the host cell genome, replication-deficient AAV vectors generally persist as episomes, thus limiting the risk of insertional mutagenesis or activation of oncogenes; and (v) in contrast to other vector systems, AAV vectors do not trigger a significant immune response (see ii), thus granting long-term expression of the therapeutic trans genes (provided their gene products are not rejected).

Self-complementary adeno-associated virus (scAAV) is a viral vector engineered from the naturally occurring adeno-associated virus (AAV) for use in gene therapy. scAAV is termed "self-complementary" because the coding region has been designed to form an intramolecular double-stranded DNA template. A rate-limiting step in gene expression for the standard single strand AAV genome involves the second-strand synthesis, since the typical AAV genome is a single-stranded DNA template. However, this is not the case for scAAV genomes. Upon infection, rather than waiting for cell mediated synthesis of the second strand, the two complementary halves of scAAV will associate to form one double stranded DNA (dsDNA) unit that is ready for immediate replication and transcription.

Spinal muscular atrophy (SMA) is a severe neuromuscular disease caused by a genetic defect in the SMN1 gene—leading to the loss of motor neurons and resulting in progressive muscle weakness and paralysis. SMA is divided into sub-categories—SMA Types 1, 2, 3, and 4—based on disease onset and severity, which generally correlate to survival motor neuron (SMN) protein levels.

Gene therapy via use of viral vectors (as the delivery vector) is a well-suited approach for the treatment of SMA due to the monogenic nature of the disease—meaning it is caused by the deletion of, or mutations in, a single gene. It has been previously determined that AAV9 is a suitable viral vector for gene therapy of SMA, where it has been used for SMA type 1 and SMA type 2. This viral vector has been shown to deliver a fully functional human SMN gene into target motor neuron cells, to produce sufficient levels of SMN protein required to improve motor neuron function, and to provide a rapid onset of effect in addition to sustained SMN protein expression.

Nevertheless, there is a need for the development of a robust and quantitative in vitro cell-based assay for determining the relative potency intended for lot disposition of an AAV9 drug product. The development of a robust and quantitative cell-based in vitro potency assay has been hindered by the fact that none of transformed or primary cells (human or murine) tested so far are shown to be permissive to AAV9 vector including the commonly used HeLa RC32 cell line in testing for Infectious Titer using AAV9-based viral vectors.

In the present disclosure, provided for the first time are terminally differentiated, non-dividing cells derived from neural progenitor cells under the SMN1–/– genetic background (terminally differentiated cells derived from NPCs, hereafter referred to as mTD-NPC-Δ7) that are capable of being effectively transduced by non-replicating AAV9 vectors. More importantly, these cells were used an in vitro cell model system, to develop a quantitative cell-based assay to measure dose-dependent increase of expression of a protein of interest upon transduction of AAV9 vector at increasing multiplicity of infection (MOI) by a high content imaging system using a monoclonal antibody specific for the protein of interest.

SUMMARY OF THE INVENTION

In one aspect, the disclosure provides methods for measuring transgene expression, the method comprising the steps of: (a) culturing a plurality of cells, wherein the cells comprise a viral vector, wherein the viral vector comprises a transgene, wherein the culturing is under conditions sufficient to express a protein of interest from the transgene; (b) incubating the plurality of cells to allow for transgene expression of the protein of interest to ensue; (c) contacting the plurality of cells with a molecule specific for the protein of interest; (d) imaging the cell to obtain an integrated fluorescent intensity per cell (IFI-C) assay readout; and, (e) determining the expression of the transgene based on the IFI-C readout.

In a related aspect, the disclosure provides methods of measuring or quantifying a viral infectious titer in a plurality of cells, the method comprising the steps of: (a) culturing a plurality of cells, wherein the cells comprise a viral vector, wherein the viral vector comprises a transgene, wherein the culturing is under conditions sufficient to express a protein of interest from the transgene; (b) incubating the plurality of cells to allow for transgene expression of the protein of interest to ensue; (c) contacting the plurality of cells with a molecule specific for the protein of interest; (d) imaging the cell to obtain an integrated fluorescent intensity per cell (IFI-C) assay readout; and, (e) determining the expression of the transgene based on the IFI-C readout.

In another aspect, the disclosure provides methods for measuring transgene expression, comprising: (a) providing a first plurality of terminally differentiated neural progenitor cells (NPCs); (b) transducing the first plurality of terminally differentiated NPCs with a test sample comprising a viral vector comprising a sequence encoding a protein of interest; (c) incubating the transduced first plurality of terminally differentiated NPCs under conditions sufficient to express the protein of interest; (d) contacting the first plurality of terminally differentiated NPCs from (c) with a molecule specific for the protein of interest; (e) imaging the first plurality of terminally differentiated NPCs to obtain an integrated fluorescent intensity per cell (IFI-C) assay readout; and (f) determining the expression of the protein of interest based on the IFI-C readout.

In some aspects of the methods of the disclosure, the first plurality of terminally differentiated NPCs are homozygous for a Survival Motor Neuron (SMN1)−/− mutation. In some aspects, the SMN1−/− mutation comprises a deletion of SMN1 exon 7 (Δ7). In some aspects, the incubating step c) is followed by fixing and permeabilizing the first plurality of terminally differentiated NPCs.

In another aspect, the disclosure provides methods comprising: (g) providing a second plurality of terminally differentiated NPCs; (h) transducing the second plurality of terminally differentiated NPCs with a reference standard comprising the viral vector; (i) incubating the transduced second plurality of terminally differentiated NPCs under conditions sufficient to express the protein of interest; (j) contacting the second plurality of terminally differentiated NPCs from (i) with a molecule specific for the protein of interest; (k) imaging the second plurality of terminally differentiated NPCs to obtain an integrated fluorescent intensity per cell (IFI-C) assay readout; and (l) comparing the IFI-C of the first plurality of terminally differentiated NPCs with the IFI-C of the second plurality of terminally differentiated NPCs; thereby determining the relative potency of the viral vector of the test sample relative to the reference standard.

In some aspects of the methods of the disclosure, the second plurality of terminally differentiated NPCs are homozygous for a SMN1−/− mutation. In some aspects, the SMN1−/− mutation comprises a deletion of SMN1 exon 7 (Δ7).

In some aspects, the incubating step (i) is followed by fixing and permeabilizing the second plurality of terminally differentiated NPCs.

In some aspects, said first and second pluralities of terminally differentiated NPCs are produced by terminally differentiating neural progenitor cells isolated from the cortex of an SMN1−/− mouse embryo. In some aspects, the neural progenitor cells (NPCs) were terminally differentiated by (a) culturing the NPCs in serum free culture media containing Epidermal Growth Factor (EGF) and Fibroblast Growth Factor-basic (bFGF) to form neurospheres; (b) dissociating said neurospheres to produce dissociated NPCs; and (c) culturing the dissociated NPCs in serum-enriched media without growth factors, thereby producing terminally differentiated NPCs.

In some aspects of the methods of the disclosure, said first and second pluralities of cells are transduced by the test sample and the reference standard at at least two different multiplicities of infection (MOI) of the viral vector. In some aspects, said first and second pluralities of cells are transduced at 5 different MOI of the viral vector in the test sample and reference standard. In some aspects, the 5 MOIs comprise 300,000, 150,000, 75,000, 37,500, 18,750 viral particles per cell.

In some aspects of the methods of the disclosure, the comparing step (l) comprises plotting a standard curve of MOI versus IFI-C for each of the test sample and the reference standard. In some aspects, the comparing step (l) comprises calculating a linear regression of log MOI versus IFI-C for each of the test sample and the reference standard, thereby deriving a test sample slope and a reference standard slope.

In some aspects of the methods of the disclosure, determining the relative potency of the viral vector is performed by parallel line analysis (PLA), and wherein the PLA comprises measuring a slope ratio of the test sample slope against the reference standard slope. In some aspects, the reference standard slope is greater than or equal to 1.02E+05. In some aspects, the slope ratio is between 0.69-1.45. In some aspects, the slope ratio is between 0.75 and 1.33.

In some aspects of the methods of the disclosure, the methods comprise calculating a coefficient of variance of the linear regression of the sample. In some aspects, the coefficient of variance is between 15.6% and 29.5%. In some aspects, the coefficient of variance is less than or equal to 40%, less than or equal to 30%, or less than or equal to 20%.

In some aspects of the methods of the disclosure, the methods comprise calculating an $R^2$ value for the linear regression of the test sample and the reference standard. In some aspects, the $R^2$ value for the test sample and the reference standard is greater than or equal to 0.95.

In some aspects of the methods of the disclosure, the methods comprise calculating an assay dynamic window of the reference standard. In some aspects, the assay dynamic window is greater than or equal to 2.69.

In some aspects of the methods of the disclosure, the protein of interest is a survival motor neuron (SMN1) protein. In some aspects, the SMN1 protein comprises an amino acid sequence of SEQ ID NO: 3.

In some aspects of the methods of the disclosure, the viral vector is an adeno-associated virus serotype 9 (AAV9). In some aspects, the viral vector comprises a sequence encoding cytomegalovirus (CMV) enhancer/chicken-β-actin-hybrid promoter (CB) operably linked to the sequence encoding the SMN1 protein. In some aspects, the viral vector comprises AAV inverted terminal repeats (ITR) from the AAV serotype 2 (AAV2) DNA. In some aspects, the viral vector comprises a sequence of SEQ ID NO: 1.

In some aspects of the methods of the disclosure, the cells are passaged 8 to 15 times prior to transduction with the viral vector.

In some aspects of the methods of the disclosure, the step of incubating the terminally differentiated NPCs following transduction is performed for about 69-75 hours (hrs).

In some aspects of the methods of the disclosure, the molecule that is specific for the protein of interest comprises an antibody, an antibody fragment, or an aptamer. In some aspects, the antibody comprises an antibody specific for the protein of interest. In some aspects, the anti-protein of interest antibody is provided at a concentration of about 4 μg/mL. In some aspects, the anti-protein of interest antibody is provided at a concentration of about 2 µg/mL. In some aspects, the molecule comprises a detectable label.

In some aspects of the methods of the disclosure, the methods further comprise contacting the terminally differentiated NPCs with a second molecule that specifically recognizes the molecule specific for the protein of interest. In some aspects, the second molecule comprises a detectable label. In some aspects, the second molecule comprises an antibody, an antibody fragment or an aptamer.

In some aspects of the methods of the disclosure, the terminally differentiated NPCs are contacted with an anti-nuclear detectable label following the fixing and permeabilizing step.

In some aspects of the methods of the disclosure, the terminally differentiated NPCs are on a solid surface. In some aspects, the solid surface is coated with Poly-D-Lysin. In some aspects, the terminally differentiated NPCs are seeded at a density of 20,000 cells per well.

In another aspect, the method of measuring or quantifying a viral infectious titer in a plurality of cells further comprises optimizing a multiplicity of infection (MOI) of the plurality of cells.

In another related aspect, the plurality of cells are transduced with the viral vector prior to step a). In another aspect, the incubating step b) is followed by fixing and permeabilizing the plurality of cells.

In another related aspect, the step of determining the relative potency of a viral vector test sample is performed by parallel line analysis (PLA) against a standard curve of a reference standard after linear regression data fit.

In another aspect, the viral vector is an adeno-associated virus serotype 9 (AAV9) comprising a cDNA expressing SMN1 protein under the control of the cytomegalovirus (CMV) enhancer/chicken-β-actin-hybrid promoter (CB), and AAV inverted terminal repeats (ITR) from the AAV serotype 2 (AAV2) DNA.

In another related aspect, the cell transduced with a viral vector is a terminally differentiated non-dividing cell.

In another aspect, the cell is derived from neural progenitor cells under the SMN1 genetic background (mTD-NPC-Δ7).

In another aspect, the IFI-C readout reflects a measurement of protein expression.

In another aspect, the molecule that is specific for the protein of interest comprises an antibody, an antibody fragment, or an aptamer. In another aspect, the antibody comprises an antibody specific for the protein of interest.

In another aspect, the molecule comprises a detectable label.

In another aspect, the method further comprises washing the cells to remove the molecule specific for the protein of interest.

In another aspect, the method further comprises contacting the cells with a second molecule that specifically recognizes the molecule specific for the protein of interest. In another aspect, the second molecule comprises a detectable label. In another aspect, the second molecule comprises an antibody, an antibody fragment or an aptamer. In another aspect, the cell is contacted with an anti-nuclear detectable label following the fixing and permeabilizing step.

In another aspect, the method allows a quantitative measurement of dose-dependent increase in the level of the protein of interest.

In another aspect, the protein of interest is a survival motor neuron (SMN1) protein.

The disclosure provides kits comprising: (a) a plurality of cells capable of being transduced with a viral vector; (b) a viral vector encoding protein of interest; (c) a first molecule capable of binding the protein of interest; (d) a second molecule capable of binding the first molecule, wherein the second molecule comprises a detectable label; and, (e) instructions for use in an imaging assay.

The disclosure provides methods of producing a pharmaceutical composition comprising a viral vector comprising a transgene, the method comprising: (a) producing the viral vector comprising the transgene (b) assaying said viral vector according to the methods for measuring the transgene of the instant disclosure; and (c) formulating the viral vector comprising the transgene in a pharmaceutical composition.

The disclosure provides methods of treating a patient in need thereof with a therapy comprising a viral vector comprising a transgene, the method comprising: (a) assaying said viral vector comprising a transgene according to the method of measuring transgene expression of the instant disclosure; and (b) administering the viral vector comprising a transgene to said patient.

In some aspects of the methods of the disclosure, the relative potency of the viral vector is at least 40%, at least 50%, at least 60%, at least 70%, at least 80%, at least 90%, at least 91%, at least 92%, at least 93%, at least 94%, at least 95%, at least 96%, at least 97%, at least 98%, at least 99%, at least 99.5%, at least 99.9%, at least 100%, at least 110%, at least 120%, at least 130% or at least 140% relative to a reference standard. In some aspects, the relative potency of the viral vector is at least 90% relative to the reference standard.

In some aspects of the methods of the disclosure, the potency of the viral vector in the pharmaceutical formulation is within 5% of the potency of the reference standard, within 10% of the potency of the reference standard, or within 20% of the potency of the reference standard.

Any of the above aspects can be combined with any other aspect.

Unless otherwise defined, all technical and scientific terms used herein have the same meaning as commonly understood by one of ordinary skill in the art to which this disclosure belongs.

As used herein, the singular forms of a word also include the plural form of the word, unless the context clearly dictates otherwise; as examples, the terms "a," "an," and "the" are understood to be singular or plural and the term "or" is understood to be inclusive. By way of example, "an element" means one or more element.

Throughout the specification the word "comprising," or variations such as "comprises," will be understood to imply the inclusion of a stated element, integer or step, or group of elements, integers or steps, but not the exclusion of any other element, integer or step, or group of elements, integers or steps. Throughout the specification the word "consisting of," or variations such as "consists of," will be understood to imply the inclusion of a stated element, integer or step, or group of elements, integers or steps, and the exclusion of any other element, integer or step, or group of elements, integers or steps. Throughout the specification the word "consisting essentially of," or variations such as "consists essentially of," will be understood to imply the inclusion of a stated element, integer or step, or group of elements, integers or steps, and any other element, integer or step, or group of elements, integers or steps that do not materially affect the basic and novel characteristics of the claimed invention.

About can be understood as within 10%, 9%, 8%, 7%, 6%, 5%, 4%, 3%, 2%, 1%, 0.5%, 0.1%, 0.05%, or 0.01% of the stated value. Unless otherwise clear from the context, all numerical values provided herein are modified by the term "about."

Although methods and materials similar or equivalent to those described herein can be used in the practice or testing of the present disclosure, suitable methods and materials are described below. All publications, patent applications, patents, and other references mentioned herein are incorporated by reference in their entirety. The references cited herein are not admitted to be prior art to the claimed disclosure. In the case of conflict, the present Specification, including definitions, will control. In addition, the materials, methods, and examples are illustrative only and are not intended to be limiting. Other features and advantages of the disclosure will be apparent from the following detailed description and claim.

BRIEF DESCRIPTION OF THE DRAWINGS

Any of the above aspects and embodiments can be combined with any other aspect or embodiment as disclosed here in the Summary and/or Detailed Description sections.

Various objects and advantages and a more complete understanding of the present invention are apparent and more readily appreciated by reference to the following Detailed Description and to the appended claims when taken in conjunction with the accompanying Drawing wherein:

(FIG. 3A) NPCs were derived from mouse SMN-/- embryonic cortex at ~e14.5 (middle image) and (FIG. 3B) grown as proliferating neurospheres in the presence of mitogens (growth factors EGF and FGF). (FIG. 3C) Neurospheres can be dissociated and terminally differentiated into CNS cells including GFAP+ astrocytes when removed from growth factors and placed in a serum-based media.

FIGS. 5A-5B illustrates a montage of images covering about 40% of a well at a cell density of 20,000 cells per well (nuclei staining) (FIG. 5A), and at a cell density of 10,000 cells per well (nuclei staining) (FIG. 5B).

FIG. 7 illustrates images of GFP and SMN 1 staining for mTD-NPC-Δ7 transduced with AAAV9 vector lot NCHAAV9SMN0613 (top) (Bottom Panel is a Control Group).

FIGS. 8A-8B illustrates nuclei staining for mTD-NPC-Δ7 seeded on an un-coated plates (a montage of images covering 40% of a well) (FIG. 8A), and nuclei staining for mTD-NPC-Δ7 seeded on a poly-D-lysin-coated plates (a montage of images covering 40% of a well) (FIG. 8B).

FIGS. 15A-15C illustrates the application of the in vitro relative potency assay for AAV9 vector in a quantitative infectivity assay using the mNPC-based assay platform.

FIG. 20A shows cells stained with anti-SMN1 antibody. Open circles indicate control cells transduced with SMN1 encoding AAV9 vector, filled circles indicate cells transduced with MECP2 encoding AAV9 vector. The x-axis shows log 2 MOI (multiplicity of infection), and the y-axis shows integrated fluorescent intensity per cell (IFI-C). FIG. 20B shows cells transduced with MECP2 encoding AAV9 vector and stained with anti-MECP2 antibody. The x-axis shows log 2 MOI, and the y-axis shows IFI-C. Specificity was demonstrated by dose-dependent increase in IFI-C signal indicative of exogenous SMN1 protein expression with increasing doses of MOIs when AAV9-SMN1 vector transduced, but not AAV9-MECP2 vector transduced cells were stained by anti-SMN1 antibody even though AAV9-MECP2 was shown to successfully transduce the cells when stained with anti-MECP2 antibody as indicated by the dose-dependent increase in IFI-C.

FIG. 28 shows a summary of cell processing details for the selection of HEK293 cells for exceptional adherence and pre-master cell bank (MCB) banking.

FIGS. 37A and 37B show recovery of viral vector and host cell protein (HCP) clearance at the TFF1 step.

FIGS. 42A-42B provide a table that illustrates the comparability and manufacturing consistency results—Process A (Phase 1) and Process B (Phase 3) Products. Process B products are shown to have additional benefits as compared to Process A. [1]NCH Phase 1 Lot AAV9SMN0613 was manufactured prior to the current "Proposed Test Limit" for genomic titer by ddPCR. Genomic titer value for this lot was re-established August 2017 using improved SOP-137 (v3). [2]Differences in Genomic Titer results between Process A and Process B lots are due to different manufacturing target concentrations. Lot NCH AAV9SMN0613 was originally formulated at a lower target titer concentration now determined to be $1.1 \times 10^{13}$ vg/mL by the currently used ddPCR assay (SOP-137), while AAV9-SMN1 lots 600156 and 600307 were formulated with a target titer concentration of $4.0 \times 10^{13}$ vg/mL when measured by the same method. [3]Adjusted result per $1.0 \times 10^{13}$ vg/mL to enable appropriate specifications across range of acceptable concentrations from $2.0 \times 10^{13}$ vg/mL to $6.0 \times 10^{13}$ vg/mL. Actual values have been multiplied by the following factors to provide values per $1.0 \times 10^{13}$ vg/mL: 1/1.06 (Lot NCH AAV9SMN0613), 1/3.7 (Lot 600156) and 1/4.0 (Lot 600307). [4]Differences in appearance results between Process A and Process B are due to different vector concentrations (genomic titer. Lot NCH AAV9SMN0613 has a significantly lower vector concentration than the Process B lots. As a result, Lot NCH AAV9SMN0613 is more dilute leading to a more clear and colorless solution while the colorless to white and slightly opaque observations for Process B lots results from a close to 4 times concentration of viral particles in solution per mL. [5]Actual result not adjusted to $1.0 \times 10^{13}$ vg/mL because results are below LOQ of the respective methods. [6]Lot NCHAAV9SMN0613 is designated as the initial potency Reference Standard for SOP-285 with an assigned potency value of 100%. All results generated using SOP-285 v5.

FIG. 43 shows the comparability between Process A and Process B using pair-wise comparison of Process A (Phase 1 Lot NCHAAV9SMN0613) and Process B (Phase 3 Lot 600156). Process B products are shown to have additional benefits as compared to Process A.

FIG. 44 shows the manufacturing consistency assessment by pair-wise comparison of Process B (Phase 3) lots 600156 and 600307.

FIG. 45 shows the stability profile for NCH Lot NCHAAV9SMN0613 stored at real-time storage condition ≤−60° C. over 12 months.

DETAILED DESCRIPTION

Figure 1:
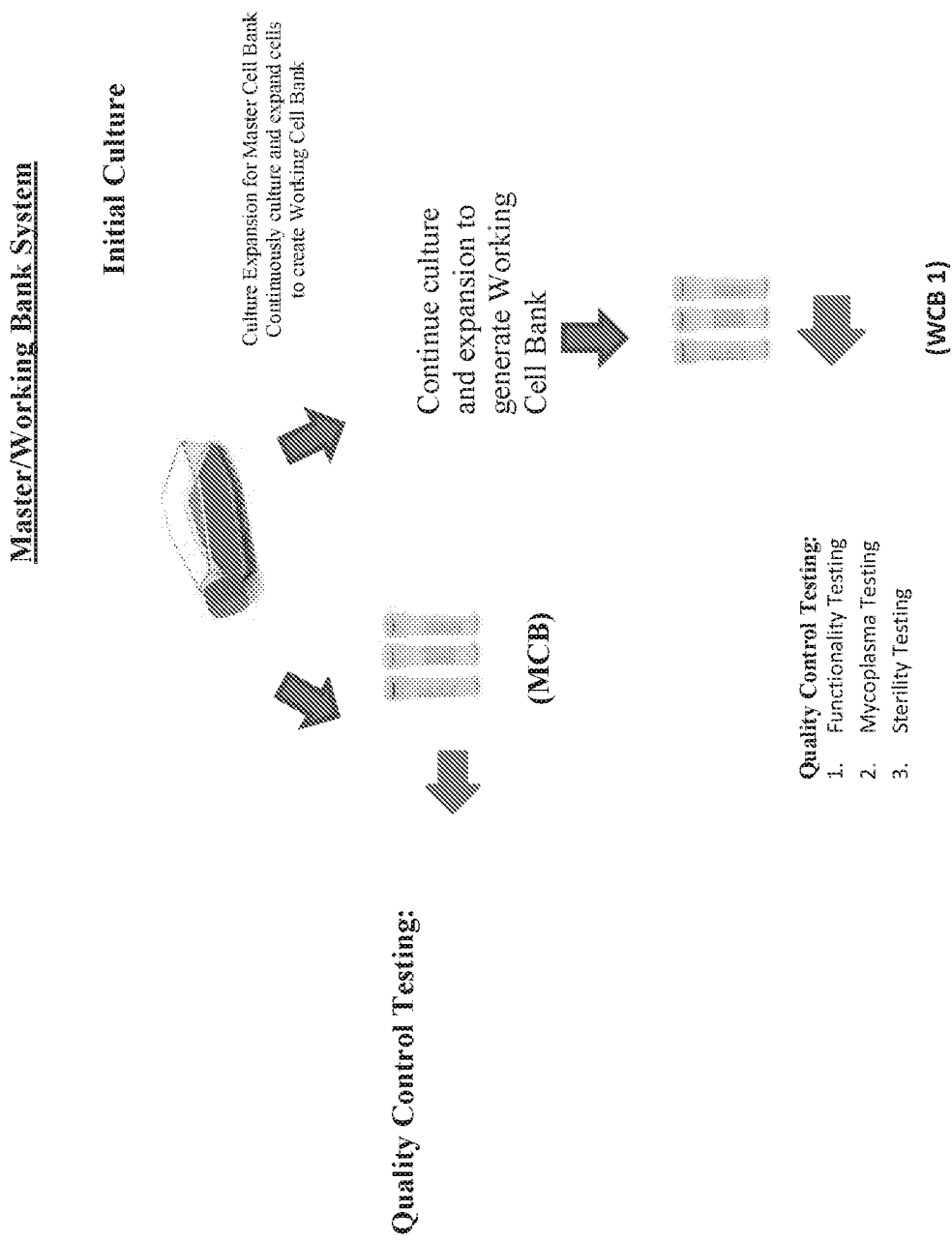
FIG. 1 illustrates a master/working bank system.

The present invention disclosure provides a quantitative cell-based in vitro potency assay using cells that are permissive to AAV9 vector transduction for assessing the potency intended for lot disposition of the protein of interest-expressing AAV9 drug product. In another embodiment, the viral vector drug product is an AAV9 vector that expresses an SMN1 protein. The assay makes use of terminally differentiated, non-dividing cells derived from neural progenitor cells under the SMN1−/− genetic background (terminally differentiated cells derived from NPCs, hereafter referred to as mTD-NPC-Δ7) with the capability to be effectively transduced by non-replicating AAV9 vector. Using mTD-NPC-Δ7 as an in vitro cell model system, a 5-day, quantitative cell-based assay was developed to measure dose-dependent increase of SMN1 protein level upon transduction of SMN1-encoding AAV9 vector at increasing multiplicity of infection (MOI) by a high content imaging system using a commercially available monoclonal antibody specific for SMN protein. In some embodiments, the in vitro cell based assay can measure the potency of a vector sample relative a reference standard.

Cell-Based Assays

The present disclosure provides in vitro cell based assays for measuring the potency of AAV vectors encoding a protein of interest. In some embodiments, the protein of interest is SMN1 and the expression of SMN1 from the vector in terminally differentiated, non-dividing cells lacking SMN1 is measured using the methods described herein.

The present disclosure provides, in one embodiment, methods for measuring transgene expression, the methods comprising the steps of: (a) culturing a plurality of cells, wherein the cells comprise a viral vector, wherein the viral vector comprises a transgene, wherein the culturing is under conditions sufficient to express a protein of interest from the transgene; (b) incubating the plurality of cells to allow for transgene expression of the protein of interest to ensue; (c) contacting the plurality of cells with a molecule specific for the protein of interest; (d) imaging the cell to obtain an integrated fluorescent intensity per cell (IFI-C) assay readout; and, (e) determining the expression of the transgene based on the IFI-C readout.

In another embodiment, provided are methods of measuring or quantifying a viral infectious titer in a plurality of cells, the method comprising the steps of: (a) culturing a plurality of cells, wherein the cells comprise a viral vector, wherein the viral vector comprises a transgene, wherein the culturing is under conditions sufficient to express a protein of interest from the transgene; (b) incubating the plurality of cells to allow for transgene expression of the protein of interest to ensue; (c) contacting the plurality of cells with a molecule specific for the protein of interest; (d) imaging the cell to obtain an integrated fluorescent intensity per cell (IFI-C) assay readout; and, (e) determining the expression of the transgene based on the IFI-C readout.

In another embodiment, the methods of measuring or quantifying a viral infectious titer in a plurality of cells further comprise optimizing a multiplicity of infection (MOI) of the plurality of cells. In another embodiment, provided is an infectivity assay for measuring or quantifying a viral infectious titer in a plurality of cells.

In another embodiment, the plurality of cells are transduced with the viral vector prior to step (a). In another embodiment, the incubating step (b) is followed by fixing and permeabilizing the plurality of cells.

In another embodiment, the step of determining the relative potency of a viral vector is performed by parallel line analysis (PLA) against a standard curve of a reference standard after linear regression data fit. A parallel-line assay is a method to calculate a relative potency. In some embodiments, the relative potency is calculated for a dilution assay.

In some embodiments, the methods comprise (a) providing a first plurality of terminally differentiated neural progenitor cells (NPCs); (b) transducing the first plurality of terminally differentiated NPCs with a test sample comprising a viral vector comprising a sequence encoding a protein of interest; (c) incubating the transduced first plurality of terminally differentiated NPCs under conditions sufficient to express the protein of interest; (d) contacting the first plurality of terminally differentiated NPCs from (c) with a molecule specific for the protein of interest; (e) imaging the first plurality of terminally differentiated NPCs to obtain an integrated fluorescent intensity per cell (IFI-C) assay readout; and (0 determining the expression of the protein of interest based on the IFI-C readout.

As used herein, a "test sample" refers to a sample comprising an AAV viral vector comprising a sequence encoding a protein of interest whose titer and/or potency are unknown, and will be determined using the methods described herein.

In some embodiments, the methods comprise (g) providing a second plurality of terminally differentiated NPCs; (h) transducing the second plurality of terminally differentiated NPCs with a reference standard comprising the viral vector; (i) incubating the transduced second plurality of terminally differentiated NPCs under conditions sufficient to express the protein of interest; (j) contacting the second plurality of terminally differentiated NPCs from (i) with a molecule specific for the protein of interest; (k) imaging the second plurality of terminally differentiated NPCs to obtain an integrated fluorescent intensity per cell (IFI-C) assay readout; and (l) comparing the IFI-C of the first plurality of terminally differentiated NPCs with the IFI-C of the second plurality of terminally differentiated NPCs; thereby determining the relative potency of the viral vector of the test sample relative to the reference standard.

In some embodiments, the methods comprise providing a third plurality of terminally differentiated NPCs, transducing the third plurality of terminally differentiated NPCs with an assay control comprising the viral vector, incubating the transduced third plurality of terminally differentiated NPCs under conditions sufficient to express the protein of interest; contacting the third plurality of terminally differentiated NPCs with a molecule specific for the protein of interest; imaging the third plurality of terminally differentiated NPCs to obtain an integrated fluorescent intensity per cell (IFI-C) assay readout; and comparing the IFI-C of the third plurality of terminally differentiated NPCs with the IFI-C of the first and/or second plurality of terminally differentiated NPCs; thereby determining the effectiveness of the in vitro potency assay. In some embodiments, the assay control is a positive control.

In some embodiments, the pluralities of terminally differentiated NPCs are cultured, transduced with the test sample, the reference sample, and optionally the assay control, incubated, stained and imaged in parallel. For example, pluralities of terminally differentiated NPCs can be cultured, transduced with the test sample, the reference sample, and optionally the assay control and undergo further downstream processing in the same 96 well plate.

In some embodiments, said first and second pluralities of cells are transduced by viral vector from the test sample and the reference standard at least two different multiplicities of infection (MOD. In some embodiments, the at least two different MOIs comprise at least 2, at least 3, at least 4, at least 5, at least 6, at least 7, at least 8, at least 9, at least 10, at least 11 or at least 12 MOI. In some embodiments, the at least two different MOIs comprise 5 different MOIs. In some embodiments, the 5 MOI comprise 300,000, 150,000, 75,000, 37,500, 18,750 viral particles per cell.

In some embodiments, the methods further comprise transducing a third plurality of In another embodiment, the viral vector or a pharmaceutical composition comprising the same, retains a potency of between ±20%, between ±15%, between ±10%, preferably ±5%, of a reference standard. In one embodiment, the potency is assessed as against a reference standard using the methods disclosed herein. Any suitable reference standard may be used.

As used herein, a "reference standard" refers to a composition comprising an AAV vector encoding a protein of interest, whose concentration and/or potency is known. An exemplary reference standard comprises AAV-SMN1 vector that is stored at less than or equal to −60° C. until use, thawed once, and stored at 2-8° C. for less than one week.

In some embodiments, the relative potency of the viral vector is at least 40%, at least 50%, at least 60%, at least 70%, at least 80%, at least 90%, at least 91%, at least 92%, at least 93%, at least 94%, at least 95%, at least 96%, at least 97%, at least 98%, at least 99%, at least 99.5%, at least 99.9%, at least 100%, at least 110%, at least 120%, at least 130% or at least 140% relative to a reference standard. In some embodiments, the relative potency of the viral vector is at least 90% relative to a reference standard.

The present methods assay the potency of the protein expressed by the transgene present in the viral vector disclosed herein, where the transgene is intended for delivery to the brain. Areas of the brain contemplated for delivery include, but are not limited to, the motor cortex and the brain stem. In some embodiments, the transgene is delivered to the spinal cord. In some embodiments, the transgene is delivered to a lower motor neuron. Embodiments of the invention employ rAAV9 to deliver transgenes to nerve and glial cells. In some embodiments, the glial cell is a microglial cell, an oligodendrocyte or an astrocyte. In some embodiments, the rAAV9 is used to deliver a transgene to a Schwann cell.

Use of viral vectors disclosed herein is indicated, for example, for treatment of lower motor neuron diseases such as SMA and ALS as well as Pompe disease, lysosomal storage disorders, Glioblastoma multiforme and Parkinson's disease. Lysosomal storage disorders include, but are not limited to, Activator Deficiency/GM2 Gangliosidosis, Alphamannosidosis, Aspartylglucosaminuria, Cholesteryl ester storage disease, Chronic Hexosaminidase A Deficiency, Cystinosis, Danon disease, Fabry disease, Farber disease, Fucosidosis, Galactosialidosis, Gaucher Disease (Type I, Type II, Type III), GM1 gangliosidosis (Infantile, Late infantile/Juvenile, Adult/Chronic), I-Cell disease/Mucolipidosis II, Infantile Free Sialic Acid Storage Disease/ISSD, Juvenile Hexosaminidase A Deficiency, Krabbe disease (Infantile Onset, Late Onset), Metachromatic Leukodystrophy, Mucopolysaccharidoses disorders (Pseudo-Hurler polydystrophy/Mucolipidosis IIIA, MPSI Hurler Syndrome, MPSI Scheie Syndrome, MPS I Hurler-Scheie Syndrome, MPS II Hunter syndrome, Sanfilippo syndrome Type A/MPS III A, Sanfilippo syndrome Type B/MPS III B, Sanfilippo syndrome Type C/MPS III C, Sanfilippo syndrome Type D/MPS III D, Morquio Type A/MPS WA, Morquio Type B/MPS IVB, MPS IX Hyaluronidase Deficiency, MPS VI Maroteaux-Lamy, MPS VII Sly Syndrome, Mucolipidosis 1/Sialidosis, Mucolipidosis IIIC, Mucolipidosis type IV), Multiple sulfatase deficiency, Niemann-Pick Disease (Type A, Type B, Type C), Neuronal Ceroid Lipofuscinoses (CLN6 disease (Atypical Late Infantile, Late Onset variant, Early Juvenile), Batten-Spielmeyer-Vogt/Juvenile NCL/CLN3 disease, Finnish Variant Late Infantile CLN5, Jansky-Bielschowsky disease/Late infantile CLN2/TPP1 Disease, Kufs/Adult-onset NCL/CLN4 disease, Northern Epilepsy/variant late infantile CLN8, SantavuoriHaltia/Infantile CLN1/PPT disease, Beta-mannosidosis, Pompe disease/Glycogen storage disease type II, Pycnodysostosis, Sandhoff Disease/Adult Onset/GM2 Gangliosidosis, Sandhoff Disease/GM2 gangliosidosis—Infantile, Sandhoff Disease/GM2 gangliosidosis-Juvenile, Schindler disease, Salla disease disease/Sialic Acid Storage Disease, Tay-Sachs/GM2 gangliosidosis, Wolman disease.

Use of viral vectors disclosed herein is indicated, for example, for treatment of SMA.

In further embodiments, use of the methods and materials is indicated for treatment of nervous system disease such as Rett Syndrome, Alzheimer's Disease, Parkinson's Disease, Huntington's Disease, or for treatment of nervous system injury including spinal cord and brain trauma/injury, stroke, and brain cancers.

"Treatment" comprises the step of administering intravenously, or via the intrathecal route, an effective dose, or effective multiple doses, of a composition comprising a rAAV of the invention to an animal (including a human being) in need thereof. If the dose is administered prior to development of a disorder/disease, the administration is prophylactic. If the dose is administered after the development of a disorder/disease, the administration is therapeutic. In embodiments of the invention, an effective dose is a dose that alleviates (either eliminates or reduces) at least one symptom associated with the disorder/disease state being treated, that slows or prevents progression to a disorder/disease state, that slows or prevents progression of a disorder/disease state, that diminishes the extent of disease, that results in remission (partial or total) of disease, and/or that prolongs survival. Examples of disease states contemplated for treatment by methods of the invention are set out above. Terminally Differentiated Neural Progenitor Cells (NPCs)

Provided herein are protocols for producing terminally differentiated NPCs, and using terminally differentiated NPCs in an in vitro cell based potency assay to determine the relative potency of an AAV vector encoding a protein of interest. In some embodiments, the potency of the AAV vector is determined relative to a reference standard. The protocols provided herein can be used to assay the potency of the AAV-SMN1 vector in pharmaceutical compositions, for example drug substance and drug product compositions, as well as assess vector stability.

Materials used to carry out the protocols will be known to the person of ordinary skill in the art. Exemplary materials include tissue-culture treated flasks (T75, T150, and T175), polypropylene centrifuge tubes, 15 and 50 mL with cap, pipets (single channel P1000, P200, and P20 and 8 or 12 channel P1000 and P300), Corning BioCoat Poly-D-Lysine 96-Well Plate (Corning 354640), Optically clear plate seal (Fisherbrand 8408240), Reagent reservoir, PIPET-AID, Cellometer slides (Nexcelom, CHT4-SD100-002), 96-Well DeepWell™ Polypropylene Microplates, Low-binding 1.5 mL Microcentrifuge Tubes, 70% (v/v) Isopropanol (IPA) and Dry Ice. However, equivalent materials and reagents may be used.

As provided in the Examples herein, NPCs are collected from the cortex of an embryo from SMA Δ7 (SMN1−/−) mouse strain at embryonic stage ~14.5 (e14.5). These cells may then be dissociated into single cells. During the culture, cells form neurospheres which are 3-dimensional colonies of undifferentiated cells. After approximately 3-5 days, neurospheres may then be passaged by dissociating into single cells and allowed to form secondary spheres. To terminally differentiate NPCs, the neurospheres may then be dissociated and seeded at 1E+06 cells/well in 0.5 mL (24-well plates, Falcon) or at 2E+05 cells/well in 100 μL (96-well plates, Corning) serum-enriched media without growth factors. At about 24 hrs post-differentiation, the cells become terminally differentiated primarily into a glial lineage.

As used herein, the term "cell line" refers to a population of cells capable of continuous or prolonged growth and division in vitro. It is further known in the art that spontaneous or induced changes can occur in karyotype during storage or transfer of such clonal populations. Therefore, cells derived from the cell line referred to may not be precisely identical to the ancestral cells or cultures, and the cell line referred to includes such variants.

In one embodiment, the terminally differentiated, non-dividing cells disclosed herein for use in the disclosed cell-based assay are derived from neural progenitor cells under the SMN1−/− genetic background (terminally differentiated cells derived from NPCs, referred to herein as "mTD-NPC-Δ7"). These cells possess the capability to be effectively transduced by non-replicating AAV9 vector.

In some embodiments, NPC-Δ7 cells that are isolated from mouse embryonic cortex and cultured as described herein are frozen (e.g., at less than or equal to −60° C.) prior to use in the in vitro cell based potency assay.

In some embodiments, NPC-Δ7 cells are thawed using the following protocol. Complete Growth Media is pre-warmed in a 37° C. water bath or equivalent for at least 30 minutes prior to use. A frozen cryovial of mNPC cells is removed from the liquid nitrogen storage. The vial is kept on dry ice until it is ready to be thawed, then quickly thawed in 37° C. water bath, swirling occasionally to ensure thawing. The vial surface is wiped with 70% (v/v) Isopropanol (IPA), then the contents are transferred to a 50 mL centrifuge tube using a sterile pipette in a BSC. After thawing cells, the cryoprotectant is slowly diluted to prevent osmotic shock. About 10-20 mL is usually sufficient to overcome toxic effects. 10-20 mL of warmed Complete Growth Media is added in a dropwise manner while mixing gently by swirling, followed by centrifugation at 300×g for 5 minutes at 20° C. The supernatant is aspirated, and then the tube is gently agitated to break up the cell pellet. The appropriate volume (e.g. 1.0-2.0 mL) of warm Complete Growth Media is added to cells and mixed.

In some embodiments, a live cell count and viability is obtained. In some embodiments, a live cell count is ≥60.0% viable in order to proceed.

In some embodiments, the cells are transferred to a tissue culture flask, 10.0 mL of complete growth media is added, and the flask is rocked to gently to ensure even distribution. The flask is then incubated at 37° C. and 5% $CO_2$, for at least 72 hours, before testing for growth and viability.

Culture of NPC Cells

In some embodiments, the NPC cells are homozygous for a mutation in SMN1 (SMN1−/−). In some embodiments, the mutation in SMN1−/− is a null mutation. In some embodiments, the SMN1−/− is a deletion of exon 7 (Δ7) and the cells are referred to as NPC-Δ7 cells. In some embodiments, the NPCs are isolated or derived from mouse embryonic cortex.

In some embodiments, NPC-Δ7 cells are cultured through one or more rounds of passage prior to use in the in vitro cell based potency assays described herein.

In some embodiments, NPC-Δ7 cells are used in an assay starting at the second passage after thaw.

In some embodiments, NPC-Δ7 cells are used at passages 8-15 in the in vitro cell based potency assays described herein. Thawing is not considered a passage. In some embodiments, cells are used up to passage 15. For example, if the working cell bank was frozen at or after passage 6 (P6), when the cells were thawed, they retained the passage number as P6. After the appropriate number of days for cell proliferation, cells were passaged by being dissociated with Accumax and became P7. At P7, cells cannot be used for an assay.

In some embodiments, NPC-Δ47 cells are passaged by being dissociated with Accumax (P8), and can then be used in the in vitro potency assay.

As cells proliferate in suspension, they form 3-dimensional colonies called neurospheres. In some embodiments, for example to prevent the neurospheres from growing too large and becoming necrotic in the center, cells are passaged every 4±1 days.

An exemplary cell passaging protocol is described as follows. Base Media and Complete Growth Media are pre-warmed in a 37° C. water bath or equivalent for 30 minutes prior to use. An exemplary Base Media comprises DMEM/F12, GlutaMAX Supplement, 2% B27 Supplement (50×), and 1% antibiotic-antimycotic. An exemplary Complete Growth Media comprises Base Media, 0.1% Heparin (5 mg/mL), 0.02% bFGF (fibroblast growth factor-basic) Recombinant Human Protein at 100 g/mL and 0.005% EGF (epidermal growth factor) Recombinant Human Protein Solution at 1 mg/mL.

In some embodiments, to passage cells, the flask containing the cells is removed from the incubator and the surface of the flask is rinsed using the media containing cells. Cells are transferred from flask to a 50 mL conical tube and centrifuged for 5 minutes at 300×g. The supernatant is aspirated without disturbing the cell pellet and 200.0 μL of Accumax is added. The cell pellet was gently triturated, then incubated for 30±10 minutes at room temperature.

At the end of the Accumax incubation, the Accumax is neutralized by pre-warmed Base Media. In some embodiments, 400.0 µL of pre-warmed Base Media is added, and the cells are gently triturated to fully dissociate to single cells.

In some embodiments, an additional 400.0 µL of pre-warmed Base Media is added to make a total volume of 1.0 mL.

In some embodiments, cells are diluted to an acceptable cell density range. An exemplary cell density range comprises a range of 5.00E+05 cells/mL to 1.00E+07 for cell counting. However, the ordinarily skilled artisan will be able to adjust cell density range to the appropriate cell counting method.

In some embodiments, sells from multiple flasks of the same cell reference/lot at the same passage number are pooled before cell counting.

In some embodiments, cells are mixed and then a sample of the cells is removed to determine the viable cell count and the viability.

In some embodiments, mTD NPC-Δ7 (terminally differentiated NPCΔ7) plates are prepared when the viability for each of the cell counts is ≥60.0%, ≥70.0%, ≥80.0%, or ≥90.0%. In some embodiments, mTD NPC-Δ7 (terminally differentiated NPCΔ7) plates are prepared when the viability for each of the cell counts is ≥80.0%.

In some embodiments, the in vitro potency assay proceeds only if the viability for each of the cell counts is ≥70.0% viable.

Terminally Differentiating NPCs

The disclosure provides methods of terminally differentiating NPCs to produce terminally differentiated NPCs to use in the in vitro cell based potency assays described herein. In some embodiments, the terminally differentiated NPCs comprise a homozygous deletion of exon 7 of SMN1 (mTD NPC-Δ7 cells).

In some embodiments, Plate Media is used to terminally differentiate the NPCs. Exemplary plate media comprises DMEM/F12, GlutaMAX supplement, 2% B27 Supplement (50x), 1% antibiotic-antimycotic and 10% FBS.

In some embodiments, cells are diluted to a density of 20,000 cells/well/100 µL (or 2.00×10$^5$ cells/mL) in Plate Media. In some embodiments, cells are diluted to a density of 5,000 cells/well/100 µL, 10,000 cells/well/100 µL, 15,000 cells/well/100 µL, 20,000 cells/well/100 µL, 25,000 cells/well/100 µL or 30,000 cells/well/100 µL, In some embodiments, 100 µL cells are gently mixed and added to wells of 96-well Poly-D-Lysine coated plate.

In some embodiments, the plate(s) are rested at ambient temperature for 25±5 minutes prior to placing plated cells in a 37° C., 5% CO$_2$ incubator.

In some embodiments, plated cells are placed in a 37° C., 5% CO$_2$ incubator for 24 hours±2 hours prior to transduction.

Transduction

In one embodiment, the term "transfection" is used interchangeably herein with the term "transduction", and either term or grammatical equivalents thereof is used to refer to the uptake of foreign DNA by a cell, and a cell has been "transfected" or "transduced" refers to when exogenous DNA has been introduced inside the cell membrane. A number of transfection techniques are generally known in the art. See, e.g., Graham et al. (1973) Virology, 52:456, Sambrook et al. (1989) Molecular Cloning, a laboratory manual, Cold Spring Harbor Laboratories, New York, Davis et al. (1986) Basic Methods in Molecular Biology, Elsevier, and Chu et al. (1981) Gene 13: 197. Such techniques can be used to introduce one or more exogenous DNA moieties into suitable host cells.

Suitable methods for the transduction of cells are known in the art. In one embodiment, cells are transduced in vitro by combining a viral vector with cells. In one embodiment, cells are transduced in vitro by combining an AAV9 vector with cells. In one embodiment, cells are transduced in vitro by combining an SMN1-encoding AAV9 vector with cells. In one embodiment, AAV9 is combined with the cell about 24-hrs post differentiation. In another embodiment it is combined with the cell about 12-24 hrs post differentiation. In another embodiment it is combined with the cell about 24-32 hrs post differentiation.

In one embodiment, any suitable transfection media may be used. In one embodiment, the DMEM serum-free growth medium used for cell expansion is replaced with a modified DMEM transfection media. In one embodiment, the transfection media is DMEM with no FBS, no calcium, no L-glutamine and 4.5 g/l glucose.

In a particular embodiment, the step of incubating the cells following transduction is performed for about 69-75 hrs. In some embodiments, the step of incubating the cells following transduction is performed for about 24-48 hrs, 48-69 hrs, or about 75-90 hrs.

In one embodiment, transduction of cells of a patient with rAAV of the invention results in sustained expression of polypeptide or RNA encoded by the rAAV.

In another embodiment, the cell transduced with a viral vector is a terminally differentiated non-dividing cell. In another embodiment, the cell transduced with a viral vector is a terminally differentiated non-dividing primary cell, such as an mTD NPC-Δ7 cell.

In some embodiments, mTD NPC-Δ7 cells are transduced with a test sample and a reference standard comprising an AAV vector comprising a transgene encoding an SMN1 protein. In some embodiments, mTD NPC-Δ7 cells are transduced with a test sample, a reference standard and an assay control (e.g., a positive control, sometimes referred to as Control) comprising an AAV vector comprising a transgene encoding an SMN1 protein.

In some embodiments, the AAV9-SMN1 vector Reference Standard (RS), Control (Crtl) and Test Samples are prepared as follows. Aliquots of the Reference Standard (RS), Control, and Test Samples are thawed at ambient temperature. The Formulation Buffer and Plate Media are pre-warmed in a 37° C. water bath or equivalent for at least 30 minutes prior to use. The samples are pre-diluted to 1.00E+12 vg/mL (the protocol may be adapted for other concentrations) in a 1.5 mL microcentrifuge tube using the appropriate pre-warmed Formulation Buffer.

In some embodiments, serial dilutions are performed to prepare the different MOI to generate the MOI versus IFI-C plot. For example, a starting concentration of 300K MOI can be serially diluted to generate RS, test and assay/positive control samples at 150K MOI, 75K MOI, 37.5K MOI, and 18.75K MOI.

In some embodiments, the prepared samples at the prepared MOI are gently mixed and immediately dispensed at an angle to the wall of the corresponding wells of the 96 well plate. Plates are transferred to the incubator (37±1° C., 5±1% CO2). Plates were incubated for 72±2 hours.

Cell Staining

Provided herein are methods of staining cells for a protein of interest, e.g. a SMN protein such as SMN1 or SMN2, e.g., SMN1. The methods of staining cells can be used in the in vitro cell based potency assays described herein.

In one embodiment, the molecule that is specific for the protein of interest comprises an antibody, an antibody fragment, or an aptamer. In another embodiment, the antibody comprises an antibody specific for the protein of interest.

Antibodies exist as intact immunoglobulins or as a number of well characterized fragments produced by digestion with various peptidases. Thus, for example, pepsin digests an antibody below the disulfide linkages in the hinge region to produce F(ab')2, a dimer of Fab which itself is a light chain joined to VH-CH1 by a disulfide bond. The F(ab')2 may be reduced under mild conditions to break the disulfide linkage in the hinge region thereby converting the F(ab')2dimer into an Fab' monomer. The Fab' monomer is essentially an Fab with part of the hinge region (see, Fundamental Immunology, W. E. Paul, ed., Raven Press, New York (1999), for a more detailed description of other antibody fragments). While various antibody fragments are defined in terms of the digestion of an intact antibody, one of skill will appreciate that such Fab' fragments, etc. may be synthesized de novo either chemically or by utilizing recombinant DNA methodology. Thus, the term antibody, as used herein also includes antibody fragments either produced by the modification of whole antibodies or synthesized de novo using recombinant DNA methodologies. Antibodies include single chain antibodies, including single chain Fv (sFv or scFv) antibodies in which a variable heavy and a variable light chain are joined together (directly or through a peptide linker) to form a continuous polypeptide.

As explained above (see, Definitions, supra) the antibodies used herein optionally comprise F(ab)2, F(ab')2, Fab, Fab', scFv, etc. depending upon the specific requirements of the embodiment. Some embodiments utilize alternate immunoglobins such as IgM, IgA, IgD, and IgE. Furthermore, all possible isotypes of the various immunoglobins are also encompassed within the current embodiments. Thus, IgG1, IgG2, IgG3, etc. are all possible molecules for use in the in the invention.

In one embodiment, the anti-protein of interest antibody is provided at a concentration of about 4 µg/mL. In another embodiment, the anti-protein of interest antibody is provided at a concentration of about 1-4 µg/mL, 4-8 µg/mL, 8-12 µg/mL, or 12-16 µg/mL. In one embodiment, the anti-protein of interest antibody is provided at a concentration of about 2 µg/mL.

In another embodiment, the molecule comprises a detectable label to enable detection. Labels include for example chelated lanthanide series metals like europium, platinum group metals like ruthenium, fluorochromes, including inter alia xanthene derivatives like fluorescein and rhodamine, or any derivatives of both, fluorescent proteins like green fluorescent protein (GFP) and its derivatives yellow fluorescent protein (YFP) and red fluorescent protein (RFP), radiolabels like iodine-125 and actinium-225, and other like detectable labels known in the art. In some embodiments, a detectable label that removes the need to perform a washing step is used.

Fluorescent labeling groups are generally distinguishable from each other based upon one or more of their excitation spectra, emission spectra or fluorescent lifetimes. By separately directing excitation light of different wavelengths at the cells, one could then determine the level of fluorescence resulting from the any one or more different detectable labels. Alternatively, the detectable labels are selected to have distinguishable fluorescent emission maxima, e.g., they emit light or fluoresce at substantially different wavelengths. In operation, a single light source is directed at the cells. The fluorescent emissions from the cells are then passed through optical filters, which separate the different fluorescent emissions, which are then separately quantified. In selecting either distinguishable excitation or emission maxima, it is generally preferred that the excitation or emission spectrum of one label, e.g., a reference label, does not appreciably overlap with the excitation or emission spectrum of the other label. Specifically, while there is generally a maximum excitation or emission wavelength for different labels, there is typically a broader range of wavelengths at which there is some excitation or emission. Typically, labels are selected such that there is substantially no overlap between the excitation or emission spectra of the two labels, e.g., in detection of one label, less than 10% of the fluorescence is due to overlap from the other label.

In one embodiment, measurement of the intensity of fluorescence provides a measure of expression of a protein of interest that has taken place inside the cell. In another embodiment, integrated fluorescent intensity per cell (IFI-C) values are calculated for every dose of viral vector provided in the cell-based assay disclosed herein and replicate. In another embodiment, the IFI-C readout reflects a measurement of expression of a protein of interest.

In one embodiment, the method provided herein further comprises washing the cells to remove the molecule specific for the protein of interest. In another embodiment, after washing, the method further comprises contacting the cells with a second molecule that specifically recognizes the molecule specific for the protein of interest. In another embodiment, the second molecule comprises a detectable label. In another embodiment, the second molecule comprises an antibody, an antibody fragment or an aptamer.

In another embodiment of the methods provided herein, the cell is contacted with an anti-nuclear detectable label following the fixing and permeabilizing step. Detectable labels that are used for detecting the nucleus may include, but are not limited to, DAPI, propidium iodide (PI), Hoechst, NucSpot® 470, RedDot™2 Far-Red Nuclear Stains, or Dye NucFix™ Red. In another embodiment, NucSpot® Live 488 and NucSpot® Live 650 Nuclear Stains are used. NucSpot® Live Nuclear Stains specifically stain nuclei in live or fixed cells with no need for washing.

In one embodiment, following staining with at least one detectable label disclosed herein, the method further comprises the step of acquiring one or more images of cells, wherein the images display expression of the protein of interest within the cells, as determined via detection of a detectable signal provided by at least one of the detectable labels upon excitation with light. Further, the step of obtaining the images is followed by performing image analysis.

In one embodiment, the cells disclosed herein are assessed for viability following isolation and/or prior to performing the cell-based assay disclosed herein. Methods for assessing cell viability are well known in the art and include, for example, Trypan Blue stain (or equivalent cell viability reagent depending on cell counter used), microscopic observation, and the like.

In one embodiment, the plurality of cells are seeded on a solid surface. In another embodiment, the solid surface comprise any type of plates known in the art, including 24 or 96 well plates. In another embodiment, the plates that are used in the assay are amenable for imaging the cells. In another embodiment, the solid surface is coated with Poly-D-Lysin.

In another embodiment, the cells are seeded at a density of 20,000 cells on the solid surface. In another embodiment, the cells are seeded at a density of 10,000 cells on the solid surface. In another embodiment, the cells are seeded at a density of 10,000-20,000 cells on the solid surface. In another embodiment, the cells are seeded at a density of 20,000 cells per well. In another embodiment, the cells are seeded at a density of 10,000 cells per well. In another embodiment, the cells are seeded at a density of 10,000-20,000 cells per well.

In one embodiment, the transgene comprises a polynucleotide encoding a survival motor neuron (SMN1) protein. In another embodiment, the protein of interest expressed by a cell transduced with a viral vector disclosed herein is a survival motor neuron (SMN1) protein.

In some embodiments, transduced plates comprising the terminally differentiated and transduced cells described herein are removed from the incubator at 72 hours±2 hours for cell staining.

In some embodiments, cells are fixed according to the protocol described below. 50.0 μL of 4% Paraformaldehyde, or an appropriate volume and concentration, are gently added to the wells. Plates were then incubated, for example 5 to 7 minutes at ambient room temperature. Following incubation, the 4% Paraformaldehyde is aspirated from each well, and wells are washed with 250.0 μL DPBS (Dulbecco's Phosphate-Buffered Saline).

In some embodiments, the plate can be stored in 2-4° C. In some embodiments, the plate can be stored for up to 3 days. When the plate is stored, DPBS is removed and 250.04 of fresh DPBS was added before storing the plate.

In some embodiments, cells are permeabilized with Triton X-100. In some embodiments, DPBS was gently aspirated from each well, and 50.0 μL of 0.1% Triton X-100 is gently added. Plates can then be incubated, for example 5 to 7 minutes at ambient room temperature, the 0.1% Triton X-100 aspirated from each well, and the wells washed with DPBS.

Primary Antibody Incubation

Exemplary primary antibodies include mouse monoclonal anti-SMN antibody (Clone 2B1), Santa Cruz sc-32313 XS Lot #C2818 at 1:500 dilution, Santa Cruz sc-32313 XS Lot #F2118 at 1:1000 dilution, and EMD Millipore Lot #3054700 at 1:500 dilution. For example, to prepare 4.0 mL of staining solution for 1:500 dilution of antibody, 8.0 μL of anti-SMN antibody is added to 4.0 mL of 1% BSA in DPBS.

In some embodiments, are incubated for 120 to 150 minutes with primary antibody at ambient room temperature.

In some embodiments, cells are washed with DPBS following primary antibody incubation.

Secondary Antibody Incubation

Exemplary secondary antibodies include 2 μg/mL final of goat anti-mouse IgG (H+L) Alexa Fluor Plus 488 at 1:1000 dilution and 2 μg/mL of nuclear dye Hoechst 33342 (1:5000 dilution) in 1% BSA in DPBS. Hoechst 33342 Nuclear Dye can be pre-diluted by adding 10.0 μL of the Hoechst 33342 nuclear dye into 40.0 μL of Distilled Water.

In some embodiments, cells are incubated for 60 to 80 minutes in secondary antibody at ambient room temperature, protected from light (example: covered in foil).

The secondary antibody solution is aspirated from each well, and cells washed with DPBS.

In some embodiments, plates are then sealed with a clear optic plate seal, and imaged.

Calculating Relative Potency

The disclosure provides methods of determining the potency of a vector in a test sample. In some embodiments, the potency of the vector in the test sample is determined relative to a reference standard (RS). In some embodiments, the reference standard comprises the same vector as the test sample, but the characteristics of the reference standard (vector concentration, potency and the like) are known.

In some embodiments, the relative potency calculation of the vector in the test sample compared to the vector in the reference standard is carried out using parallel lines analysis (PLA). PLA is a method used to compare dose response curves, for example IFI-C as a result of MOI, or log MOI.

In some embodiments, the PLA comprises fitting an individual linear model to the $Log_2$ MOI versus IFI-C for each of the test sample and the reference standard. In some embodiments, the IFI-C of an assay control, for example a positive control, is also measured at the same time, and the MOI or $Log_2$ MOI versus IFI-C is also calculated for the assay control. In some embodiments, the IFI-C for each of the test sample, the reference standard and optionally, the assay control is averaged from multiple assay readouts at each MOI (for example, 2, 3, 4, 5 or more replicates).

In some embodiments, the R-squared value ($R^2$), intercept, and slope estimate of the linear regression are calculated using a least squares method for the test sample, the reference standard and the assay control.

In some embodiments, the ratio of the test sample slope estimate relative to the reference standard ($\hat{\beta}_{sample}/\hat{\beta}_{RS}$)) is used to assess parallelism between the test sample and reference standard. The sample slope is parallel to the slope of reference standard if the slope ratio is within the empirical range established between assay control sample and reference standard, where:

$$y = \alpha + \beta \log_2(MOI) + e \qquad (M2.1)$$

where y is the Integrated Fluorescence Intensity per Cell from a given MOI level; α and β are intercept and slope of the linear regression line, respectively, and e is the residual error.

In some embodiments, a common slope model is used in the PLA. In some embodiments, for each test sample and the reference standard, and optionally the assay control, the linear regression model with individual intercept and common slope (M2.2) is fitted to the assay readout of Integrated Fluorescence Intensity per Cell (IFI-C) vs $\log_2$ transformed expected MOI values on the plate, where:

$$y = \alpha + \beta \log_2(MOI) + e \qquad (M2.1)$$

and where $y_i$ is the Integrated Fluorescence Intensity per Cell from give MOI level for sample i, i∈{sample, reference standard}; $\alpha_i$ is the individual intercept for sample i, i∈{sample, reference standard}; β is the common slope and e is the residual error.

In some embodiments, the IFI-C for each of the test sample and the reference sample, and optionally the assay control, is averaged from multiple assay readouts at each MOI (for example, 2, 3 or more replicates).

In some embodiments, relative potency is calculate as follows: the relative potency of the test sample is calculated from the intercept of slope estimates from model (M2.2) as $$\text{Relative Potency} = 2 \wedge \left( \frac{\hat{\alpha}_{sample} - \hat{\alpha}_{reference\ standard}}{\hat{\beta}} \right)$$

In some embodiments, an assay plate is considered valid if the percent coefficient of variance (% CV) of the IFI-C of the test sample, $R^2$ value of the linear regression fit, the assay dynamic window of the reference standard (RS), the slope ratio for an assay control (e.g. a positive control) versus the RS, the relative potency of the assay control, and the slope ratio of the test sample versus the RS meet certain criteria.

In some embodiments, the % CV of IFI-C of the test sample is less than or equal to 40%, is less than or equal to 30%, is less than or equal to 20%, is less than or equal to 10% or is less than or equal to 10%. In some embodiments, the % CV of IFI-C of the test sample is less than or equal to 20%.

In some embodiments, the $R^2$ upon linear regression fit is ≥0.99, ≥0.95, ≥0.90, ≥0.89, or ≥0.85.

In some embodiments, the $R^2$ upon linear regression fit is ≥0.95.

In some embodiments, the reference standard (RS) has an assay dynamic window (maximal signal to background signal cells only) that is ≥2.0, ≥2.1, ≥2.2, ≥2.3, ≥2.4, ≥2.5, ≥2.6, ≥2.69, ≥2.8, ≥2.9 or ≥3.0. In some embodiments, reference standard (RS) has an assay dynamic window (maximal signal to background signal cells only) that is ≥2.69.

In some embodiments, reference standard (RS) has a slope that is ≥1.02E+05.

In some embodiments, the slope ratio for the assay control (e.g., a positive control) versus the reference standard is within 0.60-1.5. In some embodiments, the slope ratio for the assay control (e.g., a positive control) versus the reference standard is within 0.70-1.4. In some embodiments, the slope ratio for the assay control (e.g., a positive control) versus the reference standard is within 0.75-1.33.

In some embodiments, for each test sample, the mean ($\hat{\mu}$) and standard deviation ($\hat{\sigma}$) and associated 95% confidence limits are estimated for the natural log transformed relative potency results; and the geometric mean relative potency ($e^{\hat{\mu}}$) and percent coefficient of variation (CV %= $\sqrt{e^{\hat{\sigma}^2}-1} \times 100\%$) are calculated.

In some embodiments, $\log(y_{ij})=\mu_i+\epsilon_{ij}$ (M2.1) is calculated across test samples, where, $y_{ij}$ is the relative potency from recovery sample i; $\mu_i$ is the mean log-transformed relative potency of recovery sample i, and $\epsilon_{ij}\sim$Normal (0, $\sigma_{intra-assay}^2$) is the random intra-assay residual error.

In some embodiments, the overall intermediate precision ($\sigma_{inter-assay}^2+\sigma_{intra-assay}^2$) is calculated across test samples. In some embodiments, intermediate precision is calculated using $\log(y_{ijk})=\mu_i+\theta_j+\epsilon_{ijk}$ (M2.2); where $y_{ijk}$ is the relative potency from recovery sample i; $\mu_i$, is the mean log-transformed relative potency of recovery sample i; $\theta_j\sim$Normal (0, $\sigma_{inter-assay}^2$) is the random inter-assay effect from assay run j; and $\epsilon_{ijk}\sim$Normal (0, $\sigma_{intra-assay}^2$) is the random intra-assay residual error.

In some embodiments, the overall reproducibility is calculated across test samples. In some embodiments, overall reproducibility is calculated using $\log(y_{iljk})=\mu_i+\alpha_l+\epsilon_{ijk}$ (M2.3); where $y_{ijk}$ is the relative potency from recovery sample i; $\mu_i$ is the mean log-transformed relative potency of recovery sample i; $\alpha_l\sim$Normal (0, $\sigma_{inter-lab}^2$) is the random inter-lab effect from lab l; $\theta_{j[l]}\sim$Normal (0, $\sigma_{inter-assay}^2$) is the random inter-assay effect from assay run j nested in lab l; and $\epsilon_{ijk}\sim$Normal (0, $\sigma_{intra-assay}^2$) is the random intra-assay residual error.

In some embodiments, the parallelism of the slope ratio is assessed. The parallelism of in-vitro relative potency assay can be measured by the ratio of slopes of the test sample and reference standard, i.e. $\text{slope}_{sample}/\text{slope}_{standard}$, where the slope is estimated from linear regression model between IFI-c and log 2 transformed MOI levels.

In some embodiments, the slope ratios are log transformed for analysis. In some embodiments, the mean ($\hat{\mu}$) and standard deviation ($\hat{\sigma}$) are estimated for the natural log transformed slope ratios for each test sample and an assay control (e.g., positive control) sample, and the geometric mean relative potency ($e^{\hat{\mu}}$) and percent coefficient of variation (CV %= $\sqrt{e^{\hat{\sigma}^2}-1} \times 100\%$) are then calculated.

Methods of carrying out the statistical analysis described herein will be known to the person of ordinary skill in the art. For example, statistical analysis can be performed using statistical software JMP Pro 13.2.1, R, Matlab, or the like.

Vector Stability

Provided herein are methods of assessing the stability of a vector using the in vitro cell based potency assay described herein.

In some embodiments, the methods comprise holding a vector stability sample at a particular temperature (for example 20-25° C.) for a length of time, and then comparing the relative potency of the vector stability sample to a reference standard that has not been held at the particular temperature. For example, a vector stability sample may be held at 20-25° C. for 1 week, 2 weeks, 3 weeks, 1 month, 2, months, 3 months or 4, months, and the potency of the vector stability sample compared to a reference standard that was held at or below −60° C. for the same length of time using the methods provided herein.

Vectors

The disclosure provides viral vectors as gene therapy biological products intended to be developed for the treatment of pediatric patients diagnosed with a disease. The potency of the vectors provided herein, and pharmaceutical compositions comprising same can be assayed using the in vitro cell based potency assay described herein. In one embodiment, the disease is SMA, e.g., SMA Type 1, SMA Type 2, SMA Type 3, SMA Type 4 or combinations thereof. In one embodiment, the disease is SMA Type 1, a severe neuromuscular disease characterized by the loss of motor neurons due to a genetic defect in the SMN 1 gene important for survival of motor neurons. In some embodiments, the viral vector is comprised of a non-replicating and non-integrating recombinant self-complementary adeno-associated virus serotype 9 (AAV9) comprising the cDNA expressing SMN1 protein under the control of the cytomegalovirus (CMV) enhancer/chicken-β-actin-hybrid promoter (CB), and two AAV inverted terminal repeats (ITR) from the AAV serotype 2 (AAV2) DNA.

In one embodiment, the term "vector" refers to any genetic element, such as a plasmid, phage, transposon, cosmid, chromosome, virus, virion, etc., which is capable of replication when associated with the proper control elements and which can transfer gene sequences between cells. Thus, the term includes cloning and expression vehicles, as well as viral vectors.

In one embodiment, the term "AAV vector" refers to a vector derived from an adeno-associated virus serotype, including without limitation, AAV-1, AAV-2, AAV-3, AAV-4, AAV-5, AAV-6, AAV-7, AAV-8 and AAV-9, preferably AAV-9. AAV vectors can have one or more of the AAV wild-type genes deleted in whole or part, preferably the rep and/or cap genes, but retain functional flanking ITR sequences. Functional ITR sequences are necessary for the rescue, replication and packaging of the AAV virion. Thus, an AAV vector is defined herein to include at least those sequences required in cis for replication and packaging (e.g., functional ITRs) of the virus. The ITRs need not be the wild-type nucleotide sequences, and may be altered, e.g., by the insertion, deletion or substitution of nucleotides, so long as the sequences provide for functional rescue, replication and packaging. In a preferred embodiment the vector is an AAV-9 vector, with AAV-2 derived ITRs. Also by an "AAV vector" is meant the protein shell or capsid, which provides an efficient vehicle for delivery of vector nucleic acid to the nucleus of target cells.

In one embodiment, the term "scAAV" refers to a self-complementary adeno-associated virus (scAAV), which is a viral vector engineered from the naturally occurring adeno-associated virus (AAV) for use in gene therapy. scAAV is termed "self-complementary" because the coding region has been designed to form an intra-molecular double-stranded DNA template.

In embodiment, provided herein is a rAAV genomes. The rAAV genomes comprise one or more AAV ITRs flanking a polynucleotide encoding a polypeptide (including, but not limited to, an SMN polypeptide) or encoding siRNA, shRNA, antisense, and/or miRNA directed at mutated proteins or control sequences of their genes. The polynucleotide is operatively linked to transcriptional control DNAs, specifically promoter DNA and polyadenylation signal sequence DNA that are functional in target cells to form a gene cassette. The gene cassette may also include intron sequences to facilitate processing of an RNA transcript when expressed in mammalian cells.

The rAAV9 genome encodes in some embodiments, siRNA, shRNA, antisense, and/or miRNA for use in methods to decrease mutant Huntington protein (htt) expression for treating a neurodegenerative disorder such as Huntington's disease.

The rAAV9 genome encodes in various embodiments siRNA, shRNA, antisense, and/or miRNA for use in for treatment of neurodegenerative disorders such as ALS. Treatment results in a decrease in the expression of molecular markers of disease, such as TNF.alpha., nitric oxide, peroxynitrite, and/or nitric oxide synthase (NOS).

In some embodiments, the vectors encode short hairpin RNAs directed at mutated proteins such as superoxide dismutase for ALS, or neurotrophic factors such as GDNF or IGF1 for ALS or Parkinson's disease.

In some embodiments, use of the viral vector of the invention is indicated for treating neurodevelopmental disorders such as Rett Syndrome. For embodiments relating to Rett Syndrome, the rAAV9 genome may encode, for example, methyl cytosine binding protein 2 (MeCP2).

The rAAV genomes disclosed herein may lack AAV rep and cap DNA. AAV DNA in the rAAV genomes (e.g., ITRs) may be from any AAV serotype for which a recombinant virus can be derived including, but not limited to, AAV serotypes AAV-1, AAV-2, AAV-3, AAV-4, AAV-5, AAV-6, AAV-7, AAV-8, AAV-9, AAV-10 and AAV-11. The nucleotide sequences of the genomes of the AAV serotypes are known in the art. For example, the complete genome of AAV-1 is provided in GenBank Accession No. NC_002077; the complete genome of AAV-2 is provided in GenBank Accession No. NC 001401 and Srivastava et al., Virol., 45: 555-564 (1983): the complete genome of AAV-3 is provided in GenBank Accession No. NC_1829; the complete genome of AAV-4 is provided in GenBank Accession No. NC_001829; the AAV-5 genome is provided in GenBank Accession No. AF085716; the complete genome of AAV-6 is provided in GenBank Accession No. NC_00 1862; at least portions of AAV-7 and AAV-8 genomes are provided in GenBank Accession Nos. AX753246 and AX753249, respectively; the AAV-9 genome is provided in Gao et al., J. Virol., 78: 6381-6388 (2004); the AA V-10 genome is provided in Mol. Ther., 13(1): 67-76 (2006); and the AAV-11 genome is provided in Virology, 330(2): 375-383 (2004).

In another embodiment, the provided are DNA plasmids comprising rAAV genomes of the invention. The DNA plasmids are transferred to cells permissible for infection with a helper virus of AAV (e.g., adenovirus, EI-deleted adenovirus or herpes virus) for assembly of the rAAV genome into infectious viral particles with AAV9 capsid proteins. Techniques to produce rAAV particles, in which an AAV genome to be packaged, rep and cap genes, and helper virus functions are provided to a cell are standard in the art. Production of rAAV requires that the following components are present within a single cell (denoted herein as a packaging cell): a rAAV genome, AAV rep and cap genes separate from (i.e., not in) the rAAV genome, and helper virus functions. Production of pseudotyped rAAV is disclosed in, for example, WO01/83692 which is incorporated by reference herein in its entirety.

In various embodiments, AAV capsid proteins may be modified to enhance delivery of the recombinant vector. Modifications to capsid proteins are generally known in the art. See, for example, US 2005/0053922 and US 2009/0202490, the disclosures of which are incorporated by reference herein in their entirety.

General principles of rAAV production are reviewed in, for example, Carter, 1992, Current Opinions in Biotechnology, 1533-539; and Muzyczka, 1992, CUM Topics in Microbial. And Immunol., 158:97-129). Various approaches are described in Ratschin et al., Mol. Cell. Biol. 4:2072 (1984); Hennonat et al., Proc. Natl. Acad. Sci. USA, 81:6466 (1984); Tratschin et al., Mol. Cell. Biol. 5:3251 (1985); McLaughlin et al., J. Virol., 62:1963 (1988); and Lebkowski et al., 1988 Mol. Cell. Biol., 7:349 (1988). Samulski et al. (1989, J. Virol., 63:3822-3828); U.S. Pat. No. 5,173,414; WO 95/13365 and corresponding U.S. Pat. No. 5,658,776; WO95/13392; WO96/17947; PCT/US98/18600; WO97/09441 (PCT/US96/14423); WO97/08298 (PCT/US96/13872); WO97/21825 (PCT/US96/20777); WO97/06243 (PCT/FR96/01064); WO99/11764; Perrin et al. (1995) Vaccine 13:1244-1250; Paul et al. (1993) Human Gene Therapy 4:609-615; Clark et al. (1996) Gene Therapy 3:1124-1132; U.S. Pat. Nos. 5,786,211; 5,871,982; and 6,258,595. The foregoing documents are hereby incorporated by reference in their entirety herein, with particular emphasis on those sections of the documents relating to rAAV production. The invention thus provides packaging cells that produce infectious rAAV. In one embodiment any suitable packaging cell line may be used, such as HeLa cells, HEK-293 cells and PerC.6 cells (a cognate 293 line), preferably HEK293 cells. In other embodiments, the invention provides rAAV9 (i.e., infectious encapsidated rAAV9 particles) comprising a rAAV genome of the invention. In one aspect of the invention, the rAAV genome is a self-complementary genome.

In another embodiment, the method allows a quantitative measurement of dose-dependent increase in the level of the protein of interest.

In other embodiments, the invention provides rAAV9 (i.e., infectious encapsidated rAAV9 particles) comprising a rAAV genome of the invention. In one aspect of the invention, the rAAV genome is a self-complementary genome.

In another embodiment, rAAV are provided such as a rAAV9 named "rAAV9-SMN", or "AAV9-SMN1." The rAAV SMN genome has in sequence an AAV2 ITR, the chicken beta-actin promoter with a cytomegalovirus enhancer, an SV 40 intron, the SMN coding DNA set out in (GenBank Accession Number NM_000344.2), a polyadenylation signal sequence from bovine growth hormone and another AAV2 ITR. An exemplary SMN coding sequence comprises a sequence of:

(SEQ ID NO: 2)

```
   1    CCACAAATGT GGGAGGGCGA TAACCACTCG TAGAAAGCGT GAGAAGTTAC TACAAGCGGT
  61    CCTCCCGGCC ACCGTACTGT TCCGCTCCCA GAAGCCCCGG GCGGCGGAAG TCGTCACTCT
 121    TAAGAAGGGA CGGGGCCCCA CGCTGCGCAC CCGCGGGTTT GCTATGGCGA TGAGCAGCGG
 181    CGGCAGTGGT GGCGGCGTCC CGGAGCAGGA GGATTCCGTG CTGTTCCGGC GCGGCACAGG
 241    CCAGAGCGAT GATTCTGACA TTTGGGATGA TACAGCACTG ATAAAAGCAT ATGATAAAGC
 301    TGTGGCTTCA TTTAAGCATG CTCTAAAGAA TGGTGACATT TGTGAAACTT CGGGTAAACC
 361    AAAAACCACA CCTAAAAGAA AACCTGCTAA GAAGAATAAA AGCCAAAAGA AGAATACTGC
 421    AGCTTCCTTA CAACAGTGGA AAGTTGGGGA CAAATGTTCT GCCATTTGGT CAGAAGACGG
 481    TTGCATTTAC CCAGCTACCA TTGCTTCAAT TGATTTTAAG AGAGAAACCT GTGTTGTGGT
 541    TTACACTGGA TATGAAATA  GAGAGGAGCA AAATCTGTCC GATCTACTTT CCCCAATCTG
 601    TGAAGTAGCT AATAATATAG AACAGAATGC TCAAGAGAAT GAAAATGAAA GCCAAGTTTC
 661    AACAGATGAA AGTGAGAACT CCAGGTCTCC TGGAAATAAA TCAGATAACA TCAAGCCCAA
 721    ATCTGCTCCA TGGAACTCTT TTCTCCCTCC ACCACCCCCC ATGCCAGGGC CAAGACTGGG
 781    ACCAGGAAAG CCAGGTCTAA AATTCAATGG CCCACCACCG CCACCGCCAC CACCACCACC
 841    CCACTTACTA TCATGCTGGC TGCCTCCATT TCCTTCTGGA CCACCAATAA TTCCCCCACC
 901    ACCTCCCATA TGTCCAGATT CTCTTGATGA TGCTGATGCT TTGGGAAGTA TGTTAATTTC
 961    ATGGTACATG AGTGGCTATC ATACTGGCTA TTATATGGGT TTCAGACAAA ATCAAAAAGA
1021    AGGAAGGTGC TCACATTCCT TAAATTAAGG AGAAATGCTG GCATAGAGCA GCACTAAATG
1081    ACACCACTAA AGAAACGATC AGACAGATCT GGAATGTGAA GCGTTATAGA AGATAACTGG
1141    CCTCATTTCT TCAAAATATC AAGTGTTGGG AAAGAAAAAA GGAAGTGGAA TGGGTAACTC
1201    TTCTTGATTA AAAGTTATGT AATAACCAAA TGCAATGTGA AATATTTTAC TGGACTCTTT
1261    TGAAAAACCA TCTGTAAAAG ACTGGGGTGG GGGTGGGAGG CCAGCACGGT GGTGAGGCAG
1321    TTGAGAAAAT TTGAATGTGG ATTAGATTTT GAATGATATT GGATAATTAT TGGTAATTTT
1381    ATGGCCTGTG AGAAGGGTGT TGTAGTTTAT AAAAGACTGT CTTAATTTGC ATACTTAAGC
1441    ATTTAGGAAT GAAGTGTTAG AGTGTCTTAA AATGTTTCAA ATGGTTTAAC AAAATGTATG
1501    TGAGGCGTAT GTGGCAAAAT GTTACAGAAT CTAACTGGTG GACATGGCTG TTCATTGTAC
1561    TGTTTTTTTC TATCTTCTAT ATGTTAAAA  GTATATAATA AAAATATTTA ATTTTTTTTT
1621    A.
```

Conservative nucleotide substitutions of SMN DNA are also contemplated (e.g., a guanine to adenine change at position 625 of GenBank Accession Number NM_000344.2). In some embodiments, the genome of the rAAV lacks AAV rep and cap DNA, that is, there is no AAV rep or cap DNA between the ITRs of the genome. SMN polypeptides contemplated include, but are not limited to, the human SMN1 polypeptide set out in NCBI protein database number NP 000335.1 and its isoforms. SMN polypeptides contemplated also include, but are not limited to, the human SMN2 polypeptide and isoforms of any SMN polypeptide. Also contemplated is the SMN1-modifier polypeptide plastin-3 (PLS3) [Oprea et al., Science 320(5875): 524-527 (2008)] Sequences encoding other polypeptides may be substituted for the SMN DNA. A rAAV9 SMN vector is described in Foust et al., Nature Biotechnology 28(3): 271-274 (2010).

In one embodiment, the viral vector is an adeno-associated virus serotype 9 (AAV9) comprising a cDNA expressing SMN1 protein under the control of the cytomegalovirus (CMV) enhancer/chicken-β-actin-hybrid promoter (CB), and AAV inverted terminal repeats (ITR) from the AAV serotype 2 (AAV2) DNA. In another embodiment, the AAV is a replication defective AAV9, preferably scAAV9, with AAV2-derived ITRs. In one embodiment, the AAV vector carries an SMN transgene. In a preferred embodiment, the SMN-coding DNA is set out in GenBank Accession Number NM_000344.2. Conservative nucleotide substitutions of SMN DNA are also contemplated (e.g., a guanine to adenine change at position 625, as set forth in GenBank Accession Number NM_000344.2).

In some embodiments, the term "vector-related impurities" refers to all types of AAV particles other than bona fide recombinant AAV particles. Vector-related impurities include empty AAV capsids (also referred to as "empties", or "empty particles"), and AAV particles containing polynucleotide sequences other than the intended vector genome (also referred to as "AAV-encapsidated nucleic acid impurities" or "AAV-encapsidated DNA impurities").

In some embodiments, "recombinant virus" is meant a virus that has been genetically altered, e.g., by the addition or insertion of a heterologous nucleic acid construct into the particle. "Recombinant" may abbreviated "r", e.g., rAAV may refer to recombinant AAV. The term "AAV" as used herein is intended to encompass "recombinant AAV" or "rAAV."

In some embodiments, by "AAV virion" is meant a complete virus particle, such as a wild-type (wt) AAV virus particle (comprising a linear, single-stranded AAV nucleic acid genome associated with an AAV capsid protein coat). In this regard, single-stranded AAV nucleic acid molecules of either complementary sense, e.g., "sense" or "antisense" strands, can be packaged into any one AAV virion and both strands are equally infectious.

In some embodiments, the terms "recombinant AAV virion," "rAAV virion," "AAV vector particle," "full capsids," and "full particles" are defined herein as an infectious, replication-defective virus including an AAV protein shell, encapsidating a heterologous nucleotide sequence of interest which is flanked on both sides by AAV ITRs. A rAAV virion is produced in a suitable host cell which has had sequences specifying an AAV vector, AAV helper functions and accessory functions introduced therein. In this manner, the host cell is rendered capable of encoding AAV polypeptides that provide for packaging the AAV vector (containing a recombinant nucleotide sequence of interest) into infectious recombinant virion particles for subsequent gene delivery.

In some embodiments, the terms "empty capsid," and "empty particle," refer to an AAV virion that includes an AAV protein shell but that lacks in whole or part the polynucleotide construct comprising the heterologous nucleotide sequence of interest flanked on both sides by AAV ITRs.

The term "host cell" denotes, for example, microorganisms, yeast cells, insect cells, and mammalian cells, that can be, or have been, used as recipients of an AAV helper construct, an AAV vector plasmid, an accessory function vector, or other transfer DNA. The term includes the progeny of the original cell which has been transfected. Thus, a "host cell" as used herein generally refers to a cell which has been transfected with an exogenous DNA sequence. It is understood that the progeny of a single parental cell may not necessarily be completely identical in morphology or in genomic or total DNA complement as the original parent, due to natural, accidental, or deliberate mutation.

In another embodiment, the term "AAV helper functions" refer to AAV-derived coding sequences which can be expressed to provide AAV gene products that, in turn, function in trans for productive AAV replication. Thus, AAV helper functions include both of the major AAV open reading frames (ORFs), rep and cap. The Rep expression products have been shown to possess many functions, including, among others: recognition, binding and nicking of the AAV origin of DNA replication; DNA helicase activity; and modulation of transcription from AAV (or other heterologous) promoters. The Cap expression products supply necessary packaging functions. AAV helper functions are used herein to complement AAV functions in trans that are missing from AAV vectors.

In one embodiment, the term "AAV helper construct" refers generally to a nucleic acid molecule that includes nucleotide sequences providing AAV functions deleted from an AAV vector which is to be used to produce a transducing vector for delivery of a nucleotide sequence of interest. AAV helper constructs are commonly used to provide transient expression of AAV rep and/or cap genes to complement missing AAV functions that are necessary for AAV replication; however, helper constructs lack AAV ITRs and can neither replicate nor package themselves. AAV helper constructs can be in the form of a plasmid, phage, transposon, cosmid, virus, or virion. A number of AAV helper constructs have been described, such as the commonly used plasmids pAAV/Ad and pIM29+45 which encode both Rep and Cap expression products. See, e.g., Samulski et al. (1989) J. Virol. 63:3822-3828; and McCarty et al. (1991) J. Virol. 65:2936-2945. A number of other vectors have been described which encode Rep and/or Cap expression products. See, e.g., U.S. Pat. Nos. 5,139,941 and 6,376,237.

In another embodiment, the term "transfection" is used to refer to the uptake of foreign DNA by a cell, and a cell has been "transfected" when exogenous DNA has been introduced inside the cell membrane. A number of transfection techniques are generally known in the art. See, e.g., Graham et al. (1973) Virology, 52:456, Sambrook et al. (1989) Molecular Cloning, a laboratory manual, Cold Spring Harbor Laboratories, New York, Davis et al. (1986) Basic Methods in Molecular Biology, Elsevier, and Chu et al. (1981) Gene 13:197. Such techniques can be used to introduce one or more exogenous DNA moieties into suitable host cells.

As used herein, the term "cell line" refers to a population of cells capable of continuous or prolonged growth and division in vitro. It is further known in the art that spontaneous or induced changes can occur in karyotype during storage or transfer of such clonal populations. Therefore, cells derived from the cell line referred to may not be precisely identical to the ancestral cells or cultures, and the cell line referred to includes such variants. In some embodiments, the terms "HEK293 cells", "293 cells" or their grammatical equivalents are used interchangeably here and refer to the host/packing cell line used in the methods disclosed herein.

In some embodiments, the term "eluent" may be understood, in context, to refer to the buffer used to elute a substance. In some embodiments, the term "eluent" may be understood, in context, to refer to the eluted substance, e.g., the desired product or substance from a prior purification step, e.g., for assaying or further purification.

In some embodiments, the methods described here are performed using good manufacturing practice (GMP) and at industrial scale. GMPs are regulatory practices, e.g., those enforced by the Federal Drug Agency (FDA), for ensuring pharmaceutical quality. GMP regulations establish controls for manufacturing processes. Examples of current GMP regulations are published by FDA. In some embodiments, the methods described herein employ GMP procedures for producing AAV viral vectors at industrial scale. To date, industrial scale production of AAV viral vectors for gene therapy has been challenging because of scalability issues. Thus, in some embodiments, the methods described herein provided an advantage by producing AAV viral vectors, e.g., in adherent cells, at industrial scale and at purity levels sufficient to administer to a human. The term "industrial scale" refers to methods of producing viral vector in cells at larger than bench scale, e.g., commercial scale, e.g., where the yield is more than $5\times10^{15}$ vg, or more than $8\times10^{15}$ vg or more than $1\times10^{16}$ vg per manufacturing batch.

Imaging

As part of the cell based assay disclosed herein, image analysis may be performed using High-content imaging platform (CellInsight CX5). This platform enables quantitative measurement of intracellular protein expression on a per cell-basis (Integrated Fluorescent Intensity Per Cell). In addition, the CellInsight CX5 allows appropriate throughput for lot disposition and stability study.

In high content screening, cells are first incubated with the substance and after a period of time, structures and molecular components of the cells are analyzed. The most common analysis involves labeling proteins with fluorescent tags, and finally changes in cell phenotype are measured using automated image analysis. Through the use of fluorescent tags with different absorption and emission maxima, it is possible to measure several different cell components in parallel. Furthermore, the imaging is able to detect changes at a subcellular level (e.g., cytoplasm vs. nucleus vs. other organelles). Therefore a large number of data points can be collected per cell (see Proll G, Steinle L, Pröll F, Kumpf M, Moehrle B, Mehlmann M, Gauglitz G (August 2007). "Potential of label-free detection in high-content-screening applications". J Chromatogr A. 1161 (1-2): 2-8). High-content screens automate the extraction of multicolor fluorescence information derived from specific fluorescence-based reagents incorporated into cells (Giuliano and Taylor (1995), Curr. Op. Cell Biol. 7:4; Giuliano et al. (1995) Ann. Rev. Biophys. Biomol. Struct. 24:405). Cells are analyzed using an optical system that can measure spatial, as well as temporal dynamics. (Farkas et al. (1993) Ann. Rev. Physiol. 55:785; Giuliano et al. (1990) In Optical Microscopy for Biology. B. Herman and K. Jacobson (eds.), pp. 543-557. Wiley-Liss, New York; Hahn et al (1992)Nature 359:736; Waggoner et al. (1996) Hum. Pathol. 27:494). The concept is to treat each cell as a "well" that has spatial and temporal information on the activities of the labeled constituents.

In one embodiment, a cell screening system is provided comprising a high magnification fluorescence optical system having a microscope objective, an XY stage adapted for holding a plate with an array of locations for holding cells and having a means for moving the plate to align the locations with the microscope objective and a means for moving the plate in the direction to effect focusing; a digital camera; a light source having optical means for directing excitation light to cells in the array of locations and a means for directing fluorescent light emitted from the cells to the digital camera; and a computer means for receiving and processing digital data from the digital camera wherein the computer means includes: a digital frame grabber for receiving the images from the camera, a display for user interaction and display of assay results, digital storage media for data storage and archiving, and means for control, acquisition, processing and display of results. Methods for using such a system are disclosed in U.S. Pat. No. 6,756,207, which is incorporated herein in its entirety.

After a plate scan is complete, images and data can be reviewed with the system's image review, data review, and summary review facilities. All images, data, and settings from a scan may be archived in the system's database for later review or for interfacing with a network information management system. Data can also be exported to other third-party statistical packages to tabulate results and generate other reports. As a final phase of a complete scan, reports can be generated on one or more statistics of the measured features. Users can generate a graphical report of data summarized on a well-by-well basis for the scanned region of the plate using an interactive report generation procedure. This report may include a summary of the statistics by well in tabular and graphical format and identification information on the sample.

Methods of imaging plates will be known to the person of ordinary skill in the art. An exemplary imaging platform comprises a CellInsight High Content Screening (HCS) Platform, using HSC studio software and a standardized protocol. However, equivalent imaging and/or software platforms may also be used to practice the methods of the instant disclosure.

Exemplary CellInsight settings used for data acquisition comprise the following settings. Assay settings: Imaging Mode: Fluorescence 1 (F1) % Fluorescence 2 (F2); Acquire Brightfield Image; F1 image Cell Type: Mouse ES Cell; Description: mNPC Fluorophore AO VC-535-403; Fluorescent Exp: 700.0 msec; F2 image Cell Type: Mouse ES Cell; Description: mNPC Fluorophore P1 VC-660-503; Fluorescent Exp: 5000.0 msec; Set Dilution Factor for Assay: 2.000; Show Percent F1, F2: F1/(F1+F2)*100%. Cell Type settings: Mouse ES cells; Cell Diameter: 9.0 micron minimum, 30.0 micron maximum; Roundness: 0.10; Contrast Enhancement: 0.40; Decluster Edge Factor: 0.5; Decluster Th Factor: 1.0; Background Adjustment: 1.0. Trypan Blue Viability Parameters: Dead Cell Diameter: 8.0 micron minimum, 30 micron maximum; Sensitivity: 1.0; Uniformity: 150; Very Dim Dead Cells Contrast Enhancement: 0.60. Protocol Settings: Objective: 20×; field size: 455.4 by 455.4 microns; Camera: X1; Camera Acquisition Mode: 1104×1104 (2×2 binning); Use Software Autofocus; Software Focus Channel: 1; Autofocus interval: 1. Channel 1 Settings: channel included in the Composite, Camera Gain: 2; Light Intensity (in %): 100; Imaging Mode: Widefield; Dye: 386-23_BGR-FRN_BGRFRN; Depth Of Field: 6.563; Fixed Exposure Time; Target %: 25; Exposure Time (secs): 0.08. Channel 2 Settings: channel included in the Composite, Camera Gain: 2; Light Intensity (in %): 100; Imaging Mode: Widefield; Dye: 485-20_BGRFRN_BGRFRN; Depth Of Field: 6.563; Fixed Exposure Time; Target %: 25; Exposure Time (secs): 0.08.

Methods of Producing AAV Vectors

Provided herein are methods of producing AAV vectors, and pharmaceutical compositions comprising the same, and assaying the potency of the AAV vectors using the cell based potency assay described herein. In some embodiments, the AAV vector comprises a sequence encoding SMN1. In some embodiments, the relative potency of the viral vector is at least 40%, at least 50%, at least 60%, at least 70%, at least 80%, at least 90%, at least 91%, at least 92%, at least 93%, at least 94%, at least 95%, at least 96%, at least 97%, at least 98%, at least 99%, at least 99.9%, at least 100%, at least 110%, at least 120%, at least 130% or at least 140% relative to a reference standard.

In some embodiments, the relative potency of the viral vector is at least 90% compared to a reference standard.

The relative potency cell-based assay as described herein, can be used to determine the relative potency of AAV-SMN1 vector intended for lot disposition, and for stability testing of an AAV-SMN1 vector Drug Substance and Drug Product.

Upstream Process

In some embodiments, an upstream process is used to produce an intermediate derived from a working cell bank, wherein the upstream process comprises the steps of (a) culturing cells, e.g., adherent cells, (b) transfecting the cultured cells, e.g., adherent cells, with three plasmids, (c) harvesting the expanded viral particles from the cells after a culture period, e.g., by total cell lysis, (d) purifying the viral particles via filtration to remove any intact cells or cellular debris, (e) subjecting the eluent from step (d) to tangential flow filtration, and (f) optionally freezing the resultant intermediate preparation of purified viral particles. In some embodiments, the intermediate preparation may be frozen. In other embodiments, the intermediate preparation need not be frozen prior to downstream processing. In some embodiments, the AAV prepared with the upstream process disclosed herein is an AAV comprising a polynucleotide encoding SMN1, as described herein. In some embodiments, the upstream process is conducted under GMP and at industrial scale.

1. Cell Line Transfection and Culturing

In one aspect, disclosed herein are rAAV genomes. The rAAV genomes comprise one or more AAV ITRs flanking a polynucleotide encoding a polypeptide (including, but not limited to, an SMN polypeptide) or encoding siRNA, shRNA, antisense, and/or miRNA directed at mutated proteins or control sequences of their genes. The polynucleotide is operatively linked to transcriptional control DNAs, specifically promoter DNA, enhancer DNA and polyadenylation signal sequence DNA that are functional in target cells to form a gene cassette. The gene cassette may also include intron sequences to facilitate processing of an RNA transcript when expressed in mammalian cells.

In some embodiments, the rAAV genomes disclosed herein lack AAV rep and cap DNA. AAV DNA in the rAAV genomes (e.g., ITRs) may be from any AAV serotype for which a recombinant virus can be derived including, but not limited to, AAV serotypes AAV-1, AAV-2, AAV-3, AAV-4, AAV-5, AAV-6, AAV-7, AAV-8, AAV-9, AAV-10 and AAV-11. The nucleotide sequences of the genomes of the AAV serotypes are known in the art. For example, the complete genome of AAV-1 is provided in GenBank Accession No. NC_002077; the complete genome of AAV-2 is provided in GenBank Accession No. NC_001401 and Srivastava et al., Virol., 45: 555-564 {1983): the complete genome of AAV-3 is provided in GenBank Accession No. NC_1829; the complete genome of AAV-4 is provided in GenBank Accession No. NC_001829; the AAV-5 genome is provided in GenBank Accession No. AF085716; the complete genome of AAV-6 is provided in GenBank Accession No. NC_00 1862; at least portions of AAV-7 and AAV-8 genomes are provided in GenBank Accession Nos. AX753246 and AX753249, respectively; the AAV-9 genome is provided in Gao et al., J. Virol., 78: 6381-6388 (2004); the AAV-10 genome is provided in Mol. Ther., 13(1): 67-76 (2006); and the AAV-11 genome is provided in Virology, 330(2): 375-383 (2004).

As used herein, the "pSMN" vector plasmid comprises a polynucleotide encoding an SMN protein, i.e, a SMN cDNA expression cassette, wherein the cassette is flanked by adeno-associated virus inverted terminal repeat (ITR) sequences, e.g., "left" and "right" of the polynucleotide encoding the SMN gene. In some embodiments, the polynucleotide encoding SMN is a human SMN sequence, e.g., a naturally occurring human SMN sequence or isoforms, variants, or mutants thereof. In some embodiments, the ITR sequences are native, variant, or modified AAV ITR sequences. In some embodiments, at least one ITR sequence is a native, variant, or modified AAV2 ITR sequence. In some embodiments, the two ITR sequences are both native, variant or modified AAV2 ITR sequences. In some embodiments, the "left" ITR is a modified AAV2 ITR sequence that allows for the production of self-complementary genomes, and the "right" ITR is a native AAV2 ITR sequence. In some embodiments, the "right" ITR is a modified AAV2 ITR sequence that allows for the production of self-complementary genomes, and the "left" ITR is a native AAV2 ITR sequence. In some embodiments, the pSMN plasmid further comprises a CMV enhancer/chicken beta-actin ("CB") promoter. In some embodiments, the pSMN plasmid further comprises a Simian Virus 40 (SV40) intron. In some embodiments, the pSMN plasmid further comprises a bovine growth hormone (BGH) polyadenylation (polyA) termination signal. Exemplary sequences that may be used for one or more of the components discussed above are shown in Table 1 below. In some embodiments, all of the sequences shown in Table 1 below are used. In some embodiments, "AVXS-101," is a non-limiting example of a vector construct using all the sequences in Table 1 and falling within the scope of the term pSMN.

In some embodiments, a pSMN vector may comprise a SMN cDNA expression cassette, a modified AAV2 ITR, a chicken beta-actin (CB) promoter, a cytomegalovirus (CMV) immediate/early enhancer, a modified SV40 late 16s intron, a bovine growth hormone (BGH) polyadenylation signal, and an unmodified AAV2 ITR. The modified and unmodified ITRs may come in either orientation (i.e., 5' or 3') relative to the SMN cDNA expression cassette.

In some embodiments, e.g., during the manufacturing processes described herein the vector construct sequence is encapsidated, e.g., into AAV9 virions. In these embodiments, encapsidation is in a non-replicating, recombinant AAV9 capsid capable of delivering a stable, function transgene, e.g. a fully functional human SMN transgene. In some embodiments, the capsid is comprised of 60 viral proteins (VP1, VP2, VP3), e.g., in a ratio of 1:1:10 produced by alternate splicing such that VP2 and VP3 are two truncated forms of VP1, all with common C-terminal sequences. In some embodiments, the product of the manufacturing process, e.g., a drug product, may comprise a non-replicating, recombinant AAV9 capsid to deliver a stable, fully functional human SMN transgene. In some embodiments, the capsid is comprised of 60 viral proteins (VP1, VP2, VP3) in a ratio of 1:1:10 produced by alternate splicing such that VP2 and VP3 are two truncated forms of VP1, all with common C-terminal sequences.

The DNA sequence of an exemplary vector construct, e.g., AVXS-101 (AAV9-SMN1) is described in Table 1.

TABLE 1

AVXS-101 Vector Construct DNA Sequence Summary Component (all nucleotide start and stop positions are in relation to SEQ ID NO: 1)

| | Start Position | Stop Position | Size (nt) | Description | Non-limiting description of potential benefits |
|---|---|---|---|---|---|
| "Left" Mutated AAV2 ITR | 1 | 106 | 106 | Modification to the "left" ITR by deleting the terminal resolution site to allow hairpin formation of genome | Without being limited by theory, this mutated ITR may allow for a second-generation self-complementary vector to maximize vector potency, allowing lower systemic doses |

TABLE 1-continued

AVXS-101 Vector Construct DNA Sequence Summary Component (all nucleotide start and stop positions are in relation to SEQ ID NO: 1)

| | Start Position | Stop Position | Size (nt) | Description | Non-limiting description of potential benefits |
|---|---|---|---|---|---|
| CMV Enhancer/CB Promoter | 153 | 432 | 280 | Portion of the CMV immediate/early enhancer | Without being limited by theory, this may allow for constitutive high-level SMN expression |
| | 439 | 704 | 266 | CB core promoter | |
| SV40 Intron | 774 | 870 | 97 | Intron from the SV40 (to enhance accumulation of steady level of mRNA for translation) | Without being limited by theory, this may allow for increased gene expression |
| Human SMN cDNA | 1003 | 1887 | 885 | Modified from Genbank Accession #NM_017411 | Without being limited by theory, this may allow the for expression of a full-length SMN protein |
| BGH Poly A Termination Signal | 1973 | 2204 | 232 | BGH Poly A signal | Without being limited by theory, this may provide a Poly A of the SMN mRNA (transcription termination signal) for high-level, efficient gene expression |
| "Right" AAV2 ITR | 2217 | 2359 | 143 | Unmodified AAV2 ITR | Without being limited by theory, this AAV2 ITR in cis may provide for both viral DNA replication and packaging of the AAV vector genome |

In another aspect, the DNA sequence of the AVXS-101 vector construct is provided in SEQ ID NO: 1:

```
                                                       (SEQ ID NO: 1)
ctgcgcgctc gctcgctcac tgaggccgcc cgggcaaagc ccgggcgtcg     50
ggcgaccttt ggtcgcccgg cctcagtgag cgagcgagcg cgcagagagg    100
gagtggaatt cacgcgtgga tctgaattca attcacgcgt ggtacctctg    150
gtcgttacat aacttacggt aaatggcccg cctggctgac cgcccaacga    200
cccccgccca ttgacgtcaa taatgacgta tgttcccata gtaacgccaa    250
tagggacttt ccattgacgt caatgggtgg agtatttacg gtaaactgcc    300
cacttggcag tacatcaagt gtatcatatg ccaagtacgc cccctattga    350
cgtcaatgac ggtaaatggc ccgcctggca ttatgcccag tacatgacct    400
tatgggactt tcctacttgg cagtacatct actcgaggcc acgttctgct    450
tcactctccc catctccccc ccctccccac ccccaatttt gtatttattt    500
attttttaat tattttgtgc agcgatgggg gcggggggg gggggggggcg    550 cgcgccaggc ggggcggggc ggggcgaggg gcgggggcggg gcgaggcgga    600 gaggtgcggc ggcagccaat cagagcggcg cgctccgaaa gtttcctttt    650
atggcgaggc ggcggcggcg gcggccctat aaaaagcgaa gcgcgcggcg    700
ggcgggagcg ggatcagcca ccgcggtggc ggcctagagt cgacgaggaa    750
```

```
ctgaaaaacc agaaagttaa ctggtaagtt tagtcttttt gtcttttatt    800
tcaggtcccg gatccggtgg tggtgcaaat caaagaactg ctcctcagtg    850
gatgttgcct ttacttctag gcctgtacgg aagtgttact tctgctctaa    900
aagctgcgga attgtacccg cggccgatcc accggtccgg aattcccggg    950
atatcgtcga cccacgcgtc cgggccccac gctgcgcacc cgcgggtttg   1000
ctatggcgat gagcagcggc ggcagtggtg gcggcgtccc ggagcaggag   1050
gattccgtgc tgttccggcg cggcacaggc cagagcgatg attctgacat   1100
ttgggatgat acagcactga taaaagcata tgataaagct gtggcttcat   1150
ttaagcatgc tctaaagaat ggtgacattt gtgaacttc gggtaaacca   1200
aaaccacac ctaaaagaaa acctgctaag aagaataaaa gccaaaagaa   1250
gaatactgca gcttccttac aacagtggaa agttgggac aaatgttctg   1300
ccatttggtc agaagacggt tgcatttacc cagctaccat tgcttcaatt   1350
gattttaaga gagaaacctg tgttgtggtt tacactggat atggaaatag   1400
agaggagcaa aatctgtccg atctactttc cccaatctgt gaagtagcta   1450
ataatataga acagaatgct caagagaatg aaaatgaaag ccaagtttca   1500
acagatgaaa gtgagaactc caggtctcct ggaaataaat cagataacat   1550
caagcccaaa tctgctccat ggaactcttt tctccctcca ccaccccca   1600
tgccagggcc aagactggga ccaggaaagc caggtctaaa attcaatggc   1650
ccaccaccgc caccgccacc accaccaccc cacttactat catgctggct   1700
gcctccattt ccttctggac caccaataat tccccacca cctcccatat   1750
gtccagattc tcttgatgat gctgatgctt tgggaagtat gttaatttca   1800
tggtacatga gtggctatca tactggctat tatatgggtt ttagacaaaa   1850
tcaaaaagaa ggaaggtgct cacattcctt aaattaagga gaaatgctgg   1900
catagagcag cactaaatga caccactaaa gaaacgatca gacagatcta   1950
gaaagcttat cgataccgtc gactagagct cgctgatcag cctcgactgt   2000
gccttctagt tgccagccat ctgttgtttg ccctccccc gtgccttcct   2050
tgaccctgga aggtgccact cccactgtcc tttcctaata aaatgaggaa   2100
attgcatcgc attgtctgag taggtgtcat tctattctgg ggggtggggt   2150
ggggcaggac agcaagggg aggattggga agacaatagc aggcatgctg   2200
gggagagatc gatctgagga accctagtg atggagttgg ccactccctc   2250
tctgcgcgct cgctcgctca ctgaggccgg gcgaccaaag gtcgcccgac   2300
gcccgggctt tgcccgggcg gcctcagtga gcgagcgagc gcgcagagag   2350
ggagtggcc.                                                2359
```

In some embodiments, the amino acid sequence of the SMN protein encoded by the pSMN plasmid comprises:

(SEQ ID NO: 3)
MAMSSGGSGGGVPEQEDSVLFRRGTGQSDDSDIWDDTALIKAYDKAVASF

KHALKNGDICETSGKPKTTPKRKPAKKNKSQKKNTAASLQQWKVGDKCSA

IWSEDGCIYPATIASIDFKRETCVVVYTGYGNREEQNLSDLLSPICEVAN

NIEQNAQENENESQVSTDESENSRSPGNKSDNIKPKSAPWNSFLPPPPPM

PGPRLGPGKPGLKFNGPPPPPPPPPPHLLSCWLPPFPSGPPIIPPPPPIC

PDSLDDADALGSMLISWYMSGYHTGYYMGFRQNQKEGRCSHSLN.

In some embodiments, a modified AAV2 ITR comprises a sequence of nucleotides 1-106 of SEQ ID NO: 1. In some embodiments, a cytomegalovirus (CMV) enhancer/chicken-β-actin-hybrid promoter (CB) comprises a sequence of nucleotides 153-432 of SEQ ID NO: 1. In some embodiments, a sequence of a cDNA expressing SMN1 protein comprises a sequence of nucleotides 1003-1887 of SEQ ID NO: 1. In some embodiments, a sequence of an SV40 intron comprises a sequence of nucleotides 774-870 of SEQ ID NO: 1. In some embodiments, a sequence of bovine growth hormone (BGH) polyadenylation signal comprises a sequence of nucleotides 1973-2204 of SEQ ID NO: 1. In some embodiments, an unmodified AAV2 ITR comprises a sequence of nucleotides 2217-2359 of SEQ ID NO: 1.

In some embodiments, AAV capsid proteins VP1, VP2, VP3 are derived from the same transcript. These have alternative start sites but share a carboxy terminus. Below, VP1 specific amino acid sequences are shown in black and are bolded. Amino acid sequences common to VP1 and VP2 are underlined and in italics. Amino acids common to all three capsid proteins are bolded and in italics.

Hennonat et al., Proc. Natl. Acad. Sci. USA, 81:6466 (1984); Tratschin et al., Mol. Cell. Biol. 5:3251 (1985); McLaughlin et al., J. Virol., 62:1963 (1988); and Lebkowski et al., 1988 Mol. Cell. Biol., 7:349 (1988). Samulski et al. (1989, J. Virol., 63:3822-3828); U.S. Pat. No. 5,173,414; WO 95/13365 and corresponding U.S. Pat. No. 5,658,776; WO 95/13392; WO 96/17947; PCT/US98/18600; WO 97/09441 (PCT/US96/14423); WO 97/08298 (PCT/US96/13872); WO 97/21825 (PCT/US96/20777); WO 97/06243 (PCT/FR96/01064); WO 99/11764; Perrin et al. (1995) Vaccine 13:1244-1250; Paul et al. (1993) Human Gene Therapy 4:609-615; Clark et al. (1996) Gene Therapy 3:1124-1132; U.S. Pat. Nos. 5,786,211; 5,871,982; and 6,258,595. The foregoing documents are hereby incorporated by reference

```
                                                           (SEQ ID NO: 4)
  1  MAADGYLPDW  LEDNLSEGIR  EWWALKPGAP  QPKANQQHQD  NARGLVLPGY  KYLGPGNGLD

61  KGEPVNAADA  AALEHDKAYD  QQLKAGDNPY  LKYNHADAEF  QERLKEDTSF  GGNLGRAVFQ

121  AKKRLLEPLG  LVEEAAKTAP  GKKRPVEQSP  QEPDSSAGIG  KSGAQPAKKR  LNFGQTGDTE

181  SVPDPQPIGE  PPAAPSGVGS  LTMASGGGAP  VADNNEGADG  VGSSSGNWHC  DSQWLGDRVI

241  TTSTRTWALP  TYNNHLYKQI  SNSTSGGSSN  DNAYFGYSTP  WGYFDFNRFH  CHFSPRDWQR

301  LINNNWGFRP  KRLNFKLFNI  QVKEVTDNNG  VKTIANNLTS  TVQVFTDSDY  QLPYVLGSAH

361  EGCLPPFPAD  VFMIPQYGYL  TLNDGSQAVG  RSSFYCLEYF  PSQMLRTGNN  FQFSYEFENV

421  PFHSSYAHSQ  SLDRLMNPLI  DQYLYYLSKT  INGSGQNQQT  LKFSVAGPSN  MAVQGRNYIP

481  GPSYRQQRVS  TTVTQNNNSE  FAWPGASSWA  LNGRNSLMNP  GPAMASHKEG  EDRFFPLSGS

541  LIFGKQGTGR  DNVDADKVMI  TNEEEIKTTN  PVATESYGQV  ATNHQSAQAQ  AQTGWVQNQG

601  ILPGMVWQDR  DVYLQGPIWA  KIPHTDGNFH  PSPLMGGFGM  KHPPPQILIK  NTPVPADPPT

661  AFNKDKLNSF  ITQYSTGQVS  VEIEWELQKE  NSKRWNPEIQ  YTSNYYKSNN  VEFAVNTEGV

721  YSEPRPIGTR  YLTRNL.
```

In one embodiment, the AAV capsid proteins are derived from a transcript encoding the amino acid sequence set forth in SEQ ID NO: 4.

In another aspect, disclosed herein are DNA plasmids comprising rAAV genomes. The DNA plasmids are transferred to cells permissible for infection with a helper virus of AAV (e.g., adenovirus, E1-deleted adenovirus or herpesvirus) for assembly of the rAAV genome into infectious viral particles with AAV9 capsid proteins. Techniques to produce rAAV particles, in which an AAV genome to be packaged, rep and cap genes, and helper virus functions are provided to a cell are standard in the art. In some embodiments, production of rAAV involves the following components present within a single cell (denoted herein as a packaging cell): a rAAV genome, AAV rep and cap genes separate from (i.e., not in) the rAAV genome, and helper virus functions. Production of pseudotyped rAAV is disclosed in, for example, WO 01/83692 which is incorporated by reference herein in its entirety. In various embodiments, AAV capsid proteins may be modified to enhance delivery of the recombinant vector. Modifications to capsid proteins are generally known in the art. See, for example, US 2005/0053922 and US 2009/0202490, the disclosures of which are incorporated by reference herein in their entirety.

General principles of rAAV production are reviewed in, for example, Carter, 1992, Current Opinions in Biotechnology, 1533-539; and Muzyczka, 1992, CUM Topics in Microbial. and Immunol., 158:97-129). Various approaches are described in Ratschin et al., Mol. Cell. Biol. 4:2072 (1984);

in their entirety herein, with particular emphasis on those sections of the documents relating to rAAV production.

An exemplary method of generating a packaging cell is to create a cell line that stably expresses all the necessary components for AAV particle production. For example, a plasmid (or multiple plasmids) comprising a rAAV genome lacking AAV rep and cap genes, AAV rep and cap genes separate from the rAAV genome, and a selectable marker, such as a neomycin resistance gene, are integrated into the genome of a cell. AAV genomes have been introduced into bacterial plasmids by procedures such as GC tailing (Samulski et al., 1982, Proc. Natl. Acad. S6. USA, 79:2077-2081), addition of synthetic linkers containing restriction endonuclease cleavage sites (Laughlin et al., 1983, Gene, 23:65-73) or by direct, blunt-end ligation (Senapathy & Carter, 1984, J. Biol. Chem., 259:4661-4666). The packaging cell line is then infected with a helper virus such as adenovirus. The advantages of this method are that the cells are selectable and are suitable for large-scale production of rAAV. Other examples of suitable methods employ adenovirus or baculovirus rather than plasmids to introduce rAAV genomes and/or rep and cap genes into packaging cells.

The disclosure herein thus provides, in various embodiments, packaging cells that produce infectious rAAV. Packaging cells may be non-adherent cells cultured in suspension or adherent cells. In one embodiment any suitable packaging cell line may be used, such as HeLa cells, HEK 293 cells and PerC.6 cells (a cognate 293 line). In one embodiment, the cell line is HEK 293 cells.

To increase the viral vector production yield, adherent cells may be cultured and selected for improved adherence to culture flasks. In some embodiments, improves transfection efficiency and cell count during subsequent bioreactor seeding steps. During subculture, cells may be detached from the cell culture surface by methods known in the art. For example, cells may be lifted by scraping or by incubating in a solution comprising proteases. In an exemplary embodiment, HEK293 cells may be washed with PBS and dissociated with trypsin for ~2 minutes at room temperature. Dissociation may be stopped by adding growth media containing serum, and cell clumps may be dissociated by repeated pipetting of the suspension. Cell suspension may then be pelleted, and the isolated pellet may be resuspended in a suitable complete growth media. Cells may then be seeded in new cell culture chambers, and allowed to adhere. Cells that do not adhere to the surface after a period of time may be removed by gentle aspiration with cell culture media, before the cell culture media was completely replaced with growth media. In some embodiments, the period of time that cells are allowed to adhere may be about 2 hours, about 3 hours, about 4 hours, about 5 hours, about 6 hours or about 7 hours. When the cells have been expanded, the process may be repeated to increase the fraction of cells that adhere strongly to the culture flasks. In some embodiments, the process is repeated at least 2 times, at least 3 times, at least 4 times, at least 5 times, or any suitable number of times. In an exemplary embodiment, HEK293 cells are seeded in 75 cm$^2$ flask, allowed to adhere for 4 hours in the 37° C. incubator before weakly adherent cells are removed by aspirating and replace cell culture media. In an exemplary embodiment, the process of selecting for strongly adherent cells is repeated for three cell culture passages.

In other embodiments, rAAV9 (i.e., infectious encapsidated rAAV9 particles) comprises a rAAV genome disclosed herein. In one aspect, the rAAV genome is a self-complementary genome.

Pre-transfection, cells are expanded in suitable culture media, in flasks or a suitable bioreactor, or both. In some embodiments, cells may be expanded in bioreactors that provide continuous circulation of cell culture media. In one embodiment, cells are expanded in 200 m$^2$, 333 m$^2$, or 500 m$^2$ iCELLis bioreactors. One culture media is DMEM with 5-10% FBS, 4.5 g/L glucose, 4 mM L-glutamine. In some embodiments, adherent cells are added to media in a recirculation media bag and circulated through the bioreactor. In some embodiments, cell culture media or any other media is continuously recirculated through the bioreactor using a peristaltic pump. Cells may be seeded at a suitable density in the flasks or bioreactors for culturing and transfection. The seeding density may depend on the cell type and the amount of time till transfection. In some embodiments, cells are seeded at about 8000-16000 cells/cm$^2$. In an embodiment, HEK293 cells are seeded at 8000-12,000 cell/cm$^2$.

Suitable methods for the transduction and reintroduction of transduced cells into a subject are known in the art. In one embodiment, cells can be transduced in vitro by combining rAAV with the cells, e.g., in appropriate media, and screening for those cells harboring the DNA of interest using conventional techniques such as Southern blots and/or PCR, or by using selectable markers.

In some embodiments, a packaging cell line is transfected with three plasmids: a plasmid encoding or comprising the vector sequence to be packaged within the AAV vector (e.g., pSMN, pMECP2 transgene, or pSOD1sh), pHELP and pAAV2/9. Transfection can be performed using any of the techniques known in the art, including but not limited to electroporation, lipofection, e.g. with a lipofectamine, cationic polymers and cationic lipids. Any suitable transfection media may be used. In one embodiment of the transfection process, adherent human embryonic kidney (HEK293) cells are transfected with a triple DNA plasmid polyethylenimine (PEI) co-precipitation. In one embodiment, a scAAV9.CB.SMN vector (a self-complementary AAV9 vector comprising a CB promoter and a polynucleotide encoding SMN) is produced using triple DNA plasmid transfection into adherent HEK293 cells using a PEI co-precipitation in a large-scale adherent cell bioreactor. In one embodiment, the DMEM growth medium used for cell expansion is replaced with a modified DMEM transfection media. This media is formulated without calcium and L-glutamine. In one embodiment, the transfection media is DMEM with no FBS, no calcium, no L-glutamine and 4.5 g/L glucose.

In some embodiments, transfection media without serum (e.g., without FBS) improves transfection efficacy. In an embodiment, the transfection media is OptiMEM (Invitrogen/Thermo Fisher). In one embodiment, the three plasmids (pSMN, pHELP and pAAV2/9) are mixed together with PEI in transfection media and allowed to react. In some embodiments, the three plasmids are mixed together in about 1:1:1 molar ratio. In some embodiments, the plasmids and PEI are mixed in a ratio of 1:1 by weight of DNA:PEI. In some embodiments, the plasmids and PEI are mixed in a ratio of less than 1:1 by weight of DNA:PEI. In an embodiment, pSMN, pHELP and pAAV2/9 are mixed in 1:1:1 molar ratio in OptiMEM media. In such an embodiment, PEI is added such that DNA:PEI is 1:1 by weight. In some embodiments, the reaction is allowed to occur for 0-60 minutes, or 10-45 minutes, or 20-30 minutes. In an embodiment, the reaction is allowed to occur for 15-30 minutes.

In an embodiment, the present disclosure provides a method for manufacturing a AAV based viral vector comprising the steps of (i) culturing adherent HEK293 cells in an industrial scale bioreactor, (2) transfecting the adherent cells with plasmids for less than 60 minutes to enable production of the AAV vector, and optionally applying further processing, purification, formulation and filling steps to produce a pharmaceutical product. In one embodiment of this process, the scAAV9.CB.SMN vector is produced using triple DNA plasmid transfection using a polyethylenimine ("PEI") co-precipitation. In an embodiment, the 3 plasmids utilized for this transfection are pSMN, pAAV2/9, and pHELP.

Transfection may be performed by contacting the packaging cell line with the DNA-PEI coprecipitate. In some embodiments, the DNA-PEI coprecipitate in transfection media is filled into a media recirculation bag. In some embodiments, the DNA-PEI coprecipitate in transfection media is circulated into the bioreactor and completely displaces the growth media. In some embodiments, the DNA-PEI coprecipitate in transfection media is allowed to contact the adherent cells in the bioreactor. In some embodiments, DNA-PEI coprecipitate in transfection media is allowed to contact the adherent cells in the bioreactor for up to two hours. In some embodiments, the transfection occurs for one to two hours. In some embodiments, the transfection occurs for less than one hour, for example, 10 minutes, 20 minutes, 30 minutes, 40 minutes or 50 minutes. In some embodiments, the transfection occurs for one to two hours. In some embodiments, the transfection is stopped by recirculating complete growth media through the bioreactor and completely displacing the transfection media.

2. Harvesting the Expanded Viral Particles

After a suitable cell expansion period post-transfection, in some embodiments the cells are lysed and the viral particles harvested. In some embodiments, the cells are dissociated from the reactor before the cell lysis process is initiated. In some embodiments, the cells are lysed in situ. Optionally, the viral particles are harvested without lysing. In some embodiments, an endonuclease is added, e.g., circulated into the bioreactor to a final target concentration. The endonuclease may be one that degrades both DNA and RNA. In one embodiment, the endonuclease is a genetically engineered endonuclease from *Serratia marcescens* (Eaves, G. N. et al. J. Bact. 1963, 85, 273-278; Nestle, M. et al. J. Biol. Chem. 1969, 244, 5219-5225) that is sold under the name Benzonase® (EMD Millipore). The enzyme is produced and purified from *E. coli* strain W3110, a mutant of strain K12, containing the pNUC1 production plasmid (U.S. Pat. No. 5,173,418, which is hereby incorporated by reference in its entirety). Structurally, the protein is a dimer of identical 245 amino acid, about 30 kDa subunits with two important disulfide bonds. Benzonase® degrades all forms of DNA and RNA (single stranded, double stranded, linear and circular) and is effective over a wide range of operating conditions, digesting nucleic acids to 5'-monophosphate terminated oligonucleotides 2-5 bases in length. Benzonase® is produced under current good manufacturing practices (cGMP) and, thus, can be used in industrial scale processes for the purification of proteins and/or viral particles. Other endonucleases that are produced under cGMP conditions can likewise be used in the purification methods disclosed in this application. In one embodiment, benzonase is added to the bioreactor to a final concentration of between 50-200 U/ml, e.g., 75-150 U/ml, e.g., about 100 U/mL. In some embodiments the addition of Benzonase significantly reduces host cell DNA while allowing for high vg production in a bioreactor.

In some embodiments, the endonuclease is allowed to mix before the lysis buffer is added to the reactor. In some embodiments, the cell lysis solution is allowed to mix with the adherent cells for up to 1 hour, up to 2 hours, up to 3 hours, up to 4 hours or up to 5 hours. In some embodiments, the lysis buffer may comprise magnesium chloride and/or Tween-20 in a suitable buffer. In an exemplary embodiment, the lysis buffer is 500 mM HEPES, 10% Tween 20, 20 mM $MgCl_2$, pH 8.0. A Salt Sucrose Solution (SSS) which quenches the Benzonase reaction may be added to stop the lysis reaction. In some embodiments, the SSS is added to a harvest bag comprising rinse buffer and mixed for 15 minutes. In some embodiments, the bioreactor is rinsed with a Bioreactor Rinse Buffer, and the rinse is then collected in the harvest collection bag, along with the quenched cell lysis solution and the lysed cell contents, all of which together comprises the bulk harvest. In some embodiments, the Bioreactor Rinse Buffer may comprise Tris, MgCl2, NaCl, Tween-20 and sucrose. In an exemplary embodiment, the Bioreactor Rinse Buffer comprises 20 mM Tris, 1 mM $MgCl_2$, 500 mM NaCl, 1% Tween-20 w/v and 1% sucrose w/v at pH 8.1.

3. Purifying the Viral Particles

After harvest, the bulk harvest viral particles may be concentrated and purified, typically via filtration. In one embodiment, the viral particles are filtered by depth filtration followed by filtration through a filter that removes large molecule contaminants and cell debris, for example a 0.45 µm filter, but that permits vector genomes to pass therethrough. Any suitable depth filter may be used.

As understood in the art, depth filtration refers to the use of a porous filter medium to clarify solutions containing significant quantities of large particles (e.g., intact cells or cellular debris) in comparison to membrane filtration which would rapidly become clogged under such conditions. A variety of depth filtration media of varying pore sizes are commercially available from a variety of manufacturers such as Millipore, Pall, General Electric, and Sartorious.

The target flow rate for depth filtration may be reduced to keep the filter inlet pressure within specification. Once all bulk harvest has been filtered, the depth filter may, in certain embodiments, be chased with the diafiltration buffer used for a subsequent first tangential flow filtration step ("TFF1"). The depth filter pool is mixed. The depth filter pool may then be filtered through a 0.45 µm filter to further clarify the bulk harvest material. The 0.45 µm filter is then chased with TFF1 buffer.

4. Tangential Flow Filtration

In various embodiments, tangential flow filtration is used to concentrate the bulk harvest, and remove salts and proteins, e.g., using Tangential Flow Filtration. Tangential Flow Filtration (TFF) (also referred to as Cross Flow Filtration CFF) is well known to those of skill in the art and equipment and protocols for its implementation in a wide range of situations are commercially available from a variety of manufacturers including but not limited to the Pall Corporation, Port Washington, N.Y. and Spectrum Labs, Rancho Dominguez, Calif. Generally, TFF may involve the recirculation of the retentate across the surface of the membrane. This gentle cross flow feed can, in certain embodiments, minimize membrane fouling, maintain a high filtration rate, and provide high product recovery. In one embodiment, the TFF step may be implemented with a flat sheet system, as exemplified herein. Flat sheet systems may be used in large scale production where such systems are provided with a means (e.g., an open flow channel) to prevent excessive shear forces on the viral particles. Alternatively, the TFF step may be implemented with a hollow fiber system, as exemplified herein. In one embodiment, the Molecular Weight Cut Off (MWCO) of the TFF system is between 200-400 kDa, e.g., about 300 kDa.

In one embodiment, the TFF1 step is performed using a 300 kDa MW cut-off regenerated cellulose membrane cassette. The cassette is flushed and sanitized with NaOH solution and equilibrated with TFF1 buffer. In one embodiment, the TFF1 buffer comprises 20 mM Tris, 1 mM MgCl2, 500 mM NaCl, 1% Sucrose, pH 8.1.

In some embodiments, the concentration phase of the TFF1 step is selected to reduce the volume of the clarified harvest approximately 10×. Once the target retentate volume is reached, diafiltration operations may be started. The retentate can, in some embodiments, be diafiltered with about 6 diavolumes of TFF1 buffer. In some embodiments, the retentate is diafiltered with about 5-20, or 10-15, or 12 diavolumes of TFF1 buffer. Once 6 diavolumes of permeate total flow have been achieved, the retentate may be concentrated again and harvested. Rinses, e.g., two successive rinses of the membrane, may be executed to increase the product recovery of the intermediate drug substance.

5. Intermediate Product

In some embodiments, the intermediate drug substance may then be frozen on dry ice or in a freezer and then transferred to <−60° C. storage. In other embodiments, the intermediate product need not be frozen prior to the downstream process.

In some embodiments, multiple intermediate product substance lots are pooled together for further processing (e.g., for purification by a downstream process, e.g., as described herein). The multiple intermediate product substance lots may be pooled prior to freezing and storage. In other embodiments, the multiple intermediate product substance lots may be pooled after thawing the frozen and stored lots.

Downstream Process

In some embodiments, a downstream process is used to process the intermediate product (e.g. the pooled intermediate product) to a filtered drug substance. In some embodiments, the downstream process steps include: (a) acidification and clarification (e.g., using filtration), (b) cation exchange chromatography, (c) tangential flow filtration ("TFF2"), (d) CsCl ultracentrifugation, (e) collection of viral vector and (f) further tangential flow filtration ("TFF3") to produce a filtered drug substance where the purified AAV particles are suspended in a pharmaceutically acceptable carrier. In some embodiments, the downstream process contains the following manufacturing steps subsequent to production of the TFF1 intermediate: thaw and pool TFF1 intermediate, acidification and clarification, cation exchange chromatography (CEX), tangential flow filtration (TFF2), CsCl ultracentrifugation for Full/Empty Capsid Separation, tangential flow filtration (TFF3) for Concentration/Buffer Exchange, TFF 3 pool material filtration to generate drug substance, dilution and filtration of drug substance to produce drug product, storage of the drug product and filling of drug product into vials.

In some embodiments, the downstream process disclosed herein may be used to process an intermediate comprising an AAV SMN, as described herein.

1. Acidification and Clarification of Intermediate

In embodiments where the intermediate is frozen, the downstream process begins by thawing the TFF1 intermediate material. A detergent, e.g., Tween 20, may be used to promote flocculation of the bulk of host cell proteins and DNA under acidic pH. The pH of the TFF1 intermediate containing detergent may then be lowered. The flocculant and precipitate formed when the pH is lowered may then be removed by filtering the solution through a depth filter and a filter that removes large molecule contaminants and cell debris, for example a 0.45 µm filter, but that permits vector genomes to pass therethrough. Any suitable depth filter may be used.

In one embodiment, Tween 20 is slowly added to the TFF1 Intermediate solution to achieve final concentration of between 10-20% Tween 20. In some embodiments, the target composition after addition of Tween 20 is 36% Tween 20 solution in 20 mM Tris, 1 mM MgCl$_2$, 500 mM NaCl, 1% Sucrose m/v, pH 8.1. In some embodiments, Tween 20 is added slowly over a span of about 1-6 hours. In some embodiments, Tween 20 is added slowly over 3-6 hours. In some embodiments, Tween 20 is added slowly over 4 hours. In some embodiments, the Tween 20/TFF1 Intermediate solution is allowed to incubate overnight at room temperature. In some embodiment, the Tween 20/TFF1 Intermediate solution is allowed to incubate for 8-20 hours at room temperature. In an exemplary embodiment, the Tween 20/TFF1 Intermediate solution is allowed to incubate for 12-20 hours at room temperature.

After incubation the pH of the Tween 20 containing TFF1 Intermediate may be lowered by adding any suitable acid. In some embodiments, 1M glycine pH 2.5 is added to achieve a target pH of 3.5±0.1. In some embodiments, the target pH is pH 3.0-4.0, about pH 3.3-3.7, about pH 3.4-3.6, or about pH 3.5. Once the pH is within the acceptable range, the solution may be passed through any size filter. In an exemplary embodiment, a depth filter (e.g., Clarisolve POD) in line with a 0.45 µm filter (e.g., Opticap XL10 Durapore filter) or 0.8/0.45 µm PES filter is used.

2. Cation Exchange Chromatography

In various embodiments, a cation exchange (CEX) capture chromatography step is used, e.g., to separate the viral capsids from host cell proteins, host cell DNA, host cell lipids, Tween 20 and other process-related impurities. The principles of cation exchange chromatography are well known in the art, but, briefly, this method relies on the charge-charge interactions between the positively-charged particles to be isolated and the negatively-charged resin used. In general, the column is first equilibrated by running a few diavolumes of buffer through until pH and conductivity is stabilized. The sample is then loaded and the column is washed with a loading buffer. Finally, an elution buffer is used to elute the sample of interest off the column, and fractions containing the sample are collected. The presence of the sample of interest can be detected by optical absorbance measurements of the eluent.

In one embodiment, the CEX step utilizes a CIMmultus S03-8000 Advanced Composite Column (Sulfonyl) (2 µm pores) chromatography column. In one embodiment, the elution peak is collected starting at a sharp rise in OD280. The OD280 will begin to rise when the conductivity is between 80-85 mS/cm. The CEX eluate may be collected according to routine procedures and may be collected in two fractions. In one embodiment, the first fraction starts at the sharp rise in OD280 and is collected for 1.5 collection volumes (CVs). In another embodiment, the second fraction starts immediately after the first fraction and is collected for 1.0 CV. The two fractions are pooled and then neutralized to pH 8.0±0.30. In one embodiment, a Neutralization Buffer comprises 1.0 M Tris pH 9.1±0.1 at 20° C.

3. Tangential Flow Filtration 2

In some embodiments, a tangential flow filtration step (TFF2) is used to concentrate, remove protein impurities, and exchange the buffer to an appropriate buffer for the subsequent CsCl ultracentrifugation step. Any suitable TFF membrane may be used. In an embodiment, the TFF2 step utilizes 300 kD MWCO regenerated cellulose membranes.

In some embodiments, the concentration phase of this step is designed to reduce the volume of the CEX eluate. In one embodiment, the retentate is diluted 2-fold with a diafiltration buffer and the retentate is concentrated to its initial volume. In one embodiment, the diafiltration buffer is the TFF2 NaCl diafiltration buffer that contains 20 mM Tris, 2 mM MgCl2, 150 mM NaCl, 0.2% Poloxamer 188, 1% Sucrose, pH 8.1±0.1 at 20° C. In such embodiments, this process may be repeated until diafiltration with the new buffer is complete. In one embodiment, the retentate is diluted 2-fold with a CsCl-containing diafiltration buffer and the retentate is concentrated to its initial volume. In an embodiment, the CsCl-containing diafiltration buffer is the TFF2 CsCl diafiltration buffer that contains 20 mM Tris, 2 mM MgCl2, 3 M CsCl, 0.2% Poloxamer 188, pH 8.1±0.1 at 20° C. In such embodiments, this process may be repeated until diafiltration with the new buffer is complete. Once CsCl diafiltration is complete, the retentate may then be concentrated to a prescribed volume that is dependent on the system hold-up volume. In some embodiments, rinsing, e.g., two successive rinses of the membrane, are executed to maximize the product recovery from the TFF2 system.

4. CsCl Ultracentrifugation

In some embodiments where an AAV is used for in vivo gene transduction, the final product of rAAV may contain minimum impurities and empty particles. Two methods for purifying AAV vector are ultracentrifugation using either an iodixanol gradient or a CsCl gradient. One study comparing the two methods demonstrated that iodixanol yielded AAV vectors with higher vector purity, but had more empty viral capsids compared to CsCl. Strobel et al. "Comparative Analysis of Cesium Chloride- and Iodixanol-Based Purification of Recombinant Adeno-Associated Viral Vectors for Preclinical Applications." Human Gene Therapy Methods, 26(4):147-157. Even though the use of CsCl leads to lower amounts of empty viral capsids, CsCl may be toxic to cells and multiple purification steps may be needed to remove residual CsCl, leading to a long process time (~3.5 days) compared to shorter methods like iodixanol (~1 day). A different study has shown that the many steps to remove residual CsCl frequently results in the dramatic loss of rAAV, leading to low yields and recovery rate, often negating the other benefits of the method. Hermens et al. "Purification of Recombinant Adeno-Associated Virus by Iodixanol Gradient Ultracentrifugation Allows Rapid and Reproducible Preparation of Vector Stocks for Gene Transfer in the Nervous System." Human Gene Therapy, 10:1885-1891. Furthermore, while these two methods work well in a laboratory for producing preclinical samples, they are not scalable and thus not suitable for large-scale production of commercial products. See, e.g., Tomono et al., "Ultracentrifugation-free chromatography-mediated large-scale purification of recombinant adeno-associated virus serotype 1 (rAAV1)." Molecular Therapy—Methods & Clinical Development, 3:15058 ("purification methods using cesium chloride (CsCl) or iodixanol density ultracentrifugation are not suitable for large-scale production").

In some embodiments, an ultracentrifugation step is used, e.g., to separate empty capsids from full capsids. Unexpectedly, the CsCl ultracentrifugation method disclosed herein was scalable and suitable for large-scale production of purified AAV vectors. Ultracentrifugation may be performed by analytical ultracentrifugation, and may involve the use of gradient buffers. Examples of gradient buffers include but are not limited to CsCl, sucrose, iodixanol and others known in the art. Centrifugation can be performed in any centrifuge capable of reaching the desired g-forces, e.g., an automated Optima XPN 100 Ultra Centrifuge system or equivalent system equipped with Type 50.2 Ti rotor or equivalent rotor. After ultracentrifugation, empty capsids and full capsids separate into different bands within the tube, and may be extracted by drawing material from a specific band. In some embodiments, TFF2-purified filtered material is centrifuged at 241,600-302,000 g (~40,000-50,000 rpm in 50.2 Ti rotor). In some embodiments, TFF2-purified filtered material is centrifuged overnight. In some embodiments, TFF2-purified filtered material is centrifuged for 16-24 hours. In some embodiments, TFF2-purified filtered material is centrifuged for 20-24 hours. In some embodiments, TFF2-purified filtered material is centrifuged at 15-25° C. In an embodiment, TFF2-purified filtered material is centrifuged at 302,000 g (50,000 rpm in 50.2 Ti rotor) for 17 hours at 20° C. In some embodiments, the buffer for CsCl centrifugation can have one or more of the following ingredients, comprising (a) CsCl, further comprising one or more of (b) MgCl2, (c) Poloxamer 188 and (d) Tris. In some embodiments, the buffer for CsCl can include all of (a), (b), (c) and (d). In some embodiments, the buffer for CsCl has a pH 7.5-8.5, or pH 7.9-8.2. In an embodiment, a suitable buffer for CsCl centrifugation is 20 mM Tris, 2 mM MgCl2, 3 M CsCl, 0.2% Poloxamer 188, pH 8.1±0.10. After completion of the centrifugation step, tubes may be removed from the ultracentrifuge. In one embodiment, the highest band, Band A, contains the empty capsids. In some embodiments, the next highest bands, Bands B, C and D, contain the full capsid doublet bands. In some embodiments, the AAV viral vectors are collected using a syringe. In an embodiment, Bands B, C and D are removed by an 18G needle attached to 30 mL syringe inserted just below band D to middle of tube. In other embodiments, the bands may be assayed for the presence of full or empty capsid using techniques known in the art and/or as described herein, and the bands containing full capsid collected.

The ratio of empty to non-empty viral capsids can be measured by standard laboratory techniques. In some embodiments, the measurement is done by optical absorbance measurements. In some embodiments, the measurement is done by UV absorbance measurements. In some embodiments, the total amount of capsid proteins and total amount of DNA can be determined from UV absorbance measurements. In some embodiments, the measurement is done by optical refractive index measurements. In some other embodiments, the measurement is done by analytical ultracentrifugation.

In one embodiment, the AAV viral vector collected after ultracentrifugation has less than 8% empty capsids, less than 7% empty capsids, less than 5%, less than 3%, or less than 1%. In one embodiment, the AAV viral vector collected after ultracentrifugation has 1-10% empty capsids. In one embodiment, the AAV viral vector collected after ultracentrifugation has 2-8% empty capsids. In one embodiment, the number of empty capsids is below the limit of detection. In another embodiment, the percentage of empty capsids is determined as a percentage of total capsids.

5. Tangential Flow Filtration 3 to Generate Filtered Drug Substance

In some embodiments, a tangential flow filtration step (TFF3) is used to remove CsCl and concentrate the full vector capsids. Tangential flow filtration may be performed using suitable membranes. In one embodiment, 300 kDa MWCO regenerated cellulose membranes are used. The vector capsids may be retained by the membranes. The concentration phase of TFF3 operation may be designed to reduce the concentration of residual CsCl and volume of the ultracentrifugation pool. In some embodiments, once the target retentate volume is reached, diafiltration is started. The retentate is diafiltered with up to 10 diavolumes of a suitable TFF3 buffer. In one embodiment a suitable TFF3 buffer can include one or more of the following components, comprising (a) Tris, (b) $MgCl_2$, (c) NaCl, or (d) Poloxamer 188. In one embodiment, a suitable TFF3 buffer can include all of (a), (b), (c) and (d). In one embodiment, the TFF3 buffer has pH 7.5-8.5, pH 7.7-8.3, or pH 8.0. In an embodiment a suitable TFF3 buffer comprises 20 mM Tris, 1 mM $MgCl_2$, 200 mM NaCl, 0.001% Poloxamer 188, pH 8.0±0.1 at 20° C. In another embodiment, a suitable TFF3 buffer comprises 20 mM Tris, 1 mM $MgCl_2$, 200 mM NaCl, 0.005% Poloxamer 188, pH 8.0±0.1 at 20° C. In one embodiment, the concentrated retentate is filtered using a 0.2 μm Pall Supor® EKV Sterilizing-Grade Filter (Mini Kleenpak) Filter to produce a filtered drug substance. In some embodiments, the methods described herein yield more than $5\times10^{15}$ vg, or more than $8\times10^{15}$ vg or more than $1\times10^{16}$ vg of rAAV per manufacturing batch.

Pharmaceutical Compositions

The viral (e.g., AAV) particles purified according to the methods disclosed herein may be produced in high yield with sufficient purity that they can be administered to a human subject. In some embodiments, the potency of pharmaceutical compositions comprising the AAV particles described herein are assayed using the in vitro cell based potency assay described herein. In some embodiments, the viral vector is formulated at a concentration of between about $1\text{-}8\times10^{13}$ viral vector genomes/mL (vg/mL), or about $1.7\text{-}2.3\times10^{13}$ vg/mL. In some embodiments, the viral vector is formulated at a concentration of about $1.9\text{-}2.1\times10^{13}$ vg/mL. In some embodiments, the viral vector is formulated at a concentration of about $2.0\times10^{13}$ vg/mL.

In some embodiments, during the production process of the viral vector, empty viral capsids that do not contain nucleic acid material may be generated. Pharmaceutical compositions comprising low amounts of empty viral capsids may be advantageous, because they avoid exposing patients, e.g., infants, with immature immune systems to antigenic material (empty capsids, host cell protein, host cell DNA) unnecessarily without therapeutic benefit. In some embodiments, such pharmaceutical compositions may reduce potential infusion reactions or broader immune responses and may improve therapeutic efficacy. Compared to full viral capsids with genome material, empty capsids have different densities, allowing the two species to be separated by gradient centrifugation, or other methods known in the art. In some embodiments, the empty capsids are separated by ultracentrifugation. In some embodiments, the empty capsids are separated by CsCl gradient ultracentrifugation. In other embodiments, the empty capsids are separated by iodixanol gradient ultracentrifugation. In some embodiments, the empty capsids are separated by sucrose gradient ultracentrifugation.

The ratio of empty to non-empty viral capsids can be measured by standard laboratory techniques. In some embodiments, the ratio is measured by optical absorbance measurements. In some embodiments, the ratio is measured by UV absorbance measurements. In some embodiments, the total amount of capsid proteins and total amount of DNA can be determined by UV absorbance measurements. In some embodiments, the measurement is determined by optical refractive index measurements. In some other embodiments, the measurement is determined by analytical ultracentrifugation.

High levels of empty capsids may pose challenges for the efficacy of viral vector treatments. In one embodiment, the pharmaceutical composition has less than 10% empty capsids, less than 8% empty capsids, less than 7%, less than about 5%, less than 3%, less than 1% empty capsids. In another embodiment, the pharmaceutical composition has 1-10% empty capsids. In another embodiment, the pharmaceutical composition has 2-8% empty capsids. In another embodiment, the pharmaceutical composition has less than or equal to 6% empty capsids, 5% empty capsids, 4% empty capsids, 3% empty capsids, 2% empty capsids, or fewer. In an embodiment, the number of empty capsids is below the limit of detection. In another embodiment, the percentage of empty capsids is determined as a percentage of total capsids, e.g., using AUC. In some embodiments, these low percentage empty capsids improve efficacy of treatment and/or reduce adverse events (e.g., inflammatory responses, liver injury) after administration to a patient, e.g., as compared to compositions having higher percentage empty capsids. In some embodiments, the methods of preparing viral vectors disclosed herein provide these improved percentages of empty capsids, as compared to the levels in prior methods, e.g., those not using adherent cells and/or the purification methods described herein.

During the production process of the viral vector, residual protein from the adherent cells (e.g. HEK293 cells) used to generate the viral vectors may not be completely separated out. Residual host cell proteins pose a potential to elicit an immune response. The amount of residual host cell can be measured by any standard laboratory techniques that can distinguish between the viral capsid proteins and the residual host cell proteins. In some embodiments, the amount of residual host cell proteins can be measured by size exclusion or ion exchange chromatography. In some embodiments, the measurement can be done by a western blot with parental cell-specific antibodies. In one embodiment, the amount of residual host cell protein can be measured by enzyme-linked immunosorbent assay (ELISA). In some embodiments, the amount of residual host cell protein can be measured by a commercial ELISA kit. In some embodiments, the amount of residual host cell protein can be measured by a *Cygnus* Technologies HEK293 HCP ELISA Kit.

In another embodiment, the residual host cell protein in said pharmaceutical composition is less than or equal to $5\times10^6$ pg/ml per $1\times10^{13}$ vg/ml, less than or equal to $1.2\times10^6$ pg/ml per $1\times10^{13}$ vg/mL or $1\times10^5$ pg/ml per $1\times10^{13}$ vg/ml to $1.2\times10^6$ pg/ml per $1\times10^{13}$ vg/ml or less than or equal to 40 ng/ml per $1\times10^{13}$ vg/ml. In an embodiment, the pharmaceutical composition comprises less than or equal to 5, 4, 3, 2, 1 or fewer ng residual host cell protein per $1.0\times10^{13}$ vg. In one embodiment, the pharmaceutical composition comprises less than or equal to 4 ng residual host cell protein per $1.0\times10^{13}$ vg.

During the production process of the viral vector, residual host cell DNA from the adherent cells (e.g. HEK293 cells) or residual plasmid DNA transfected to generate the viral vectors may not be completely removed. The purification process (e.g. acidification, clarification, tangential flow filtration etc.) removes the bulk of residual host cell or plasmid DNA. In one embodiment, measurement of the amount of residual host cell or plasmid DNA is performed by PCR. In another embodiment, measurement of the amount of residual host cell or plasmid DNA is performed by quantitative PCR (qPCR) with primers specific for host cell or plasmid sequences. In another embodiment, measurement of the amount of residual host cell or plasmid DNA is performed by digital droplet PCR (ddPCR). In one embodiment, the amount of plasmid DNA is determined using a qPCR assay with primers specific to the Kanamycin resistance gene region of the plasmid. In another embodiment, the amount of residual host cell DNA is determined by commercial qPCR assay kits, for example the resD-NASEQ© Human Residual DNA Quantitation Kit by ThermoFisher, Residual DNA Quantification Supermix by Biorad, or any equivalent product. Reducing the amount of residual host cell or plasmid DNA may improve therapeutic outcomes and such compositions may be purified and/or selected for use in treatments disclosed herein.

In an embodiment, the residual host cell DNA in said pharmaceutical composition is less than or equal to $1.7\times10^6$ pg/ml per $1\times10^{13}$ vg/ml, $1\times10^5$ pg/ml per $1\times10^{13}$ vg/ml to $1.2\times10^6$ pg/ml per $1\times10^{13}$ vg/ml. In an embodiment, the residual host cell DNA in said pharmaceutical composition is less than or equal to $3\times10^5$, $2\times10^5$, $1.1\times10^5$, $1\times10^5$ pg or fewer per $1.0\times10^{13}$ vg. In embodiments, the residual host cell DNA in said pharmaceutical composition is less than or equal to $1.1\times10^5$ pg per $1.0\times10^{13}$ vg.

In another embodiment, the residual plasmid DNA in said pharmaceutical composition is less than or equal to $1.7\times10^6$ pg/ml per $1\times10^{13}$ vg/ml, $1\times10^5$ pg/ml per $1\times10^{13}$ vg/ml to $1.7\times10^6$ pg/ml per $1\times10^{13}$ vg/ml. In another embodiment, the residual plasmid DNA in said pharmaceutical composition is less than or equal to $6.8\times10^5$ pg per $1.0\times10^{13}$ vg.

In an embodiment, the residual host cell DNA in a pharmaceutical composition is less than or equal to $1.1\times10^5$ pg per $1.0 \times 10^{13}$ vg and the residual plasmid DNA in said pharmaceutical composition is less than or equal to $6.8 \times 10^5$ pg per $1.0 \times 10^{13}$ vg.

In an embodiment, the residual host cell DNA in a pharmaceutical composition is less than or equal to $1.1 \times 10^5$ pg per $1.0 \times 10^{13}$ vg, and the residual plasmid DNA in said pharmaceutical composition is less than or equal to $6.8 \times 10^5$ pg per $1.0 \times 10^{13}$ vg, and the residual host cell protein in said pharmaceutical composition is less than or equal to 4 ng per $1.0 \times 10^{13}$ vg.

In some embodiments, the amount of endotoxin in the pharmaceutical composition is less than about 1 EU/mL per $1.0 \times 10^{13}$ vg/mL, less than about 0.75 EU/mL per $1.0 \times 10^{13}$ vg/mL, less than about 0.5 EU/mL per $1.0 \times 10^{13}$ vg/mL, less than about 0.4 EU/mL per $1.0 \times 10^{13}$ vg/mL, less than about 0.35 EU/mL per $1.0 \times 10^{13}$ vg/mL, less than about 0.3 EU/mL per $1.0 \times 10^{13}$ vg/mL, less than about 0.25 EU/mL per $1.0 \times 10^{13}$ vg/mL, less than about 0.2 EU/mL per $1.0 \times 10^{13}$ vg/mL, less than about 0.15 EU/mL per $1.0 \times 10^{13}$ vg/mL, less than about 0.1 EU/mL per $1.0 \times 10^{13}$ vg/mL, less than about 0.05 EU/mL per $1.0 \times 10^{13}$ vg/mL, or, less than about 0.02 EU/mL per $1.0 \times 10^{13}$ vg/mL. Methods for determining the amount of endotoxin are known in the art, e.g., a limulus amoebocyte lysate (LAL) test. In embodiments, the endotoxin is assayed per U.S. Pharmacopiea ("USP")<85>(incorporated herein by reference in its entirety).

In one embodiment, the bovine serum albumin (BSA) in a pharmaceutical composition is less than 0.5 ng per $1.0 \times 10^{13}$ vg, less than 0.3 ng per $1.0 \times 10^{13}$ vg, or less than 0.22 ng per $1.0 \times 10^{13}$ vg. In one embodiment, the benzonase in said pharmaceutical composition is less than 0.2 ng per $1.0 \times 10^{13}$ vg, less than 0.1 ng per $1.0 \times 10^{13}$ vg, or less than 0.09 ng per $1.0 \times 10^{13}$ vg.

In one embodiment, a pharmaceutical composition disclosed herein comprises one or more of the following: less than about 0.09 ng of benzonase per $1.0 \times 10^{13}$ vg, less than about 30 µg/g (ppm) of cesium, about 20-80 ppm of Poloxamer 188, less than about 0.22 ng of BSA per $1.0 \times 10^{13}$ vg, less than about $6.8 \times 10^5$ pg of residual plasmid DNA per $1.0 \times 10^{13}$ vg, less than about $1.1 \times 10^5$ pg of residual hcDNA per $1.0 \times 10^{13}$ vg, less than about 4 ng of rHCP per $1.0 \times 10^{13}$ vg, pH 7.7-8.3, about 390-430 mOsm/kg, less than about 600 particles that are ≥25 µm in size per container, less than about 6000 particles that are ≥10 µm in size per container, about $1.7 \times 10^{13}$-$2.3 \times 10^{13}$ vg/mL genomic titer, infectious titer of about $3.9 \times 10^8$-$8.4 \times 10^{10}$ IU per $1.0 \times 10^{13}$ vg, total protein of about 100-300 µg per $1.0 \times 10^{13}$ vg, median survival of ≥24 days of Δ7SMA mice with about $7.5 \times 10^{13}$ vg/kg dose of viral vector, about 70-130% relative potency based on an in vitro cell-based assay, and/or less than about 5% empty capsid.

In one embodiment a pharmaceutical composition disclosed herein comprises one or more, e.g., all, of the following: pH 7.7-8.3 (e.g., as measured by USP <791>), about 390-430 mOsm/kg (e.g., as measured by USP <785>), less than about 600 particles that are >25 µm in size per container (e.g., as measured by USP <787>), less than about 6000 particles that are ≥10 µm in size per container (e.g., as measured by USP <787>), about $1.7 \times 10^{13}$-$2.3 \times 10^{13}$ vg/mL genomic titer, infectious titer of about $3.9 \times 10^8$-$8.4 \times 10^{10}$ IU per $1.0 \times 10^{13}$ vg, total protein of about 100-300 µg per $1.0 \times 10^{13}$ vg, median survival of ≥24 days of Δ7SMA mice with about $7.5 \times 10^{13}$ vg/kg dose of viral vector, e.g., in an in vivo functionality test, e.g., as described herein, about 70-130% relative potency based on an in vitro cell-based assay, and/or less than about 5% empty capsid. In embodiments, a pharmaceutical composition disclosed herein comprises a total purity greater than or equal to 95% (e.g., as determined by SDS-PAGE). In embodiments, a pharmaceutical composition disclosed herein comprises no single unnamed related impurity at a level greater than 2% (e.g., as determined by SDS-PAGE). In embodiments, a pharmaceutical composition disclosed herein comprises Endotoxin levels of less than or equal to 0.75 EU/mL. In embodiments, a pharmaceutical composition disclosed herein tests for no growth in a sterility test.

High levels of residual host cell protein, host cell DNA, plasmid DNA, and/or endotoxin may pose challenges for the efficacy of viral vector treatments. In some embodiments, these low amounts of residual host cell protein, host cell DNA, plasmid DNA, and/or endotoxin improve efficacy of treatment and/or reduce adverse events (e.g., inflammatory responses, liver injury) after administration to a patient, e.g., as compared to compositions having higher amounts. In some embodiments, the methods of preparing viral vectors disclosed herein provide these improved levels, as compared to the levels in prior methods, e.g., those not using adherent cells and/or the purification methods described herein. In some embodiments, the methods herein also allow for preparation of viral vectors with reduced percentages of empty capsids in addition to low amounts of residual host cell protein, host cell DNA, plasmid DNA, and/or endotoxin.

In some embodiments, the amount of residual cesium after TFF, e.g., the second TFF, is below about 50 µg/g. In some embodiments, the amount of residual cesium after the TFF, e.g., the second TFF, is below about 30 µg/g. In some embodiments, the amount of residual cesium after the TFF, e.g., the second TFF, is below about 20 ug/g. In some embodiments, the residual cesium in the pharmaceutical composition is less than or equal to 30 ug/g (ppm). In some embodiments, the amount of residual CsCl may be measured by mass spectrometry, inductively coupled plasma mass spectrometry (ICP-MS), and/or another suitable method. In some embodiments, the amount of residual cesium after the second TFF is below the limit of quantitation, e.g., using ICP-MS.

In some embodiments, the concentration of AAV viral vectors collected after the second TFF is greater than or equal to about $5 \times 10^{12}$ vg/ml, greater than or equal to about $1 \times 10^{13}$ vg/ml, or greater than or equal to about $3 \times 10^{13}$ vg/ml.

In one embodiment, a pharmaceutical composition has one or more of the following: less than 0.09 ng of benzonase per $1.0 \times 10^{13}$ vg, less than 30 µg/g (ppm) of cesium, about 20-80 ppm of Poloxamer 188, less than 0.22 ng of BSA per $1.0 \times 10^{13}$ vg, less than $6.8 \times 10^5$ pg of residual plasmid DNA per $1.0 \times 10^{13}$ vg, less than $1.1 \times 10^5$ pg of residual hcDNA per $1.0 \times 10^{13}$ vg, and less than 4 ng of rHCP per $1.0 \times 10^{13}$ vg.

In some embodiments, the potency of the pharmaceutical composition is measured using the in vitro cell based potency assay described herein. In some embodiments, the pharmaceutical composition comprises a viral vector, wherein the relative potency of the viral vector is at least 40%, at least 50%, at least 60%, at least 70%, at least 80%, at least 90%, at least 91%, at least 92%, at least 93%, at least 94%, at least 95%, at least 96%, at least 97%, at least 98%, at least 99%, at least 99.5%, at least 99.9%, at least 100%, at least 110%, at least 120%, at least 130% or at least 140% relative to a reference standard. In some embodiments, the pharmaceutical composition comprises a viral vector, wherein the relative potency of the viral vector is at the relative potency of the viral vector is at least 90% relative to a reference standard.

The virus particles purified according to the present disclosure (e.g., viral particles) can be formulated according to known methods to prepare pharmaceutically useful compositions. The compositions of the disclosure can be formulated for administration to a mammalian subject, e.g., a human, using techniques known in the art. In particular delivery systems may be formulated for intramuscular, intradermal, mucosal, subcutaneous, intravenous, intrathecal, injectable depot type devices or topical administration.

When the delivery system is formulated as a solution or suspension, the delivery system is in an acceptable carrier, e.g., an aqueous carrier. A variety of aqueous carriers may be used, e.g., water, buffered water, 0.8% saline, 0.3% glycine, hyaluronic acid and the like. These compositions may be sterilized by conventional, well known sterilization techniques, or may be sterile filtered. The resulting aqueous solutions may be packaged for use as is, or lyophilized, the lyophilized preparation being combined with a sterile solution prior to administration.

The compositions, e.g., pharmaceutical compositions, may contain pharmaceutically acceptable auxiliary substances to approximate physiological conditions, such as pH adjusting and buffering agents, tonicity adjusting agents, wetting agents and the like, for example, sodium acetate, sodium lactate, sodium chloride, potassium chloride, calcium chloride, sorbitan monolaurate, triethanolamine oleate, etc. In some embodiments, the pharmaceutical composition comprises a preservative. In some other embodiments, the pharmaceutical composition does not comprise a preservative.

The genomic titer of viral vectors, e.g., those in the compositions and formulations disclosed herein, can be determined in a number of standard ways. PCR with primers specific to the viral vector can provide relative measurements, but quantitative PCR (qPCR) may be used for smaller samples and absolute measurements. Droplet Digital PCR (ddPCR) is a method for performing digital PCR that is based on water-oil emulsion droplet technology. A sample is fractionated into tens of thousands of droplets, and PCR amplification of the template molecules occurs in each individual droplet. One does not need to make a standard curve or have primers with high amplification efficiency, hence ddPCR does not typically use as much sample as traditional PCR-based techniques. In one embodiment, the genomic titer of the viral vector is determined using PCR. In another embodiment, the genomic titer of the viral vector is determined using qPCR. In another embodiment, the genomic titer of the viral vector is determined using ddPC. The method of determining viral genomic titer using ddPCR is described, for instance, in Lock et al., "Absolute Determination of Single-Stranded and Self-Complementary Adeno-Associated Viral Vector Genome Titers by Droplet Digital PCR," Human Gene Therapy Methods, 25(2):115-125.

In some embodiments, the PCR-based methods detect and quantify encapsidated AAV9 viral genome using specifically designed primers and probes targeting the SMN gene. In other embodiments, the PCR-based methods detect and quantify encapsidated AAV9 viral genome using specifically designed primers and probes targeting the chicken beta-actin promoter. In other embodiments, the PCR-based methods detect and quantify encapsidated AAV9 viral genome using specifically designed primers and probes targeting the CMV enhancer. In other embodiments, the PCR-based methods detect and quantify encapsidated AAV9 viral genome using specifically designed primers and probes targeting the ITR sequences. In other embodiments, the PCR-based methods detect and quantify encapsidated AAV9 viral genome using specifically designed primers and probes targeting the bovine growth hormone polyadenylation signal.

In some embodiments, the pharmaceutical composition is about pH 7.7-8.3 and has an osmolality of 390-430 mOsm/kg. In some embodiments, the pH is measured using a pH meter. In some embodiments, the pH is measured potentiometrically using a micro-electrode with temperature compensation in accordance with standards set by the United States Pharmacopeia (USP), e.g., <791>(incorporated by reference in its entirety). In some embodiments, the osmolality is measured using freezing point depression in accordance with USP, e.g., USP <785>(incorporated by reference in its entirety). In some embodiments, the osmolality is measured using a vapor pressure depression osmometer. In other embodiments, the osmolality is measured using a membrane osmometer.

In one embodiment, an intravenous formulation has a pH between 7.5 and 8.5, a genomic titer of $2\times10^{13}$ vg/ml-$6\times10^{13}$ vg/ml, and an osmolality of 384-448 mOsm/kg. In another embodiment, an intravenous formulation has a pH between 7.5 and 8.5, a genomic titer of $1.5\times10^{13}$ vg/ml-$3.5\times10^{13}$ vg/ml, and an osmolality of 384-448 mOsm/kg. In another embodiment, an intravenous formulation has a pH between 7.5 and 8.5, a genomic titer of $1.8\times10^{13}$ vg/ml-$2.2\times10^{13}$ vg/ml, and an osmolality of 384-448 mOsm/kg. In an embodiment, an IV formulation comprises about 0.1-2.0 mM $MgCl_2$. In an embodiment, an IV formulation comprises about 100-300 mM NaCl. In an embodiment, an IV formulation comprises about 0.001%-0.01% w/v Poloxamer 188. In an embodiment, an IV formulation is an aqueous formulation in 10-30 mM Tris buffer, e.g., at a pH of 7.5-8.5.

In an embodiment, an IV formulation comprises 1 mM $MgCl_2$, 200 mM NaCl, 0.005% w/v Poloxamer 188, in 20 mM Tris buffer at pH 8.0. In embodiments, the IV formulation comprises a genomic titer of about $1\times10^{13}$ to $3\times10^{13}$ vg/mL or $1.7\times10^{13}$ to $2.3\times10^{13}$ vg/mL.

Uses of Pharmaceutical Compositions

The disclosure provides methods of treating a patient in need thereof with a therapy comprising a viral vector comprising a transgene, the method comprising: assaying said viral vector comprising a transgene according to the methods of the in vitro cell based potency assay described herein and administering the viral vector comprising a transgene to said patient. In some embodiments, the viral vector is formulated in a pharmaceutical composition.

In other embodiments, disclosed herein are methods for delivery of a polynucleotide to the central nervous system of a patient comprising administering a rAAV9 with a genome including the polynucleotide. In some embodiments, the delivery is intrathecal delivery of a polynucleotide to the central nervous system of a patient comprising administering a rAAV9 with a genome including the polynucleotide. In some embodiments, a non-ionic, low-osmolar contrast agent is also administered to the patient. The non-ionic, low-osmolar contrast agent increases transduction of target cells in the central nervous system of the patient. In some embodiments, the rAAV9 genome is a self-complementary genome. In other embodiments, the rAAV9 genome is a single-stranded genome.

In some embodiments, a non-ionic, low-osmolar contrast agent is also administered to the patient. More specifically, the invention provides methods of delivering a vector to the central nervous system of a patient in need thereof comprising intrathecal delivery of rAAV9 and a non-ionic, low-osmolar contrast agent to the patient, wherein the rAAV9 comprises a polynucleotide encoding a protein of interest. In some embodiments, the protein of interest is SMN1. The polynucleotide is delivered to, for example, the brain, the spinal cord, a glial cell, an astrocyte and/or a lower motor neuron. The non-ionic, low-osmolar contrast agent is, for example, iobitridol, iohexol, iomeprol, iopamidol, iopentol, iopromide, ioversol or ioxilan. In some embodiments, the polynucleotide is a survival motor neuron (SMN) polynucleotide. An exemplary iohexol radioopaque agent comprises [Omnipaque™ (iohexol, N,N'-Bis(2,3-dihydroxypropyl)-5-[N(2,3-dihydroxypropyl)-acetamido]-2,4,6-trioldo-isophthalamide), GE Healthcare, Waukesha, Wis.]. In some embodiments, the vector and the contrast agent are administered intrathecally, and intrathecal sread is recorded with real-time continuous fluoroscopy.

In some embodiments, the polynucleotide is delivered to a brain region. Areas of the brain contemplated for delivery include, but are not limited to, the motor cortex and the brain stem. In some embodiments, the polynucleotide is delivered to the spinal cord. In some embodiments, the polynucleotide is delivered to a lower motor neuron. Embodiments of the disclosure employ rAAV9 to deliver polynucleotides to nerve and glial cells. In some embodiments, the glial cell is a microglial cell, an oligodendrocyte or an astrocyte. In some embodiments, the rAAV9 is used to deliver a polynucleotide to a Schwann cell.

In some embodiments, use of the methods and materials is indicated for treatment of spinal muscular atrophy (SMA).

There are four types of SMA, which are conventionally classified by age of onset and highest motor function achieved. All forms of SMA are autosomal recessive inheritance and caused by mutations of the survival motor neuron 1 (SMN1) gene. Humans also carry a second nearly identical copy of the SMN gene called SMN2. Lefebvre et al. "Identification and characterization of a spinal muscular atrophy-determining gene." *Cell*, 80(1):155-65. Monani et al. "Spinal muscular atrophy: a deficiency in a ubiquitous protein; a motor-neuron specific disease." *Neuron*, 48(6): 885-896. Both the SMN1 and SMN2 genes express SMN protein, however SMN2 contains a translationally silent mutation in exon 7, which results in inefficient inclusion of exon 7 in SMN2 transcripts. Thus, SMN2 produces both full-length SMN protein and a truncated version of SMN lacking exon 7, with the truncated version as the predominant form. As a result, the amount of functional full-length protein produced by SMN2 is much less (by 70-90%) than that produced by SMN1. Lorson et al. "A single nucleotide in the SMN gene regulates splicing and is responsible for spinal muscular atrophy." *PNAS*, 96(11) 6307-6311. Monani et al, "A single nucleotide difference that alters splicing patterns distinguishes the SMA gene SMN1 from the copy gene SMN2." *Hum Mol Genet* 8(7):1177-1183. Although SMN2 cannot completely compensate for the loss of the SMN1 gene, patients with milder forms of SMA generally have higher SMN2 copy numbers. Lefebvre et al., "Correlation between severity and SMN protein level in spinal muscular atrophy." *Nat Genet* 16(3):265-269. Park et al., "Spinal muscular atrophy: new and emerging insights from model mice." *Curr Neurol Neurosci Rep* 10(2):108-117. A caveat is that SMN2 copy number is not the sole phenotypic modifier. In particular, the c.859G>C variant in exon 7 of the SMN2 gene has been reported as a positive disease modifier. Patient with this particular mutation have less severe disease phenotypes. Prior et al., "A positive modified of spinal muscular atrophy in the SMN2 gene." *Am J Hum Genet* 85(3):408-413.

Type I SMA (also called infantile onset or Werdnig-Hoffmann disease) is when SMA symptoms are present at birth or by the age of 6 months. In this type, babies typically have low muscle tone (hypotonia), a weak cry and breathing distress. They often have difficulty swallowing and sucking, and do not reach the developmental milestone of being able to sit up unassisted. They often show one or more of the SMA symptoms selected from hypotonia, delay in motor skills, poor head control, round shoulder posture and hypermobility of joints. Typically, these babies have two copies of the SMN2 gene, one on each chromosome 5. Over half of all new SMA cases are SMA type I.

Type II or intermediate SMA is when SMA has its onset between the ages of 7 and 18 months and before the child can stand or walk independently. Children with type 2 SMA generally have at least three SMN2 genes. Late-onset SMA (also known as types III and IV SMA, mild SMA, adult-onset SMA and Kugelberg-Welander disease) results in variable levels of weakness. Type III SMA has its onset after 18 months, and children can stand and walk independently, although they may require aid. Type IV SMA has its onset in adulthood, and people are able to walk during their adult years. People with types III or IV SMA generally have between four and eight SMN2 genes, from which a fair amount of full-length SMN protein can be produced.

In one embodiment, the term "treatment" comprises the step of administering intravenously, or via the intrathecal route, an effective dose, or effective multiple doses, of a composition comprising a rAAV as disclosed herein to an animal (including a human being) in need thereof. If the dose is administered prior to development of a disorder/disease, the administration is prophylactic. If the dose is administered after the development of a disorder/disease, the administration is therapeutic. In embodiments, an effective dose is a dose that alleviates (either eliminates or reduces) at least one symptom associated with the disorder/disease state being treated, that slows or prevents progression to a disorder/disease state, that slows or prevents progression of a disorder/disease state, that diminishes the extent of disease, that results in remission (partial or total) of disease, and/or that prolongs survival. Examples of disease states contemplated for treatment are set out herein.

In one embodiment, the compositions comprising rAAV of the disclosure are administered intravenously to a patient in need thereof having SMA, for example, SMA type I. In some embodiments, the patient having SMA is less than 2 years of age. In some embodiments, the patient has bi-allelic mutations in the SMN1 gene. In another embodiment, the compositions comprising rAAV of the disclosure are administered intrathecally to a patient in need thereof having SMA types II, III, or IV. In some embodiments, the compositions comprising rAAV of the disclosure are used for the treatment of pediatric patients less than 2 years of age with SMA with bi-allelic mutations in the SMN1 gene.

A method of treating SMA, e.g., type I SMA, in a patient in need thereof, by administering the AAV9 viral vector via an intrathecal or intravenous route is disclosed herein. In some embodiments, the patient is 0-9 months of age. In some other embodiments, the patient is 0-6 months of age. In some embodiments, the patient is less than 2 years of age. In some embodiments, the patient is less than 2 years of age with bi-allelic mutations in the SMN1 gene. In some embodiments where the viral vector is used for treating SMA, e.g., type I SMA, in a patient, the weight of the patient is determined. In some embodiments, the patient has a body weight of less than 13.5 kg. In some embodiments, the patient has a body weight of less than 8.5 kg. In some embodiments, the patient has a body weight of more than 2.6 kg. In some embodiments, the patient has a body weight of 2.6-8.5 kg. In some embodiments, the patient has a body weight of 2.6-13.5 kg.

In some embodiments, the patient has mutations, e.g., a null mutation, in one copy of the SMN1 gene (encompassing any mutation that renders the encoded SMN1 nonfunctional). In some embodiments, the patient has mutations, e.g., a null mutation, in two copies of the SMN1 gene. In some embodiments, the patient has mutations, e.g., a null mutation, in all copies of the SMN1 gene. In some embodiments, the patient has a deletion in one copy of the SMN1 gene. In some embodiments, the patient has a deletion in two copies of the SMN1 gene. In some embodiments, the patient has biallelic SMN1 mutations, that is, either a deletion or substitution of SMN1 in both alleles of the chromosome. In some embodiments, the patient has at least one functional copy of the SMN2 gene. In some embodiments, the patient has at least two functional copies of the SMN2 gene. In some embodiments, the patient has at least two functional copies of the SMN2 gene. In some embodiments, the patient has at least three functional copies of the SMN2 gene. In some embodiments, the patient has at least four functional copies of the SMN2 gene. In some embodiments, the patient has at least five functional copies of the SMN2 gene. In some embodiments, the patient does not have a c.859G>C substitution in exon 7 of at least one copy of the SMN2 gene. In some embodiments, the genetic sequence of the SMN1 or SMN2 gene may be determined by full genome sequencing. In other embodiments, the genetic sequence and copy number of the SMN1 or SMN2 gene may be determined by high-throughput sequencing. In some embodiments, the genetic sequence and copy number of the SMN1 or SMN2 gene may be determined by microarray analysis. In some embodiments, the genetic sequence and copy number of the SMN1 or SMN2 gene may be determined by Sanger sequencing. In some embodiments, the copy number of the SMN1 or SMN2 gene may be determined by fluorescence in-situ hybridization (FISH).

In some embodiments, the patient shows one or more SMA symptoms. SMA symptoms can include hypotonia, delay in motor skills, poor head control, round shoulder posture and hypermobility of joints. In some embodiments, poor head control is determined by placing the patient in a ring sit position with assistance given at the shoulders (front and back). Head control is assessed by the patient's ability to hold the head upright. In some embodiments, spontaneous movement is observed when the patient is in a supine position and motor skills is assessed by the patient's ability to lift their elbows, knees, hands and feet off the surface. In some embodiments, the patient's grip strength is measured by placing a finger in the patient's palm and lifting the patient until their shoulder comes off the surface. Hypotonia and grip strength is measured by how soon/long the patient maintains grasp. In some embodiments, head control is assessed by placing the patient's head in a maximum available rotation and measuring the patient's ability to turn head back towards midline. In some embodiments, shoulder posture may be assessed by sitting patient down with head and trunk support, and observing if patient flexes elbows or shoulder to reach for a stimulus that is placed at shoulder level at arms length. In some embodiments, shoulder posture may also be assessed by placing patient in a side-lying position, and observing if patient flexes elbows or shoulder to reach for a stimulus that is placed at shoulder level at arms length. In some embodiments, motor skills are assessed by observing if the patients flex their hips or knees when their foot is stroked, tickled or pinched. In some embodiments, shoulder flexion, elbow flexion, hip adduction, neck flexion, head extension, neck extension, and/or spinal incurvation may be assessed by known clinical measures, e.g., CHOP INTEND. Other SMA symptoms may be evaluated according to known clinical measures, e.g., CHOP INTEND.

In some embodiments, patients are treated after they show symptoms of SMA, e.g., type I SMA (e.g., one or more symptoms), as determined using one of the tests described herein. In some embodiments, patients are treated before they show symptoms of SMA, e.g., type I SMA. In some embodiments, patients are diagnosed with SMA, e.g., type I SMA, based on genetic testing, before they are symptomatic.

Combination therapies are also contemplated herein. Combination as used herein includes either simultaneous treatment or sequential treatments. Combinations of methods can include the addition of certain standard medical treatments (e.g., riluzole in ALS), as are combinations with novel therapies. For example, other therapies for SMA include antisense oligonucleotides (ASOs) that alter bind to pre-mRNA and alter their splicing patterns. Singh. et al., "A multi-exon-skipping detection assay reveals surprising diversity of splice isoforms of spinal muscular atrophy genes." Plos One, 7(11):e49595. In one embodiment, nusinersen (US U.S. Pat. Nos. 8,361,977 and 8,980,853, incorporated herein by, reference) may be used. Nusinersen is an approved ASO that target intron 6, exon 7 or intron 7 of SMN2 pre-mRNA, modulating the splicing of SMN2 to more efficiently produce full-length SMN protein. In some embodiments, the method of treatment comprising the AAV9 viral vector is administered in combination with a muscle enhancer. In some embodiments, the method of treatment comprising the AAV9 viral vector is administered in combination with a neuroprotector. In some embodiments, the method of treatment comprising the AAV9 viral vector is administered in combination with an antisense oligonucleotide-based drug targeting SMN. In some embodiments, the method of treatment comprising the AAV9 viral vector is administered in combination with nusinersen. In some embodiments, the method of treatment comprising the AAV9 viral vector is administered in combination with a myostatin-inhibiting drug. In some embodiments, the method of treatment comprising the AAV9 viral vector is administered in combination with stamulumab.

While delivery to an individual in need thereof after birth is contemplated, intrauteral delivery to a fetus is also contemplated.

Methods of treating SMA, e.g., type I SMA, patients using the pharmaceutical compositions comprising the viral vector are contemplated. In some embodiments, the viral vector is formulated at a concentration of about $1-8 \times 10^{13}$ AAV9 viral vector genomes/mL (vg/mL). In some embodiments, the viral vector is formulated at a concentration of about $1.7-2.3 \times 10^{13}$ vg/mL. In some embodiments, the viral vector is formulated at a concentration of about $1.9-2.1 \times 10^{13}$ vg/mL. In some embodiments, the viral vector is formulated at a concentration of about $2.0 \times 10^{13}$ vg/mL.

In some embodiments where the viral vector is used for treating SMA, e.g., type I SMA, in a patient, the AAV viral vector (e.g. AAV SMN) is administered to the patient at a dose of about $1.0-2.5 \times 10^{14}$ vg/kg. In some embodiments where the viral vector is used for treating SMA, e.g., type I SMA, in a patient, the AAV viral vector is administered to the patient at a dose of about $1.1 \times 10^{14}$ vg/kg. In some embodiments where the viral vector is used for treating SMA, e.g., type I SMA, in a patient, the AAV viral vector is infused into the patient over about 45-70 min. In some embodiments where the viral vector is used for treating SMA, e.g., type I SMA, in a patient, the AAV viral vector is infused into the patient over about 60 min. In some embodiments where the viral vector is used for treating SMA, e.g., type I SMA, in a patient, the AAV viral vector is infused into the patient using an infusion pump, a peristaltic pump or any other equipment known in the art. In some embodiments where the viral vector is used for treating SMA, e.g., type I SMA, in a patient, the AAV viral vector is infused into the patient using a syringe pump.

Titers of rAAV viral vector to be administered will vary depending, for example, on the particular rAAV, the mode of administration, the treatment goal, the individual, and the cell type(s) being targeted, and may be determined by methods standard in the art. Titers of rAAV may range from about $1 \times 10^6$, about $1 \times 10^7$, about $1 \times 10^8$, about $1 \times 10^9$, about $1 \times 10^{10}$, about $1 \times 10^{11}$, about $1 \times 10^{12}$, about $1 \times 10^{13}$, about $1 \times 10^{14}$, or more DNase resistant particles (DRP) per ml. Dosages may also be expressed in units of vector genomes (vg). The genomic titer can be determined using ddPCR as described in this application, in Lock et al., or any other methods known in the art.

Dosages may also vary based on the timing of the administration to a human. These dosages of rAAV may range from about $1 \times 10^{11}$ vg/kg, about $1 \times 10^{12}$ vg/kg, about $1 \times 10^{13}$ vg/kg, about $1 \times 10^{14}$ vg/kg, about $1 \times 10^{15}$ vg/kg, about $1 \times 10^{16}$ vg/kg, or more vector genomes per kilogram body weight in an adult. For a neonate, the dosages of rAAV may range from about $1 \times 10^{11}$ vg/kg, about $1 \times 10^{12}$ vg/kg, about $3 \times 10^{12}$ vg/kg, about $1 \times 10^{13}$ vg/kg, about $3 \times 10^{13}$ vg/kg, about $1 \times 10^{14}$ vg/kg, about $3 \times 10^{14}$ vg/kg, about $1 \times 10^{15}$ vg/kg, about $3 \times 10^{15}$ vg/kg, about $1 \times 10^{16}$ vg/kg, about $3 \times 10^{16}$ vg/kg, or more vector genomes per kilogram body weight.

Dosages may also vary based on the timing of the administration to a human. These dosages of rAAV may range from about $1 \times 10^{11}$ vg/kg/week, about $1 \times 10^{12}$ vg/kg/week, about $1 \times 10^{13}$ vg/kg/week, about $1 \times 10^{14}$ vg/kg/week, about $1 \times 10^{15}$ vg/kg/week, about $1 \times 10^{16}$ vg/kg/week, or more vector genomes per kilogram body weight in an adult. For a neonate, the dosages of rAAV may range from about $1 \times 10^{11}$ vg/kg/week, about $1 \times 10^{12}$ vg/kg/week, about $3 \times 10^{12}$ vg/kg/week, about $1 \times 10^{13}$ vg/kg/week, about $3 \times 10^{13}$ vg/kg/week, about $1 \times 10^{14}$ vg/kg/week, about $3 \times 10^{14}$ vg/kg/week, about $1 \times 10^{15}$ vg/kg/week, about $3 \times 10^{15}$ vg/kg/week, about $1 \times 10^{16}$ vg/kg/week, about $3 \times 10^{16}$ vg/kg/week, or more vector genomes per kilogram body weight per week. Dosages of rAAV $1 \times 10^{11}$ vg/1.5 kg/week, about $1 \times 10^{12}$ vg/1.5 kg/week, about $1 \times 10^{13}$ vg/1.5 kg/week, about $1 \times 10^{14}$ vg/1.5 kg/week, about $1 \times 10^{15}$ vg/1.5 kg/week, about $1 \times 10^{16}$ vg/1.5 kg/week, or more vector genomes per kilogram body weight in an adult. For a neonate, the dosages of rAAV may range from about $1 \times 10^{11}$ vg/1.5 kg/week, about $1 \times 10^{12}$ vg/1.5 kg/week, about $3 \times 10^{12}$ vg/kg/week, about $1 \times 10^{11}$ vg/1.5 kg/week, about $3 \times 10^{11}$ vg/1.5 kg/week, about $1 \times 10^{14}$ vg/1.5 kg/week, about $3 \times 10^{14}$ vg/1.5 kg/week, about $1 \times 10^{15}$ vg/1.5 kg/week, about $3 \times 10^{15}$ vg/1.5 kg/week, about $1 \times 10^{16}$ vg/1.5 kg/week, about $3 \times 10^{16}$ vg/1.5 kg/week, or more vector genomes per 1.5 kilogram body weight per week.

In some embodiments, the dosage retains at least 40%, at least 50%, at least 60%, at least 70%, at least 80%, at least 90%, at least 91%, at least 92%, at least 93%, at least 94%, at least 95%, at least 96%, at least 97%, at least 98%, at least 99%, at least 99.5%, at least 99.9%, at least 100%, at least 110%, at least 120%, at least 130% or at least 140% potency relative to a reference standard at the same dosage. In some embodiments, the dosage retains at least 90% potency relative to a reference standard at the same dosage. In some embodiments, the relative potency is assayed using the in vitro cell based relative potency assay described herein.

In an embodiment, the dose is about $1.1 \times 10^{14}$ vector genomes per kg (vg/kg) of patient body weight. In an embodiment, a 5 kg patient would receive a total dose of between $0.5 \times 10^{14}$ to $5.0 \times 10^{14}$ vector genomes. In an embodiment, the viral vector is administered in a Tris-buffered Saline. In an embodiment, the viral vector is administered in about 5-20 mL/kg, about 10-20 mL/kg, or about 5.5-6.5 mL/kg of Tris-buffered Saline.

The dose can be determined in a number of standard ways. PCR with primers specific to the viral vector can provide relative measurements, but qPCR may be used for smaller samples and absolute measurements. ddPCR is a method for performing digital PCR that is based on water-oil emulsion droplet technology. Baker et al., "Digital PCR hits its stride." *Nature Methods*, 9(6):541-544. Sykes et al., "Quantitation of targets for PCR by use of limiting dilution." *Biotechniques*, 13(3)444-449. A sample is fractionated into tens of thousands of droplets, and PCR amplification of the template molecules occurs in each individual droplet. One does not need to make a standard curve or have primers with high amplification efficiency, hence ddPCR does not typically use as much sample as traditional PCR-based techniques. Examples of commercially available ddPCR machines include, but are not limited to, the BioRad QX100 ddPCR and the RainDance Raindrop Digital PCR. In one embodiment, the dose is determined using PCR. In another embodiment, the dose is determined using qPCR. In another embodiment, the dose is determined using digital droplet PCR (ddPCR). In some embodiments, the PCR-based methods detect and quantify encapsidated AAV9 viral genome using specifically designed primers and probes targeting the SMN gene. In other embodiments, the PCR-based methods detect and quantify encapsidated AAV9 viral genome using specifically designed primers and probes targeting the chicken beta-actin promoter. In other embodiments, the PCR-based methods detect and quantify encapsidated AAV9 viral genome using specifically designed primers and probes targeting the CMV enhancer. In other embodiments, the PCR-based methods detect and quantify encapsidated AAV9 viral genome using specifically designed primers and probes targeting the ITR sequences. In other embodiments, the PCR-based methods detect and quantify encapsidated AAV9 viral genome using specifically designed primers and probes targeting the bovine growth hormone polyadenylation signal.

In one aspect, the dose is administered according to the following table, using $2.0 \times 10^{13}$ vg/ml as the target concentration of the drug product.

TABLE 2

| Dosing | |
|---|---|
| Patient Weight Range (kg) | Dose Volume$^a$ (mL) |
| 2.6-3.0 | 16.5 |
| 3.1-3.5 | 19.3 |
| 3.6-4.0 | 22.0 |
| 4.1-4.5 | 24.8 |
| 4.6-5.0 | 27.5 |
| 5.1-5.5 | 30.3 |
| 5.6-6.0 | 33.0 |
| 6.1-6.5 | 35.8 |
| 6.6-7.0 | 38.5 |
| 7.1-7.5 | 41.3 |
| 7.6-8.0 | 44.0 |

TABLE 2-continued

Dosing

| Patient Weight Range (kg) | Dose Volume[a] (mL) |
|---|---|
| 8.1-8.5 | 46.8 |
| 8.6-9.0 | 49.5 |
| 9.1-9.5 | 52.3 |
| 9.6-10.0 | 55.0 |
| 10.1-10.5 | 57.8 |
| 10.6-11.0 | 60.5 |
| 11.1-11.5 | 63.3 |
| 11.6-12.0 | 66.0 |
| 12.1-12.5 | 68.8 |
| 12.1-12.5 | 71.5 |
| 13.1-13.5 | 74.3 |

[a]NOTE:
Dose Volume is calculated using the upper limit of the Patient Weight Range.

In some embodiments pharmaceutical composition comprising the AAV viral vector is infused into the patient over about 20-70 minutes, for example over about 45-70 minutes. In some embodiments, the pharmaceutical composition comprising the AAV viral vector is infused into the patient over about 60 min. In some embodiments, the pharmaceutical composition comprising the AAV viral vector is infused into the patient using an infusion pump, a peristaltic pump or any other equipment known in the art. In some embodiments, the pharmaceutical composition comprising the AAV viral vector is infused into the patient using a syringe pump.

The pre-screening of patients amenable to treatment is also contemplated, as well as the administration of treatment to patients identified according to criteria disclosed herein. AAVs may give rise to both a cellular and humoral immune response. As a result, a fraction of potential patients for AAV-based gene therapy harbors pre-existing antibodies against AAV. Jeune et al., "Pre-existing anti-Adeno-Associated Virus antibodies as a challenge in AAV gene therapy." Hum Gene Ther Methods, 24(2):59-67. Boutin et al., "Prevalence of serum IgG and neutralizing factors against adeno-associated virus (AAV) types 1, 2, 5, 6, 8, and 9 in the healthy population: implications for gene therapy using AAV vectors." Hum Gene Ther, 21:704-712. Because even very low levels of antibodies can prevent successful transduction, antecedent anti-AAV antibodies pose a serious obstacle to the universal application of AAV gene therapy. In some embodiments, the levels of anti-AAV9 antibody titers in a patient is determined prior to administration of the AAV viral vector. In some embodiments, the levels of anti-AAV9 antibody titers in a patient is determined by an ELISA binding immunoassay. In some embodiments, the patient has anti-AAV9 antibody titers at or below 1:100 as determined by an ELISA binding immunoassay prior to administration of treatment. In some embodiments, the patient has anti-AAV9 antibody titers at or below 1:50 as determined by an ELISA binding immunoassay prior to administration of treatment. In some embodiments, the patient has anti-AAV9 antibody titers above 1:100 as determined by an ELISA binding immunoassay after treatment and is monitored for 1-8 weeks or until titers decrease to below 1:100. In some embodiments, the patient has anti-AAV9 antibody titers above 1:100 as determined by an ELISA binding immunoassay after treatment and is monitored for 1-8 weeks or until titers decrease to below 1:50.

One approach to overcome high anti-AAV antibody titer is the use of immunosuppressant drugs. Monoclonal anti-CD20 antibody rituximab in combination with cyclosporine A has been shown to be effective in bringing down anti-AAV titers. Mingozzi et al., "Pharmacological modulation of humoral immunity in a nonhuman primate model of AAV gene transfer for hemophilia B." Mol Ther, 20:1410-1416. Another approach is the use of plasmapheresis to deplete neutralizing antibodies prior to vector administration. Monteilhet et al., "A 10 patient case report on the impact of plasmapheresis upon neutralizing factors against adeno-associated virus (AAV) types 1, 2, 6, and 8." Mol Ther, 19(11):2084-2091. During plasmapheresis, blood is withdrawn from a patient and the plasma and blood cells are separated by either centrifugation or hollow fiber filtration. The blood cells are then returned to the patient together with either treated plasma or replacement fluids, such as a 4.5% human albumin in saline. A common use of therapeutic apheresis is the removal of undesired immunoglobulins but in this case, plasmapheresis represents an attractive approach to deplete anti-AAV antibodies. In some embodiments, the patient has anti-AAV9 antibody titers above 1:100 as determined by an ELISA binding immunoassay prior to or after treatment and is treated with plasmapheresis. In some embodiments, the patient has anti-AAV9 antibody titers above 1:50 as determined by an ELISA binding immunoassay prior to or after treatment and is treated with plasmapheresis.

Pre-existing maternal antibodies to AAV9 may be transferred to an infant patient through breast milk or placental transfer in utero. In some embodiments, the patient has anti-AAV9 antibody titers above 1:100 as determined by an ELISA binding immunoassay prior to or after treatment and is switched to formula feeding. In some embodiments, the patient has anti-AAV9 antibody titers above 1:50 as determined by an ELISA binding immunoassay prior to or after treatment and is switched to formula feeding.

Prior to and after administration of treatment, the condition of the patient may be monitored. Some patients who have received AAV-based treatments have experienced thrombocytopenia, which is a condition characterized by low platelet count. Thrombocytopenia can be detected by a full blood count using a diluted sample of blood on a hemocytometer. Thrombocytopenia can also be detected by viewing a slide prepared with the patient's blood (a thin blood film or peripheral smear) under the microscope. Normal human platelet counts range from 150,000 cells/ml to about 450,000 cells/ml.

In some embodiments, the patient has platelet counts above about 67,000 cells/ml prior to administration or above about 100,000 cells/ml, or above about 150,000 cells/ml. In some embodiments, the patient has platelet counts below about 150,000 cells/ml prior to administration or below about 100,000 cells/ml, or below about 67,000 cells/ml, and is monitored for 1-8 weeks or until platelet counts increase to above about 67,000 cells/ml, or above about 100,000 cells/ml, or above about 150,000 cells/ml. In some embodiments where platelet counts are below about 67,000 cells/ml after administration of the viral vector, the patient may be treated with platelet transfusion. In some embodiments, the patient does not have thrombocytopenia prior to administration of the viral vector. In some embodiments, the patient has thrombocytopenia after administration of the viral vector and is monitored for about 1-8 weeks or until the patient does not have thrombocytopenia. In some embodiments, the patient has thrombocytopenia after administration of the viral vector and is treated with a platelet transfusion.

Monitoring the condition of patients may also involve standard blood tests that measure levels of platelets, serum protein electrophoresis, serum gamma-glutamyl transferase (GGT), aspartate transaminase (AST) and alanine aminotransferase (ALT), total bilirubin, glucose, creatine kinase (CK), creatinine, blood urea nitrogen (BUN), electrolytes, alkaline phosphatase and amylase. Troponin I levels are a general measure for heart health, and elevated levels reflect heart damage or heart-related conditions. In some embodiments, troponin-I levels are monitored after administration of the viral vector. In some embodiments, patients may have troponin-I levels less than about 0.3, 0.2, 0.15, or 0.1 µg/ml before administration of the viral vector. In some embodiments, patients may have troponin-I levels less than about 0.176 µg/ml before administration of the viral vector. In some embodiments, patients may have troponin-I levels above about 0.176 µg/ml after administration of the viral vector. In some embodiments, patients receive cardiac monitoring after administration of the viral vector until troponin-I levels are less than about 0.176 µg/ml.

Aspartate transaminase (AST) and alanine aminotransferase (ALT) and total bilirubin are a general measure of hepatic function, while creatinine tracks renal function. Elevated levels of AST, ALT or total bilirubin may indicate hepatic malfunction. In some embodiments, the patient has normal hepatic function prior to administration of the viral vector. In some embodiments, the patient has hepatic transaminase levels less than about 8-40 U/L prior to administration of the viral vector. In some embodiments, the patient has AST or ALT levels less than about 8-40 U/L prior to administration of the viral vector. In some embodiments, the patient has bilirubin levels less than 3.0 mg/dL prior to administration of the viral vector. In some embodiments, patients have creatinine levels less than 1.8 mg/dL prior to administration of the viral vector. In some embodiments, patients have hemoglobin (Hgb) levels between 8-18 g/dL prior to administration of the viral vector. In some embodiments, the patient has white blood cell (WBC) counts less than 20000 per mm$^3$ prior to administration of the viral vector.

The efficacy of the treatment method may be determined using a variety of tests for motor skills before and after treatment. In particular, the Children's Hospital of Philadelphia Infant Test of Neuromuscular Disorders (CHOP INTEND) was developed to evaluate the motor skills of patients with type I SMA. Glanzman et al., "The Children's Hospital of Philadelphia Infant Test of Neuromuscular Disorders (CHOP INTEND): Test development and reliability." *Neuromuscular Disorders,* 20(3):155-161. The CHOP INTEND test was developed following the evaluation of 26 infants with Type I SMA, mean age 11.5 months (1.4-37.9 months) with the Test of Infant Motor Performance (TIMP) and The Children's Hospital of Philadelphia Test of Strength in SMA (CHOP TOSS), a newly devised motor assessment for SMA. Testing of treating efficacy is not limited to the CHOP INTEND test, but may also include other motor skills tests known in the art, including but not limited to TIMP, CHOP TOSS, the Peabody Development Motor Scales, the Brazelton Neonatal Behavior Assessment test, Motor Milestone Development Survey, Ability Captured Through Interactive Video Evaluation (ACTIVE), the Bayley Scale of Infant Development and measurements of compound motor action potentials (CMAP).

In some embodiments, baseline testing before treatment is performed using the CHOP INTEND scale. In one embodiment, the efficacy of treatment is determined using the CHOP INTEND scale during follow up visits. In some embodiments, the CHOP INTEND includes measures of head control, righting reactions, trunk movements in supported sitting, supine and prone positions. In some embodiments, the CHOP INTEND includes measures of anti-gravity movements in assisted rolling, ventral suspension and supported standing.

In many gene therapy studies involving AAV vectors, an antigen specific T-cell response to the AAV vector has been observed, and may be expected between 2-4 weeks following gene transfer. One possible consequence to such antigen specific T-cell response is clearance of the transduced cells and loss of transgene expression. In an attempt to dampen the host immune response to the AAV based therapy, patients may be given immune suppressants. In some embodiments, patients may be given glucocorticoids before administration of viral vector. In some embodiments, patients may be given a corticosteroid before administration of viral vector. In some embodiments, patients may be given an oral steroid before administration of viral vector. Examples of oral steroids include but are not limited to prednisone, prednisolone, methylprednisolone, triamcinolone, bethamethasone, dexamethasone and hydrocortisone. In some embodiments, the oral steroid is or comprises prednisolone. In some embodiments, the patient is started on prophylactic steroid at least 24 hours prior to administering the viral vector. In some embodiments, the patient is given oral steroid for at least 30 days after administering the viral vector. In some embodiments, the oral steroid is administered once daily. In some embodiments, the oral steroid is administered twice daily. In some embodiments, the oral steroid is given at a dose of about 0.1-10 mg/kg, e.g., about 1 mg/kg. In some embodiments, the oral steroid is given at a dose of about 0.1-10 mg/kg/day, e.g., about 1 mg/kg/day. In some embodiments, the levels of AST and ALT are monitored after administration of the viral vector. In such embodiments, the oral steroid treatment is administered when AST and ALT levels exceed twice the upper limit of normal, e.g., as determined by clinical standards and methods known in the art, or about 120 IU/L. In some embodiments, the oral steroid treatment is administered for more than 30 days as long as AST and ALT levels exceed twice the upper limit of normal, e.g., as determined by clinical standards and methods known in the art, or exceed about 120 IU/L. During sustained treatment with corticosteroids, the adrenal glands naturally decrease production of cortisol. If corticosteroid treatment is stopped abruptly, the body may experience cortisol deficiency. In some embodiments where oral steroid is given to a patient for at least 30 days, the steroid dose is slowly tapered on a schedule. In some embodiments, the oral steroid dose is tapered when AST and ALT levels fall below twice the upper limit of normal, e.g., as determined by clinical standards and methods known in the art, or about 120 IU/L. In some embodiments, tapering comprises stepped decrements to 0.5 mg/kg/day for 2 weeks followed by 0.25 mg/kg/day for 2 more weeks. In some other embodiments, tapering of the oral steroid occurs at the discretion of the doctor.

Kits

In one embodiment, provided herein is a kit comprising:
a. a plurality of cells capable of being transduced with a viral vector;
b. a viral vector encoding protein of interest;
c. a first molecule capable of binding the protein of interest;
d. a second molecule capable of binding the first molecule, wherein the second molecule comprises a detectable label; and,
e. instructions for use in an imaging assay.

In some embodiments of the kits of the disclosure, the plurality of cells comprise neural progenitor cells under the SMN1-/- genetic background (mTD-NPC-?7).

In some embodiments, the viral vector drug product is an adeno-associated virus serotype 9 (AAV9) comprising a cDNA expressing SMN1 protein under the control of the cytomegalovirus (CMV) enhancer/chicken-beta-actin-hybrid promoter (CB), and two AAV inverted terminal repeats (ITR) from the AAV serotype 2 (AAV2) DNA. In some embodiments, the vector comprises a sequence of SEQ ID NO: 2. In some embodiments, the vector comprises a sequence of SEQ ID NO: 1. In some embodiments, the vector comprises sequence encoding a SMN1 protein comprising an amino acid sequence of SEQ ID NO: 3.

In some embodiments, the first molecule comprises an anti-SMN1 antibody. Exemplary antibodies comprise mouse monoclonal antibody 2B1 antibodies.

In some embodiments, the second molecule comprises an antibody specific for said first molecule. In some embodiments, second molecule comprises a detectable label.

It must also be noted that, as used in this disclosure and the appended claims, the singular forms "a", "an", and "the" include plural referents unless the context clearly dictates otherwise. Optional or optionally means that the subsequently described event or circumstance can or cannot occur, and that the description includes instances where the event or circumstance occurs and instances where it does not. For example, the phrase optionally the composition can comprise a combination means that the composition may comprise a combination of different molecules or may not include a combination such that the description includes both the combination and the absence of the combination (i.e., individual members of the combination). Ranges may be expressed herein as from about one particular value, and/or to about another particular value. When such a range is expressed, another aspect includes from the one particular value and/or to the other particular value. Similarly, when values are expressed as approximations, by use of the antecedent about, it will be understood that the particular value forms another aspect. It will be further understood that the endpoints of each of the ranges are significant both in relation to the other endpoint, and independently of the other endpoint. All references cited in this disclosure are hereby incorporated herein in their entirety.

The present invention will now be illustrated by the following examples. It is to be understood that the foregoing are for exemplary purposes only and are not intended to limit the scope of the invention. One skilled in the art can appreciate that modification may be made without departing from the spirit or scope of the present invention as set forth in the claims.

ENUMERATED EMBODIMENTS

The invention can be understood by reference to the following enumerated embodiments:

1. A method for measuring transgene expression, comprising:
   a) providing a first plurality of terminally differentiated neural progenitor cells (NPCs);
   b) transducing the first plurality of terminally differentiated NPCs with a test sample comprising a viral vector comprising a sequence encoding a protein of interest;
   c) incubating the transduced first plurality of terminally differentiated NPCs under conditions sufficient to express the protein of interest;
   d) contacting the first plurality of terminally differentiated NPCs from (c) with a molecule specific for the protein of interest;
   e) imaging the first plurality of terminally differentiated NPCs to obtain an integrated fluorescent intensity per cell (IFI-C) assay readout; and
   f) determining the expression of the protein of interest based on the IFI-C readout.

2. The method of embodiment 1, wherein the first plurality of terminally differentiated NPCs are homozygous for a Survival Motor Neuron (SMN1)−/− mutation.

3. The method of embodiment 2, wherein the SMN1−/− mutation comprises a deletion of SMN1 exon 7 (Δ7).

4. The method of any one of embodiments 1-3, wherein the incubating step c) is followed by fixing and permeabilizing the first plurality of terminally differentiated NPCs.

5. The method of any one of embodiment 1-4, comprising:
   g) providing a second plurality of terminally differentiated NPCs;
   h) transducing the second plurality of terminally differentiated NPCs with a reference standard comprising the viral vector;
   i) incubating the transduced second plurality of terminally differentiated NPCs under conditions sufficient to express the protein of interest;
   j) contacting the second plurality of terminally differentiated NPCs from (i) with a molecule specific for the protein of interest;
   k) imaging the second plurality of terminally differentiated NPCs to obtain an integrated fluorescent intensity per cell (IFI-C) assay readout; and
   l) comparing the IFI-C of the first plurality of terminally differentiated NPCs with the IFI-C of the second plurality of terminally differentiated NPCs;
thereby determining the relative potency of the viral vector of the test sample relative to the reference standard.

6. The method of embodiment 5, wherein the second plurality of terminally differentiated NPCs are homozygous for a SMN1−/− mutation.

7. The method of embodiment 6, wherein the SMN1−/− mutation comprises a deletion of SMN1 exon 7 (Δ7).

8. The method of embodiment 4 or 5, wherein the incubating step (i) is followed by fixing and permeabilizing the second plurality of terminally differentiated NPCs.

9. The method of any one of embodiments 1-8, wherein said first and second pluralities of terminally differentiated NPCs are produced by terminally differentiating neural progenitor cells isolated from the cortex of an SMN1−/− mouse embryo.

10. The method of embodiment 9, wherein the neural progenitor cells (NPCs) were terminally differentiated by
   a. culturing the NPCs in serum free culture media containing Epidermal Growth Factor (EGF) and Fibroblast Growth Factor-basic (bFGF) to form neurospheres;
   b. dissociating said neurospheres to produce dissociated NPCs; and
   c. culturing the dissociated NPCs in serum-enriched media without growth factors;
thereby producing terminally differentiated NPCs.

11. The method of any one of embodiments 1-10, wherein said first and second pluralities of cells are transduced by the test sample and the reference standard at at least two different multiplicities of infection (MOI) of the viral vector.

12. The method of embodiment 11, wherein said first and second pluralities of cells are transduced at 5 different MOI of the viral vector in the test sample and reference standard.

13. The method of embodiment 12, wherein the 5 MOIs comprise 300,000, 150,000, 75,000, 37,500, 18,750 viral particles per cell.

14. The method of any one of embodiments 5-13, wherein the comparing step (l) comprises plotting a standard curve of MOI versus IFI-C for each of the test sample and the reference standard.

15. The method of any one of embodiments 5-14, wherein the comparing step (l) comprises calculating a linear regression of log MOI versus IFI-C for each of the test sample and the reference standard, thereby deriving a test sample slope and a reference standard slope.

16. The method of any one of embodiments 5-15, wherein determining the relative potency of the viral vector is performed by parallel line analysis (PLA), and wherein the PLA comprises measuring a slope ratio of the test sample slope against the reference standard slope.

17. The method of embodiment 16, wherein the reference standard slope is greater than or equal to 1.02E+05.

18. The method of embodiment 16 or 17, wherein the slope ratio is between 0.69-1.45.

19. The method of embodiment 16 or 17, wherein the slope ratio is between 0.75 and 1.33.

20. The method of any one of embodiments 16-19, comprising calculating a coefficient of variance of the linear regression of the sample.

21. The method of embodiment 20, wherein the coefficient of variance is between 15.6% and 29.5%.

22. The method of embodiment 20, wherein the coefficient of variance is less than or equal to 40%, less than or equal to 30%, or less than or equal to 20%.

23. The method of any one of embodiments 16-22, comprising calculating an R2 value for the linear regression of the test sample and the reference standard.

24. The method of embodiment 23, wherein the R2 value for the test sample and the reference standard is greater than or equal to 0.95.

25. The method of any one of embodiments 16-24, comprising calculating an assay dynamic window of the reference standard.

26. The method of embodiment 25, wherein the assay dynamic window is greater than or equal to 2.69.

27. The method of any one of embodiments 1-26, wherein the protein of interest is a survival motor neuron (SMN1) protein.

28. The method of embodiment 27, wherein the SMN1 protein comprises an amino acid sequence of SEQ ID NO: 3.

29. The method of embodiment 27 or 28, wherein the viral vector is an adeno-associated virus serotype 9 (AAV9).

30. The method of any one of embodiments 27-29, wherein the viral vector comprises a sequence encoding cytomegalovirus (CMV) enhancer/chicken-β-actin-hybrid promoter (CB) operably linked to the sequence encoding the SMN1 protein.

31. The method of any one of embodiments 27-30, wherein the viral vector comprises AAV inverted terminal repeats (ITR) from the AAV serotype 2 (AAV2) DNA.

32. The method of any one of embodiments 27-31, wherein the viral vector comprises a sequence of SEQ ID NO: 1.

33. The method of any one of embodiments 1-32, wherein the cells are passaged 8 to 15 times prior to transduction with the viral vector.

34. The method of any one of embodiments 1-33, wherein the IFI-C readout reflects a measurement of protein expression.

35. The method of any one of embodiments 1-34, wherein the step of incubating the terminally differentiated NPCs following transduction is performed for about 69-75 hrs.

36. The method of any one of embodiments 1-35, wherein the molecule that is specific for the protein of interest comprises an antibody, an antibody fragment, or an aptamer.

37. The method of embodiment 36, wherein the antibody comprises an antibody specific for the protein of interest.

38. The method of embodiment 37, wherein the anti-protein of interest antibody is provided at a concentration of about 4 µg/mL.

39. The method of embodiment 37, wherein the anti-protein of interest antibody is provided at a concentration of about 2 µg/mL.

40. The method of any one of embodiments 1-39, wherein the molecule comprises a detectable label.

41. The method of any one of embodiments 1-40, further comprising washing the terminally differentiated NPCs to remove the molecule specific for the protein of interest.

42. The method of any one of embodiments 1-38, further comprising contacting the terminally differentiated NPCs with a second molecule that specifically recognizes the molecule specific for the protein of interest.

43. The method of embodiment 42, wherein the second molecule comprises a detectable label.

44. The method of embodiment 42 or 43, wherein the second molecule comprises an antibody, an antibody fragment or an aptamer.

45. The method of any one of embodiments 1-44, wherein the terminally differentiated NPCs are contacted with an anti-nuclear detectable label following the fixing and permeabilizing step.

46. The method of any one of embodiments 1-45, wherein the terminally differentiated NPCs are on a solid surface.

47. The method of embodiment 46, wherein the solid surface is coated with Poly-D-Lysin.

48. The method of embodiments 46 or 47, wherein the terminally differentiated NPCs are seeded at a density of 20,000 cells per well.

49. The method of any one of embodiments 1-48, wherein the method allows a quantitative measurement of dose-dependent increase in the level of the protein of interest.

50. A kit comprising:
 a. a plurality of cells capable of being transduced with a viral vector;
 b. a viral vector encoding protein of interest;
 c. a first molecule capable of binding the protein of interest;
 d. a second molecule capable of binding the first molecule, wherein the second molecule comprises a detectable label; and,
 e. instructions for use in an imaging assay.

51. The kit of embodiment 50, wherein the plurality of cells comprise neural progenitor cells (NPCs).

52. The kit of embodiment 51, wherein the NPCs are homozygous for an SMN1−/− mutation.

53. The kit of embodiment 51, wherein the SMN1−/− mutation is a deletion of exon 7 (Δ7).

54. The kit of any one of embodiments embodiment 50-53, wherein the viral vector is an adeno-associated virus serotype 9 (AAV9) comprising a cDNA expressing SMN1 protein under the control of the cytomegalovirus (CMV) enhancer/chicken-β-actin-hybrid promoter (CB), and two AAV inverted terminal repeats (ITR) from the AAV serotype 2 (AAV2) DNA.

55. The kit of any one of embodiments 50-54, wherein the first molecule comprises an anti-SMN1 antibody.

56. The kit of any one of embodiments 50-55, wherein the second molecule comprises an antibody specific for said first molecule.

57. The kit of embodiment 56, wherein the second molecule comprises a detectable label.

58. The kit of any one of embodiments 50-57, wherein the protein of interest is a Survival Motor Neuron (SMN1) protein.

59. A method of producing a pharmaceutical composition comprising a viral vector comprising a transgene, the method comprising:
   a. producing the viral vector comprising the transgene;
   b. assaying said viral vector according to the method for measuring the transgene of any one of embodiments 1-49; and
   c. formulating the viral vector comprising the transgene in a pharmaceutical composition.

60. The method of embodiment 59, wherein producing the viral vector comprises:
   a. culturing adherent cells;
   b. transfecting the adherent cells with plasmid(s) to enable production of the AAV viral vector;
   c. lysing the adherent cells to isolate the AAV viral vector;
   d. acidifying and clarifying the cell lysate of (c);
   e. purifying the product of (d) using cation exchange chromatography (CEX);
   f. filtering the product of (e) using tangential flow filtration (TFF);
   g. ultracentrifuging the product of (0 in a cesium chloride (CsCl) buffer; and
   h. collecting the AAV viral vectors from the product of (g).

61. The method of embodiment 60, wherein the AAV is AAV9.

62. The method of embodiment 60 or 61, wherein the AAV is self-complementary (scAAV).

63. The method of any one of embodiments 60-61, wherein the adherent cells are HEK293 cells.

64. The method of any one of embodiments 60-63, wherein the adherent cells are selected for adherence prior to culturing.

65. The method of any one of embodiments 60-64, wherein the selection comprises subculturing the adherent cells multiple times to select for adherence.

66. The method of any one of embodiments 60-65, wherein the adherent cells are seeded in a bioreactor for culturing.

67. The method of embodiment 66, wherein the bioreactor is a large-scale bioreactor that can provide continuous circulation of cell culture media.

68. The method of embodiments 66 or 67, wherein the bioreactor is a 200 m$^2$, a 333 m$^2$ or a 500 m$^2$ bioreactor.

69. The method of any one of embodiments 66-68, wherein the adherent cells are added to media in a recirculation media bag and circulated through the bioreactor.

70. The method of embodiment 69, wherein the cells are circulated using a peristaltic pump.

71. The method of embodiment 70, wherein the peristaltic pumping is continuous while the adherent cells are seeded in a bioreactor for culturing.

72. The method of embodiment 71, wherein the seeding density is about 8,000-12,000 cells/cm$^2$.

73. The method of any one of embodiments 60-72, wherein the transfection step comprises adding a transfection medium to the recirculation media bag and circulating the transfection medium through the bioreactor.

74. The method of embodiment 73, wherein the transfection medium is circulated using a peristaltic pump.

75. The method of embodiment 73 or 74, wherein the circulating occurs between 15-25° C.

76. The method of any one of embodiments 60-75, wherein the transfection step comprises contacting the adherent cell with an adenovirus helper plasmid (pHELP).

77. The method of any one of embodiments 60-76, wherein the transfection step comprises contacting the adherent cell with a plasmid encoding an AAV rep gene.

78. The method of any one of embodiments 60-77, wherein the transfecting step comprises contacting the adherent cell with a plasmid encoding an AAV cap gene.

79. The method of any one of embodiments 60-78, wherein the transfection step comprises contacting the adherent cell with a plasmid encoding an AAV rep gene and an AAV cap gene on the same plasmid (pAAV).

80. The method of embodiment 77 or embodiment 79, wherein the AAV rep gene is rep2.

81. The method of embodiment 78 or 79, wherein the AAV cap gene is cap9.

82. The method of any one of embodiments 60-81, wherein the transfection step comprises contacting the adherent cell with the transfection agent polyethylenimine (PEI).

83. The method of embodiment 82, wherein the ratio of PEI to at least one of the plasmids is less than 1:1 by weight.

84. The method of embodiment 82, wherein the ratio of PEI to at least one of the plasmids is about 1:1 by weight.

85. The method of any one of embodiments 73-84, wherein the transfection step comprises contacting the adherent cell with a transfection medium that does not contain serum.

86. The method of any one of embodiments 60-85, wherein the transfection step comprises contacting the adherent cell with a transfection medium that does not contain calcium.

87. The method of any one of embodiments 60-86, wherein the transfecting step comprises contacting the adherent cell with a transfection medium that does not contain glutamine.

88. The method of any one of embodiments 60-87, wherein the transfecting step is performed for 10-60 minutes, 10-30 minutes, 20-30 minutes, 15-30 minutes or for less than 30 minutes.

89. The method of any one of embodiments 60-88, wherein the lysing step comprises total cell lysis.

90. The method of any one of embodiments 60-89, wherein the lysing step comprises using a lysis buffer supplemented with an endonuclease.

91. The method of embodiment 90, wherein the endonuclease is benzonase.

92. The method of any one of embodiments 60-91, wherein the lysing step comprises using a lysis buffer supplemented with TWEEN.

93. The method of any one of embodiments 60-92, wherein the lysing step is performed between 15-25° C.

94. The method of any one of embodiments 60-93, further comprising freezing the cell lysate of step (c) prior to the acidification step of (d).

95. The method of any one of embodiments 60-94, wherein the CsCl buffer is a 2-4M CsCl buffer.

96. The method of any one of embodiments 60-94, wherein the CsCl is at a concentration of about 3 M.

97. The method of any one of embodiments 60-96, further comprising (i) filtering the product of (g) through tangential flow filtration.

98. The method of any one of embodiments 60-98, wherein the acidification step comprises acidifying the cell lysate to a pH of about 3.0-4.0, about 3.3-3.7, or about 3.4-3.6.

99. The method of embodiment 98, wherein the acidification step comprises acidifying the cell lysate to a pH of about 3.5.

100. The method of any one of embodiments 60-99, wherein the ultracentrifugation is performed between about 40,000-50,000 rpm or between about 43,000-46,000 rpm.

101. The method of any one of embodiments 60-100, wherein the ultracentrifugation is performed between 15-25° C.
102. The method of any one of embodiments 60-101, wherein the ultracentrifugation is performed for 16-24 hours or for 20-24 hours.
103. The method of any one of embodiments 60-102, wherein the cell lysate is incubated with Tween prior to the acidification step.
104. The method of any one of embodiments 60-103, wherein the cell lysate is incubated with Tween for about 8-20 hours prior to the acidification step.
105. The method of any one of embodiments 60-104, wherein the clarification step comprises filtering the cell lysate through a depth filter.
106. The method of any one of embodiments 60-105, wherein the clarification step comprises filtering the cell lysate through a 0.45 micron filter.
107. The method of any one of embodiments 60-106, wherein the CEX comprises a sulfonyl resin.
108. The method of any one of embodiments 60-107, wherein at least one TFF step comprises using cellulose membranes with a molecular weight cutoff of 300 kDa MW.
109. The method of any one of embodiments 60-108, wherein the TFF step reduces the eluate volume of the cation exchange step by at least six-fold.
110. The method of any one of embodiments 60-109, wherein the CsCl buffer comprises Tris, MgCl2, and Poloxamer 188.
111. The method of embodiment 110, wherein the CsCl buffer comprises about 20 mM Tris. 112. The method of embodiment 110 or 111, wherein the CsCl buffer comprises about 2 mM MgCl2.
113. The method of any one of embodiments 110-112, wherein the CsCl buffer comprises Poloxamer 188, optionally about 0.2% w/v Poloxamer 188.
114. The method of any one of embodiments 60-113, wherein the CsCl buffer is between about pH 7.5-8.5 or between about pH 7.9-8.2.
115. The method of any one of embodiments 60-114, wherein the number of empty viral capsid is less than 7%, less than 5%, less than 3% or less than 1% of the total viral capsids after collecting the AAV viral vectors from the ultracentrifuged cell lysate.
116. The method of embodiment 115, wherein the number of empty viral capsid is measured by analytical ultracentrifugation (AUC).
117. The method of any one of embodiments 60-116, wherein the AAV viral vectors are collected from the ultracentrifuged cell lysate using a syringe.
118. The method of any one of embodiments 60-117, wherein the AAV viral vectors collected after the second TFF step are stored in a solution comprising Tris, MgCl2, NaCl, and Poloxamer 188.
119. The method of embodiment 118, wherein the solution comprises about 20 mM Tris.
120. The method of embodiment 118 or 119, wherein the solution comprises about 1 mM MgCl2.
121. The method of any one of embodiments 118-120, wherein the solution comprises about 200 mM NaCl.
122. The method of any one of embodiments 118-121, wherein the solution comprises about 0.005% w/v Poloxamer 188.
123. The method of any one of embodiments 118-122, wherein the solution is between about pH 7.5-8.5 or between about pH 7.7-8.3.
124. The method of any one of embodiments 60-123, wherein the AAV viral vectors collected after the second TFF contain less than about 30 μg/g or less than about 20 μg/g of CsCl.
125. The method of any one of embodiments 60-124, wherein the concentration of AAV viral vectors collected after the second TFF is greater than or equal to about $3\times10^{13}$ vg/ml.
126. The method of any one of embodiments 60-125, wherein host cell proteins and/or host cell DNA are removed from the cell lysate using flocculation with a detergent.
127. The method of any one of embodiments 60-120, wherein the AAV viral vector comprises a polynucleotide encoding a survival motor neuron (SMN) protein.
128. The method of any one of embodiments 76-127, wherein the plasmid encoding the SMN protein, the plasmid encoding the pAAV, and the plasmid encoding the pHELP are transfected at a ratio of 1:1:1.
129. The method of any one of embodiments 60-128 wherein the pharmaceutical composition comprises:
   a. between $1-8\times10^{13}$ AAV9 viral vector genomes/mL (vg/mL);
   b. less than about 7% empty viral capsids;
   c. less than about 100 ng/mL host cell protein per $1\times10^{13}$ vg/mL;
   d. less than about $5\times10^{6}$ μg/mL residual host cell DNA per $1\times10^{13}$ vg/mL; and
   wherein at least about 80% of the $1-8\times10^{13}$ AAV9 viral vector genomes/mL are functional.
130. The method of embodiment 129, wherein the pharmaceutical composition comprises between $1.7-2.3\times10^{13}$ AAV9 vg/mL or between $1.9-2.1\times10^{13}$ AAV9 vg/mL.
131. The method of embodiment 129, wherein the pharmaceutical composition comprises about $2\times10^{13}$ AAV9 vg/mL.
132. The method of any one of embodiments 129-131, wherein the pharmaceutical composition comprises comprising less than about 5% empty capsids, less than about 3% empty capsids or less than about 1% empty capsids.
133. The method of any one of embodiments 129-132, wherein the pharmaceutical composition comprises or consists of $1-2\times10^{14}$ vg of the AAV9 viral vector or $1.1\times10^{14}$ vg of the AAV9 viral vector.
134. The method of any one of embodiments 129-132, wherein the pharmaceutical composition consists of $1.7\times10^{14}$ vg of the AAV9 viral vector.
135. The method of any one of embodiments 129-134, wherein the pharmaceutical composition is an aqueous pharmaceutical formulation.
136. The method of embodiment 135, wherein the formulation comprises a Tris buffer, magnesium chloride, sodium chloride, and a poloxamer, and wherein the pharmaceutical composition does not comprise a preservative.
137. The method of embodiment 136, wherein the poloxamer comprises poloxamer 188.
138. The method of any one of embodiments 135-137, wherein the pH of the formulation is about 7.7 to about 8.3.
139. The method of embodiment 138, wherein the pH is about pH 8.0.
140. The method of any one of embodiments 136-139, wherein the magnesium chloride concentration is about 0.5-1.5 mM.
141. The method of embodiment 140, wherein the magnesium chloride concentration is about 1 mM.
142. The method of any one of embodiments 136-141, wherein the sodium chloride concentration is about 100-300 mM.

143. The method of embodiment 142, wherein the sodium chloride concentration is about 200 mM.

144. The method of any one of embodiments 136-143, wherein the formulation comprises about 0.005% w/v poloxamer 188.

145. The method of any one of embodiments 136-144, wherein the formulation has an osmolality of 390-430 mOsm/kg.

146. The method of any one of embodiments 60-145, wherein the pharmaceutical formulation comprises at least one of the following:
  a. less than about 0.09 ng of benzonase per $1.0 \times 10^{13}$ vg,
  b. less than about 30 µg/g (ppm) of cesium,
  c. about 20-80 ppm of Poloxamer 188,
  d. less than about 0.22 ng of BSA per $1.0 \times 10^{13}$ vg,
  e. less than about $6.8 \times 10^5$ pg of residual plasmid DNA per $1.0 \times 10^{13}$ vg,
  f. less than about $1.1 \times 10^5$ pg of residual hcDNA per $1.0 \times 10^{13}$ vg,
  g. less than about 4 ng of rHCP per $1.0 \times 10^{13}$ vg,
  h. about pH 7.7-8.3,
  i. about 390-430 mOsm/kg,
  j. less than about 600 particles that are ≥25 µm in size per container,
  k. less than about 6000 particles that are ≥10 µm in size per container,
  l. about $1.7 \times 1013$-$2.3 \times 10^{13}$ vg/mL genomic titer,
  m. infectious titer of about $3.9 \times 10^8$-$8.4 \times 10^{10}$ IU per $1.0 \times 10^{13}$ vg,
  n. total protein of about 100-300 µg per $1.0 \times 10^{13}$ vg,
  o. relative potency of about 70-130%, and
  p. less than about 5% empty capsid.

147. The method of any one of embodiments 60-145, wherein the pharmaceutical formulation comprises at least one of the following:
  a. about pH 7.7-8.3,
  b. about 390-430 mOsm/kg,
  c. less than about 600 particles that are ≥25 µm in size per container,
  d. less than about 6000 particles that are ≥10 µm in size per container,
  e. about $1.7 \times 10^{13}$-$2.3 \times 10^{13}$ vg/mL genomic titer,
  f. infectious titer of about $3.9 \times 10^8$-$8.4 \times 10^{10}$ IU per $1.0 \times 10^{13}$ vg,
  g. total protein of about 100-300 µg per $1.0 \times 10^{13}$ vg,
  h. Pluronic F-68 content of about 20-80 ppm,
  i. relative potency of about 70-130%,
  j. median survival in a delta7SMN mouse model greater than or equal to 24 days, at a dose of $7.5 \times 10^{13}$ vg/kg,
  k. less than about 5% empty capsid,
  l. and a total purity of greater than or equal to about 95%, and
  m. less than or equal to about 0.75 EU/mL Endotoxin.

148. The method of any one of embodiments 60-145, wherein the pharmaceutical formulation comprises at least one of the following:
  a. less than about 0.09 ng of benzonase per $1.0 \times 10^{13}$ vg,
  b. less than about 30 µg/g (ppm) of cesium,
  c. about 20-80 ppm of Poloxamer 188,
  d. less than about 0.22 ng of BSA per $1.0 \times 10^{13}$ vg,
  e. less than about $6.8 \times 105$ pg of residual plasmid DNA per $1.0 \times 10^{13}$ vg,
  f. less than about $1.1 \times 10^5$ pg of residual hcDNA per $1.0 \times 10^{13}$ vg, and
  g. less than about 4 ng of rHCP per $1.0 \times 10^{13}$ vg.

149. The method of any one of embodiments 59-148, wherein the relative potency of the viral vector is at least 40%, at least 50%, at least 60%, at least 70%, at least 80%, at least 90%, at least 91%, at least 92%, at least 93%, at least 94%, at least 95%, at least 96%, at least 97%, at least 98%, at least 99%, at least 99.5%, at least 99.9%, at least 100%, at least 110%, at least 120%, at least 130% or at least 140% relative to a reference standard.

150. The method of any one of embodiments 59-148, wherein the relative potency of the viral vector is at least 90% relative to the reference standard.

151. The method of any one of embodiments 59-148, wherein the potency of the viral vector in the pharmaceutical formulation is within 5% of the potency of the reference standard, within 10% of the potency of the reference standard, or within 20% of the potency of the reference standard.

152. A method of treating a patient in nee d thereof with a therapy comprising a viral vector comprising a transgene, the method comprising:
  a. assaying said viral vector comprising a transgene according to the method of measuring transgene expression for any one of embodiments 1-49; and
  b. administering the viral vector comprising a transgene to said patient.

153. The method of embodiment 152, wherein the viral vector is formulated in a pharmaceutical composition.

154. The method of embodiment 146, wherein the pharmaceutical composition comprises:
  a. between $1$-$8 \times 10^{13}$ AAV9 viral vector genomes/mL (vg/mL);
  b. less than about 7% empty viral capsids;
  c. less than about 100 ng/mL host cell protein per $1 \times 10^{13}$ vg/mL; and
  d. less than about $5 \times 10^6$ µg/mL residual host cell DNA per $1 \times 10^{13}$ vg/mL;
  wherein at least about 80% of the $1$-$8 \times 10^{1^t}$ AAV9 viral vector genomes/mL are functional.

155. The method of any one of embodiments 152-154, wherein the patient in need thereof has SMA, e.g., type I spinal muscular atrophy (SMA).

156. The method of embodiment 155, wherein the in a patient in need thereof:
  a. is two years or younger, optionally, nine months old or younger;
  b. has a body weight of at least about 2.6 kg;
  c. has bi-allelic SMN1 null mutations or deletions; and
  d. has at least one functional copy of SMN2.

157. The method of any one of embodiments 153-156, wherein the composition is administered to the patient by an intrathecal or intravenous route.

158. The method of any one of embodiments 152-157, wherein the viral vector is administered at a dose of about $1$-$2.5 \times 10^{14}$ vg/kg.

159. The method of any one of embodiments 152-157, wherein the viral vector is administered at a dose of about $1.1 \times 10^{14}$ vg/kg.

160. The method of embodiments 158 or 159, wherein the amount of viral vector genome is measured using ddPCR.

161. The method of any one of embodiments 155-160, wherein the patient has a body weight of no more than about 13.5 kg, optionally no more than about 8.5 kg.

162. The method of any one of embodiments 155-161, wherein the patient does not have a c.859G>C substitution in exon 7 of at least one copy of the SMN2 gene.

163. The method of any one of embodiments 155-162, wherein the treatment is administered to the patient before the age of 2 years, optionally before the age of 6 months.

164. The method of any one of embodiments 155-163, wherein the treatment is administered to the patient before the onset of one or more SMA symptoms selected from hypotonia, delay in motor skills, poor head control, round shoulder posture and hypermobility of joints.

165. The method of any one of embodiments 155-164, wherein the patient has anti-AAV9 antibody titers at or below 1:100 or 1:50 as determined by an ELISA binding immunoassay prior to administration.

166. The method of any one of embodiments 155-164, wherein the patient has anti-AAV9 titers above 1:100 as determined by an ELISA binding immunoassay after administration and is monitored for about 1-8 weeks or until titers decrease to below 1:100.

167. The method of any one of embodiments 155-164, wherein the patient has anti-AAV9 titers above 1:100 as determined by an ELISA binding immunoassay after administration and is monitored for about 1-8 weeks or until titers decrease to below 1:50.

168. The method of any one of embodiments 155-164, wherein the patient has anti-AAV9 titers above 1:100 as determined by an ELISA binding immunoassay before or after administration and is switched to formula feeding.

169. The method of embodiment 168, wherein the patient is switched to formula feeding prior to or after administration.

170. The method of any one of embodiments 155-164, wherein the patient has anti-AAV9 titers above 1:50 as determined by an ELISA binding immunoassay before or after administration and is switched to formula feeding.

171. The method of embodiment 170, wherein the patient is switched to formula feeding prior to or after administration.

172. The method of any one of embodiments 155-171, wherein the patient has anti-AAV9 titers above 1:100 or above 1:50 as determined by an ELISA binding immunoassay after administration and is treated using plasmapheresis.

173. The method of any one of embodiments 155-172, wherein the patient has platelet counts above about 67,000 cells/ml prior to administration or above about 100,000 cells/ml, or above about 150,000, cells/ml.

174. The method of any one of embodiments 155-173, wherein the patient has platelet counts below about 67,000 cells/ml after administration, or below about 100,000 cells/ml, or below about 150,000, cells/ml, and is monitored for about 1-8 weeks or until platelet counts increase to about 67,000 cells/ml, or above about 100,000 cells/ml, or above about 150,000, cells/ml.

175. The method of any one of embodiments 155-174, wherein the patient has platelet counts below about 67,000 cells/ml after administration and is treated with a platelet transfusion.

176. The method of any one of embodiments 155-175, wherein the patient does not have thrombocytopenia prior to administration.

177. The method of any one of embodiments 155-175, wherein the patient has thrombocytopenia after administration and is monitored for about 1-8 weeks or until the patient does not have thrombocytopenia.

178. The method of any one of embodiments 155-175, wherein the patient has thrombocytopenia after administration and is treated with a platelet transfusion.

179. The method of any one of embodiments 155-178, wherein the patient has troponin-I levels less than about 0.176 ug/ml before administration of the viral vector.

180. The method of any one of embodiments 155-179, wherein the levels of troponin-I in the patient is monitored after administration of the viral vector.

181. The method of embodiment 179 or embodiment 180, wherein monitoring is performed after administration until troponin-I levels in the patient are less than about 0.176 ug/ml.

182. The method of any one of embodiments 155-181, wherein the patient has normal hepatic function prior to administration.

183. The method of embodiment 182, wherein the patient has hepatic transaminase levels less than about 8-40 U/L prior to administration.

184. The method of embodiment 183, wherein the hepatic transaminase is selected from alanine transaminase (AST), aspartate transaminase (ALT), and a combination thereof 185. The method of any one of embodiments 155-184, wherein the patient has bilirubin levels less than 3.0 mg/dL, creatinine levels less than 1.8 mg/dL, Hgb levels between 8-18 g/dL, and/or white blood cell counts of less than about 20000 per mm3 prior to administration.

186. The method of any one of embodiments 155-185, wherein the viral vector is administered in a Tris-buffered saline.

187. The method of any one of embodiments 155-186, wherein the viral vector is administered in about 5-20 mL/kg, about 10-20 mL/kg, or about 5.5-6.5 mL/kg of Tris-buffered saline.

188. The method of any one of embodiments 155-187, wherein the viral vector is infused over about 45-75 minutes.

189. The method of any one of embodiments 155-188, wherein the viral vector is infused over about 60 minutes.

190. The method of embodiment 188 or embodiment 189, wherein the infusion comprises a syringe pump.

191. The method of any one of embodiments 155-189, wherein the patient is administered an oral steroid at least 24 hours before administering the viral vector.

192. The method of any one of embodiments 155-191, wherein the patient is administered an oral steroid for at least 30 days after administering the viral vector.

193. The method of embodiment 192, wherein the oral steroid is administered once daily.

194. The method of embodiment 193, wherein the oral steroid is administered twice daily.

195. The method of any one of embodiments 191-194, wherein the patient is monitored for elevated levels of ALT and/or AST after the administration of the viral vector, and wherein the oral steroid continues to be administered after 30 days until AST and/or ALT levels are below twice the upper limit of normal or below about 120 IU/L.

196. The method of any one of embodiments 191-195, wherein the patient is administered an oral steroid until AST and/or ALT levels are below twice the upper limit of normal or below about 120 IU/L.

197. The method of any one of embodiments 191-195, wherein the oral steroid is administered at a dose of about 1 mg/kg.

198. The method of any one of embodiments 191-197, further comprising tapering the oral steroid administration after AST and ALT are below twice the upper limit of normal or below about 120 IU/L.

199. The method of embodiment 198, wherein the tapering comprises stepped increments to 0.5 mg/kg/day for 2 weeks followed by 0.25 mg/kg/day for 2 more weeks.

200. The method of any one of embodiments 191-198, comprising administering the oral steroid for 30 days at a dose of about 1 mg/kg and then tapering down to 0.5 mg/kg/day for 2 weeks followed by 0.25 mg/kg/day for 2 more weeks.

201. The method of any one of embodiments 191-200, wherein the oral steroid is prednisolone or an equivalent.
202. The method of any one of embodiments 155-201, comprising administering a muscle enhancer or neuroprotector to the patient.
203. The method of any one of embodiments 155-202, comprising administering an antisense oligonucleotide targeting SMN to the patient.
204. The method of any one of embodiments 155-203, comprising administering nusinersen to the patient.
205. The method of any one of embodiments 155-204, comprising administering stamulumab to the patient.
206. The method of any one of embodiments 155-205, wherein efficacy is determined using the CHOP-INTEND scale.
207. The method of any one of 155-206, wherein the patient is with or without disease onset.
208. The method of any one of embodiments 155-207 comprising:
　a. determining the weight of the patient;
　b. obtaining a kit containing vials of an AAV9 viral vector pharmaceutical composition,
　　wherein the viral vector concentration in each vial is about $2.0 \times 10^{13}$ vg/mL; and
　　wherein the number and volume of the vials in the kit is selected from the group consisting of:
　　　2 vials at 7.9-8.8 mL of the composition per vial when the weight of the patient is 2.6 to 3 kg, 2 vials at 5.1 to 5.9 mL of the composition per vial and 1 vial at 7.9-8.8 mL of the composition per vial when the patient is between 3.1 and 3.5 kg, 1 vial at 5.1 to 5.9 mL of the composition per vial and 2 vials at 7.9-8.8 mL of the composition per vial when the patient is between 3.6 and 4.0 kg, 3 vials at 7.9-8.8 mL of the composition per vial when the patient is between 4.1 and 4.5 kg, 2 vials at 5.1 to 5.9 mL of the composition per vial and 2 vials at 7.9-8.8 mL of the composition per vial when the patient is between 4.6 and 5.0 kg, 1 vial at 5.1 to 5.9 mL of the composition per vial and 3 vials at 7.9-8.8 mL of the composition per vial when the patient is between 5.1 and 5.5 kg, 4 vials at 7.9-8.8 mL of the composition per vial when the patient is between 5.6 and 6.0 kg, 2 vials at 5.1 to 5.9 mL of the composition per vial and 3 vials at 7.9-8.8 mL of the composition per vial when the patient is between 6.1 and 6.5 kg, 1 vial at 5.1 to 5.9 mL of the composition per vial and 4 vials at 7.9-8.8 mL of the composition per vial when the patient is between 6.6 and 7.0 kg, 5 vials at 7.9-8.8 mL of the composition per vial when the patient is between 7.1 and 7.5 kg, 2 vials at 5.1 to 5.9 mL of the composition per vial and 4 vials at 7.9-8.8 mL of the composition per vial when the patient is between 7.6 and 8.0 kg, 1 vial at 5.1 to 5.9 mL of the composition per vial and 5 vials at 7.9-8.8 mL of the composition per vial when the patient is between 8.1 and 8.5 kg, 6 vials at 7.9-8.8 mL of the composition per vial when the patient is between 8.6 and 9.0 kg, 2 vials at 5.1 to 5.9 mL of the composition per vial and 5 vials at 7.9-8.8 mL of the composition per vial when the patient is between 9.1 and 9.5 kg, 1 vial at 5.1 to 5.9 mL of the composition per vial and 6 vials at 7.9-8.8 mL of the composition per vial when the patient is between 9.6 and 10.0 kg, 7 vials at 7.9-8.8 mL of the composition per vial when the patient is between 10.1 and 10.5 kg, 2 vials at 5.1 to 5.9 mL of the composition per vial and 6 vials at 7.9-8.8 mL of the composition per vial when the patient is between 10.6 and 11.0 kg, 1 vial at 5.1 to 5.9 mL of the composition per vial and 7 vials at 7.9-8.8 mL of the composition per vial when the patient is between 11.1 and 11.5 kg, 8 vials at 7.9-8.8 mL of the composition per vial when the patient is between 11.6 and 12.0 kg, 2 vials at 5.1 to 5.9 mL of the composition per vial and 7 vials at 7.9-8.8 mL of the composition per vial when the patient is between 12.1 and 12.5 kg, 1 vial at 5.1 to 5.9 mL of the composition per vial and 8 vials at 7.9-8.8 mL of the composition per vial when the patient is between 12.6 and 13.0 kg, and 9 vials at 7.9-8.8 mL of the composition per vial when the patient is between 13.1 and 13.5 kg; and c. administering the AAV9 viral vector from the vials to the patient.
209. The method of embodiment 208, wherein the AAV viral vector is administered by infusion at a dose of about $1.0 \times 10^{14}$-$2.5 \times 10^{14}$ vg/kg.
210. The method of 208 or 209, wherein the AAV viral vector is administered by infusion at a dose of about $1.1 \times 10^{14}$ vg/kg.
211. The method of embodiment 209 or 210 wherein the viral vector is infused over about 45-70 minutes.
212. The method of any one of embodiments 209-211, wherein the viral vector is infused over about 60 minutes.
213. The method of any one of embodiments 209-212, wherein the infusion comprises a syringe pump.
214. The method of any one of embodiments 209-213, wherein the amount of viral vector genome is measured using ddPCR.
215. The method of any one of embodiments 209-214, wherein a dose titer of AAV9 viral vector is measured by ddPCR.
216. The method of any one of embodiments 155-215, comprising administering a dose volume of: 16.5 mL when the patient weighs 2.6-3.0 kg, 19.3 mL when the patient weighs 3.1-3.5 kg, 22.0 mL when the patient weighs 3.6-4.0 kg, 24.8 mL when the patient weights 4.1-4.5 kg, 27.5 mL when the patient weighs 4.6-5.0 kg, 30.3 mL when the patient weighs 5.1-5.5 kg, 33.0 mL when the patient weighs 5.6-6.0 kg, 35.8 mL when the patient weighs 6.1-6.5 kg, 38.5 mL when the patient weighs 6.6-7.0 kg, 41.3 mL when the patient weighs 7.1-7.5 kg, 44.0 mL when the patient weighs 7.6-8.0 kg, 46.8 mL when the patient weighs 8.1-8.5 kg, 49.5 when the patient weighs 8.6-9.0 kg, 52.3 mL when the patient weighs 9.1-9.5 kg, 55.0 when the patient weighs 9.6-10.0 kg, 57.8 mL when the patient weighs 10.1-10.5 kg, 60.5 when the patient weighs 10.6-11.0 kg, 63.3 mL when the patient weighs 11.1-11.5 kg, 66.0 when the patient weighs 11.6-12.0 kg, 68.8 mL when the patient weighs 12.1-12.5 kg, 71.5 when the patient weighs 12.6-13.0 kg, and 74.3 mL when the patient weighs 13.1-13.5 kg.
217. The method of any one of embodiments 155-216, wherein the pharmaceutical composition comprises:
　a. a self-complementary AAV9 viral vector comprising a modified AAV2 ITR, a chicken beta-actin (CB) promoter, a cytomegalovirus (CMV) immediate/early enhancer, a modified SV40 late 16s intron, a sequence encoding an SMN1 polypeptide, a bovine growth hormone (BGH) polyadenylation signal, and an unmodified AAV2 ITR;
　b. 20 mM Tris at pH 8.0;
　c. 1 mM MgCl2;
　d. 200 mM NaCl; and
　e. 0.005% Poloxamer 188;
wherein the patient is less than 2 years old.

218. The method of embodiment 217, wherein the composition does not comprise a preservative.

219. The method of any one of embodiments 152-218, wherein the relative potency of the viral vector is at least 40%, at least 50%, at least 60%, at least 70%, at least 80%, at least 90%, at least 91%, at least 92%, at least 93%, at least 94%, at least 95%, at least 96%, at least 97%, at least 98%, at least 99%, at least 99.5%, at least 99.9%, at least 100%, at least 110%, at least 120%, at least 130% or at least 140% relative to a reference standard.

220. The method of any one of embodiments 152-218, wherein the relative potency of the viral vector is at least 90% relative to the reference standard.

221. The method of any one of embodiments 152-218, wherein the potency of the viral vector in the pharmaceutical formulation is within 5% of the potency of the reference standard, within 10% of the potency of the reference standard, or within 20% of the potency of the reference standard.

EXAMPLES

Example 1: Generation of Marine Delta 7 Cells

Purpose

This procedure describes the generation of cells lines and banks created from mouse primary neural progenitor cells (mNPCs) for use in the assay qualification, validation, release and stability testing of the manufactured, gene replacement drug material.

Scope

This specifically applies to the generation of mouse primary neural progenitor cell line defective in expressing SMN 1 protein derived from SMA delta 7 mouse with exon 7 deleted from SMN gene leading to Type I Spinal Muscular Atrophy (SMA) disease resembling human Type I SMA disease.

Procedure

Generation of Primary Neural Progenitor Cells (NPCs)

A pregnant delta 7 (+/−) mouse at embryology day 14±2 (E14±2) was given a lethal dose of isoflurane. After wiping with ethanol, the abdomen was opened with scissors and embryos were removed. The embryos were placed in a petri dish layered with cold Hanks balanced buffer saline solution (HBSS). Embryos were isolated one at a time by cutting with scissors, placing in a clean petri dish, and removing from amniotic sac with forceps.

The tail was removed and placed in an Eppendorf tube for genotyping. The cortex was separated from the brain and the meninges were removed as much as possible. The cortex was chopped into fine pieces and placed into a 15 mL conical tube with 14 mL of cold HBSS. These steps (in this paragraph) were repeated for each embryo, using clean tools to avoid contamination of DNA and cells.

The conical tubes containing the dissected tissue were centrifuged at 300 g for 5 minutes.

Isolation of Neural Progenitor Cells

Buffer solution was aspirated from each conical tube using a clean aspiration pipette between each tube. 200 µL of accumax was added to each sample and incubated at room temperature for 30 minutes as part of the cell dissociation process. 400 µL of complete media was then added to the individual sample and tissue was triturated by pipetting up and down to dissociate cells. This procedure was performed on each sample prior to moving to the next step.

An additional 400 µL of complete media was added to make total volume of 1 mL. The cells were filtered into a new 15 mL conical tube using 70 µm cell strainer.

Cells were counted using an automated cell counter by adding a volume of cells to a volume of Trypan Blue stain (or equivalent cell viability reagent depending on cell counter used) and adding the appropriate volume to a slide that is inserted into the automated cell counter.

The total volume of cells (1 mL) were added to 9 mL of complete media in individually labeled T-75 tissue culture flasks and placed in an incubator at 37° C., 5% $CO_2$. The mouse primary cells were directly isolated from the embryotic cortex of SMA delta 7 mouse and are designated as passage 0 (P0). To ensure that the cell line(s) from at least one dissected embryo is defective in expressing SMN1 protein due to its carrying 2 alleles of SMN 1 gene with its exon 7 deleted (delta 7), at least 4 embryos were collected and dissected. The cell line containing homozygote SMN1 (delta7) were confirmed by PCR genotyping per SOP-269. The cell lines continue to be passaged in parallel as described in Passaging section below until SMN 1 delta 7 genotype and proper cell growth is confirmed for one cell line. The rest of the cell lines are terminated and the selected cell line (SMN1 delta 7) continues to be passaged to generate the master cell bank(s) and working cell bank(s), as appropriate.

Passaging and Freezing Cells

Suggested Volumes:

| Flask | Surface Area (cm$^2$) | Total Volume Medium (mL) |
|---|---|---|
| T-75 | 75 | 10-15 |
| T-150 | 150 | 20-25 |
| T-175 | 175 | 25-40 |

Neurospheres

When the cells are ready for passaging (i.e., before the cells reached close to maximal recommended density), the flask was removed from the incubator and mixed well.

Cells were transferred from the flask to a 50 mL conical tube and were centrifuged for 5 minutes at 300 g. If a larger volume of cells in medium is collected, the time of centrifuging may be increased. For example, if 50 mL is collected, the cells may be centrifuged for 8 minutes at 300 g.

The supernatant was aspirated and 200 µL of accumax was added. The cell pellet was agitated and triturated one to three times, then incubated for 30 minutes at room temperature.

The accumax was then neutralized by adding 400 µL of complete growth media and the cells were triturated 10-15 times to dissociate to single cells.

An additional 400 µL of complete media was added to make a total volume of 1 mL. An additional volume of complete media could be added to dilute cells for ease of counting.

A small sample of the cells was removed to determine the total number of cells and the viability per above (using trypan blue and an automated cell counter). The derived cells were designated as passage 1 (P1).

The P1 cell suspension were diluted to 100,000 cells per mL and the appropriate volume was transferred (via pipette) into new cell culture vessels, and incubated at 37° C., 5% CO2.

The above passage steps were repeated and with each passage cycle one passage number was added to the previous passage.

Freezing Cells

Cells were microscopically examined for cell morphology, viability, density cell concentration), and microbial contamination, prior to freezing in cryogenic vials.

Cells were frozen in freezing medium and stored in cryogenic vials at in a cryopreservation container at a −80° C. freezer for 24-72 hours.

After initial freeze, the vials were transferred to a liquid nitrogen freezer.

Cell Banking

Master Cell Bank (MCB)

Figure 2:
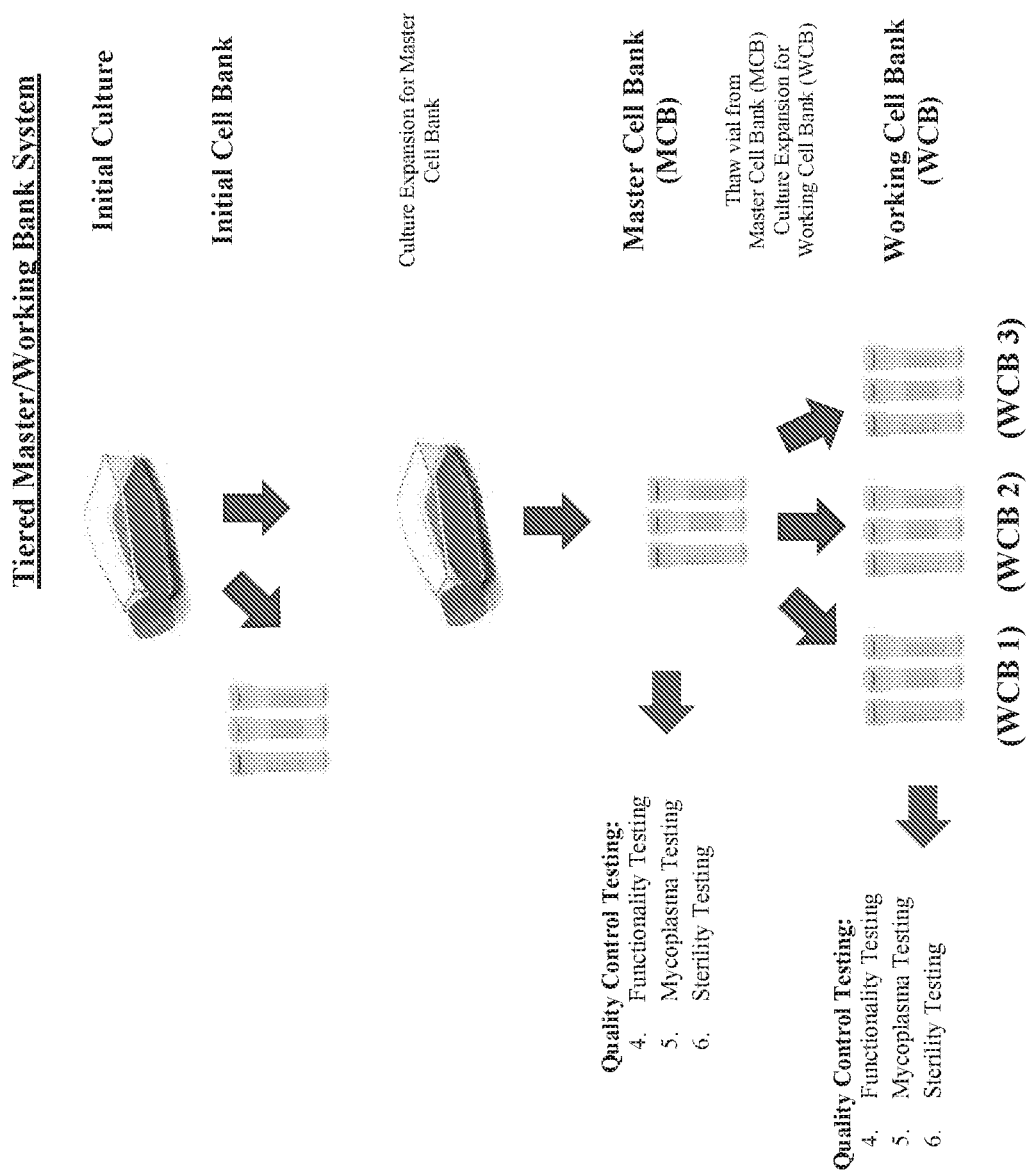
FIG. 2 illustrates tiered master/working bank system.
Figure 3A:
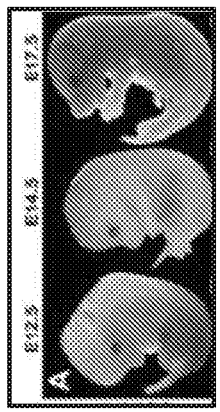
FIGS. 3A-3C illustrates terminal differentiation of NPCs derived from the embryonic cortex of SMN Δ7 mouse.
Figure 3B:
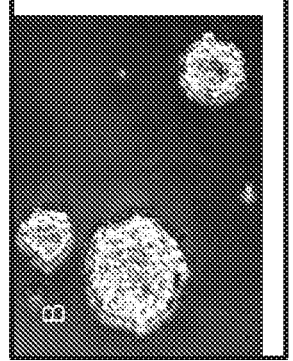
Figure 3C:
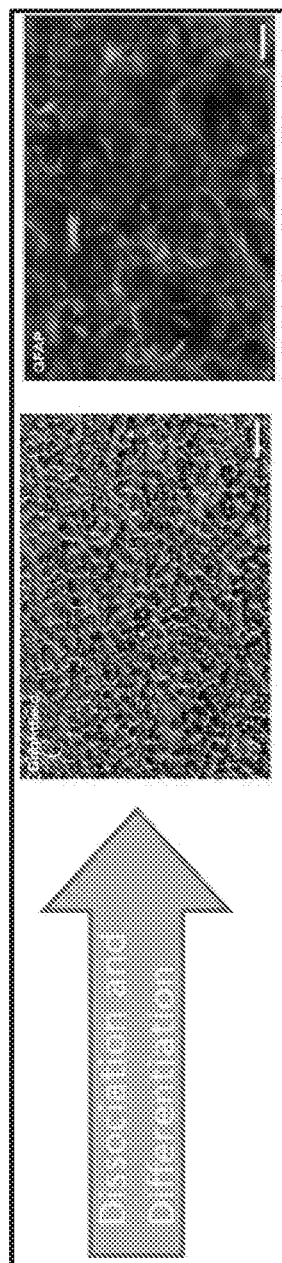

A Master Cell Bank (MCB) was created from expansion of cells from the initial source and after quality control (QC) testing, the expansion was continued from the initial source that was used to make master cell bank and was expanded to establish a working cell bank (see FIG. 1-FIG. 2).

A small portion of the Master Cell Bank and Working Cell Banks were segregated and maintained in a location remote from all other material. The cells may be frozen and then thawed and passaged for use as needed for the assay disclosed herein.

Example 2: Method Development of a Robust Quantitative Relative Potency Cell-Based Assay Materials and Methods Isolation and Passaging of Neural Progenitor Cells (NPCs)

NPCs were collected from the cortex of an embryo from SMA Δ7 mouse strain (Jackson Laboratories) at embryonic stage ~14.5 (e14.5). These cells were dissociated into single cells by incubating in Accumax (STEMCELL Technologies) for 30 minutes at the room temperature and cultured in serum-free media (DMEM/F12, Gibco) containing EGF (Corning) and bFGF (Corning) as growth factors in non-adherent tissue culture flasks at a 5% $CO_2$ incubator. During the culture, cells form neurospheres which are 3-dimensional colonies of undifferentiated cells. After approximately 3-5 days, neurospheres were dissociated into single cells by incubating in Accumax (STEMCELL Technologies) for 30 minutes at the room temperature and allowed to form secondary spheres, a process known as "passaging".

Differentiation of NPCs

To terminally differentiate NPCs, the neurospheres were dissociated by incubating in Accumax (STEMCELL Technologies) for 30 minutes at the room temperature and plated at 1E+06 cells/well in 0.5 mL (24-well plates, Falcon) or at 2E+05 cells/well in 100 μL (96-well plates, Corning) serum-enriched media without growth factors. At 24 hr post-differentiation, the cells were terminally differentiated primarily into a glial lineage.

Transduction of mTD-NPC-Δ7

At 24 hr post-differentiation, media was removed from the cells and 100 μL of media containing AAV9 vectors was added to cells. AAV9 vectors used in these studies are AAV9-eGFP batch SAB-138, and SMN1-encoding AAV9 (AAV9-SMN1) vector drug product batches NCHAAV9SMN0613 (reference standard), 816836 and 600156.

SMN1 Staining

Cells were fixed at the indicated time point after the transduction by adding 50 μL of 4% paraformaldehyde in PBS (Alfa Aesar) in each well of 96-well plates (Corning). Cells were incubated in 4% paraformaldehyde for 5 min at the room temperature (RT) and then washed with 250 μL of PBS per well. Then, cells were permeabilized for 5 min at RT using 0.1% Triton X-100 (ThermoScientific) in PBS followed by a wash using 250 μL of PBS. For the staining of SMN1, a mouse monoclonal antibody 2B1 (ThermoFisher) was used at 4 μg/mL. Cells were incubated with the 50 μl of antibodies diluted in 1% BSA (Fisher) in PBS for 2 hours at RT and then washed with 250 μL of PBS. Finally, cells were incubated for 1 hour at RT with secondary antibodies (goat anti-mouse IgG Alexa488, ThermoFisher) and a nuclear stain (Hoechst33342, Invitrogen) in a 50 μL of 1% BSA in PBS. After the cells were washed with 250 μL of PBS, the plate was sealed with an optically clear plate seal (ThermoFisher) and imaged as described below.

Image Acquisition and Analysis

The CellInsight CX5 (ThermoFisher, hereafter designated CX5) was used for the acquisition of images. The CX5 is an automated high-content imaging instrument allowing measurements of biological activity in single cells in multi-well plates. The CX5 is operated using HCS Studio (ThermoFisher) to configure parameters such as an objective and exposure time. Images were acquired with a fixed exposure time using 20× objective for a high dynamic range of fluorescence detection. Captured images were then analyzed using the HCS Studio. The HCS Studio defines each cell using nuclei staining using sets of algorithms and filters, and then identifies cells using this nuclei staining as a seed. The integrated fluorescent intensity within each cell after the SMN1 staining was analyzed using the HCS Studio. This software also calculates an average of the measurement across the whole cell population per well, which represents the biological changes within the well. For the data analysis, the Integrated Fluorescent Intensity Per Cell (IFI-C) was used as a measurement of SMN1 protein expression.

Results

Transduction of Mouse Terminally Differentiated Cells Derived from Neural Progenitor Cells (mTD-NPC-Δ7)

Figure 4:
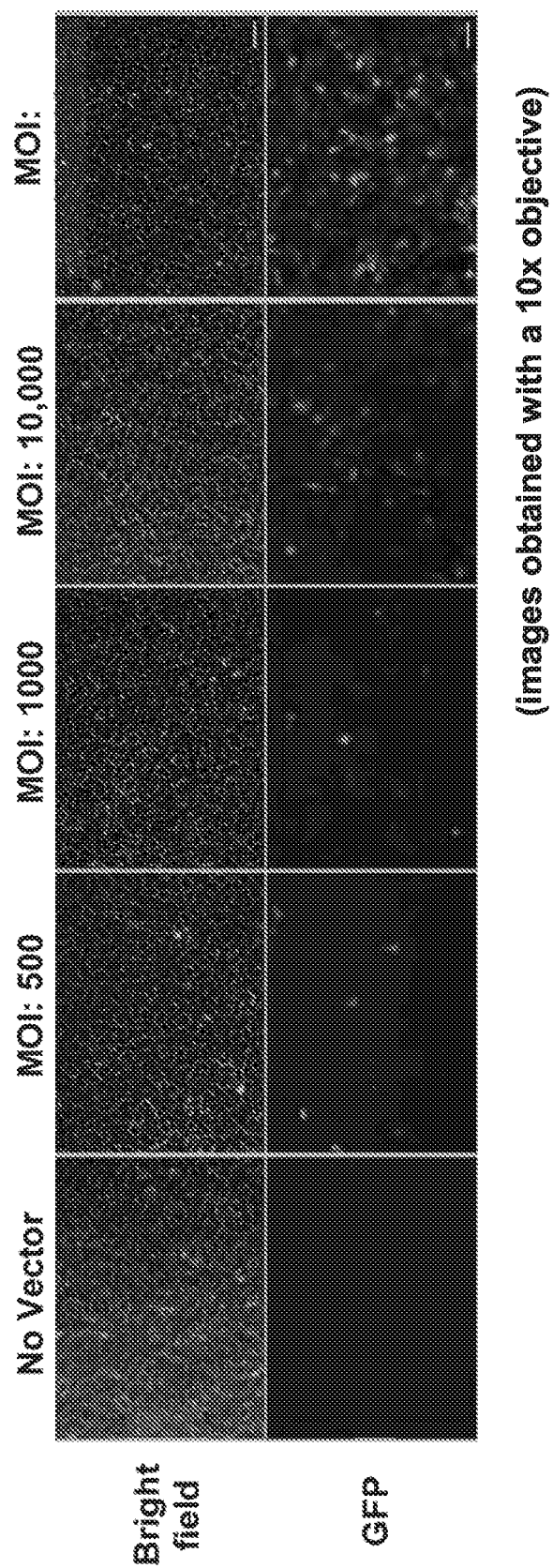
FIG. 4 illustrates images of mTD-NPC-Δ7 transduced with AAV9-eGFP at indicated MOI.
Figure 6:
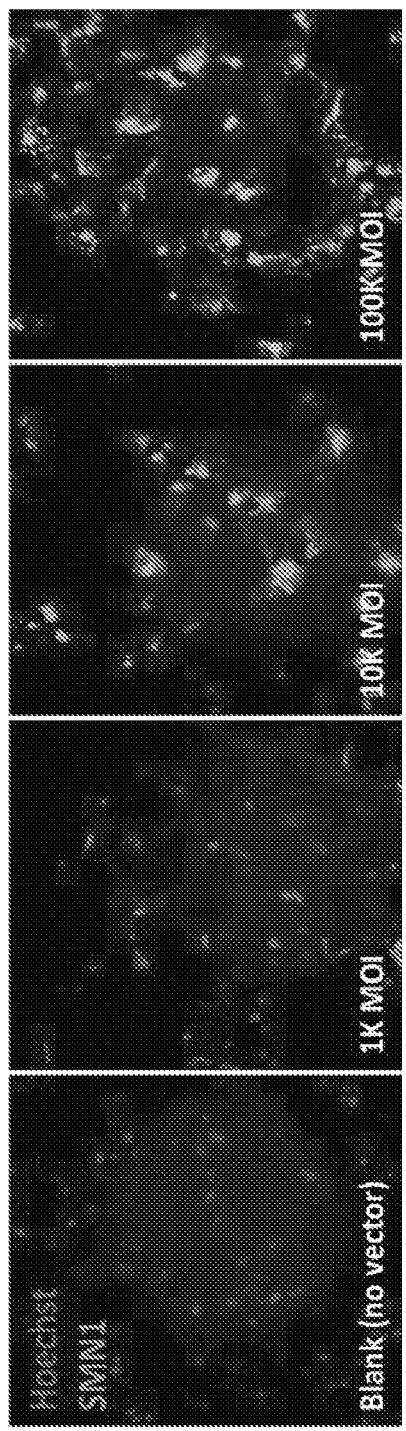
FIG. 6 illustrates images of SMN1 (2B1) and nuclei (Hoechst33342) staining at 72-hours post-transduction with AAV9 vector (Lot #NCHAAV9SMN0613).
Figure 9A:
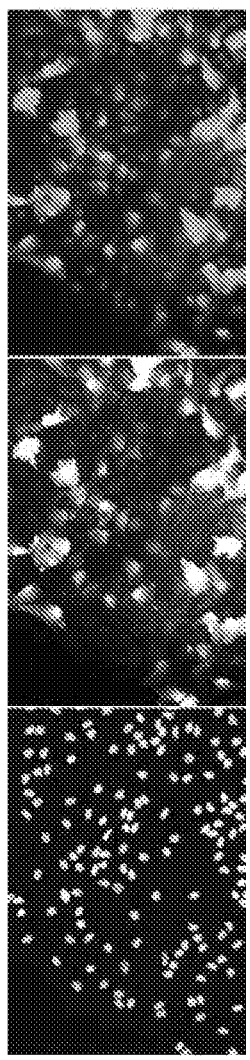
FIGS. 9A-9B illustrates images of AAV9-eGFP Transduced mTD-NPC-Δ7 at 72-hours post-transduction (FIG. 9A) and images of AAV9-eGFP Transduced mTD-NPC-Δ7 at 48-hours post-transduction (FIG. 9B).
Figure 9B:
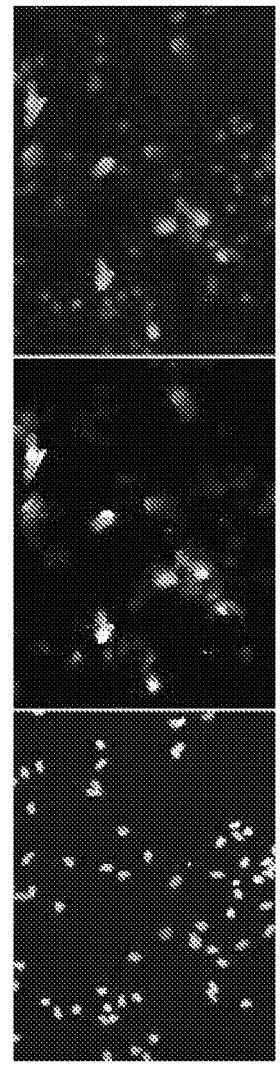

To assess the permissiveness of mTD-NPC-Δ7 to non-replicating, self-complementary AAV9-SMN1 (AVXS-101), AAV9-eGFP vector was used to transduce mTD-NPC-Δ7 in a 24-well plate format. Transduction was monitored using green fluorescent signal from eGFP expressed in transduced cells and images were obtained at 24 hr post-transduction. MOI-dependent eGFP expression demonstrated that mTD-NPC-Δ7 cells are permissive to the AAV9 vector without requiring a chemical treatment or engineering of cells. FIG. 4 shows a rise in eGFP positive cells with the increase of multiplicity of infection (MOI).

Feasibility of Using a 96-Well Plate Format for mTD-NPC-Δ7-Based Assay

To have reasonable throughput for an assay that could be used as the potency assay for lot disposition, the feasibility of using a 96-well plate format was assessed.

Evenness of Cell Distribution on 96-Well Plates and Determination of Cell Plating Density To be able to accurately capture biological changes using imaging technology, it is critical to have appropriate cell density per well. We tested and compared 20,000 cells per well (FIG. 5A) and 10,000 cells per well (FIG. 5B). At the density of 20,000 cells per well, cells were close enough to each other to foster an appropriate biological environment without extensively touching each other for an optimal image analysis.

Establishment of a SMN1 Staining Method for AAV9 Vector Transduced mTD-NPC-Δ7 in a 96-Well Plate Format Staining of SMN1 in mTD-NPC-Δ7

A few mouse monoclonal antibodies from commercial sources (data not shown) were screened for the detection of SMN1 protein using immuno-staining, and identified a mouse monoclonal antibody (2B1) that showed low background with a consistently good dynamic range of detection.

Specificity of SMN1 Monoclonal Antibody (2B1)

To ensure that the protein detected by 2B1 is not from AAV9 vector or from artifacts of transduction procedure, AAV9-eGFP-transduced mTD-NPC-Δ7 were stained with 2B1. Cells transduced at a MOI of 100,000 did not show any detectable signal when stained by 2B1, while successful AAV9 transduction was demonstrated which was confirmed by GFP expression (FIG. 7).

Assessment of the Tissue Culture Plate Coated with Poly-D-Lysin

To ensure minimal loss of cells during staining procedure, we evaluated the need for using Poly-D-Lysin coated 96-well plates. FIG. 8A and FIG. 8B show the comparison of uncoated and typical tissue culture treated 96-well plates (FIG. 8A) and Poly-D-Lysin coated plates (FIG. 8B). When cells were plated and stained on uncoated plates, loss of cells was observed with many of remaining cells sluffing off. However, cells plated on Poly-D-Lysin did not show this phenomena after all the staining procedures were completed. Therefore, we decided to use Poly-D-Lysin coated plates for further assay development experiments.

Establishment of a Quantitative mTD-NPC-Δ7-Based Imaging Assay that Measures SMN1 Protein Level Determination of an Assay Duration Time for the Detection of Transgene Expression.

Assay duration time for the detection of the transgene expression was determined to be 72 hr post-transduction. Because mTD-NPC-Δ7 are terminally differentiated and non-dividing, transgene SMN1 expression is accumulated after the transduction which reflects the transgene expression in non-dividing motor neuron upon SMN1-encoding AAV9 vector transduction in SMAΔ7 disease model or SMA patients in vivo. For the assessment, we used AAV9-eGFP as a tool to monitor transgene expression at two time-points, 48 hr post-transduction and 72 hr post-transduction. At 72 hr post-transduction, the majority of cells (up to 80%) were positive for GFP with high fluorescent signal per cell basis, which provides a good assay window. However, at 48 hr post-transduction, much fewer cells were positive for GFP with much lower fluorescent signal per cell basis.

Figure 10:
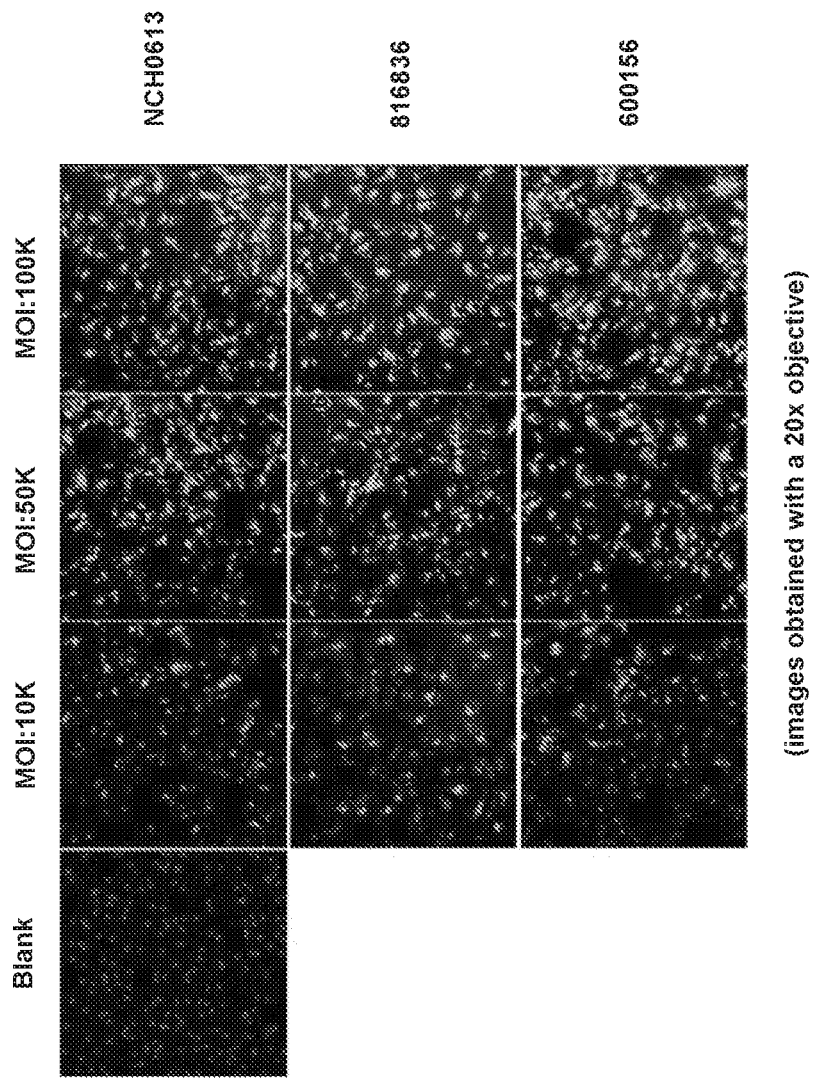
FIG. 10 illustrates images of SMN1 (Green) and nuclei (Blue) staining for SMN1-encoding AAV9 vector transduced mTD-NPC-Δ7 (72-hours post-transduction).

Detection and Analysis of MOI-Dependent Increase in SMN1 Protein Expression for Three AAV9 Vector Batches Using the established assay conditions, mTD-NPC-Δ7 were transduced with three SMN1 expressing AAV9 vector lots (NCHAAV9SMN0613, 816836 or 600156) at three different MOIs, and the cells were stained with anti-SMN1 2B1monoclonal antibodies. The images obtained after staining showed increased SMN1 expression with increasing MOIs. To determine whether fluorescent signals from immuno-staining can be used to quantitatively assess SMN1 expression, the integrated fluorescent intensity for each cell was analyzed (Integrated Fluorescent Intensity Per Cell, IFI-C). This experiment was carried out with n=3. For each of the clinical lots tested, the IFI-C increased with increasing MOI (Table 3). The data demonstrated comparable SMN1 expression upon transduction of the three clinical lots at three given MOIs (Table 3). FIG. 10 shows representative images of mTD-NPC-Δ7 at 72 hr post-transduction.

TABLE 3

Fluorescent Intensity Per Cell Data for Each Batch

| | n = 3 | Avg | CV |
|---|---|---|---|
| SMN1-encoding AAV9 VECTOR Lot NCHAAV9SMN0613 | | | |
| Blank | 2.83E+05; 3.06E+05; 2.86E+05 | 2.92E+05 | 4.11 |
| 10K | 7.50E+05; 8.71E+05; 7.35E+05 | 7.86E+05 | 9.39 |
| 50K | 1.42E+06; 1.19E+06; 1.38E+06 | 1.33E+06 | 9.27 |
| 100K | 1.58E+06; 1.67E+06; 1.69E+06 | 1.65E+06 | 3.64 |
| SMN1-encoding AAV9 VECTOR Lot 816836 | | | |
| Blank | 2.83E+05; 3.06E+05; 2.86E+05 | 2.92E+05 | 4.11 |
| 10K | 7.97E+05; 7.98E+05; 7.78E+05 | 7.91E+05 | 1.40 |
| 50K | 1.46E+06; 1.54E+06; 1.46E+06 | 1.49E+06 | 3.03 |
| 100K | 1.87E+06; 1.82E+06; 1.86E+06 | 1.85E+06 | 1.54 |
| SMN1-encoding AAV9 VECTOR Lot 600156 | | | |
| Blank | 2.83E+05; 3.06E+05; 2.86E+05 | 2.92E+05 | 4.11 |
| 10K | 7.09E+05; 6.91E+05; 7.37E+05 | 7.13E+05 | 3.28 |
| 50K | 1.29E+06; 1.31E+06; 1.22E+06 | 1.27E+06 | 3.86 |
| 100K | 1.56E+06; 1.63E+06; 1.44E+06 | 1.54E+06 | 6.19 |

TABLE 4

Fluorescent Intensity Per Cell Data Comparison Across Batches

| | NCH0613 | 816836 | 600156 | CV |
|---|---|---|---|---|
| 10k | 7.86E+05 | 7.91E+05 | 7.13E+05 | 5.75 |
| 50k | 1.33E+06 | 1.49E+06 | 1.27E+06 | 8.08 |
| 100k | 1.65E+06 | 1.85E+06 | 1.54E+06 | 9.28 |

Figure 11:
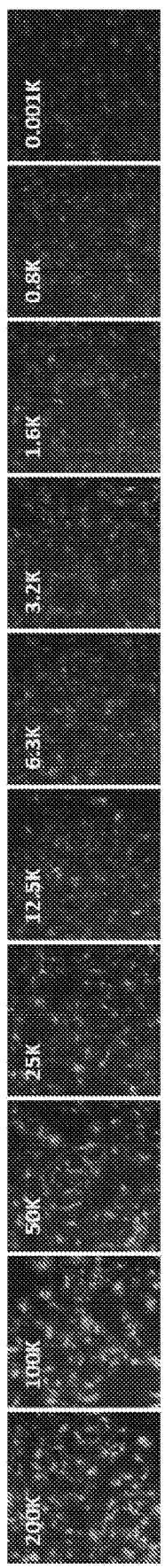
FIG. 11 illustrates images of SMN1 (Green) and nuclei (Blue) staining for mTD-NPC-Δ7 transduced with NCH0613 at various multiplicities of infections (MOIs) (72-hours post-transduction).
Figure 12:
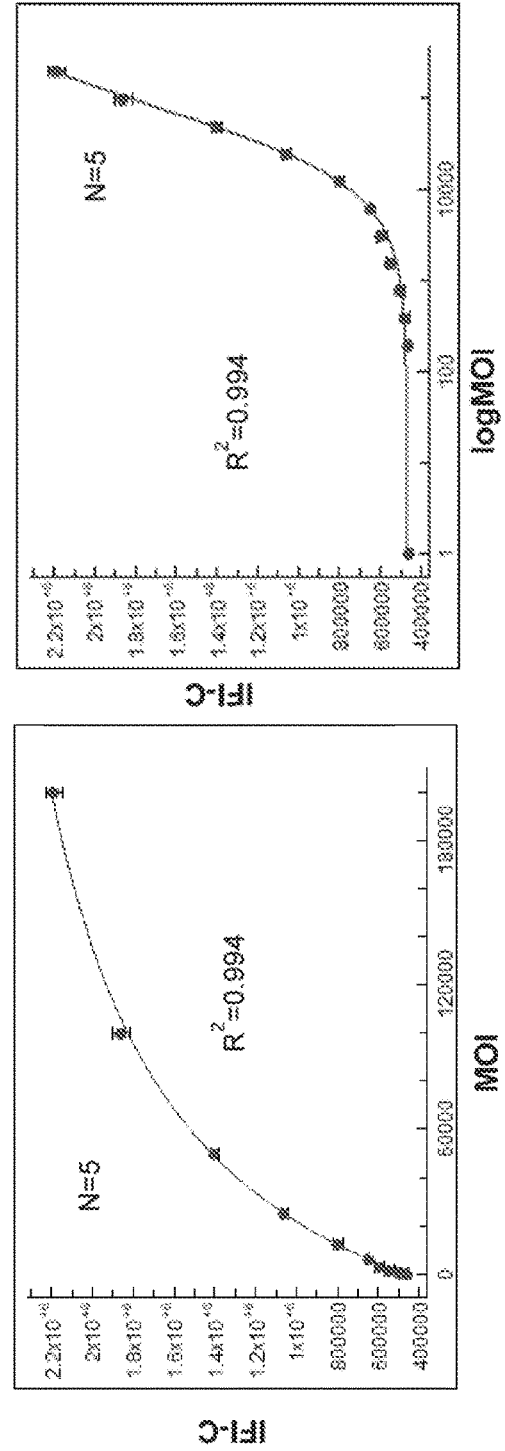
FIG. 12 illustrates curve fit for 12-point dose data of integrated fluorescent intensity per cell (IFI-C) (left: non-transformed, right: log-transformed on x-axis).
Figure 13:
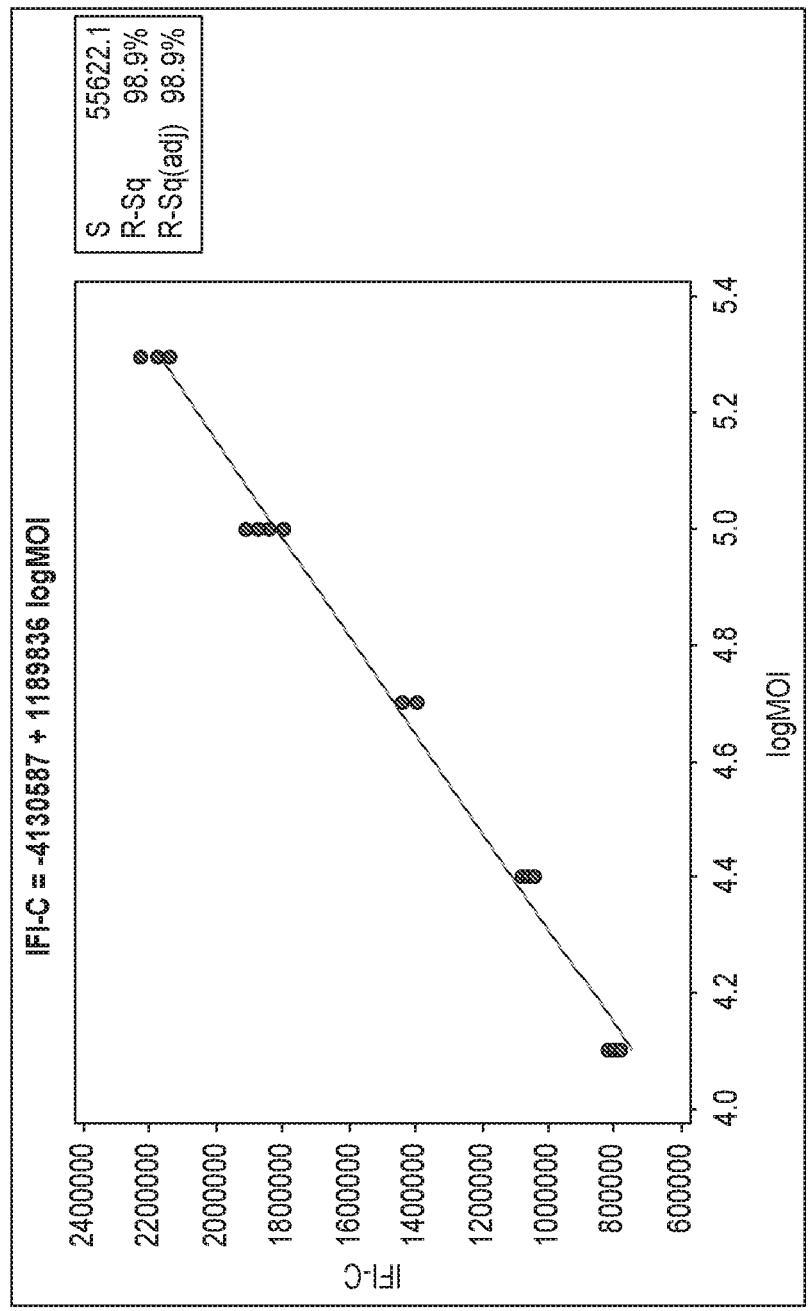
FIG. 13 illustrates a fitted line plot of log MOI versus IFI-C.
Figure 14:
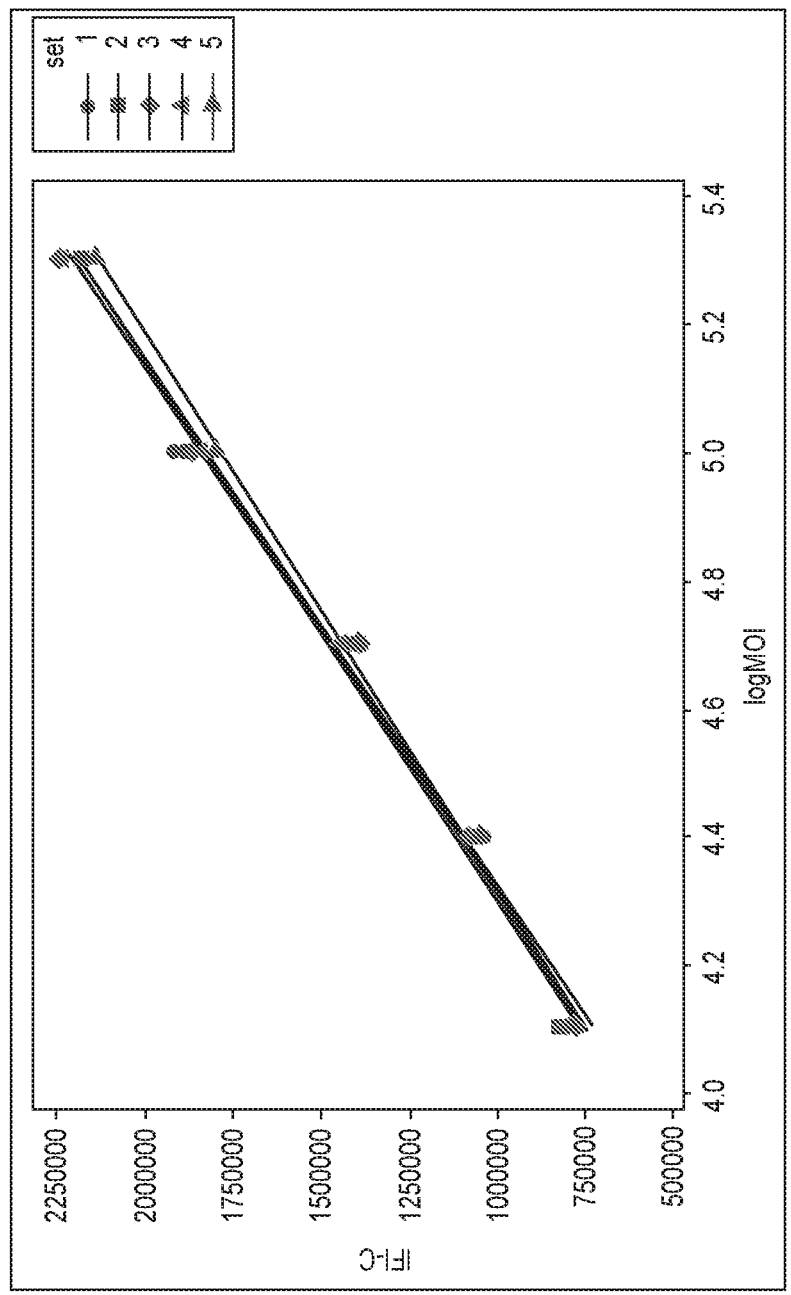
FIG. 14 illustrates a scatterplot of IFI-C vs log MOI, showing that lines for all five replicates are very close. All five replicates passed pairwise parallelism test (all p-values >0.25).
Figure 16B:
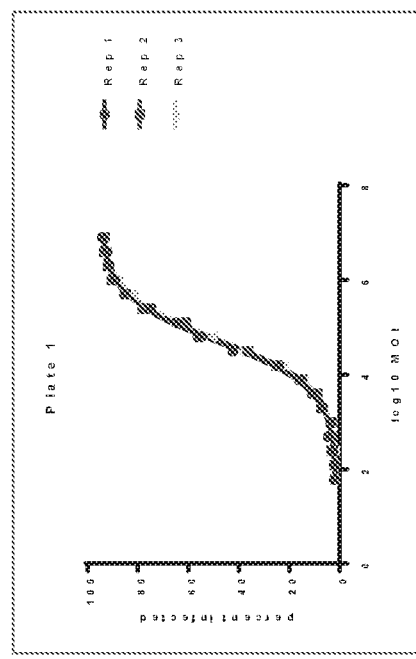
FIGS. 16A-16B illustrates proof of concept studies to establish AAV9 vector infectivity assay for infectious titer $EC_{50}$.
Figure 16A:
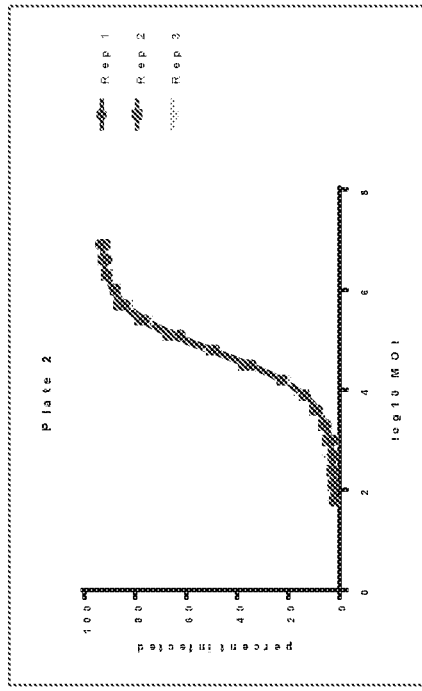

Proof of Concept Data Demonstrating that mTD-NPC-Δ7-Based Assay is a Dose-Dependent, Quantitative Assay in a 96-Well Format To determine the quantitative characteristics of this assay, 12-point MOI transduction of the AAV9-SMN1 vector lot NCHAAV9SMN0613 (n=5) was performed in 2-fold dilutions of vector using the developed mTD-NPC-Δ7-based assay. From the background (MOI=1) to the highest MOI (MOI=200K), there is a 4.8-fold increase in the IFI-C, demonstrating an acceptable background to signal ratio. As shown in Table 3, the relative standard deviation (RSD) (or CV %) of SMN1 IFI-C from 5 replicates across 12 MOIs was below 5% (from 0.5% to 4%). The initial proof of concept (POC) data showed that the assay is precise. FIG. 11 shows visual confirmation of MOI-dependent increase in SMN1 expression with the increase of MOI (only 10 MOIs are shown). To further evaluate whether the assay is quantitative, thus potentially suitable as a cell-based potency assay, 12-point data were analyzed with appropriate curve fitting algorism. As shown in FIG. 12, the assay shows a good curve fit ($R^2$=0.994) using a hyperbolic model. When x-axis is log-transformed, MOIs (from 200K to 12.5K) fell within a linear range.

The dose-dependent fitting data posed the potential to utilize the image-based assay to determine the relative potency of the AAV9-SMN1 vector by parallel line analysis (PLA).

In addition, along with the data comparing three AAV9-SMN1 vector clinical batches, these data support the proof of concept that a robust and quantitative measurement of SMN 1 can be achieved using an in vitro cell based assay.

TABLE 5

12-point MOI IFI-C Data

| | MOI | | | | | | | | | | | |
|---|---|---|---|---|---|---|---|---|---|---|---|---|
| | 200K | 100K | 50K | 25K | 12.5K | 6.25K | 3.125K | 1.6K | 0.8K | 0.4K | 0.2K | 0.001K |
| Avg | 2.19E+06 | 1.86E+06 | 1.40E+06 | 1.06E+06 | 7.98E+05 | 6.45E+05 | 5.95E+05 | 5.49E+05 | 5.00E+05 | 4.78E+05 | 4.64E+05 | 4.57E+05 |
| CV (%) | 1.84 | 2.49 | 1.56 | 1.75 | 2.62 | 0.47 | 3.87 | 4.38 | 3.70 | 3.95 | 2.38 | 1.72 |

Statistical Methods

To assess the suitability of mTD-NPC-Δ7-based imaging assay as a potential lot disposition potency assay, we determined 5 MOIs that support parallel line analysis (PLA). The following statistical analysis demonstrated that parallel line analysis (PLA) can be used to calculate the relative potency of the AAV9-SMN1 vector using the linear regression model.

Integrated Fluorescent Intensity Per Cell (IFI-C)

Integrated Fluorescent Intensity Per Cell (IFI-C) values were calculated for every dose and replicate. The IFI-C is the assay readout for each dose.

Linear Dose Response Model

Five replicates were obtained for every MOI measured and a linear regression model was applied and demonstrated a good fitting with R2 of 98.9% after a log-transformation of x-axis (dose).

Proof-of-Concept Study for the Use of PLA to Determine the Relative Potency (RP)

The five sets of the SMN1 IFI-C vs log MOI data were used to conduct the "mock" relative potency calculation in a pairwise analysis with one set of the data as "Mock Reference Standard" against the other set of the data as "Mock Test Article". With this approach, there are ten possible pairwise combinations as listed below (Table 6). The relative potency (%) of the 10 mock test articles were within the range of 93.6% to 101.8% with % CV less than 5%. The statistical analysis demonstrated that the newly developed assay is quantitative with the 16-fold linear range covering 5 MOIs of 2-fold apart.

Assay robustness, qualification and validation is determined prior to the final assessment of the utility of this assay as the potency assay intended for lot disposition of AAV9 drug product.

TABLE 6

Relative Potency Calculation Data

| Comparison Between Replicates | Relative Potency (%) |
|---|---|
| 1 vs 2 | 100.6 |
| 1 vs 3 | 99.7 |
| 1 vs 4 | 101.3 |
| 1 vs 5 | 93.6 |
| 2 vs 3 | 100.8 |
| 2 vs 4 | 99.3 |
| 2 vs 5 | 107.4 |
| 3 vs 4 | 98.5 |
| 3 vs 5 | 106.5 |
| 4 vs 5 | 108.2 |
| Mean | 101.6 |
| StDev | 4.5 |

Assessment of the Optimal SMN Antibody (2B1) Concentration for Immuno-Staining of mTD-NPC-Δ7

The interim PLA tool was used to further assess the effect of different anti-SMN (2B1) antibody concentrations for the staining of mTD-NPC-Δ7 transduced with the AAV9-SMN1 vector. Acceptable concentrations of primary and secondary antibodies used in image-based assays are generally wider compared to other immuno-assays such as ELISA. This is due to the capability of image-based assays achieved by instrument's high-sensitive camera to detect wide range of signals by adjusting exposure time to light source. Therefore, the main goal of antibody concentration optimization was to ensure that the primary or secondary antibody concentrations chosen were not a limiting factor for quantifying protein level of interest (e.g., SMN1) as determined by the dose-dependent response.

Figure 17:
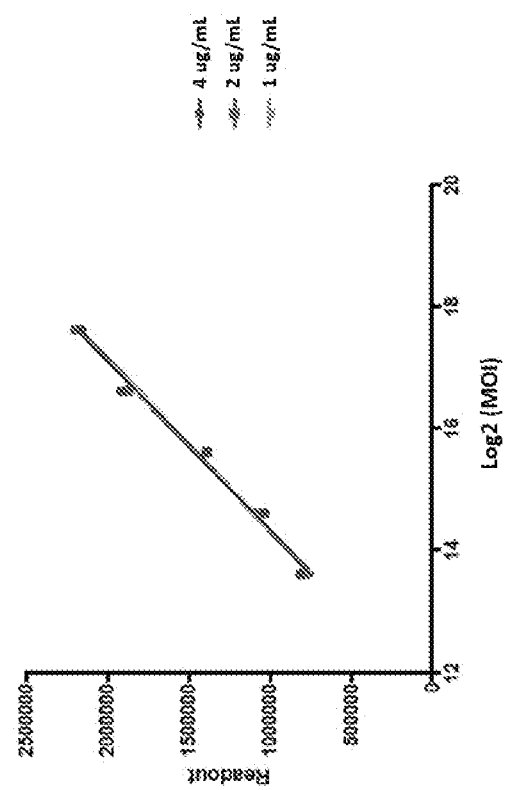
FIG. 17 is a plot that illustrates the equivalent dose-dependent increase in SMN using three different anti-SMN antibody concentrations.

For that purpose, three different concentrations of SMN (2B1) antibody were tested (4 μg/mL, 2 μg/mL and 1 μg/mL) to assess the linearity of the dose-dependent response determined by linear regression. In brief, 12 MOI doses prepared from an the SMN1-encoding AAV9 vector lot were added into the wells as shown in Table 7 and then cells were immuno-stained by 2 μg/mL, 1 μg/mL and 4 μg/mL of SMN antibody according to the plate layout. 5 doses ranging from 200K MOI to 12.5K MOI were fitted into a linear regression as described above and showed excellent linearity of dose-dependent increase in SMN protein level for all three conditions tested ($R^2=0.98$). Additionally, the data were analyzed using interim PLA by taking 2 μg/mL condition as a Reference Standard and comparing 4 μg/mL and 1 μg/mL conditions against the Reference Standard to calculate % relative potency. In this analysis, the three conditions of SMN antibody concentration demonstrated to be comparable with relative potency values at 99.8%, 100% and 97.2% and the slope ratios (slope of tested conditions to that of Reference Standard) at 0.991, 1.000 and 0.980 for 4 μg/mL, 2 μg/mL (Reference Standard) and 1 μg/mL, respectively (FIG. 17 and Table 8). Taken together, these data demonstrated that the SMN1 antibody was not a limiting factor in the quantitative determination of SMN protein expressed in mTD-NPC-Δ7 cells.

Given the equivalent data obtained from three different concentrations of SMN1 antibody, the mid-point of 2 μg/mL was chosen to establish In-Vitro cell-based relative potency for SMN1-encoding AAV9 vector. This concentration was chosen to avoid excessive consumption of SMN (2B1) antibody but to ensure that a slight variation in primary antibody concentration would not compromise the assay performance.

The concentration of secondary antibody use was determined to be at 2 μg/mL based on vendor's recommendation to ensure that the secondary antibody is not a limiting factor in the detection of the primary antibody that is bound to target protein in cells plated on a microplate setting. Data shown in the FIG. 17 and Table 8 establishes the quantitation of dose-dependent increase in SMN with excellent linearity ($R^2$ of 0.98) and with comparable slopes as shown by slope ratio in Table 8, confirming that there is a sufficient amount of secondary antibody for immunostaining.

TABLE 7

Plate Layout for the Comparison of Three Different anti-SMN Antibody Concentrations

| | 1 | 2 | 3 | 4 | 5 | 6 | 7 | 8 | 9 | 10 | 11 | 12 |
|---|---|---|---|---|---|---|---|---|---|---|---|---|
| A | | N = 1 | | | N = 1 | | | N = 2 | | | N = 1 | N = 2 |
| B | 200K | 3.125K | 200K | 3.125K | 200K | 3.125K | 200K | 3.125K | 200K | 3.125K | | |
| C | 100K | 1.6K | 100K | 1.6K | 100K | 1.6K | 100K | 1.6K | 100K | 1.6K | | |
| D | 50K | 0.8K | 50K | 0.8K | 50K | 0.8K | 50K | 0.8K | 50K | 0.8K | | |
| E | 25K | 0.4K | 25K | 0.4K | 25K | 0.4K | 25K | 0.4K | 25K | 0.4K | | |
| F | 12.5K | 0.2K | 12.5K | 0.2K | 12.5K | 0.2K | 12.5K | 0.2K | 12.5K | 0.2K | | |
| G | 6.25K | 0.001K | 6.25K | 0.001K | 6.25K | 0.001K | 6.25K | 0.001K | 6.25K | 0.001K | | |
| H | SMN Ab at 4 µg/mL | | | SMN Ab at 2 µg/mL | | | | SMN Ab at 1 µg/mL | | | | |

TABLE 8

Comparison of the Three SMN Antibody Concentrations by PLA

| SMN Antibody Concentration | % RP | Slope Ratio of RS vs Sample |
|---|---|---|
| 4 ug/mL | 99.8% | 0.991 |
| 2 ug/mL (used as Reference Standard) | 100% | NA |
| 1 ug/mL | 97.2% | 0.980 |

Conclusion

The above studies describe the successful identification of a novel primary mouse cell model system permissive to AAV9; the development of an in vitro cell based method for the measurement of transgene (SMN1) expression by using a quantitative high content image-based system; and the POC data to demonstrate the potential suitability of the developed mTD-NPC-Δ7-based assay as a lot disposition potency assay upon the completion of assay validation.

In addition, it has been shown that the newly established cell-based assay system possessed the following characteristics:
- Rapidly replicating NPCs enabled generation of cell banks with the progenitor cell phenotypes conserved before they are differentiated;
- mTD-NPC-Δ7s were naturally permissible for AAV9 transduction and were MOA-reflective;
- Measurement of SMN1 expression level in mTD-NPC-Δ7s showed a good assay window (signal: background >4) because TD-NPCs have a low background (derived from SMN−/− mice) and these cells are non-dividing (allowing accumulation of transgene product);
- The assay window allowed a quantitative measurement of dose-dependent increase in SMN1 protein level;
- The assay measuring IFI-C was robust and provides a throughput in a 96-well plate format;
- The statistical analysis supported PLA for the calculation of relative potency with accuracy and repeatability.

Example 3: New Method Development for AAV9 Infectivity in mNPC

A robust, quantitative, mechanism of action (MOA)-reflective AAV9 infectivity assay utilizing SMN−/− Δ7 mouse neural progenitor cell line (mNPC) and high content imaging system CellInsight was established. The in vitro relative potency assay for AAV9 vector was developed into a robust, quantitative infectivity assay using the mNPC-based assay platform.

Proof of concept data was obtained showing its superiority to current TCID50 infectivity assay in the aspects such as its quantitative nature and easier and less cumbersome assay process.

Proof of Concept studies were performed to establish AAV9 vector infectivity assay for infectious titer $EC_{50}$

TABLE 9

$EC_{50}$ as infectious titer

| Replicate | Plate # | EC50 vg/mL | Geomean $EC_{50}$ vg/mL | CV % Inter-plate |
|---|---|---|---|---|
| R1 | 1 | 6.34E+08 | 7.13E+08 | 7.8% |
| R2 | 1 | 7.12E+08 | | |
| R3 | 1 | 7.10E+08 | | |
| R1 | 2 | 7.44E+08 | | |
| R2 | 2 | 7.28E+08 | | |
| R3 | 3 | 7.48E+08 | | |

The full dose range of multiplicity of infections (MOIs) to cover both low plateau upper plateau was identified with excellent 4-p fit (0 to 8000K MOI).

$EC_{50}$ value in viral genomes per milliliter (vg/mL) was used as infectious titer of an AAV9 vector drug product and this replaces tedious and variable TCID50 assay.

Advantages of this Infectivity Assay Using SMN−/− mNPC Cells Over the Current TCID50-Based Assay Using HeLaRC32 Cells

TABLE 10

Comparison of the two methods used to determine AAV9 vector infectious titer.

| Parameter | mNPC-based (EC50 by HCI imaging) | HeLaRC-32 Cell-based (TCID50 by qPCR) |
|---|---|---|
| MOA-reflective | Partially | No |
| Precision & robustness | Precise (<10% CV); Quantitative (4-p fit) | >100% variability Semi-quantitative |
| Turn-around time | 5 days | 4-5 days |

Example 4: Determination of In-Vitro Relative Potency for SMN1 Encoding AAV9 Vector Drug Substance and Drug Product The relative potency of an AAV9-SMN1 vector Drug Substance and Drug Product was determined using the in-vitro quantitative cell-based relative potency assay developed in Examples 1-3.

The relative potency cell-based assay is a robust and quantitative in-vitro assay for determining the relative potency intended for lot disposition and stability testing of an SMN1-encoding AAV9 vector Drug Substance and Drug Product. The cells used in this assay were derived from mouse primary neural progenitor cells (NPCs) that were isolated from the cortex of SMNΔ7 mice as described in Examples 1 and 2. SMNΔ7 mice are an in vivo animal model of SMA disease homozygous for an of SMN1 gene knockout allele and homozygous for an allele of SMN2 with a deletion of its exon 7, leading to no expression of SMN protein in cells. The cell model system used in this assay was the terminally differentiated NPCs (mTD-NPC-Δ7). In mTD-NPC-Δ7 transduced with increasing doses of the SMN1-encoding AAV9 vector, increasing levels of SMN protein expression was measured by staining using a monoclonal antibody specific to SMN.

The relative potency of the samples relative to the reference standard (RS) was calculated using parallel line analysis (PLA) described by the following equation, where α (intercept) and β (slope) are estimates of the linear regression line from the common slope model:

$$\text{Relative Potency} = 2 \wedge \left( \frac{\hat{\alpha}_{sample} - \hat{\alpha}_{reference\ standard}}{\hat{\beta}} \right)$$

The high-content imaging platform (CellInsight CX5) used in this assay enabled quantitative measurement of intracellular protein expression on a per cell-basis (Integrated Fluorescent Intensity Per Cell). In addition, the CellInsight CX5 platform allowed appropriate throughput for lot disposition and stability study.

The following equipment was used to carry out the cell-based relative potency assay: a Biological Safety Cabinet (BSC), a CellInsight CX5 (ThermoFisher CX51110), a Humidified $CO_2$ incubator set at 37±1° C. with 5% $CO_2$, a water bath set at 37° C. or equivalent, a Centrifuge with temperature control, a Cellometer K2 Image Cytometer and a microscope.

The following materials were used to carry out the cell-based relative potency assay: Tissue-culture treated flasks (T75, T150, and T175), polypropylene centrifuge tubes, 15 and 50 mL with cap, pipets (single channel P1000, P200, and P20 and 8 or 12 channel P1000 and P300), Corning BioCoat Poly-D-Lysine 96-Well Plate (Corning 354640), Optically clear plate seal (Fisherbrand 8408240), Reagent reservoir, PIPET-AID, Cellometer slides (Nexcelom, CHT4-SD100-002), 96-Well DeepWell™ Polypropylene Microplates, Low-binding 1.5 mL Microcentrifuge Tubes, 70% (v/v) Isopropanol (IPA) and Dry Ice.

The reagents listed in Table 11 below were used to carry out the cell-based relative potency assay. Reagents adhered to manufacturer's suggested expiry date unless otherwise noted or retested.

TABLE 11

| | Reagents |
|---|---|
| Cell | Working cell bank (WCB) of Mouse Neural Progenitor Cells Δ7 (mNPC Δ7) generated under GMP protocol. Example: AD_WCB001-1 Storage: stored in validated liquid nitrogen tank until thawed out and cultured. |
| Primary Antibody | Mouse anti-SMN (Clone 2B1): ThermoFisher MA15878, Santa Cruz sc-32313 XS or EMD Millipore 05-1532 or equivalent Expiration and storage: Expiration is assigned per the manufacturer. Refer to the product label for expiration dating. Reagent is stored per the manufacturer's recommendation. |
| Reference Standard (for SMN1 encoding AAV9 vector) | Expiration and storage: Expiration is assigned per batch/lot number. Refer to the product label for expiration dating. Reference standard is stored frozen at ≤−60° C. until use. Once thawed, the expiration is 1 week stored at 2-8° C. |
| Control (for SMN1 encoding AAV9 vector) | Expiration and storage: Expiration is assigned per batch/lot number. Refer to the product label for expiration dating. Control is stored frozen at ≤−60°C until use. Once thawed, the expiration is 1 week stored at 2-8° C. |
| Base Media | DMEM/F12, GlutaMAX Supplement (Gibco 10565-018) 2% (v/v) B27 Supplement (50×) (Gibco 17504001) 1% (v/v) Antibiotic-Antimycotic (100×) (Gibco 15240062) Expiration and storage: 3 weeks stored at 2-8° C. from date of preparation or earliest expiration of components, whichever comes first. |
| Complete Growth Media | Base Media 0.1% (v/v) Heparin (5mg/mL from powder) (Fisher H19) 0.02% (v/v) bFGF Recombinant Human Protein at 100 g/mL (PeproTech 100-18B) 0.005% (v/v) EGF Recombinant Human Protein Solution at 1 mg/mL (Gibco PHG0311L) Expiration and storage: 1 week stored at 2-8° C. from date of preparation or earliest expiration of components, whichever comes first. |
| Plate Media | Base Media 10% (v/v) FBS (Gibco 16000-044) Expiration and storage: 1 week stored at 2-8° C. from date of preparation or earliest expiration of components, whichever comes first. |
| Dissociation Reagent | Accumax (Invitrogen 00-4666-56) Expiration and storage: 2 weeks stored at 2-8° C. once thawed. |

TABLE 11-continued

| Reagents | |
|---|---|
| ViaStain AO/PI Staining Solution | Expiration and storage: 6 months stored at 2-8° C. from date of receipt per manufacturer's recommendation. |
| Fetal Bovine Serum (FBS) (Gibco 16000-044) | Expiration and storage: Expiration is assigned by the manufacturer and stored long-term at ≤−15° C. Once thawed, the expiration is 1 month stored at 2-8° C. |
| 4% Paraformaldehyde (Alfa Aesar J61899) | Expiration and storage: Expiration is assigned 1 year from date of receipt and stored at 2-8° C. |
| Secondary Antibody | Goat anti-mouse IgG (H + L) Alexa Fluor Plus 488 (ThermoFisher A32723) Expiration and storage: Expiration is assigned 1 year from date of receipt and stored at 2-8° C. |
| DPBS (1×) (Gibco 14190-136) | Expiration and storage: Expiration is assigned 2 years from the open date, or manufacturer's expiration date, whichever is earlier. Reagent is stored long-term at ambient temperature. |
| Distilled Water (Gibco 15230-147) | Expiration and storage: Expiration is assigned 2 years from the open date, or manufacturer's expiration date, whichever is earlier. Reagent is stored long-term at ambient temperature. |
| 1% BSA in DPBS | Expiration and storage: 1 month stored at 2-8° C. from date of preparation or earliest expiration of components, whichever is first. |
| 0.1% Triton X-100 in DPBS | Expiration and storage: 6 months stored at ambient temperature from date of preparation or earliest expiration of components, whichever is first. |
| Formulation Buffer (TFF3) for AAV9 vectors | Expiration and storage: Expiration is assigned per batch/lot number, 1 month from date of preparation. Refer to the product label for expiration dating. Reagent is stored at ambient temperature. |
| Hoechst 33342 Nuclear Dye (Invitrogen H3570) | Expiration and storage: Expiration is assigned 6 months after opening and stored at 2-8° C. |
| BSA (Fisher BP1600-100) | Expiration and storage: Expiration is assigned 1 year from date of receipt and stored at 2-8° C. |
| Test Samples | For both release and stability testing, use genomic titer obtained during release testing for dilution calculation in preparing the SMN1-encoding AAV9 vector Reference Standard, Control and Test Samples, during Sample Preparation. Expiration and storage: Expiration is assigned per batch/lot number, if applicable. Refer to the product label for expiration dating and storage. After samples have been tested, store them per receipt instructions. For example, if a sample needs to be stored at ≤−60°C, freeze it after being thawed out for testing. |

Assay Procedure

NPC-Δ7 cells were thawed using the protocol outlined below.

Complete Growth Media was pre-warmed in a 37° C. water bath or equivalent for at least 30 minutes prior to use.

A frozen cryovial of mNPC cells was removed from the liquid nitrogen storage. The vial was kept on dry ice until it was ready to be thawed. The vial was quickly thawed in 37° C. water bath, swirling occasionally to ensure thawing.

The vial surface was wiped with 70% (v/v) Isopropanol (IPA) then the contents were transferred to a 50 mL centrifuge tube using a sterile pipette in a BSC. After thawing cells, the cryoprotectant was slowly diluted to prevent osmotic shock. About 10-20 mL is usually sufficient to overcome toxic effects.

10-20 mL of warmed Complete Growth Media was added in a dropwise manner while mixing gently by swirling, followed by centrifugation at 300×g for 5 minutes at 20° C.

The supernatant was aspirated, and then the tube was gently agitated to break up the cell pellet.

The appropriate volume (suggested 1.0-2.0 mL) of warm Complete Growth Media was added to cells and mixed gently with pipette.

A live cell count and viability was obtained, using protocol "NPCd7 Count Viability (AO/PI)" in the Cellometer K2 software. The viability for each of the counts was expected to be ≥60.0% viable.

The cells were transferred to a T75 tissue culture flask, and the cell volume collected was documented. 10.0 mL of complete growth media was added, and the flask was rocked to gently to ensure even distribution.

The flask was then placed in an incubator set at 37° C. and 5% $CO_2$, and incubated for at least 72 hours of culture at 37° C., 5% $CO_2$ before testing for growth and viability. Cells were passaged every 4±1 days.

Culture of NPC-Δ7 Cells

Cells were used in an assay starting at the second passage after thaw. Thawing was not considered a passage. Cells were used up to passage 15. For example, if the working cell bank was frozen at or after passage 6 (P6), when the cells were thawed, they retained the passage number as P6. After the appropriate number of days for cell proliferation, cells were passaged by being dissociated with Accumax and became P7. At P7, cells cannot be used for an assay. When cells are passaged again by being dissociated with Accumax (P8), these cells can be used in the assay.

TABLE 12

Example of Passage Designation When Thawing and Passaging Cells[1]

|  | Passage Number at which Cells were frozen | Passage Number at Thaw | Passage Number at Dissociation 1 | Passage Number at Dissociation 2 (Begin Use in the Assay) | Maximum Passage Number to be Used in the Assay |
|---|---|---|---|---|---|
| Passage Designation | P6 | P6 | P7 | P8 | P15 |
|  | P8 | P8 | P9 | P10 | P15 |
|  | P9 | P9 | P10 | P11 | P15 |

[1]Reference to passage at which cells are frozen in this table are examples only.

As cells proliferate in suspension, they form 3-dimensional colonies called neurospheres. To prevent the neurospheres from growing too large and becoming necrotic in the center, cells were passaged every 4±1 days.

Cell Passaging Procedure

Cells were passaged according to the procedure described below.

Base Media and Complete Growth Media were pre-warmed in a 37° C. water bath or equivalent for 30 minutes prior to use.

To passage cells, the flask containing the cells was removed from the incubator and the surface of the flask was rinsed using the media containing cells.

Cells were transferred from flask to a 50 mL conical tube and centrifuged for 5 minutes at 300×g.

The supernatant was aspirated without disturbing the cell pellet and 200.0 µL of Accumax was added. The cell pellet was gently triturated by pipetting up/down multiple times until the pellet was disassociated, then incubated for 30±10 minutes at room temperature.

At the end of the Accumax incubation, the Accumax was neutralized by adding 400.0 µL of pre-warmed Base Media. The cells were gently triturated (e.g. 10-15 times) to fully dissociate to single cells.

An additional 400.0 µL of pre-warmed Base Media was added to make a total volume of 1.0 mL. The additional volume of Base media diluted cells to the acceptable cell density range of 5.00E+05 cells/mL to 1.00E+07 for cell counting. Cells from multiple flasks of the same cell reference/lot at the same passage number were optionally pooled at this point, after the cells had been dissociated with Accumax and neutralized with Base Media separately. A total of 1.0 mL of each cell suspension (cells in 200.0 µL of Accumax neutralized by 800.0 µL of Base Media) could be combined. An additional volume of Base media was added to dilute cells to the acceptable cell density range of 5.00E+05 cells/mL to 1.00E+07 for cell counting (For example 1.0 mL of cells from Flask 1 and 1.0 mL of cells from Flask 2 were mixed, and then an additional 3.0 mL of Base Media was added to further dilute cells).

Cells were mixed and then a small sample of the cells was removed to determine the viable cell count and the viability using protocol "NPCd7 Count Viability (AO/PI)" in the Cellometer K2 software. mTD NPC-Δ7 (terminally differentiated NPCΔ7) plates were prepared when the viability for each of the cell counts was ≥80.0%. To continue culture of the cells, the viability for each of the cell counts had to be ≥70.0% viable.

If the cell suspension was too concentrated, an additional volume of Base Media was added, and mixed well and viable cell count and viability was re-determined.

The cell suspension was diluted to 100,000 cells per mL in pre-warmed Complete Growth Media. The appropriate volume was pipetted into new cell culture vessels and the cells were returned to the incubator at 37±1° C., 5% $CO_2$ for 4±1 days.

Example calculation per flask:

Total Volume: 20.0 mL, Average Viable Cell Density: 4.50×10⁶ cells/mL $$\text{Vol of Cells Needed}: \frac{1.00 \times 10^5 \text{ cells/mL}}{\left(4.50 \times 10^6 \text{ cells/mL}\right)} \times (20.0 \text{ mL}) =$$

(0.4 mL) Cells

Volume of Complete Growth Medium Needed $$\underbrace{(20.0 \text{ mL})}_{\text{Total Volume}} - \underbrace{(0.4 \text{ mL})}_{\text{Volume of cells needed}} = \underbrace{(7.6 \text{ mL}) \text{ Complete Growth Medium}}_{\text{Volume of Complete Growth Medium}}$$

TABLE 13

Suggested volumes for tissue culture flasks

| Flask | Surface Area (cm²) | Total Volume Medium (mL) |
|---|---|---|
| T-75 | 75 | 10-15 |
| T-150 | 150 | 20-25 |
| T-175 | 175 | 25-40 |

The passaging protocol was optionally repeated, with each passage cycle adding one passage number to the previous passage.

Preparation of mTD NPC-Δ7 (Terminally Differentiated NPCΔ7) Plates

Cells were plated using Plate Media, which was different from the media used to passage cells. Plate Media terminally differentiates the NPC cells. At least 7 mL of cells in Plate Media were prepared per plate.

The viable cell counts were recorded, and the appropriate volume of cells to be used for plating was determined.

Cells were diluted to a density of 20,000 cells/well/100 µL (or 2.00×10⁵ cells/mL) in Plate Media.

Example Calculation per plate:

Total Volume: 8.0 mL, average Viable Cell Density: 4.50×10⁶ cells/mL $$\text{Vol of Cells Needed}: \frac{2.00 \times 10^5 \text{ cells/mL}}{(4.50 \times 10^6 \text{ cells/mL})} \times (8.0 \text{ mL}) = (0.4 \text{ mL}) \text{ Cells}$$

Volume of Plate Medium Needed:

$$\underset{\text{Total Volume}}{(8.0 \text{ mL})} - \underset{\text{Volume of cells needed}}{(0.4 \text{ mL})} = \underset{\text{Volume of Plate Medium}}{(7.6 \text{ mL}) \text{ Plate Medium}}$$

100.0 µL of cells at $2.00 \times 10^5$ cells/mL were gently mixed, and at an angle to the wall of the wells, slowly pipetted to the inner 60 wells of a 96-well Poly-D-Lysine coated plate. Reverse pipetting is recommended in this step.

100.0 µL DPBS (1×) was added to the edge wells (Row A, Row H, Column 1, Column 12) of each plate.

The plate(s) were rested at ambient temperature for 25±5 minutes prior to placing plated cells in a 37° C., 5% $CO_2$ incubator. Start and end times were recorded, and the incubator was verified as meeting assay requirements at 37±1° C., 5% $CO_2$. Plated cells were then placed in a 37° C., 5% $CO_2$ incubator for 24 hours±2 hours prior to transduction, and the start and end times recorded. Incubator temperature and % $CO_2$ level were also recorded.

Transduction of mTD NPC-Δ7 Cells in the 96-Well Plate(s)
Preparation of Plate Media Sufficient Plate Media for the number of plates was prepared. Each plate of mTD-NPCΔ7 cells required a minimum of 10 mL of Plate Media.

Preparation of AAV9-SMN1 Vector Reference Standard (RS), Control and Test Samples The AAV9-SMN1 vector Reference Standard (RS), Control (Crtl) and Test Samples (51, S2, S3 etc.) were prepared as follows.

Aliquots of the Reference Standard (RS), Control, and Test Samples were thawed at ambient temperature. The Formulation Buffer and Plate Media was pre-warmed in a 37° C. water bath or equivalent for at least 30 minutes prior to use.

The samples were pre-diluted to 1.00E+12 vg/mL in a 1.5 mL microcentrifuge tube using the appropriate pre-warmed Formulation Buffer. To ensure pipetting accuracy, a minimum volume of 10.0 µL was taken from the sample vial for sample pre-dilution.

To prepare the dose A (MOI of 300K), the samples were further diluted 16.67 fold to 6.00E+10 vg/mL using Plate Media.

2-fold serial dilutions were performed to prepare doses B-E. For example, after gently mixing the Dose A solution with a P-300 µL pettor, transfer 250.0 µL from the Dose A solution and combine with 250.0 µL of Plate Media (diluent) to prepare Dose B. Repeat serial dilutions to prepare doses C, D and E. Each dose was prepared with sufficient remaining volume (250.0 µL) after serial dilution so that duplicate wells at each dose were transduced at 100.0 µL each. See Table 14 as an example.

TABLE 14

Example for Preparation of the Reference Sample

| Dose | Dose (MOI) | Fold Dilution | Dilution buffer volume (µL) | Sample volume (µL) | Genomic titer (vg/mL) |
|---|---|---|---|---|---|
| A | 300K | 16.67 | 470.0 | 30.0 | 6.00E+10 |
| Proceed with prep of doses B-E by serial dilution |
| B | 150K | 2 | 250.0 | 250.0 of A | 3.00E+10 |
| C | 75K | 2 | 250.0 | 250.0 of B | 1.50E+10 |
| D | 37.5K | 2 | 250.0 | 250.0 of C | 7.50E+09 |
| E | 18.75K | 2 | 250.0 | 250.0 of D | 3.75E+09 |

Transduction

The prepared differentiated cell plate(s) were removed from the incubator and transferred to a BSC. Incubator temperature and % $CO_2$ was recorded and verified that it met assay requirements at 37±1° C., 5% $CO_2$.

Wells of each 96-well plate were assigned for use with the single reference and test sample(s). See Table 15 as an example of a plate map. Edge wells (Row A, Row H, Column 1, Column 2) contained 0.1 mL of DPBS (filled during plate seeding). The edge wells were not aspirated.

Using a multichannel pipette, the Plate Media was gently removed from wells containing cells. To prevent drying of cells, Plate Media can be removed from 2 columns at a time.

Using a multichannel pipette, 100.0 µL of the prepared samples were gently mixed and immediately dispensed at an angle to the wall of the corresponding wells per plate map.

For the Cells Only (Background) assigned wells (non-transduction controls), 100.0 µL of fresh Plate Media was added. If only one sample was tested, 100.0 µL of fresh Plate Media were added to non-transduction wells. These wells were not used for calculations.

Plates were transferred to the incubator (37±1° C., 5±1% $CO_2$). Plates were incubated for 72±2 hours, and the start and end times recorded. Incubator temperature and % $CO_2$ level were recorded, and it was verified that the incubator met assay requirements at 37±1° C., 5% $CO_2$.

TABLE 15

Plate format for AAV9-SMN1 vector Reference Standard, Control, and Test Samples

| | 1 | Rep 1 2 | Rep 2 3 | Rep 1 4 | Rep 2 5 | Rep 1 6 | Rep 2 7 | Rep 1 8 | Rep 2 9 | Rep 1 10 | Rep 2 11 | 12 |
|---|---|---|---|---|---|---|---|---|---|---|---|---|
| A | | RS | | Ctrl | | S1 | | S2 | | S3 | | |
| B | | 300K | | 300K | | 300K | | 300K | | 300K | | |
| C | | 150K | | 150K | | 150K | | 150K | | 150K | | |
| D | | 75K | | 75K | | 75K | | 75K | | 75K | | |

TABLE 15-continued

Plate format for AAV9-SMN1 vector Reference Standard, Control, and Test Samples

| | 1 | Rep 1 2 | Rep 2 3 | Rep 1 4 | Rep 2 5 | Rep 1 6 | Rep 2 7 | Rep 1 8 | Rep 2 9 | Rep 1 10 | Rep 2 11 | 12 |
|---|---|---|---|---|---|---|---|---|---|---|---|---|
| E | | 37.5K | | 37.5K | | 37.5K | | 37.5K | | 37.5K | | |
| F | | 18.75K | | 18.75K | | 18.75K | | 18.75K | | 18.75K | | |
| G | | | | | | Cells Only (background) | | | | | | |
| H | | | | | | | | | | | | |

Cell Staining Procedure

Transduced plates were removed at 72 hours±2 hours for cell staining. Incubator temperature and % $CO_2$ level were recorded, and it was verified that the incubator met assay requirements at 37±1° C., 5% $CO_2$. Edge wells were processed for cell staining. All inner 60 wells, including the wells without samples, were stained.

Cell Fixation

Cells were fixed according to the protocol described below.

The media was aspirated from the wells to be stained. Controlled pipetting was used to avoid loss of cells.

50.0 µL of 4% Paraformaldehyde were gently added to the inner 60 wells at an angle to the wall of the wells.

Plates were then incubated for 5 to 7 minutes at ambient room temperature. Start and end times were recorded.

Following incubation, the 4% Paraformaldehyde was aspirated from each well, and the inner 60 wells were washed with 250.0 µL DPBS. At this point, the plate can be stored in 2-4° C. for up to 3 days if the following steps cannot immediately follow. In this case, the 250.0 µL DPBS used to wash was removed and 250.0 µL of fresh DPBS was added before storing the plate. A plate seal was used to prevent evaporation during the storage.

Cell Permeabilization

The DPBS was gently aspirated from each well, and 50.0 µL of 0.1% Triton X-100 was gently added to the inner 60 wells at an angle to the wall of the wells.

Plates were incubated for 5 to 7 minutes at ambient room temperature, and the start and end times were recorded.

The 0.1% Triton X-100 was aspirated from each well, and the inner 60 wells were washed with 250.0 µL DPBS.

Primary Antibody Incubation

Mouse monoclonal anti-SMN antibody (Clone 2B1) stored at 2-8° C., was used. The amount of working antibody required for staining was calculated by adding the number of reference, test, and control samples to be stained, and multiplied by a volume of a volume of 50.0 µL for each sample. Enough excess volume was prepared to be sufficient for pipetting volume loss.

A primary antibody staining solution of the mouse anti-SMN antibody was prepared using 1% BSA in DPBS solution as the diluent. Santa Cruz sc-32313 XS Lot #C2818 was used at 1:500 dilution, Santa Cruz sc-32313 XS Lot #F2118 was used at 1:1000 dilution, and EMD Millipore Lot #3054700 was used at 1:500 dilution based on the development data. Primary antibody solution preparation can be scaled up or down as needed. For example, to prepare 4.0 mL of staining solution for 1:500 dilution of antibody, 8.0 µL of anti-SMN antibody was added to 4.0 mL of 1% BSA in DPBS.

The DPBS from each well, and 50.0 µL of the primary antibody staining solution was gently added to the inner 60 wells at an angle to the wall of the wells.

The plate(s) were incubated for 120 to 150 minutes at ambient room temperature, and start and end times recorded.

Following incubation, the primary antibody solution was aspirated from each well. The inner 60 wells were washed with 250.0 µL DPBS. Before removing the DPBS in the washing step, the secondary antibody staining solution was prepared.

Secondary Antibody Incubation

Secondary antibody solution preparation can be scaled up or down as needed, and the container was covered with aluminum foil when not in use. A secondary antibody staining solution containing 2 µg/mL final of goat anti-mouse IgG (H+L) Alexa Fluor Plus 488 at 1:1000 dilution and 2 µg/mL of nuclear dye Hoechst 33342 (1:5000 dilution) in 1% BSA in DPBS was prepared. Hoechst 33342 Nuclear Dye was pre-diluted by adding 10.0 µL of the Hoechst 33342 nuclear dye into 40.0 µL of Distilled Water. The pre-diluted Hoechst 33342 was made fresh for each staining. For 1 plate, a recommended 5 mL Secondary Antibody Solution was prepared by adding 5.0 µL of pre-diluted Hoechst and 5.0 µL of the secondary antibody into 1% BSA in DPBS.

The DPBS was aspirated from each well, and 50.0 µL of the secondary antibody solution was added to each well at an angle to the wall of the wells. The plates were incubated for 60 to 80 minutes at ambient room temperature, protected from light (example: covered in foil), and start and end times recorded.

The secondary antibody solution was aspirated from each well, and the inner 60 wells were washed with 250.0 µL DPBS.

The DPBS wash was aspirated from each well, and 250.0 µL DPBS was added to the inner 60 wells. Plates were then sealed with a clear optic plate seal, which was firmly pressed onto each well. Plate(s) protected were from light until image acquisition could take place. Plate(s) were kept at ambient temperature and were read on the same day as they were stained.

Image Acquisition and Analysis

Images of the plates were acquired using a CellInsight High Content Screening (HCS) Platform, using HSC studio software and a standardized protocol.

The top of the plate seal and the bottom of the plate were wiped with KimWipes pre-wet with 70% alcohol to remove dust, and plates were loaded into the HCS receptacle, aligning A1 of the plate with A1 of the receptacle.

Figure 18:
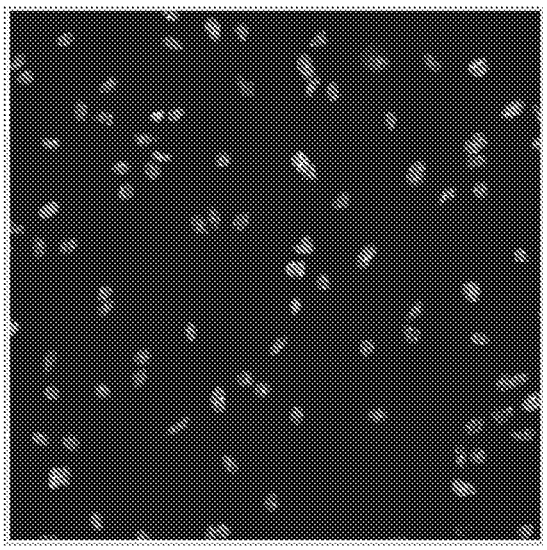
FIG. 18 is an example image of nuclei taken using the CellInsight High Content Screening system.

Autofocus was used to acquire cells, and it was visually confirmed that the nuclei were in focus. An example of in focus nuclei captured using this system is shown in FIG. 18.

The CellInsight settings described as follows were used for data acquisition. Assay settings: Imaging Mode: Fluorescence 1 (F1) % Fluorescence 2 (F2); Acquire Brightfield Image; F1 image Cell Type: Mouse ES Cell; Description: mNPC Fluorophore AO VC-535-403; Fluorescent Exp: 700.0 msec; F2 image Cell Type: Mouse ES Cell; Description: mNPC Fluorophore P1 VC-660-503; Fluorescent Exp: 5000.0 msec; Set Dilution Factor for Assay: 2.000; Show Percent F1, F2: F1/(F1+F2)*100%. Cell Type settings: Mouse ES cells; Cell Diameter: 9.0 micron minimum, 30.0 micron maximum; Roundness: 0.10; Contrast Enhancement: 0.40; Decluster Edge Factor: 0.5; Decluster Th Factor: 1.0; Background Adjustment: 1.0. Trypan Blue Viability Parameters: Dead Cell Diameter: 8.0 micron minimum, 30 micron maximum; Sensitivity: 1.0; Uniformity: 150; Very Dim Dead Cells Contrast Enhancement: 0.60. Protocol Settings: Objective: 20×; field size: 455.4 by 455.4 microns; Camera: X1; Camera Acquisition Mode: 1104×1104 (2×2 binning); Use Software Autofocus; Software Focus Channel: 1; Autofocus interval: 1. Channel 1 Settings: channel included in the Composite, Camera Gain: 2; Light Intensity (in %): 100; Imaging Mode: Widefield; Dye: 386-23BGRFRN_BGR-FRN; Depth Of Field: 6.563; Fixed Exposure Time; Target %: 25; Exposure Time (secs): 0.08. Channel 2 Settings: channel included in the Composite, Camera Gain: 2; Light Intensity (in %): 100; Imaging Mode: Widefield; Dye: 485-20_BGRFRN_BGRFRN; Depth Of Field: 6.563; Fixed Exposure Time; Target %: 25; Exposure Time (secs): 0.08.
Analysis of Assay Results An excel spreadsheet was used to streamline and automate the calculation of % relative potency values of test samples against the reference standard using the statistical methods described below.

Relative Potency Calculation Using Parallel Line Analysis
Individual Linear Model For each sample, the linear regression model (M2.1) was fitted to the average of duplicate assay readouts (Integrated Fluorescence Intensity per Cell) vs $\log_2$ transformed expected MOI values on the plate.

The R-squared value ($R^2$), intercept (for RS only), and slope estimate of the linear regression line using least squares method were provided for all samples (RS, Ctrl and 51, S2, S3 etc).

For each sample (assay control and test samples), the ratio of sample slope estimate relative to the reference standard ($\hat{\beta}sample/\hat{\beta}_{RS}$)) was used to assess parallelism between the sample and reference standard.

The sample slope is parallel to the slope of reference standard if the slope ratio is within the empirical range established between assay control sample and reference standard, where:

$$y = \alpha + \beta \log_2(\text{MOI}) + e \quad (M2.1)$$

- y is the Integrated Fluorescence Intensity per Cell from given MOI level
- α and β are intercept and slope of the linear regression line, respectively
- e is the residual error Common Slope Model For each sample (assay control and test samples) and the reference standard sample, the linear regression model with individual intercept and common slope (M2.2) was fitted to the average of duplicate assay readout of Integrated Fluorescence Intensity per Cell vs $\log_2$ transformed expected MOI values on the plate, where:

$$y = \alpha + \beta \log_2(\text{MOI}) + e \quad (M2.1)$$

- $y_i$ is the Integrated Fluorescence Intensity per Cell from give MOI level for sample i, i∈{sample, reference standard}
- $\alpha_i$ is the individual intercept for sample i, i∈{sample, reference standard}
- β is the common slope
- e is the residual error Relative Potency Calculation The relative potency of sample (assay control and test samples) was calculated from the intercept of slope estimates from model (M2.2) as $$\text{Relative Potency} = 2 \wedge \left( \frac{\hat{\alpha}_{sample} - \hat{\alpha}_{reference\ standard}}{\hat{\beta}} \right)$$

System Suitability Criteria

An assay plate was considered valid if the following criteria were met.

All Samples met the following acceptance criteria: % CV of IFI-C ≤20% and the $R^2$ upon linear regression fit was ≥0.95.

The Assay Reference Standard (RS) met the following Suitability Criteria. The assay dynamic window (maximal signal to background signal cells only) was ≥2.69, and the Slope was ≥1.02E+05.

The Assay Control met the following Suitability Criteria: the slope ratio for the assay control vs RS was within 0.75-1.33, and the relative potency of the assay control was within 100%±40%.

The Test Sample (test article) met the following suitability criterion: the slope ratio of the test sample vs RS must be within 0.69-1.45.

Failure of System Suitability

If any of the system suitability associated with reference standard or assay control was not met, the plate was deemed to be invalid, and samples were re-tested.

Failure of Sample System Suitability Criteria

If any test sample(s) did meet acceptance criteria of the sample system suitability as described above (CV %, $R^2$ and slope ratio), the sample result was deemed as invalid, no result generated and the sample was retested.

Reportable Values (% RP)

The reportable value was defined as the mean of three independent valid assay results unless otherwise specified.

The mean, standard deviation and % CV (RSD) of % RP from the three sample assay results was calculated. If the % CV was ≥30%, no reportable value will be generated, and three additional valid assays were performed and he mean and % CV for the second set of tests was calculated.

Final sample result was reported based on the calculation below, if the Reference Standard % RP was not 100%:

Sample % RP Reported Result=Sample % RP
(PLA)×current WRS or PRS assigned % RP

Where PLA: Parallel Line Analysis
WRS: Working Reference Standard
PRS: Primary Reference Standard Example 5: Validation of In-Vitro Relative Potency Cell-Based Assay for AAV9-SMN1 Vector Drug Product A comprehensive validation study was conducted to assess a wide array of performance parameters including accuracy, precision (repeatability, intermediate precision and reproducibility), linearity, parallelism, assay range and specificity as well as limit of quantitation (LOQ) of the in-vitro relative potency cell-based assay. The pre-defined acceptance criteria, some of which were more stringent in the validation protocol than those in the initial qualification protocol, were established based upon the statistical analysis utilizing the qualification data.

As summarized in Table 16, the results from the validation study met all the pre-defined acceptance criteria. This demonstrated that the validated method was precise with intermediate precision at the % RSD (relative standard deviation) range of 15.6%-29.5% and combined % RSD of 23.5% (Table 16 & Table 18), repeatability at the % RSD range of 4.9%-15.6% and combined % RSD of 11.0% (Table 16 & Table 22), and reproducibility at the % RSD range of 13.2%-22.7% and combined % RSD of 19.7% (Table 16 & Table 19).

Figure 19:
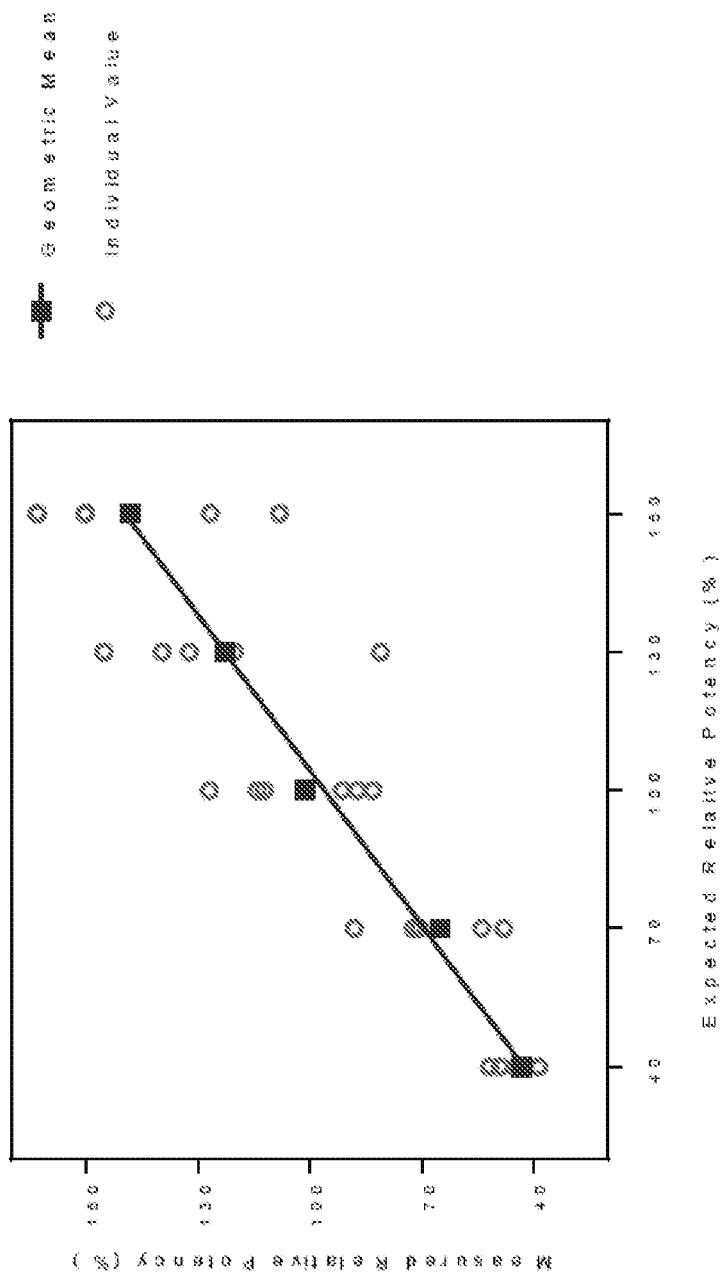
FIG. 19 is a plot demonstrating linearity between measured versus expected relative potency. Squares indicate the geometric mean, circles indicate the individual values. The x-axis shows expected relative potency (%), the y-axis shows the measured relative potency (%).

In addition, the method was accurate with relative bias at the range of −7.5% to 8.3% (Table 16 & Table 20) or % recovery at the range of 92.5%-108.3% (Table 19). The accuracy was also demonstrated by the excellent linear relationship of the geometric mean of measured relative potency versus the expected relative potency with the slope of 0.890 and $R^2$ value of 0.99 from 5 recovery samples covering the range of relative potency from 40% to 160% (Table 21 & FIG. 19). The method was also specific since it could only detect the dose-dependent increase in the cells transduced by the AAV9-SMN1 vector, but not in cells transduced by AAV9 vector expressing a protein irrelevant to SMN1 (FIG. 20). In addition, the validated assay range concluded that the lower limit of quantitation (LLOQ) and upper limit of quantitation (ULOQ) of the method are approximately 40% and 160%, respectively.

Furthermore, it was evident that the potency method was robust since its assay performance was not affected by deliberately varied conditions of the key assay parameters such as cell seeding density, passage cell number (P8 to P15), the use of different vials from the same working cell bank, antibody concentration and assay incubation times (Table 17).

Taken together, the validated potency method warrants its suitability for lot disposition of clinical and licensed drug product as well as for the stability studies given its stability indicating characteristics.

Additionally, studies on the potential plate effect showed little or no systematic bias in the relative potency values measured at three different sample positions (S1, S2 and S3) as defined in the plate layout (for example, see Table 15). Therefore, the plate layout was acceptable for the intended use in the in vitro cell-based potency assay.

TABLE 16

Summary of Method Validation Results

| Parameter | Acceptance Criteria | Results[a] | Pass/Fail |
|---|---|---|---|
| Precision | Intermediate Precision: % RSD ≤40% for each of the five recovery samples and combined | The % RSD values for the five recovery samples of expected Relative Potency values at 40%, 70%, 100%, 130% and 160% are 15.6%, 25.9%, 17.7%, 29.5%, 21.5%, respectively (n = 4 per sample). Refer to Table 16. The combined % RSD value with all data from the five recovery samples combined (n = 20) is 23.5%. Refer to Table 16. | Pass |
| | Repeatability: % RSD ≤20% for each of the three recovery samples and combined | The % RSD values for the three recovery samples of expected Relative Potency values at 40%, 100% and 160% are 15.6%, 9.7%, 4.9% respectively (n = 3 per sample). Refer to Table 20. The combined % RSD with all data from the three recovery samples combined (n = 9) is 11.0%. Refer to Table 20. | Pass |
| | Reproducibility % RSD ≤45% for each of the five recovery samples and combined | The % RSD values for five recovery samples of Expected Relative Potency values at 40%, 70%, 100%, 130% and 160% are 13.2%, 22.1%, 17.3%, 22.7%, 19.4%, respectively (n = 6 per sample). Refer to Table 17. The combined %RSD value with all data from the five recovery samples combined (n = 30) is 19.7%. Refer to Table 17. | Pass |
| Accuracy | Accuracy: Relative bias[b] within ± 40% of expected Relative Potency at 40%, 70%, 100%, 130% or 160% of each of the 5 recovery samples | The Relative bias[b] values for the five recovery samples of expected Relative values at 40%, 70%, 100%, 130% and 160% (n = 6 per sample) are 8.3%, −7.0%, 1.3%, −5.6%, -7.5%, respectively. Refer to Table 18. | Pass |
| Linearity | The linear regression fitting of the measured relative potencies vs the expected relative potencies of 5 recovery samples from two analysts. $R^2 \geq 0.9$ | $R^2$ = 0.99 Refer to Table 19 & FIG. 19. Slope estimate of the linear regression model = 0.890. Refer to Table 19. | Pass |

TABLE 16-continued

Summary of Method Validation Results

| Parameter | Acceptance Criteria | Results[a] | Pass/Fail |
|---|---|---|---|
| | The range of the slope estimate of the linear regression model: 1.0 ± 0.25 | | |

TABLE 17

Summary of Method Robustness Results

| Parameter Evaluated | Condition Specifics | Acceptance Criteria | Results | Impact upon the Assay Performance |
|---|---|---|---|---|
| Cell Seeding Density per mL | 2.0E+5 ± 5.0E+4 Cells/mL | Meet the system suitability % relative potency of the sample is within 60% to 140% | The system suitability all met (Table 21) Acceptance Criteria for Relative Potency values of the sample at varied conditions for each parameter met (Table 21) | No Impact Observed |
| Cell Passaging Number | P8 vs P15 | | | |
| Vial to vial variability | 3 vials from WCB-NPCΔ7.2.6 cells | | | |
| Differentiation time | 24 ± 2 hrs | | | |
| Incubation Time after AAV9 vector Transduction | 72 ± 2 hrs | | | |
| Concentration of mouse anti-SMN1 monoclonal antibody | 2.0 ± 0.4 µg/mL | | | |

Materials and Methods

Unless otherwise specified, the test method and the experimental designs are described in Example 4.

The cell-based potency method allowed the quantitative determination of % relative potency (% RP) of SMN1-encoding AAV9 vector drug product or the stability samples by measuring the ability of drug product (DP) containing AAV9-SMN1 vector to transduce the mouse primary cells and express the SMN1 protein. A high content image system was used to measure the immuno-stained SMN1 protein in the terminally differentiated cells from a mouse neural progenitor cell line defective in expressing endogenous SMN1 protein (mTD-NPCΔ7.2.6). The % RP values of the recovery samples against the Reference Standard (RS), which was designated as 100%, were calculated using parallel line analysis (PLA) using a validated and locked excel template.

Results

Assessment of Method's Intermediate Precision, Reproducibility, Accuracy, Linearity, Assay Range and Limit of Quantitation The 5 recovery sample data derived from 2 independent runs performed by two analysts (2 runs per analyst, N=4) were used to determine the intermediate precision. The intermediate precision of the method was illustrated by its % RSD values ranging from 15.6% to 29.5% with combined % RSD of 23.5% (see Table 18 and Example 6) which met the acceptance criterion for intermediate precision of % RSD ≤40%.

The data derived from 2 independent runs performed by three analysts in two laboratories (2 runs per analyst, N=6) were used to assess the reproducibility. The reproducibility of the method measured as % RSD associated with five recovery samples ranged from 13.2% to 22.7% with combined % RSD of 19.7% which met the acceptance criterion for reproducibility of % RSD ≤45%.

The method's accuracy was demonstrated by its % recovery or % relative bias values using the data generated by three analysts (N=6) from the five recovery samples. The geometric mean values of measured % RP values of the 5 recovery samples corresponding to the expected relative potency at 40%, 70%, 100%, 130% and 160% were 43.3%, 65.1%, 101.3%, 122.7% and 148.1%, respectively. The % recovery values ranged from 92.6% to 108.3% (Table 19). The relative bias values ranged from −7.5% to 8.3% (Table 20 and Example 6).

Furthermore, the linearity of the method was evaluated by applying the linear regression model (see Example 6) to the geometric mean of measured % Relative Potency (% RP) vs expected % Relative Potency within a range from 40% to 160% using the data from three analysts (N=6). It is evident that the measured vs expected % RP values at 40%, 70%, 100%, 130% and 160% shows excellent linear relationship with a slope of 0.890 and $R^2$ value of 0.99 as seen in Table 21 and FIG. 19 (also see Example 6). In addition, the successful studies using recovery samples concluded that the assay lower limit of quantitation (LLOQ) and upper limit of quantitation (ULOQ) of the method were approximately 40% and 160%, respectively. Therefore, the method warrants accurate and precise determination of % RP values within the assessed assay range from 40% to 160%.

Determination of the Method's Repeatability

The repeatability was assessed using three recovery samples with their expected % RP at 40%, 100% and 160%. The results were derived from two runs of experiments due to the failed system suitability of two plates in the first run (See Exceptional Conditions section for the explanation). As summarized in Table 22, % RSD values from these three recovery samples (N=3 per sample) were 15.6%, 9.7%, 4.9%, respectively, and combined % RSD was 11.0% (N=9) (Also see Example 6). All % RSD values met the acceptance criterion defined for repeatability at % RSD ≤20%, demonstrating intra-plate precision of the method.

Method's Specificity

Figure 20B:
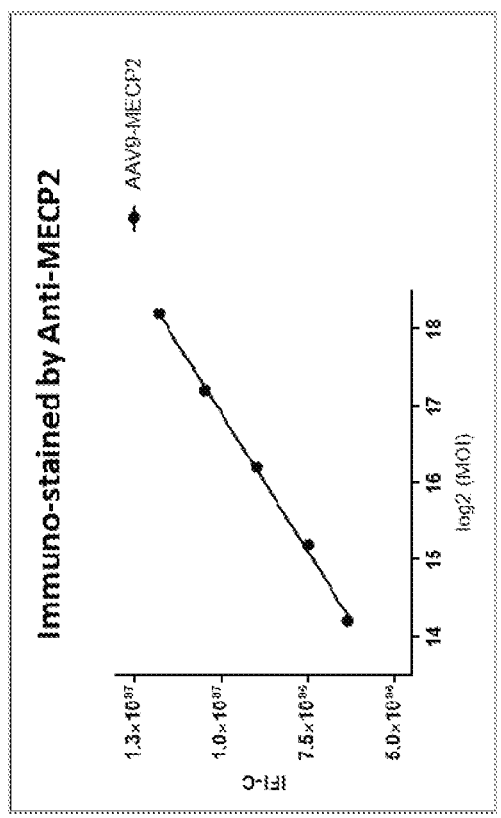
FIGS. 20A-20B are a pair of plots showing specificity demonstrated by staining cells transduced SMN1 encoding AAV9 vector or MECP2 encoding AAV9 vector using the SMN1 antibody.
Figure 20A:
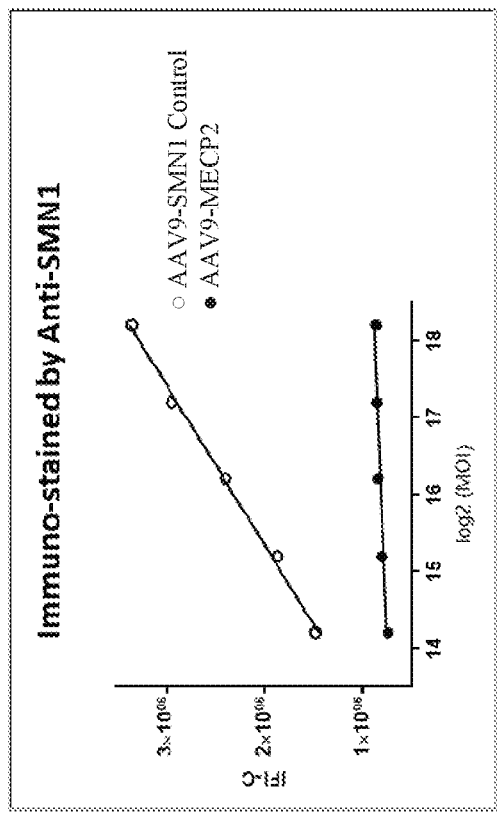

To further determine whether the cell-based potency assay is specific for quantifying the relative potency of SMN1-encoding AAV9 DP expressing SMN1, but not AAV9 vectors expressing irrelevant protein, SMN1-encoding AAV9 or MECP2-AAV9 expressing MeCP2 protein was used to transduce mTD-NPCΔ7s. The transduced cells were then stained by mouse anti-SMN1 (clone 2B1). Integrated fluorescence intensity per cell (IFI-C), which is indicative of SMN1 protein expression level, remained at background level (comparable to Cell only) in AAV9-MECP2 transduced cells (FIG. 20A). To confirm the finding of background level IFI-C readout from AAV9-MECP2 transduced cells was not due to unsuccessful transduction, the AAV9-MECP2-transduced cells were stained by anti-MeCP2 antibody. As shown in FIG. 20B, a dose dependent increase in IFI-C indicative of MeCP2 protein expression was observed confirming that AAV9-MECP2 indeed was successfully transduced into the cells.

Robustness of the Method

Robustness of the method was evaluated by deliberately varying assay conditions that have potential impact upon the assay performance. Each robustness study was designed to assess one assay condition per plate by measuring the relative potency of a sample at 100% relative potency. The results in Table 23 demonstrated that the assay performance was not affected by the varied conditions since the measured relative potency values all met the acceptance criteria which fell within ±40% of targeted 100%. Therefore, the method is considered robust under the assay conditions assessed which include cell seeding density, cell passage number, cell vials from working cell bank, SMN1 antibody concentration, cell differentiation time and duration of infection.

Parallelism of the Method

Parallelism is measured by the ratio of slopes of samples relative to the slope of the reference standard. Appropriate establishment of the slope ratio criterion, which ensures the parallelism, is crucial for the accurate and precise quantitation of relative potency. The criterion of slope ratio was determined using the distribution of slope ratios from assay control samples as assay control is prepared the same as reference standard. The slope ratio criterion for qualification study was determined as 0.69-1.45 using plates generated in assay development and pre-qualification after removing the outlier plates. The criterion was later narrowed down to 0.75-1.33 for validation study by exclusion of assay development and inclusion of assay qualification plates. In the validation study, among samples that passed all the other system suitability criteria, only two samples (both from repeatability study using 40% recovery samples) did not meet the tightened sample slope ratio criterion of 0.75-1.33, and these two samples did meet sample slope ratio criterion used in qualification study (0.69-1.45).

Further assessment of the slope ratios of five recovery samples and the assay control derived from the qualification and validation studies revealed that the failure of these two 40% recovery samples was due to the slightly lower slope ratio and higher variability associated with the 40% recovery sample (Table 24). Despite the lower slope ratio and higher variability of the 40% recovery sample, the assay performance in precision, accuracy and linearity were all successfully demonstrated for this sample in both assay qualification and validation studies (Example 6). Therefore, the observed slope ratio range (Mean±3SD range: 0.67 to 1.09, Table 24) for the 40% recovery sample is deemed acceptable and to have minimal impact in relative potency assay results. Taken together, it is demonstrated that the adjusted sample slope ratio acceptance criterion as shown in Table 25 still ensures the parallelism of the method suitable for the accurate and precise measurement of relative potency.

The deviation associated with the adjusted sample slope ratio was documented in the section entitled "Exceptional Conditions" of this example.

TABLE 18

Summary of Measured Relative Potencies from the Recovery Study for Intermediate Precision
Relative Potency %[a]

| Analyst | Assay Run | 40% of target (nominal) | 70% of target (nominal) | 100% of target (nominal) | 130% of target (nominal) | 160% of target (nominal) |
|---|---|---|---|---|---|---|
| 1 | 1 | 38.6 | 70.6 | 91.3 | 132.3 | 160.1 |
|   | 2 | 38.7 | 48.0 | 87.3 | 81.0 | 108.1 |
| 2 | 1 | 51.8 | 88.2 | 126.9 | 155.2 | 173.0 |
|   | 2 | 49.0 | 72.3 | 112.3 | 139.6 | 160.3 |
| Geometric Mean Measured | | 44.1 | 68.2 | 103.2 | 123.4 | 148.0 |
| Expected Potency % | | 40.0 | 70.0 | 100.0 | 130.0 | 160.0 |
| RSD (%) | | 15.6 | 25.9 | 17.7 | 29.5 | 21.5 |
| Combined % RSD = 23.5 (N = 20) | | | | | | |

[a]Potency Measurements are expressed as % Relative Potency

The study used 1.0E+12 vg/mL AVXS-101 as the target concentration (designated as relative potency of 100%). The intermediate precision was assessed with five recovery samples over a range of 40-160% of the relative potency against 100% (at the concentration of 1.0 E+12 vg/mL) by two analysts (N=4 per sample). % RSD per sample (N=4) and combined % RSD (N=20) were determined respectively. In this case, AVXS-101 reference material was diluted to nominal concentrations of 0.4 E+12, 0.7E+12, 1.0E+12, 1.3E+12, and 1.6E+12 vg/ml and the genomic titers of the diluted samples were confirmed by ddPCR determination.

TABLE 19

Summary of Measured Relative Potencies from the Recovery Study for Reproducibility Study
Relative Potency %

| Analyst | Assay Run | QC Lab | 40% of target (nominal) | 70% of target (nominal) | 100% of target (nominal) | 130% of target (nominal) | 160% of target (nominal) |
|---|---|---|---|---|---|---|---|
| 1 | 1 | 1 | 38.6 | 70.6 | 91.3 | 132.3 | 160.1 |
|   | 2 | 1 | 38.7 | 48.0 | 87.3 | 81.0 | 108.1 |
| 2 | 1 | 1 | 51.8 | 88.2 | 126.9 | 155.2 | 173.0 |
|   | 2 | 1 | 49.0 | 72.3 | 112.3 | 139.6 | 160.3 |
| 3 | 1 | 2 | 44.7 | 53.9 | 114.1 | 120.2 | 173.2 |
|   | 2 | 2 | 38.9 | 65.4 | 83.2 | 122.5 | 126.7 |
| Geometric Mean Measured Potency % (n = 6) | | | 43.3 | 65.1 | 101.3 | 122.7 | 148.1 |
| Expected Potency % | | | 40.0 | 70.0 | 100.0 | 130.0 | 160.0 |
| Recovery %[a] | | | 108.3 | 93.0 | 101.3 | 94.4 | 92.6 |
| RSD (%) | | | 13.2 | 22.1 | 17.3 | 22.7 | 19.4 |
| Combined % RSD = 19.7 (N = 30) | | | | | | | |

[a]Recovery (%) = (geometric mean measured potency ÷ expected potency) × 100

TABLE 20

Accuracy of the Method Demonstrated by Relative Bias (N = 6)

| Recovery Sample ID | Expected Relative Potency | Measured Geometric Mean Relative Potency | Relative Bias [Measured/Expected]-1 |
|---|---|---|---|
| S1 | 40% | 43.3% | 8.3% |
| S2 | 70% | 65.1% | −7.0% |
| S3 | 100% | 101.3% | 1.3% |
| S4 | 130% | 122.7% | −5.6% |
| S5 | 160% | 148.1% | −7.5% |

TABLE 21

Linearity Demonstrated by the Slope and $R^2$ Value with Linear Regression Model

| [1]Intercept | | [1]Slope | | [1]$R^2$ |
|---|---|---|---|---|
| Estimate | 95% CI | Estimate | 95% CI | |
| 7.05 | (−7.46, 21.56) | 0.890 | (0.757, 1.024) | 0.99 |

[1]The linear regression model was applied to the geometric mean of the measured relative potency results versus expected relative potency ranging from 40% to 160% of the 5 recovery samples.

TABLE 22

Repeatability Data from Three Recovery Samples

| Sample ID | Expected Relative Potency | Measured Relative Potency | | | Geometric Mean | % RSD |
|---|---|---|---|---|---|---|
| | | R1 | R2 | R3 | | |
| [1]S1 | 40% | 39.2% | 45.5% | 53.5% | 45.7% | 15.6% |
| S3 | 100% | 109.1% | 90.0% | 100.1% | 99.4% | 9.7% |
| [1]S5 | 160% | 153.1% | 140.4% | 140.7% | 144.6% | 4.9% |

Combined % RSD = 11.0% (N = 9)

[1]Two runs of experiments were performed for repeatability study since the initial run yielded a valid plate for S3 (100%), but resulted in invalid plates for S1 and S5 due to failed system suitability, requiring a re-test run for the failed plates. Re-test runs were successful and valid results were generated for S1 and S5 (see the "Exceptional Conditions" section for the deviation and data re-analysis for S1). 3% RP values per sample are summarized in the table.

TABLE 23

Robustness Data Summary

| Parameters | % Relative Potency of Test Sample[1] | | | Impact upon Assay Performance |
|---|---|---|---|---|
| | Condition 1 | Condition 2 | Condition 3 | |
| Cell Seeding Density (cells/mL) at 1.5E+5; 2.0E+5; or 2.5E+5 | 105.8% | 84.4% | 76.5% | None |
| Cell Passage Number at P8 or P15 | 91.0% | 90.4% | NA | None |
| Vial to Vial Variability in WCB-NPC Δ7.2.6 Cells Vial 1; Vial 2, or Vial 3 | 91.0% | 85.5% | 90.6% | None |
| Differentiation Time (hrs) at 22; 24; or 26 | 136.3% | 99.6% | 120.4% | None |
| Incubation Time After AVXS-101 Transduction (hrs) at 70; 72, or 74 | 89.6% | 111.7% | 95.5% | None |

TABLE 23-continued

Robustness Data Summary

| | % Relative Potency of Test Sample[1] | | | Impact upon Assay |
|---|---|---|---|---|
| Parameters | Condition 1 | Condition 2 | Condition 3 | Performance |
| Concentration of Mouse Anti-SMNI Monoclonal Antibody 2B1 (µg/mL) at 1.6; 2.0; or 2.4 | 103.4% | 104.4% | 107.6% | None |

[1]The sample used for the robustness study were from SMN1-encoding AAV9 drug product Lot 600443. In addition, each of the assay plates met the system suitability as described in Example 4.

TABLE 24

Summary of Slope Ratio Estimates of Sample to Reference Standard

| | Assay | Recovery Sample | | | | |
|---|---|---|---|---|---|---|
| | Control | 40% | 70% | 100% | 130% | 160% |
| N | 48 | 20 | 12 | 34 | 12 | 20 |
| Geometric Mean | 1.00 | 0.85 | 0.97 | 0.98 | 1.00 | 0.99 |
| CV % | 5.1% | 8.1% | 5.1% | 6.3% | 5.6% | 9.2% |
| 95% Confidence Interval | 0.98 to 1.01 | 0.82 to 0.89 | 0.94 to 1.01 | 0.96 to 1.00 | 0.97 to 1.04 | 0.95 to 1.03 |
| Comparison with Assay Control (p-Value) [a] | — | <0.0001 | 0.7093 | 0.6950 | 0.9999 | 0.9686 |
| Mean ± 3SD [b] | 0.86 to 1.16 | 0.67 to 1.09 | 0.84 to 1.14 | 0.81 to 1.18 | 0.85 to 1.19 | 0.75 to 1.30 |
| % within 0.75-1.33 | 100% | 90% | 100% | 100% | 100% | 100% |
| % within 0.69-1.45 | 100% | 100% | 100% | 100% | 100% | 100% |

TABLE 25

Summary of Assay System Suitability Criteria

| | | Criteria | | |
|---|---|---|---|---|
| Sample | Parameter | Qualification Study | Validation Study | Validation Study |
| Reference Standard | $R^2$ | ≥0.95 | ≥0.95 | ≥0.95 |
| | Slope | ≥1.02E+05 | ≥1.02E+05 | ≥1.02E+05 |
| | Assay Dynamic Window | ≥2.69 | ≥2.69 | ≥2.69 |
| Assay Control | $R^2$ | ≥0.95 | >0.95 | ≥0.95 |
| | Slope Ratio | 0.69 to 1.45 | 0.75 to 1.33 | 0.75 to 1.33 |
| | Relative Potency | 50% to 150% | 60% to 140% | 60% to 140% |
| Test Samples | $R^2$ | ≥0.95 | ≥0.95 | ≥0.95 |
| | Slope Ratio | 0.69 to 1.45 | 0.75 to 1.33 | 0.69 to 1.45 |
| All Samples | CV % of IFI-C at each MOI dose | ≤20% | ≤20% | ≤20% |

Conclusion

Taken together the data derived from the comprehensive validation study and their statistical analysis (Example 6), it was demonstrated that the potency method described in example 4 for AAV9-SMN1 vector was accurate with relative bias values within the range of −7.5%-8.3% and precise with the combined intermediate precision at % RSD of 23.5% (N=20), combined reproducibility at % RSD of 19.7% (N=30), and combined repeatability at % RSD of 11.0% (N=9). The method also showed excellent linearity within the assay range of % RP from 40% to 160% with the slope and $R^2$ at 0.890 and 0.99, respectively when the relationship of measured % RP vs the expected % RP from the 5 recovery samples at 40%, 70%, 100%, 130% and 160% was statistically analyzed with the linear regression (Example 6). Furthermore, the validated assay range concluded that the assay LLOQ and ULOQ are approximately 40% and 160%, respectively.

In addition to the assay performance shown by this method validation study, a recent study with thermally stressed samples demonstrated that the in vitro cell-based potency method described in example 4 was stability-indicating (Example 9). In this study, the thermal stress sample of GMP lot 100656 of SMN1-encoding AAV9 vector held at 20-25° C. for 3 months (T=3 M) lost more than half of its potency with measured % RP of 42.2%, while the control GMPS sample (T0) and the thermal stress sample held at the same temperature for 1 month (T=1 M) were fully potent. Furthermore, the studies on assessing the potential plate effect demonstrated that no systematic bias for the potency measurement is observed using the plate layout designed for sample testing per the protocol described in Example 4 (See Examples 6 and 7).

Therefore, the validated and stability-indicating in vitro cell-based potency method described in example 4 was deemed to be suitable for lot disposition of clinical and licensed SMN1 encoding AAV9 vector drug product (DP) and for evaluating potency of stability samples.

Exceptional Conditions

Deviation

During validation of the in vitro Relative Potency Cell-based Assay, the repeatability study was performed using three recovery samples (at target potency of 40%, 100% and 160%). It was observed that the sample system suitability from the plate containing 40% samples failed even though the plate passed all the assay system suitability criteria associated with the reference standard and assay control.

On each plate of repeatability study, the three % RP values were obtained from sample positions designed as S1, S2 and S3 in the plate layout. To obtain valid data from each sample, system suitability required that the slope ratio of the test sample versus the reference standard to be within 0.75-1.33, and its R2 value to be ≥0.95 among other assay parameter acceptance criteria (see Example 4). However, the slope ratios of S2 and S3 in the assay of the plate containing 40% samples were 0.72 and 0.66, respectively. In addition, the Revalue of S3 was 0.9311. The two samples with failed sample system suitability were not used to generate % RP values. Therefore, only one % RP value was generated from this assay plate. Given that the repeatability assessment requires three % RP values on each plate, the repeatability study using 40% recovery sample was repeated. Upon retest, the slope ratio of S1 (0.73) again failed the sample slope ratio criterion. Data review and statistical analysis were initiated.

Root Causes and Justifications

An investigation was conducted on the failure of the sample system suitability criteria for tested samples in repeatability study as described in the Deviation.

The common assay parameter that did not meet the system suitability criterion across three individual samples that failed (2 from original and 1 from repeated assays for the 40% repeatability study) was the slope ratio. In addition, the only additional invalid assay during the validation (repeatability study using 160% recovery samples) was due to a failure in % CV of one dose point of a sample which was immediately determined to have been caused by an artifact on the assay plate. In the comprehensive validation study including total 34 plates, the rest of system suitability per Example 4 and predefined acceptance criteria were all met. The validation results as reported here also demonstrated acceptable robustness, precision, accuracy, linearity and assay range of the SMN1 encoding AAV9 vector in-vitro Relative Potency Cell-based Assay. Therefore, the investigators postulated that the acceptance criterion for the sample slope ratio in the validation protocol may not have been suitable and may have been established stringently post-assay qualification and pre-assay validation protocols (from 0.69-1.45 to 0.75-1.33).

The investigators reviewed how the system suitability acceptance criteria were established for qualification and then revised for validation with more stringent criteria. The system suitability acceptance criteria for qualification were determined based on available assay development and pre-qualification data obtained during 1-month period where the slope ratio was defined to be 0.69-1.45. The revised system suitability criteria for validation which were tightened for a few assay parameters including the slope ratio range (from 0.69-1.45 to 0.75-1.33) were based on pre-qualification and qualification data. Furthermore, tightening the system suitability criteria did not consider additional analyst-to-analyst, lab-to-lab, instrument-to-instrument variabilities introduced during the method validation (Table 26).

TABLE 26

Differences Between the Method Qualification and Method Validation

| | Qualification | Validation |
|---|---|---|
| Number of Labs | 1 | 2 (both are different from the lab used for qualification) |
| Number of Analysts | 2 | 4 |
| Level of Analysts | Highly experienced who developed the assay | Varying range in experience |
| Instrument | Original instrument | Two new instruments |

After the investigation, it was determined that the slope ratio system suitability criterion was based on assay controls from a very short history of performing the assay and then were further tightened immediately after the method qualification without additional confirmatory data. Especially, the slope ratio criterion determined using assay controls did not reflect more variable and on average lower slope ratio range shown by 40% recovery samples (refer to Table 24). In addition, the comparison between execution environment for the method qualification and validation showed that the method validation environment included additional variables. Therefore, investigators concluded that the tightening the sample system suitability acceptance criteria immediately after the very successful method qualification with limited assay experience was premature and not well justified, leading to the failure of the sample slope ratio during the method validation that harbor many differences in the execution environment compared to the method qualification.

Despite the slightly lower slope ratio for the 40% recovery sample, the assay performance in precision, accuracy and linearity was all successfully demonstrated for this sample both in assay qualification and validation studies. Therefore, the observed slope ratio range (Mean±3SD range: 0.67 to 1.09) for the 40% recovery sample was deemed acceptable and has minimal impact in relative potency assay results. Furthermore, to accommodate higher variability in slope ratios in test samples and slightly lower slope ratio of 40% recovery sample, wider sample slope range of 0.69-1.45, which was used for assay qualification study, was applied for the analysis of validation study data. The slope ratio range for assay control (0.75-1.33) remained unchanged as well as all the other system suitability acceptance criteria to ensure no impact on the data quality. The validation data analyzed using the reverted sample slope ratio criterion demonstrated desired accuracy, precision, linearity, robustness and specificity of the assay (Example 6). Taken together, this shows that applying the sample slope ratio acceptance criterion of 0.69-1.45 warrants the data quality in the measurement of relative potency.

Example 6: Statistical Analysis of the Validation of the In-Vitro Relative Potency Cell-Based Assay for SMN1 Encoding AAV9 Vector Drug Product The results from the validation study of the in vitro relative potency cell based assay for SMN1-AAV9 (Example 5) that was carried out using the methods described in Example 4 were assessed for statistical significance.

The results of the validation study were assessed for precision (repeatability, intermediate precision, and reproducibility), accuracy, linearity, assay range and specificity.

The results are summarized in Table 27 below. The assay range of relative potency from 40% to 160% was successfully validated in assay precision, accuracy, linearity and specificity. The successful method validation study concluded the assay range as 40% to 160%, which represent assay LLOQ and ULOQ respectively.

The parallelism of in-vitro relative potency assay was measured by the ratio of slopes of samples relative to the reference standard. The criterion for slope ratio was determined using the distribution of slope ratios from assay control samples, as assay controls were prepared the same as reference standard. The slope ratio criterion for qualification study was determined as 0.69-1.45 using plates generated in assay development and pre-qualification after removing outlier plates. The criterion was later narrowed down to 0.75-1.33 for validation study by exclusion of assay development plates and inclusion of assay qualification plates (Table 28).

Figure 25:
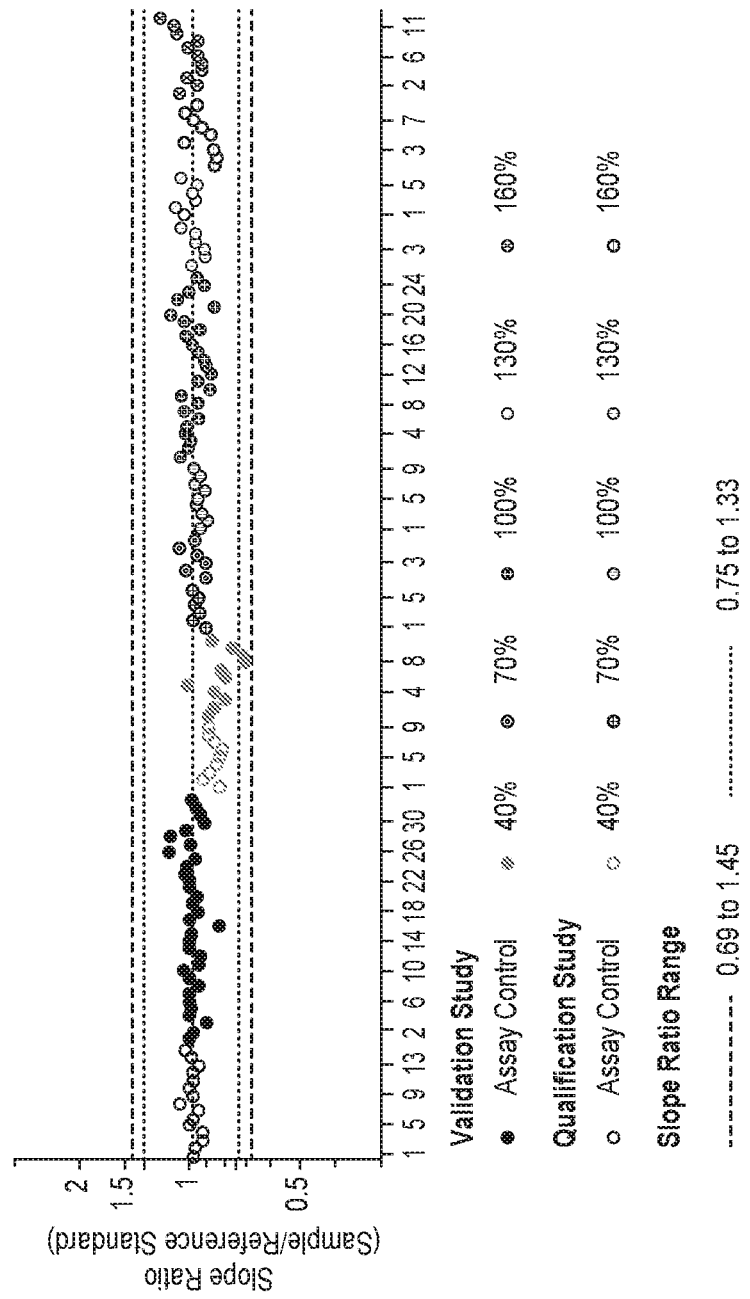
FIG. 25 is a plot illustrating the summary of slope ratio estimates of sample to reference standard.

In the assay validation study (Example 5), for samples that passed all other system suitability criteria, sample slope ratios were all within the range of 0.75-1.33 except for two 40% recovery sample replicates which were both within the range of 0.69-1.45 (Table 29 & FIG. 25). The failure of these two 40% recovery sample replicates were due to (1) the slope ratio of the 40% recovery sample was on average lower and (2) higher variability in slope ratios is observed for the 40% recovery sample (Table 29).

Despite the slightly lower slope ratio for the 40% recovery sample, the assay performance in precision, accuracy and linearity were all successfully demonstrated for this sample in both assay qualification and validation studies. Therefore, the observed slope ratio range (Mean±3SD range: 0.67 to 1.09, Table 29) for the 40% recovery sample was deemed acceptable and to have minimal impact in relative potency assay results. For the validation study (Example 5), the adjusted slope ratio criterion was implemented (Table 28). For the adjusted criteria, the slope ratio range of 0.75-1.33 remained for the assay control sample, while the wider range of 0.69-1.45, which was used for assay qualification study, was applied to test samples to accommodate higher variability in slope ratios in test samples and slightly lower slope ratios as shown in the 40% recovery sample (Tables 28 & 29). The deviation associated with the adjusted slope ratio criteria is described in the "Exceptional Conditions" section of Example 5.

TABLE 27

Summary of assay validation study results

| Parameter | Acceptance Criteria | Results | Pass/Fail? |
|---|---|---|---|
| Precision | Intermediate Precision<br>% RSD ≤40% for each of the five recovery samples and combined | RSD %[a]:<br>By sample: 15.6% to 29.5% | Pass |
|  | Repeatability:<br>% RSD ≤20% for each of the three recovery samples and combined | RSD%[a].<br>By sample: 4.9% to 15.6%<br>3 samples combined: 11.0% | Pass |
|  | Reproducibility:<br>%RSD ≤45% for each of the five recovery samples and combined | RSD%[a]:<br>By sample: 13.2% to 22.7% 5 samples combined: 19.7% | Pass |
| Accuracy | Relative bias[b] within ±40% of expected Relative Potency at 40%, 70%, 100%, 130% or 160% of each of the 5 recovery samples | Relative bias[b]:<br>By sample: −7.5% to 8.3% | Pass |
| Linearity | $R^2$ ≥0.9<br>The slope estimate of the linear regression model within the range of: 1 ± 0.25 | $R^2$ = 0.99<br>Slope = 0.890 | Pass |
| Specificity | Lack of a dose-dependent increase of IFI-C is demonstrated in mTD-NPCΔ7 cells that are transduced with AAV9-MECP2 followed by staining with anti-SMN1 antibody indicative of no specific staining.<br>When stained by anti-MECP2 (Columns 8-9), the efficient transduction of AAV9-MECP2 into the cells is demonstrated by the dose-dependent increase of fluorescence signal indicative of MECP2 expression in the transduced cells. | Mean IFI-C for the 5 doses of the transduced AAV9-MECP2 stained with anti-SMN1 2B1 ranged from 7.4E+05 to 8.71E+05 and no dose response trend is observed. AAV9-MECP2 transduced cells stained by anti-MECP2: Dose-dependent increase of IFI-C is demonstrated. | Pass |

[a]RSD % (relative standard deviation) is also known as CV % (coefficient of variance)

[b]relative bias = $\left(\dfrac{\text{Measured}}{\text{Expected}} - 1\right) * 100\%$

TABLE 28

Summary of Assay System Suitability Criteria

| Sample | Parameter | Criteria | | |
|---|---|---|---|---|
| | | Qualification Study | Validation Study | Validation Study Adjusted |
| Reference Standard | $R^2$ | ≥0.95 | ≥0.95 | ≥0.95 |
| | Slope | ≥1.02E+05 | ≥1.02E+05 | ≥1.02E+05 |
| | Assay Dynamic Window | ≥2.69 | ≥2.69 | ≥2.69 |
| Assay Control | $R^2$ | ≥0.95 | ≥0.95 | ≥0.95 |
| | Slope Ratio | 0.69 to 1.45 | 0.75 to 1.33 | 0.75 to 1.33 |
| | Relative Potency | 50% to 150% | 60% to 140% | 60% to 140% |
| Test Samples | $R^2$ | ≥0.95 | ≥0.95 | ≥0.95 |
| | Slope Ratio | 0.69 to 1.45 | 0.75 to 1.33 | 0.69 to 1.45 |
| All Samples | CV % of IFI-C at each MOI dose | ≤20% | ≤20% | ≤20% |

TABLE 29

Summary of slope ratio estimates of sample to reference standard

| | Assay Control | Recovery Sample | | | | |
|---|---|---|---|---|---|---|
| | | 40% | 70% | 100% | 130% | 160% |
| N | 48 | 20 | 12 | 34 | 12 | 20 |
| Geometric Mean | 1.00 | 0.85 | 0.97 | 0.98 | 1.00 | 0.99 |
| CV % | 5.1% | 8.1% | 5.1% | 6.3% | 5.6% | 9.2% |
| 95% Confidence Interval | 0.98 to 1.01 | 0.82 to 0.89 | 0.94 to 1.01 | 0.96 to 1.00 | 0.97 to 1.04 | 0.95 to 1.03 |
| Comparison with Assay Control (p-Value)[a] | — | <0.0001 | 0.7093 | 0.6950 | 0.9999 | 0.9686 |
| Mean ± 3SD[b] | 0.86 to 1.16 | 0.67 to 1.09 | 0.84 to 1.14 | 0.81 to 1.18 | 0.85 to 1.19 | 0.75 to 1.30 |
| % within 0.75-1.33 | 100% | 90% | 100% | 100% | 100% | 100% |
| % within 0.69-1.45 | 100% | 100% | 100% | 100% | 100% | 100% |

[a] p-value from multiple comparison with assay control using Dunnett's method
[b] mean ± 3SD range is calculated using natural log transformed slope ratios and anti-log transformed back to the original scale.

TABLE 30

Summary of repeatability study

| Sample | Expected Relative Potency | Geometric Mean | Repeatability (RSD %[a]) | |
|---|---|---|---|---|
| | | | Estimate | one-sided 95% Upper Confidence Limit |
| S1 | 40% | 45.7% | 15.6% | 77.6% |
| S3 | 100% | 99.4% | 9.7% | 44.6% |
| S5 | 160% | 144.6% | 4.9% | 22.1% |
| S1, S3 & S5 Combined | | | 11.0% | 21.2% |

[a] RSD % (relative standard deviation) is also known as CV % (coefficient of variation)

Intermediate Precision

The intermediate precision data included 5 recovery samples each with 4 relative potency results generated from Repeatability The repeatability data included 3 recovery samples, each with 3 relative potency results generated from the same assay run. The repeatability data is listed in Table 30. The relative potency was assumed to follow a log-normal distribution in this analysis.

For each recovery sample, the mean ($\hat{\mu}$) and standard deviation ($\hat{\sigma}$) and associated 95% confidence limits are estimated for the natural log transformed relative potency results; and the geometric mean relative potency ($\hat{\mu}$) and percent coefficient of variation (CV %=$\sqrt{e^{\hat{\sigma}^2}-1}\times 100\%$) were then calculated and summarized in Table 31. The CV % estimates for repeatability ranged from 4.9% to 15.6%.

For the combination of 3 recovery samples, model (M2.1) was fitted to the pooled data to estimate the overall repeatability across the 3 recovery samples. The overall repeatability using pooled data from 3 recovery sample was 11.0% (Table 30).

$$\log(y_{ij}) = \mu_i + \epsilon_{ij} \quad (M2.1)$$

where, $y_{ij}$ is the relative potency from recovery sample i; $\mu_i$ is the mean log-transformed relative potency of recovery sample i, and $\epsilon_{ij}$~Normal (0, $\sigma_{intra-assay}^2$) is the random intra-assay residual error.

4 independent assays by 2 analysts on two assay days. The samples were analyzed to assess intermediate precision of the in-vitro potency assay. The data from intermediate precision study are listed in Table 41. The relative potency was assumed to follow a log-normal distribution in this analysis.

For each recovery sample, the mean ($\hat{\mu}$) and standard deviation ($\hat{\sigma}$) and associated 95% confidence limits were estimated for the natural log transformed relative potency results; and the geometric mean relative potency ($e^{\hat{\mu}}$) and percent coefficient of variation (CV %=$\sqrt{e^{\hat{\sigma}^2}-1}\times 100\%$) were then calculated and summarized in Table 31. The CV % estimates ranged from 15.6% to 29.5%.

For the combination of 5 recovery samples, model (M2.2) was fitted to the pooled data to estimate the overall intermediate precision ($\sigma_{inter-assay}^2 + \sigma_{intra-assay}^2$) across 5 recovery samples. The overall intermediate precision using pooled data from 5 recovery samples was 23.5% (Table 30).

$$\log(y_{ijk}) = \mu_i + \theta_j + \epsilon_{ijk} \quad (M2.2)$$

where $y_{ijk}$ is the relative potency from recovery sample i; $\mu_i$ is the mean log-transformed relative potency of recovery sample i;

$\theta_j$~Normal (0, $\sigma_{inter\text{-}assay}^2$) is the random inter-assay effect from assay run j; and $\epsilon_{ijk}$~Normal (0, $\sigma_{intra\text{-}assay}^2$) is the random intra-assay residual error.

TABLE 31

Summary of intermediate precision, by recovery sample

| Sample | Geometric Mean Relative Potency | Intermediate Precision (RSD %) | |
|---|---|---|---|
| | | Estimate | one-sided 95% Upper Confidence Limit |
| 40% Recovery | 44.1% | 15.6% | 47.6% |
| 70% Recovery | 68.2% | 25.9% | 85.8% |
| 100% Recovery | 103.2% | 17.7% | 55.0% |
| 130% Recovery | 123.4% | 29.5% | 101.7% |
| 160% Recovery | 148.0% | 21.5% | 68.6% |

$^a$RSD % (relative standard deviation) is also known as CV % (coefficient of variation)

TABLE 32

Summary of overall intermediate precision, 5 recovery samples combined

| | Assay variability (RSD %$^a$) | | |
|---|---|---|---|
| | Inter-assay | Intra-assay | Total (intermediate precision |
| Estimate | 22.1% | 7.8% | 23.5% |
| One-sided 95% Upper Confidence Limit | 46.3% | 12.9% | 44.0% |

$^a$RSD % (relative standard deviation) is also known as CV % (coefficient of variation)

Reproducibility

The reproducibility data included 5 recovery samples each with 6 relative potency results generated from 4 independent assays, by two analysts, on two assay days from a first lab and 2 independent assays, by one analyst, on two assay days from a second lab. The data were analyzed to assess assay reproducibility of the in-vitro potency assay. The data for reproducibility, accuracy and linearity are listed in Table 41. The relative potency was assumed to follow a log-normal distribution in this analysis.

For each recovery sample, the mean ($\hat{\mu}$) and standard deviation ($\hat{\sigma}$) and associated 95% confidence limits were estimated for the natural log transformed relative potency results; and the geometric mean relative potency ($e^{\hat{\mu}}$) and percent coefficient of variation (CV %=$\sqrt{e^{\hat{\sigma}^2}-1} \times 100\%$) were then calculated and summarized in Table 33. The CV % estimates ranged from 13.2% to 22.7%.

For the combination of 5 recovery samples, model (M2.3) was fitted to the pooled data to estimate the overall reproducibility ($\sigma_{inter\text{-}lab}^2 + \sigma_{inter\text{-}assay}^2 + \sigma_{intra\text{-}assay}^2$) across 5 recovery samples. The overall intermediate precision using pooled data from 5 recovery samples was 19.7% (Table 34).

$$\log(y_{iljk}) = \mu_i + \alpha_l \theta_j + \epsilon_{ijk} \quad (M2.3)$$

where $y_{ijk}$ is the relative potency from recovery sample i;

$\mu_i$ is the mean log-transformed relative potency of recovery sample i;

$\alpha_l$~Normal (0, $\sigma_{inter\text{-}lab}^2$) is the random inter-lab effect from lab l;

$\theta_{j[l]}$~Normal (0, $\sigma_{inter\text{-}assay}^2$) is the random inter-assay effect from assay run j nested in lab l; and $\epsilon_{ijk}$~Normal (0, $\sigma_{intra\text{-}assay}^2$) is the random intra-assay residual error.

TABLE 33

Summary of reproducibility, by recovery sample

| Sample | Geometric Mean Relative Potency | Intermediate Precision (RSD %$^a$) | |
|---|---|---|---|
| | | Estimate | One-sided 95% Upper Confidence Limit |
| 40% Recovery | 43.3% | 13.2% | 27.9% |
| 70% Recovery | 65.1% | 22.1% | 48.1% |
| 100% Recovery | 101.3% | 37.0% | 55.0% |
| 130% Recovery | 122.7% | 22.7% | 49.4% |
| 160% Recovery | 148.1% | 19.4% | 41.8% |

$^a$RSD % (relative standard deviation) is also known as CV % (coefficient of variation)

TABLE 34

Summary of overall reproducibility, 5 recovery samples combined

| | Assay variability (RSD %$^a$) | | | |
|---|---|---|---|---|
| | Inter-lab | Inter-assay | Intra-assay | Total (intermediate precision |
| Estimate | 0% | 18.2% | 7.6% | 19.7% |
| One-sided 95% Upper Confidence Limit | 0% | 30.8% | 10.9% | 30.4% |

$^a$RSD % (relative standard deviation) is also known as CV % (coefficient of variation)

Accuracy

The relative bias for each recovery sample was estimated from the geometric mean relative potency and expected relative potency as $$\frac{\exp(\hat{\mu})}{\text{Expected Relative Potency}} - 1 \times 100\%$$

and the results are summarized in Table 35. The relative bias estimates range from −7.5% to 8.3%.

TABLE 35

Summary of relative bias

| | Geometric Mean Relative Potency | | Relative Bias | |
|---|---|---|---|---|
| Sample | Estimate | 95% CI | Estimate | 95% CI |
| 40% Recovery | 43.3% | (37.7%, 49.7%) | 8.3% | (−5.6%, 24.2%) |
| 70% Recovery | 65.1% | (51.8%, 81.9%) | −7.0% | (−26.0%, 17.0%) |
| 100% Recovery | 101.3% | (84.6%, 121.2%) | 1.3% | (−15.4%, 21.2%) |

TABLE 35-continued

Summary of relative bias

| | Geometric Mean Relative Potency | | Relative Bias | |
|---|---|---|---|---|
| Sample | Estimate | 95% CI | Estimate | 95% CI |
| 130% Recovery | 122.7% | 97.0%, 155.2%) | −5.6% | (−25.3%, 19.4%) |
| 160% Recovery | 148.1% | 121.0%, 181.1%) | −7.5% | (−24.4%, 13.2%) |

Linearity

The linear regression model was fitted to the geometric mean of measured relative potency as in Table 35 and expected potency. The linearity results are summarized in Table 36 and the data are graphed in FIG. 19. The R2 of the linear regression model was 0.99 and the estimated slope was 0.890.

TABLE 36

Summary of linearity

| Intercept | | Slope | | |
|---|---|---|---|---|
| Estimate | 95% CI | Estimate | 05% CI | $R^2$ |
| 7.05 | (−7.46, 21.56) | 0.890 | (0.757, 1.024) | 0.99 |

Specificity

The specificity was demonstrated in two sets of data from SMN1 and MeCP2 staining, respectively, and data as analyzed are listed in Table 42. In the first data set, the cells transduced with AAV9-SMN1 or AAV9-MECP2 vector with MOI dose range from 18.75 k to 300 k were stained with mouse anti-SMN1 2B1 antibody. The mean IFI-C readouts from duplicate wells transduced with AAV9-MECP2 at each MOI dose level did not show dose-dependent increasing trend while the AVXS-101 control showed linear dose response trend as expected (FIG. 20A). FIG. 20A shows a summary of the dose response trend of AAV9-SMN1 and AAV9-MECP2 transduction stained by anti-SMN1 mouse monoclonal antibody 2B1.

In the second data set, the cells transduced with AAV9-MECP2 with MOI dose range from 18.75K to 300K were stained with anti-MeCP2 rabbit monoclonal antibody. In this data, the efficient transduction of AAV9-MECP2 into the cells was demonstrated by the dose-dependent increase of fluorescence signal indicative of MECP2 expression in the transduced cells (FIG. 20B). FIG. 20B shows a summary of the dose response trend of AAV9-SMN1 and AAV9-MECP2 transduction stained by anti-MeCP2 rabbit monoclonal antibody.

Validation Study Result Summary

The analysis results of the assay validation study including precision (repeatability, intermediate precision and reproducibility), accuracy, linearity and specificity are summarized in Table 37. The assay validation study passed all pre-specified study criteria.

TABLE 37

Summary of Assay Validation Study Results

| Parameter | Acceptance Criteria | Results | Pass/Fail? |
|---|---|---|---|
| Precision | Intermediate Precision | RSD%[a]: | Pass |
| | % RSD ≤40% for each of the five recovery samples and combined | By sample: 15.6% to 29.5% 5 samples combined: 23.5% | |
| | Repeatability: | RSD%[a]: | Pass |
| | % RSD ≤20% for each of the three recovery samples and | By sample: 4.9% to 15.6% 5 samples combined: 11.0%% | |
| | Reproducibility: | RSD%[a]: | Pass |
| | % RSD ≤45% for each of the five recovery samples and combined | By sample: 13.2% to 22.7% 5 samples combined: 19.7% | |
| Accuracy | Relative biash within ±40% of expected Relative Potency at 40%, 70%, 100%, 130% or 160% of each of the 5 recovery samples | Relative bias: By sample: −7.5% to 8.3% | Pass |
| Linearity | $R^2 \geq 0.9$ | $R^2 = 0.99$ | Pass |
| | The slope estimate of the linear regression model within the range of: 1 ± 0.25 | Slope = 0.890 | |
| Specificity | Lack of a dose-dependent increase of IFI-C is demonstrated in mTD-NPCΔ7 cells that are transduced with AAV9-MECP2 followed by staining with anti-SMN1 antibody indicative of no specific staining. When stained by anti-MECP2 (Columns 8-9), the efficient transduction of AAV9-MECP2 | Mean IFI-C for the 5 doses of the transduced AAV9-MECP2 stained with anti0-SMN1 2B1 ranged from 7.4E+05 to 8.71E+05 and no dose response trend is observed. AAV9-MECP2 transduced cells stained by anti-MECP2: | Pass |

TABLE 37-continued

Summary of Assay Validation Study Results

| Parameter | Acceptance Criteria | Results | Pass/Fail? |
|---|---|---|---|
| | into the cells is demonstrated by the dose-dependent increase of fluorescence signal indicative of MECP2 expression in the transduced cells | dose-dependent increase of IFI-C is demonstrated | | aRSD % (relative standard deviation) is also known as CV % (coefficient of variation)

$^b$relative bias = $\frac{\text{Measured}}{\text{Expected}} - 1 \times 100\%$

Parallelism of Slope Ratio Assessment

The parallelism of in-vitro relative potency assay was measured by the ratio of slopes of test sample and reference standard, i.e. $\text{slope}_{sample}/\text{slope}_{standard}$, where the slope was estimated from linear regression model between IFI-c and log 2 transformed MOI levels.

The system suitability criteria for assay qualification and validation studies are listed in Table 38. The criterion for slope ratio was determined using distribution of slope ratios from assay control samples as assay control is prepared the same as reference standard. The slope ratio criterion for qualification study was determined as 0.69-1.45 using plates generated in assay development and pre-qualification after removing outlier plates and the criterion was later narrowed down to 0.75-1.33 for assay validation study by exclusion of assay development plates and inclusion of assay qualification plates.

Slope ratios from assay results generated in an assay qualification study and a validation study were pooled and analyzed to evaluate overall parallelism of samples relative to reference standard. The slope ratios were log transformed for analysis. For assay control and each recovery sample, the mean ($\hat{\mu}$) and standard deviation ($\hat{\sigma}$) were estimated for the natural log transformed slope ratios; and the geometric mean relative potency ($e^{\hat{\mu}}$) and percent coefficient of variation (CV %=$\sqrt{e^{\hat{\sigma}^2}-1} \times 100\%$) were then calculated and summarized in Table 39. Comparing to assay control sample, there was no significance difference in geometric mean slope ratio for 70%, 100%, 130% and 160% recovery samples; but the slope ratio for 40% recovery sample were lower than assay control (p<0.0001). The data also suggest higher variability in slope ratios for 40% and 160% recovery sample (CV %: 8.1% and 9.2% for 40% and 160% respectively, Table 39).

In the assay validation study, for samples that passed all other system suitability criteria, sample slope ratios were within the range of 0.75-1.33, except for two 40% recovery sample replicates which were both within the range of 0.69-1.45 (Table 39 & FIG. 25). The failure of these two 40% recovery sample replicates were due to (1) the slope ratio of the 40% recovery sample was on average lower and (2) higher variability in slope ratios was observed for the 40% recovery sample (Table 39).

Despite the slightly lower slope ratio for the 40% recovery sample, the assay performance in precision, accuracy and linearity were all successfully demonstrated for this sample in both assay qualification and validation studies. Therefore, the observed slope ratio range (Mean±3SD range: 0.67 to 1.09, Table 39) for the 40% recovery sample was deemed acceptable and have minimal impact in relative potency assay results. For validation study, the adjusted slope ratio criterion was implemented (Table 39). For the adjusted criteria, the slope ratio range of 0.75-1.33, remained for the assay control sample, while the wider range of 0.69-1.45, which was used for the assay qualification study, was applied to test samples to accommodate higher variability in slope ratios in test samples and slightly lower slope ratios as shown in the 40% recovery sample (Tables 38 & 39).

TABLE 38

Summary of Assay System Suitability Criteria

| | | Criteria | | |
|---|---|---|---|---|
| Sample | Parameter | Qualification Study | Validation Study | Validation Study Adjusted |
| Reference Standard | $R^2$ | ≥0.95 | ≥0.95 | ≥0.95 |
| | Slope | ≥1.02E+05 | ≥1.02E+05 | ≥1.02E+05 |
| | Assay Dynamic Window | ≥2.69 | ≥2.69 | ≥2.69 |
| Assay Control | $R^2$ | ≥0.95 | ≥0.95 | ≥0.95 |
| | Slope Ratio | 0.69 to 1.45 | 0.75 to 1.33 | 0.75 to 1.33 |
| | Relative Potency | 50% to 150% | 60% to 140% | 60% to 140% |
| Test Samples | $R^2$ | ≥0.95 | ≥0.95 | ≥0.95 |
| | Slope Ratio | 0.69 to 1.45 | 0.75 to 1.33 | 0.69 to 1.45 |
| All Samples | CV % of IFI-C at each MOI dose | ≤20% | ≤20% | ≤20% |

TABLE 39

Summary of slope ratio estimates of sample to reference standard

| | Assay Control | Recovery Sample | | | | |
|---|---|---|---|---|---|---|
| | | 40% | 70% | 100% | 130% | 160% |
| N | 48 | 20 | 12 | 34 | 12 | 20 |
| Geometric | 1.00 | 0.85 | 0.97 | 0.98 | 1.00 | 0.99 |
| CV % | 5.1% | 8.1% | 5.1% | 6.3% | 5.6% | 9.2% |
| 95% Confidence Interval | 0.98 to 1.01 | 0.82 to 0.89 | 0.94 to 1.01 | 0.96 to 1.00 | 0.97 to 1.04 | 0.95 to 1.03 |

TABLE 39-continued

| | Summary of slope ratio estimates of sample to reference standard | | | | | |
|---|---|---|---|---|---|---|
| | Assay | Recovery Sample | | | | |
| | Control | 40% | 70% | 100% | 130% | 160% |
| Comparison with Assay Control (p-Value)[a] | — | <0.0001 | 0.7093 | 0.6950 | 0.9999 | 0.9686 |
| Mean ± 3SD[b] | 0.86 to 1.16 | 0.67 to 1.09 | 0.84 to 1.14 | 0.81 to 1.18 | 0.85 to 1.19 | 0.75 to 1.30 |
| % within 0.75-1.33 | 100% | 90% | 100% | 100% | 100% | 100% |
| % within 0.69-1.45 | 100% | 100% | 100% | 100% | 100% | 100% |

[a] p-value from multiple comparison with assay control using Dunnett's method
[b] Mean ± 3SD range is calculated using natural log transformed slope ratios and anti-log transformed back to the original scale.

Statistical Software

The statistical analyses for assay qualification study and system suitability were performed using statistical software JMP Pro 13.2.1.

Data

TABLE 40

Repeatability Data Listing of Assay Validation Study

| Date | Analyst | Plate ID | Sample Name | Relative Potency |
|---|---|---|---|---|
| 9 Jul. 2018 | 1 | AVXS101-V033 | S1 (40% Recovery Sample) | 39.2% |
| 9 Jul. 2018 | 1 | AVXS101-V033 | S1 (40% Recovery Sample) | 45.5% |
| 9 Jul. 2018 | 1 | AVXS101-V033 | S1 (40% Recovery Sample) | 53.5% |
| 2 Jul. 2018 | 2 | AVXS101-V019 | S3 (100% Recovery Sample) | 109.1% |
| 2 Jul. 2018 | 2 | AVXS101-V019 | S3 (100% Recovery Sample) | 90.0% |
| 2 Jul. 2018 | 2 | AVXS101-V019 | S3 (100% Recovery Sample) | 100.1% |
| 9 Jul. 2018 | 3 | AVXS101-V034 | S5 (160% Recovery Sample) | 153.1% |
| 9 Jul. 2018 | 3 | AVXS101-V034 | S5 (160% Recovery Sample) | 140.4% |
| 9 Jul. 2018 | 3 | AVXS101-V034 | S5 (160% Recovery Sample) | 140.7% |

TABLE 41

Intermediate Precision, Reproducibility, Accuracy, and Linearity Data Listing of Assay Validation

| Date | Analyst | Lab | Plate ID | Sample Name | Relative Potency |
|---|---|---|---|---|---|
| 25 Jun. 2018 | 1 | 1 | AVXS101-V001 | S1 (40% Recovery Sample) | 38.6% |
| 25 Jun. 2018 | 1 | 1 | AVXS101-V001 | S3 (100% Recovery Sample) | 91.3% |
| 25 Jun. 2018 | 1 | 1 | AVXS101-V001 | S5 (160% Recovery Sample) | 160.1% |
| 25 Jun. 2018 | 1 | 1 | AVXS101-V002 | S2 (70% Recovery Sample) | 70.6% |
| 25 Jun. 2018 | 1 | 1 | AVXS101-V002 | S4 (130% Recovery Sample) | 132.3% |
| 25 Jun. 2018 | 2 | 1 | AVXS101-V003 | S1 (40% Recovery Sample) | 51.8% |
| 25 Jun. 2018 | 2 | 1 | AVXS101-V003 | S3 (100% Recovery Sample) | 126.9% |
| 25 Jun. 2018 | 2 | 1 | AVXS101-V003 | S5 (160% Recovery Sample) | 173.0% |
| 25 Jun. 2018 | 2 | 1 | AVXS101-V004 | S2 (70% Recovery Sample) | 88.2% |
| 25 Jun. 2018 | 2 | 1 | AVXS101-V004 | S4 (130% Recovery Sample) | 155.2% |
| 25 Jun. 2018 | 3 | 2 | AVXS101-V005 | S1 (40% Recovery Sample) | 44.7% |
| 25 Jun. 2018 | 3 | 2 | AVXS101-V005 | S3 (100% Recovery Sample) | 114.1% |
| 25 Jun. 2018 | 3 | 2 | AVXS101-V005 | S5 (160% Recovery Sample) | 173.2% |
| 25 Jun. 2018 | 3 | 2 | AVXS101-V006 | S2 (70% Recovery Sample) | 53.9% |
| 25 Jun. 2018 | 3 | 2 | AVXS101-V006 | S4 (130% Recovery Sample) | 120.2% |
| 29 Jun. 2018 | 1 | 1 | AVXS101-V008 | S1 (40% Recovery Sample) | 38.7% |
| 29 Jun. 2018 | 1 | 1 | AVXS101-V008 | S3 (100% Recovery Sample) | 87.3% |
| 29 Jun. 2018 | 1 | 1 | AVXS101-V008 | S5 (160% Recovery Sample) | 108.1% |
| 29 Jun. 2018 | 1 | 1 | AVXS101-V009 | S2 (70% Recovery Sample) | 48.0% |
| 29 Jun. 2018 | 1 | 1 | AVXS101-V009 | S4 (130% Recovery Sample) | 81.0% |
| 29 Jun. 2018 | 2 | 1 | AVXS101-V010 | S1 (40% Recovery Sample) | 49.0% |
| 29 Jun. 2018 | 2 | 1 | AVXS101-V010 | S3 (100% Recovery Sample) | 112.3% |
| 29 Jun. 2018 | 2 | 1 | AVXS101-V010 | S5 (160% Recovery Sample) | 160.3% |

TABLE 41-continued

Intermediate Precision, Reproducibility, Accuracy, and Linearity Data Listing of Assay Validation

| Date | Analyst | Lab | Plate ID | Sample Name | Relative Potency |
|---|---|---|---|---|---|
| 29 Jun. 2018 | 2 | 1 | AVXS101-V011 | S2 (70% Recovery Sample) | 72.3% |
| 29 Jun. 2018 | 2 | 1 | AVXS101-V011 | S4 (130% Recovery Sample) | 139.6% |
| 29 Jun. 2018 | 3 | 2 | AVXS101-V012 | S1 (40% Recovery Sample) | 38.9% |
| 29 Jun. 2018 | 3 | 2 | AVXS101-V012 | S3 (100% Recovery Sample) | 83.2% |
| 29 Jun. 2018 | 3 | 2 | AVXS101-V012 | S5 (160% Recovery Sample) | 126.7% |
| 29 Jun. 2018 | 3 | 2 | AVXS101-V013 | S2 (70% Recovery Sample) | 65.4% |
| 29 Jun. 2018 | 3 | 2 | AVXS101-V013 | S4 (130% Recovery Sample) | 122.5% |

TABLE 42

Specificity Data Listing of Assay Validation Study

| | anti-SMN1 mouse monoclonal antibody 2B1 | | | | anti-MeCP2 rabbit monoclonal antibody | |
|---|---|---|---|---|---|---|
| MOI | AAV9-SMN1 | | AAV9-MECP2 | | AAV9-MECP2 | |
| 300000 | 3427433 | 3267705 | 866953 | 874747 | 11714219 | 11866665 |
| 150000 | 2872508 | 3018082 | 886063 | 838872 | 10413037 | 10519063 |
| 75000 | 2336219 | 2459001 | 837106 | 859511 | 9052826 | 8881358 |
| 37500 | 1873698 | 1864302 | 808724 | 816856 | 7428714 | 7545245 |
| 18750 | 1457402 | 1511124 | 719832 | 759054 | 6256194 | 6446120 |

TABLE 43

Slope Ratio and Relative Potency of Assay Qualification and Validation Studies

| Study | Date | Analyst | Plate ID | Sample Name | $R^2$ | Slope Ratio (Sample/RS) | Relative Potency |
|---|---|---|---|---|---|---|---|
| Qualification | 23 Apr. 2018 | 1 | AVXS101-001 | Assay Control | 1.00 | 0.99 | 102.3% |
| Qualification | 23 Apr. 2018 | 1 | AVXS101-001 | S1 (40% Recovery Sample) | 0.98 | 0.84 | 44.7% |
| Qualification | 23 Apr. 2018 | 1 | AVXS101-001 | S3 (100% Recovery Sample) | 1.00 | 0.95 | 101.1% |
| Qualification | 23 Apr. 2018 | 1 | AVXS101-001 | S5 (160% Recovery Sample) | 0.98 | 0.87 | 154.9% |
| Qualification | 23 Apr. 2018 | 1 | AVXS101-002 | Assay Control | 0.99 | 0.98 | 97.1% |
| Qualification | 23 Apr. 2018 | 1 | AVXS101-002 | S2 (70% Recovery Sample) | 1.00 | 0.92 | 72.3% |
| Qualification | 23 Apr. 2018 | 1 | AVXS101-002 | S4 (130% Recovery Sample) | 1.00 | 1.00 | 136.0% |
| Qualification | 27 Apr. 2018 | 2 | AVXS101-003 | Assay Control | 0.99 | 0.94 | 92.0% |
| Qualification | 27 Apr. 2018 | 2 | AVXS101-003 | S1 (40% Recovery Sample) | 1.00 | 0.93 | 42.5% |
| Qualification | 27 Apr. 2018 | 2 | AVXS101-003 | S3 (100% Recovery Sample) | 1.00 | 0.91 | 99.8% |
| Qualification | 27 Apr. 2018 | 2 | AVXS101-003 | S5 (160% Recovery Sample) | 0.99 | 0.86 | 150.8% |
| Qualification | 27 Apr. 2018 | 2 | AVXS101-004 | Assay Control | 0.98 | 0.94 | 98.3% |
| Qualification | 27 Apr. 2018 | 2 | AVXS101-004 | S2 (70% Recovery Sample) | 1.00 | 0.99 | 70.8% |
| Qualification | 27 Apr. 2018 | 2 | AVXS101-004 | S4 (130% Recovery Sample) | 0.98 | 0.92 | 138.4% |
| Qualification | 27 Apr. 2018 | 1 | AVXS101-005 | Assay Control | 1.00 | 1.01 | 89.5% |
| Qualification | 27 Apr. 2018 | 1 | AVXS101-005 | S1 (40% Recovery Sample) | 0.99 | 0.89 | 41.9% |
| Qualification | 27 Apr. 2018 | 1 | AVXS101-005 | S3 (100% Recovery Sample) | 1.00 | 0.94 | 93.2% |
| Qualification | 27 Apr. 2018 | 1 | AVXS101-005 | S5 (160% Recovery Sample) | 0.99 | 0.87 | 130.1% |

TABLE 43-continued

Slope Ratio and Relative Potency of Assay Qualification and Validation Studies

| Study | Date | Analyst | Plate ID | Sample Name | $R^2$ | Slope Ratio (Sample/RS) | Relative Potency |
|---|---|---|---|---|---|---|---|
| Qualification | 27 Apr. 2018 | 1 | AVXS101-006 | Assay Control | 0.99 | 0.99 | 95.3% |
| Qualification | 27 Apr. 2018 | 1 | AVXS101-006 | S2 (70% Recovery Sample) | 1.00 | 0.96 | 67.7% |
| Qualification | 27 Apr. 2018 | 1 | AVXS101-006 | S4 (130% Recovery Sample) | 0.98 | 0.93 | 121.5% |
| Qualification | 30 Apr. 2018 | 2 | AVXS101-007 | Assay Control | 1.00 | 0.96 | 98.6% |
| Qualification | 30 Apr. 2018 | 2 | AVXS101-007 | S1 (40% Recovery Sample) | 1.00 | 0.86 | 39.9% |
| Qualification | 30 Apr. 2018 | 2 | AVXS101-007 | S3 (100% Recovery Sample) | 0.99 | 0.97 | 114.5% |
| Qualification | 30 Apr. 2018 | 2 | AVXS101-007 | S5 (160% Recovery Sample) | 1.00 | 1.05 | 177.5% |
| Qualification | 30 Apr. 2018 | 2 | AVXS101-008 | Assay Control | 0.99 | 1.07 | 102.4% |
| Qualification | 30 Apr. 2018 | 2 | AVXS101-008 | S2 (70% Recovery Sample) | 1.00 | 0.98 | 67.0% |
| Qualification | 30 Apr. 2018 | 2 | AVXS101-008 | S4 (130% Recovery Sample) | 0.99 | 0.98 | 127.5% |
| Qualification | 30 Apr. 2018 | 1 | AVXS101-009 | Assay Control | 0.99 | 0.99 | 94.3% |
| Qualification | 30 Apr. 2018 | 1 | AVXS101-009 | S1 (40% Recovery Sample) | 0.99 | 0.84 | 38.7% |
| Qualification | 30 Apr. 2018 | 1 | AVXS101-009 | S3 (100% Recovery Sample) | 1.00 | 0.96 | 95.4% |
| Qualification | 30 Apr. 2018 | 1 | AVXS101-009 | S5 (160% Recovery Sample) | 0.96 | 0.89 | 134.2% |
| Qualification | 30 Apr. 2018 | 1 | AVXS101-010 | Assay Control | 0.99 | 1.02 | 104.2% |
| Qualification | 30 Apr. 2018 | 1 | AVXS101-010 | S2 (70% Recovery Sample) | 0.99 | 0.96 | 70.1% |
| Qualification | 30 Apr. 2018 | 1 | AVXS101-010 | S4 (130% Recovery Sample) | 0.99 | 0.98 | 136.7% |
| Qualification | 1 May 2018 | 2 | AVXS101-011 | Assay Control | 0.99 | 1.00 | 107.1% |
| Qualification | 1 May 2018 | 2 | AVXS101-011 | S1 (40% Recovery Sample) | 0.99 | 0.83 | 41.3% |
| Qualification | 1 May 2018 | 2 | AVXS101-011 | S3 (100% Recovery Sample) | 1.00 | 0.93 | 106.1% |
| Qualification | 1 May 2018 | 2 | AVXS101-011 | S5 (160% Recovery Sample) | 0.99 | 0.94 | 162.9% |
| Qualification | 1 May 2018 | 2 | AVXS101-012 | Assay Control | 1.00 | 1.00 | 113.2% |
| Qualification | 1 May 2018 | 2 | AVXS101-012 | S2 (70% Recovery Sample) | 1.00 | 1.00 | 92.2% |
| Qualification | 1 May 2018 | 2 | AVXS101-012 | S4 (130% Recovery Sample) | 0.98 | 1.07 | 178.6% |
| Qualification | 4 May 2018 | 1 | AVXS101-013 | Assay Control | 1.00 | 0.96 | 95.9% |
| Qualification | 4 May 2018 | 1 | AVXS101-013 | S1 (40% Recovery Sample) | 0.99 | 0.87 | 41.4% |
| Qualification | 4 May 2018 | 1 | AVXS101-013 | S1 (40% Recovery Sample) | 1.00 | 0.90 | 44.8% |
| Qualification | 4 May 2018 | 1 | AVXS101-013 | S1 (40% Recovery Sample) | 0.99 | 0.90 | 41.6% |
| Qualification | 4 May 2018 | 1 | AVXS101-014 | Assay Control | 0.99 | 1.01 | 94.5% |
| Qualification | 4 May 2018 | 1 | AVXS101-014 | S3 (100% Recovery Sample) | 1.00 | 0.98 | 97.7% |
| Qualification | 4 May 2018 | 1 | AVXS101-014 | S3 (100% Recovery Sample) | 1.00 | 0.96 | 105.6% |
| Qualification | 4 May 2018 | 1 | AVXS101-014 | S3 (100% Recovery Sample) | 1.00 | 0.99 | 94.4% |
| Qualification | 4 May 2018 | 1 | AVXS101-015 | Assay Control | 0.99 | 1.04 | 93.0% |
| Qualification | 4 May 2018 | 1 | AVXS101-015 | S5 (160% Recovery Sample) | 0.99 | 0.99 | 146.8% |
| Qualification | 4 May 2018 | 1 | AVXS101-015 | S5 (160% Recovery Sample) | 0.99 | 1.04 | 151.6% |
| Qualification | 4 May 2018 | 1 | AVXS101-015 | S5 (160% Recovery Sample) | 0.99 | 0.97 | 141.0% |
| Validation | 25 Jun. 2018 | 2 | AVXS101-V001 | Assay Control | 0.99 | 1.02 | 92.5% |

TABLE 43-continued

Slope Ratio and Relative Potency of Assay Qualification and Validation Studies

| Study | Date | Analyst | Plate ID | Sample Name | $R^2$ | Slope Ratio (Sample/RS) | Relative Potency |
|---|---|---|---|---|---|---|---|
| Validation | 25 Jun. 2018 | 2 | AVXS101-V001 | S1 (40% Recovery Sample) | 0.99 | 0.90 | 38.6% |
| Validation | 25 Jun. 2018 | 2 | AVXS101-V001 | S3 (100% Recovery Sample) | 1.00 | 1.07 | 91.3% |
| Validation | 25 Jun. 2018 | 2 | AVXS101-V001 | S5 (160% Recovery Sample) | 1.00 | 1.08 | 160.1% |
| Validation | 25 Jun. 2018 | 2 | AVXS101-V002 | Assay Control | 0.99 | 0.99 | 98.2% |
| Validation | 25 Jun. 2018 | 2 | AVXS101-V002 | S2 (70% Recovery Sample) | 0.99 | 0.91 | 70.6% |
| Validation | 25 Jun. 2018 | 2 | AVXS101-V002 | S4 (130% Recovery Sample) | 1.00 | 1.05 | 132.3% |
| Validation | 25 Jun. 2018 | 1 | AVXS101-V003 | Assay Control | 1.00 | 0.92 | 107.8% |
| Validation | 25 Jun. 2018 | 1 | AVXS101-V003 | S1 (40% Recovery Sample) | 0.99 | 0.87 | 51.8% |
| Validation | 25 Jun. 2018 | 1 | AVXS101-V003 | S3 (100% Recovery Sample) | 1.00 | 1.02 | 126.9% |
| Validation | 25 Jun. 2018 | 1 | AVXS101-V003 | S5 (160% Recovery Sample) | 1.00 | 0.97 | 173.0% |
| Validation | 25 Jun. 2018 | 1 | AVXS101-V004 | Assay Control | 1.00 | 1.02 | 109.3% |
| Validation | 25 Jun. 2018 | 1 | AVXS101-V004 | S2 (70% Recovery Sample) | 0.98 | 1.04 | 88.2% |
| Validation | 25 Jun. 2018 | 1 | AVXS101-V004 | S4 (130% Recovery Sample) | 0.99 | 1.10 | 155.2% |
| Validation | 25 Jun. 2018 | 3 | AVXS101-V005 | Assay Control | 1.00 | 1.00 | 97.7% |
| Validation | 25 Jun. 2018 | 3 | AVXS101-V005 | S1 (40% Recovery Sample) | 0.98 | 0.81 | 44.7% |
| Validation | 25 Jun. 2018 | 3 | AVXS101-V005 | S3 (100% Recovery Sample) | 0.99 | 1.01 | 114.1% |
| Validation | 25 Jun. 2018 | 3 | AVXS101-V005 | S5 (160% Recovery Sample) | 0.99 | 1.03 | 173.2% |
| Validation | 25 Jun. 2018 | 3 | AVXS101-V006 | Assay Control | 0.99 | 1.01 | 79.2% |
| Validation | 25 Jun. 2018 | 3 | AVXS101-V006 | S2 (70% Recovery Sample) | 1.00 | 0.91 | 53.9% |
| Validation | 25 Jun. 2018 | 3 | AVXS101-V006 | S4 (130% Recovery Sample) | 1.00 | 0.98 | 120.2% |
| Validation | 29 Jun. 2018 | 2 | AVXS101-V008 | Assay Control | 0.99 | 1.02 | 98.9% |
| Validation | 29 Jun. 2018 | 2 | AVXS101-V008 | S1 (40% Recovery Sample) | 0.99 | 0.87 | 38.7% |
| Validation | 29 Jun. 2018 | 2 | AVXS101-V008 | S3 (100% Recovery Sample) | 0.99 | 1.04 | 87.3% |
| Validation | 29 Jun. 2018 | 2 | AVXS101-V008 | S5 (160% Recovery Sample) | 0.99 | 0.94 | 108.1% |
| Validation | 29 Jun. 2018 | 2 | AVXS101-V009 | Assay Control | 1.00 | 0.96 | 73.3% |
| Validation | 29 Jun. 2018 | 2 | AVXS101-V009 | S2 (70% Recovery Sample) | 0.99 | 0.97 | 48.0% |
| Validation | 29 Jun. 2018 | 2 | AVXS101-V009 | S4 (130% Recovery Sample) | 0.99 | 0.99 | 81.0% |
| Validation | 29 Jun. 2018 | 1 | AVXS101-V010 | Assay Control | 0.99 | 1.02 | 103.1% |
| Validation | 29 Jun. 2018 | 1 | AVXS101-V010 | S1 (40% Recovery Sample) | 1.00 | 1.03 | 49.0% |
| Validation | 29 Jun. 2018 | 1 | AVXS101-V010 | S3 (100% Recovery Sample) | 0.99 | 1.03 | 112.3% |
| Validation | 29 Jun. 2018 | 1 | AVXS101-V010 | S5 (160% Recovery Sample) | 0.99 | 0.94 | 160.3% |
| Validation | 29 Jun. 2018 | 1 | AVXS101-V011 | Assay Control | 0.99 | 1.06 | 106.7% |
| Validation | 29 Jun. 2018 | 1 | AVXS101-V011 | S2 (70% Recovery Sample) | 0.99 | 1.08 | 72.3% |
| Validation | 29 Jun. 2018 | 1 | AVXS101-V011 | S4 (130% Recovery Sample) | 0.97 | 0.97 | 139.6% |
| Validation | 29 Jun. 2018 | 3 | AVXS101-V012 | Assay Control | 1.00 | 0.96 | 92.2% |
| Validation | 29 Jun. 2018 | 3 | AVXS101-V012 | S1 (40% Recovery Sample) | 0.99 | 0.81 | 38.9% |
| Validation | 29 Jun. 2018 | 3 | AVXS101-V012 | S3 (100% Recovery Sample) | 1.00 | 0.96 | 83.2% |

TABLE 43-continued

Slope Ratio and Relative Potency of Assay Qualification and Validation Studies

| Study | Date | Analyst | Plate ID | Sample Name | $R^2$ | Slope Ratio (Sample/RS) | Relative Potency |
|---|---|---|---|---|---|---|---|
| Validation | 29 Jun. 2018 | 3 | AVXS101-V012 | S5 (160% Recovery Sample) | 1.00 | 0.96 | 126.7% |
| Validation | 29 Jun. 2018 | 3 | AVXS101-V013 | Assay Control | 1.00 | 0.95 | 97.1% |
| Validation | 29 Jun. 2018 | 3 | AVXS101-V013 | S2 (70% Recovery Sample) | 0.99 | 0.98 | 65.4% |
| Validation | 29 Jun. 2018 | 3 | AVXS101-V013 | S4 (130% Recovery Sample) | 1.00 | 1.07 | 122.5% |
| Validation | 29 Jun. 2018 | 4 | AVXS101-V014 | Assay Control | 0.95 | 1.02 | 103.9% |
| Validation | 29 Jun. 2018 | 4 | AVXS101-V014 | S3 (100% Recovery Sample) | 1.00 | 1.05 | 90.4% |
| Validation | 29 Jun. 2018 | 4 | AVXS101-V015 | Assay Control | 1.00 | 1.02 | 103.5% |
| Validation | 29 Jun. 2018 | 4 | AVXS101-V015 | S3 (100% Recovery Sample) | 1.00 | 0.97 | 91.0% |
| Validation | 29 Jun. 2018 | 4 | AVXS101-V016 | Assay Control | 0.98 | 1.01 | 96.7% |
| Validation | 29 Jun. 2018 | 4 | AVXS101-V016 | S3 (100% Recovery Sample) | 1.00 | 1.07 | 85.5% |
| Validation | 29 Jun. 2018 | 4 | AVXS101-V017 | Assay Control | 1.00 | 0.85 | 92.2% |
| Validation | 29 Jun. 2018 | 4 | AVXS101-V017 | S3 (100% Recovery Sample | 0.99 | 0.89 | 90.6% |
| Validation | 2 Jul. 2018 | 2 | AVXS101-V018 | Assay Control | 0.99 | 1.01 | 107.6% |
| Validation | 2 Jul. 2018 | 2 | AVXS101-V018 | S1 (40% Recovery Sample) | 0.99 | 0.83 | 41.7% |
| Validation | 2 Jul. 2018 | 2 | AVXS101-V018 | S1 (40% Recovery Sample) | 0.99 | 0.72 | 37.1% |
| Validation | 2 Jul. 2018 | 2 | AVXS101-V019 | Assay Control | 0.99 | 0.97 | 107.2% |
| Validation | 2 Jul. 2018 | 2 | AVXS101-V019 | S3 (100% Recovery Sample) | 0.99 | 0.96 | 109.1% |
| Validation | 2 Jul. 2018 | 2 | AVXS101-V019 | S3 (100% Recovery Sample) | 0.95 | 0.89 | 90.0% |
| Validation | 2 Jul. 2018 | 2 | AVXS101-V019 | S3 (100% Recovery Sample) | 1.00 | 0.92 | 100.1% |
| Validation | 2 Jul. 2018 | 2 | AVXS101-V020 | Assay Control | 1.00 | 1.00 | 91.6% |
| Validation | 2 Jul. 2018 | 2 | AVXS101-V020 | S5 (160% Recovery Sample) | 1.00 | 1.02 | 126.6% |
| Validation | 2 Jul. 2018 | 2 | AVXS101-V020 | S5 (160% Recovery Sample) | 0.99 | 0.97 | 133.8% |
| Validation | 2 Jul. 2018 | 3 | AVXS101-V021 | Assay Control | 1.00 | 0.97 | 109.4% |
| Validation | 2 Jul. 2018 | 3 | AVXS101-V021 | S3 (100% Recovery Sample) | 1.00 | 0.93 | 103.4% |
| Validation | 2 Jul. 2018 | 3 | AVXS101-V022 | Assay Control | 1.00 | 1.02 | 103.2% |
| Validation | 2 Jul. 2018 | 3 | AVXS101-V022 | S3 (100% Recovery Sample) | 0.99 | 0.97 | 104.4% |
| Validation | 2 Jul. 2018 | 3 | AVXS101-V023 | Assay Control | 0.99 | 1.02 | 99.4% |
| Validation | 2 Jul. 2018 | 3 | AVXS101-V023 | S3 (100% Recovery Sample) | 1.00 | 1.00 | 107.6% |
| Validation | 6 Jul. 2018 | 2 | AVXS101-V024 | Assay Control | 0.99 | 1.05 | 126.1% |
| Validation | 6 Jul. 2018 | 2 | AVXS101-V024 | S3 (100% Recovery Sample) | 1.00 | 1.04 | 136.3% |
| Validation | 6 Jul. 2018 | 2 | AVXS101-V025 | Assay Control | 1.00 | 1.03 | 102.4% |
| Validation | 6 Jul. 2018 | 2 | AVXS101-V025 | S3 (100% Recovery Sample) | 1.00 | 0.95 | 99.6% |
| Validation | 6 Jul. 2018 | 2 | AVXS101-V026 | Assay Control | 0.99 | 0.98 | 111.0% |
| Validation | 6 Jul. 2018 | 2 | AVXS101-V026 | S3 (100% Recovery Sample) | 1.00 | 1.05 | 120.4% |
| Validation | 6 Jul. 2018 | 3 | AVXS101-V027 | Assay Control | 0.99 | 1.16 | 116.0% |
| Validation | 6 Jul. 2018 | 3 | AVXS101-V027 | S3 (100% Recovery Sample) | 1.00 | 1.14 | 95.5% |
| Validation | 6 Jul. 2018 | 3 | AVXS101-V028 | Assay Control | 1.00 | 1.01 | 137.8% |

TABLE 43-continued

Slope Ratio and Relative Potency of Assay Qualification and Validation Studies

| Study | Date | Analyst | Plate ID | Sample Name | $R^2$ | Slope Ratio (Sample/RS) | Relative Potency |
|---|---|---|---|---|---|---|---|
| Validation | 6 Jul. 2018 | 3 | AVXS101-V028 | S3 (100% Recovery Sample) | 0.99 | 0.87 | 111.7% |
| Validation | 6 Jul. 2018 | 3 | AVXS101-V029 | Assay Control | 0.98 | 1.15 | 84.3% |
| Validation | 6 Jul. 2018 | 3 | AVXS101-V029 | S3 (100% Recovery Sample) | 1.00 | 1.09 | 89.6% |
| Validation | 6 Jul. 2018 | 4 | AVXS101-V030 | Assay Control | 0.98 | 1.04 | 109.9% |
| Validation | 6 Jul. 2018 | 4 | AVXS101-V030 | S3 (100% Recovery Sample) | 0.99 | 1.02 | 105.8% |
| Validation | 6 Jul. 2018 | 4 | AVXS101-V031 | Assay Control | 1.00 | 0.93 | 92.5% |
| Validation | 6 Jul. 2018 | 4 | AVXS101-V031 | S3 (100% Recovery Sample) | 1.00 | 0.93 | 84.4% |
| Validation | 6 Jul. 2018 | 4 | AVXS101-V032 | Assay Control | 1.00 | 0.95 | 92.4% |
| Validation | 6 Jul. 2018 | 4 | AVXS101-V032 | S3 (100% Recovery Sample) | 0.99 | 0.97 | 76.5% |
| Validation | 9 Jul. 2018 | 4 | AVXS101-V033 | Assay Control | 0.99 | 0.98 | 96.5% |
| Validation | 9 Jul. 2018 | 4 | AVXS101-V033 | S1 (40% Recovery Sample) | 0.98 | 0.73 | 39.2% |
| Validation | 9 Jul. 2018 | 4 | AVXS101-V033 | S1 (40% Recovery Sample) | 0.98 | 0.78 | 45.5% |
| Validation | 9 Jul. 2018 | 4 | AVXS101-V033 | S1 (40% Recovery Sample) | 0.97 | 0.88 | 53.5% |
| Validation | 9 Jul. 2018 | 4 | AVXS101-V034 | Assay Control | 0.99 | 1.00 | 110.3% |
| Validation | 9 Jul. 2018 | 4 | AVXS101-V034 | S5 (160% Recovery Sample) | 1.00 | 1.10 | 153.1% |
| Validation | 9 Jul. 2018 | 4 | AVXS101-V034 | S5 (160% Recovery Sample) | 0.98 | 1.12 | 140.4% |
| Validation | 9 Jul. 2018 | 4 | AVXS101-V034 | S5 (160% Recovery Sample) | 0.98 | 1.22 | 140.7% |

Figure 21:
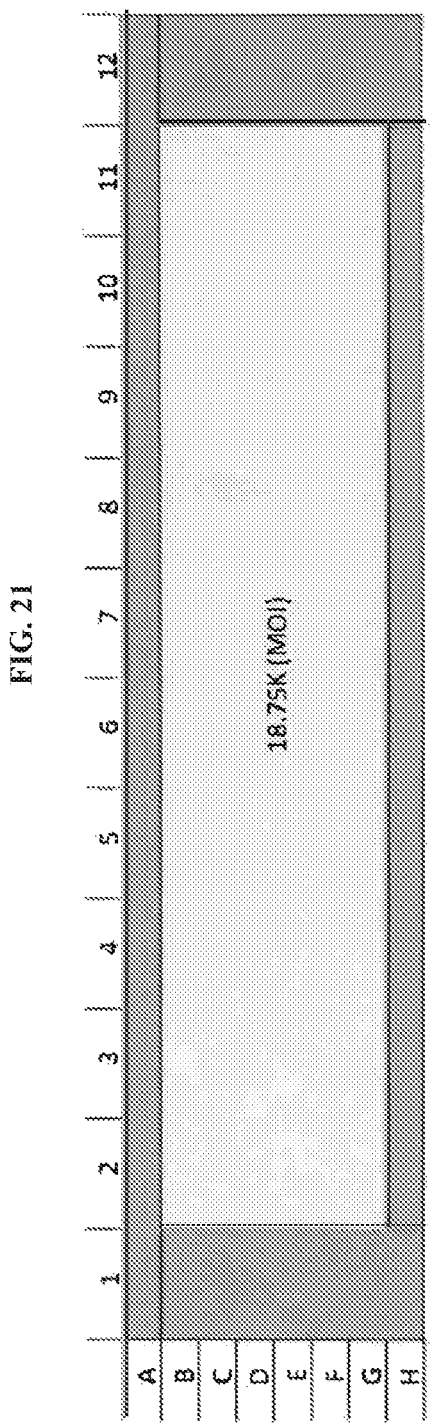
FIG. 21 illustrates the plate layout used in the uniformity study.

Example 7: Uniformity Study for the In-Vitro Relative Potency Cell-Based Assay for SMN1 Encoding AAV9 Vector Uniformity testing was performed for the in-vitro relative potency cell-based Assay for SMN1 encoding AAV9 vector. Uniformity was assessed using a single dose of MOI across wells B2-G11 of a 96 well plate, as these are the wells utilized in the assay (i.e. inner 60 wells of the plate) as shown in FIG. 21. For example, the lowest dose MOI (18.75K) of the 5-point standard curve described in Example 4 was for uniformity assessment, which corresponds to the point with the greatest sensitivity to change. Two analysts prepared three plates each, which represented the maximum number of plates an analyst can test at one time, following the procedure described in Example 4. The data were analyzed using a 3D heatmap plot, which allows for the detection of non-uniformity, if present.

The middle dose MOI (75K) was selected to evaluate uniformity of the SMN1 encoding AAV9 vector cell based potency assay. The sample was prepared by diluted the SMN1 encoding AAV9 drug product (lot 60443-05, 4.3E+13 vg/mL) to 1.0E+12 vg/mL using the formulation buffer (TFF3 buffer 50 ppm). The sample was then diluted 16.7-fold using plate media followed by two rounds of 1:2 serial dilution using plate media. These preparation steps were consistent with how the Reference Standard was prepared in Example 4.

Additional assays were performed to address the potential for plate position effect. The data from these two studies were include in the statistical analysis determining the plate effect on the in vitro cell based potency assay.

4 assays were performed according to Example 4, and the percent relative potency of the samples from 4 different positions against the reference standard was measured. The reference standard was prepared as described in Example 4, and all 4 samples were prepared the same as the reference standard. Table 44 shows the plate layout.

TABLE 44

Plate layout for plate effect assay

| | Rep 1 1 | Rep 2 2 | Rep 1 3 | Rep 2 4 | Rep 1 5 | Rep 2 6 | Rep 1 7 | Rep 2 8 | Rep 1 9 | Rep 2 10 | Rep 1 11 | Rep 2 12 |
|---|---|---|---|---|---|---|---|---|---|---|---|---|
| A | | RS | | S1 | | S2 | | S3 | | S4 | | |
| B | | 300K | | 300K | | 300K | | 300K | | 300K | | |
| C | | 150K | | 150K | | 150K | | 150K | | 150K | | |
| D | | 75K | | 75K | | 75K | | 75K | | 75K | | |
| E | | 37.5K | | 37.5K | | 37.5K | | 37.5K | | 37.5K | | |

TABLE 44-continued

| | | Rep 1 | Rep 2 | Rep 1 | Rep 2 | Rep 1 | Rep 2 | Rep 1 | Rep 2 | Rep 1 | Rep 2 | |
|---|---|---|---|---|---|---|---|---|---|---|---|---|
| | 1 | 2 | 3 | 4 | 5 | 6 | 7 | 8 | 9 | 10 | 11 | 12 |
| F | | 18.75K | | 18.75K | | 18.75K | | 18.75K | | 18.75K | | |
| G | | | | | | Cells Only (background) | | | | | | |
| H | | | | | | | | | | | | |

These data enabled the statistical analysis (Example 6) to determine whether any plate effects were associated with the plate layout used in the in-vitro relative potency cell-based assay described in Example 4. Note that SMN1 encoding AAV9 drug product GMP7 (lot 60443-05, 4.3E+13 vg/mL) was used to prepare both the Reference Standard and samples.

There was little or no systematic bias in the relative potency values measured.

Example 8: Specificity of the In-Vitro Relative Potency Cell-Based Assay for SMN1 Encoding AAV9 Vector Only a slight dose dependent increase in MeCP2 staining (IFI-C) upon transduction of mTD NPC-Δ7 cells with a MECP2 encoding AAV9 vector was initially observed.

The layout of the plate for the experiment is shown in Table 45, below.

TABLE 45

| | | Rep 1 | Rep 2 | Rep 1 | Rep 2 | Rep 1 | Rep 2 | Rep 1 | Rep 2 | Rep 1 | Rep 2 | |
|---|---|---|---|---|---|---|---|---|---|---|---|---|
| | 1 | 2 | 3 | 4 | 5 | 6 | 7 | 8 | 9 | 10 | 11 | 12 |
| A | | RS | | Control | | AAV9-MECP2 | | Control | | AAV9-MECP2 | | |
| B | | 300K | | 300K | | 300K | | 300K | | 300K | | |
| C | | 150K | | 150K | | 150K | | 150K | | 150K | | |
| D | | 75K | | 75K | | 75K | | 75K | | 75K | | |
| E | | 37.5K | | 37.5K | | 37.5K | | 37.5K | | 37.5K | | |
| F | | 18.75K | | 18.75K | | 18.75K | | 18.75K | | 18.75K | | |
| G | | Cells only (Background) stained by anti-SMN1 | | | | | | Stained by anti-MECP2 | | | | |
| H | | | | | | | | | | | | |

There are three main steps toward obtaining data for the SMN1-encoding AAV9 vector in the in vitro cell-based potency assay described in Example 4, after the assay plates are made. These steps are:

(1) image acquisition using the HCS Studio software on CellInsight CX5;

(2) Image analysis using the HCS Studio software on CellInsight CX5; and (3) Data analysis using the in vitro relative potency calculation spreadsheet.

Figure 22:
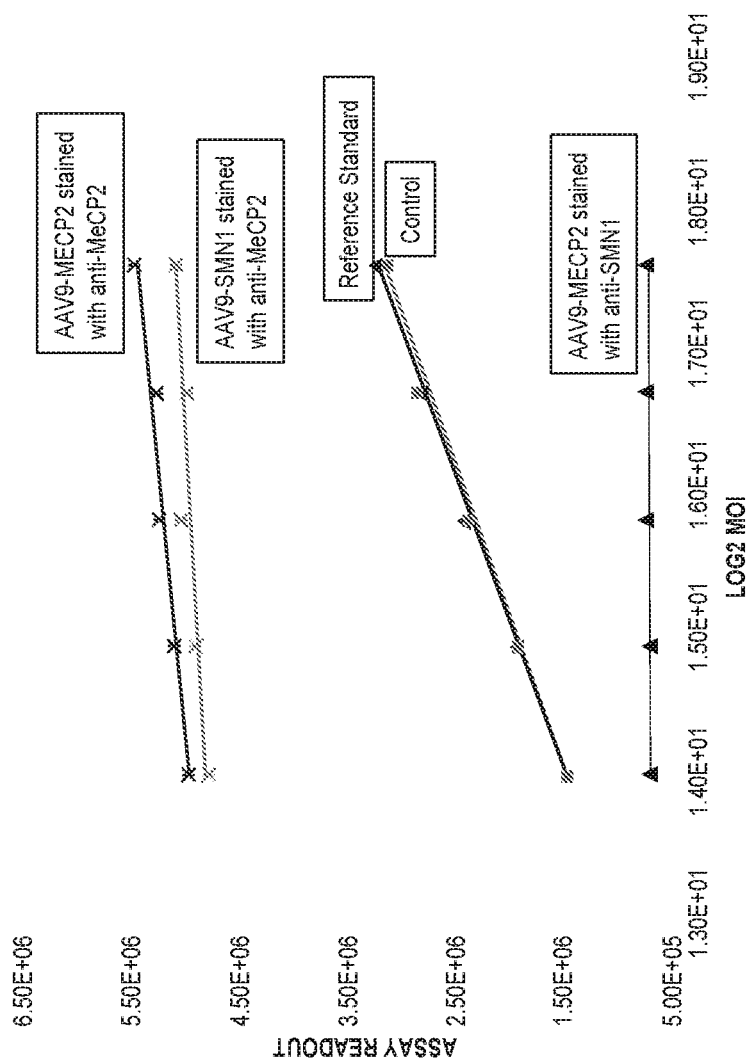
FIG. 22 is a plot illustrating dose-dependent increase in IFI-C. mTD-NPC-Δ7 cells were transduced with either AAV9-SMN1 or AAV9-MECP2 vector, stained with anti-SMN1 or anti-MeCP2, and IFI-C was measured.

The initial observation of only a marginal increase in IFI-C in columns 10-11 was made after the step (3) of data analysis (See FIG. 22).

Figure 23:
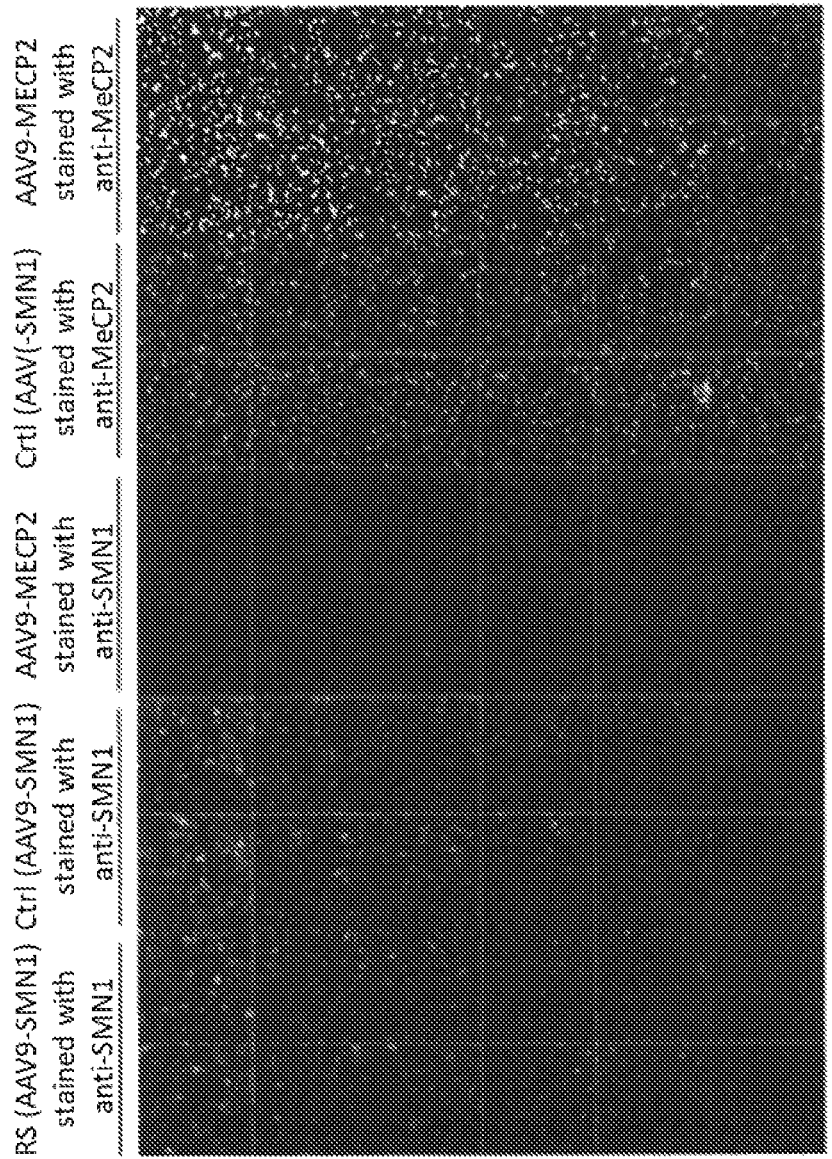
FIG. 23 is an image montage of an in vitro relative potency assay plate. Columns 1-7 are stained by anti-SMN1 antibody. Columns 8-11 are stained with anti-MeCP2 antibody.

To determine whether the observation truly reflected biological events, or resulted from the image analysis, raw image data obtained in step (1) (image acquisition) were visually verified. FIG. 23 shows an image montage of the plate shown in Table 45.

The MeCP2-stained cells were over-exposed during the image acquisition process. The over-exposure, and thereby very high IFI-C for MeCP2-stained cells resulted in the exclusion of those cells during the image analysis specifically set up for the analysis of SMN1 expression (step 2). This was due to a parameter set up specifically for SMN1 staining that appears as dispersed puncta rather than localized expression within the nucleus (MeCP2 staining).

The images initially obtained as shown in FIG. 23 were re-analyzed using an image analysis protocol modified to specifically evaluate MeCP2 stained cells. The obtained image analysis data were then used to plot a graph showing IFI-C against $Log_2$ MOI (FIG. 24).

Figure 24:
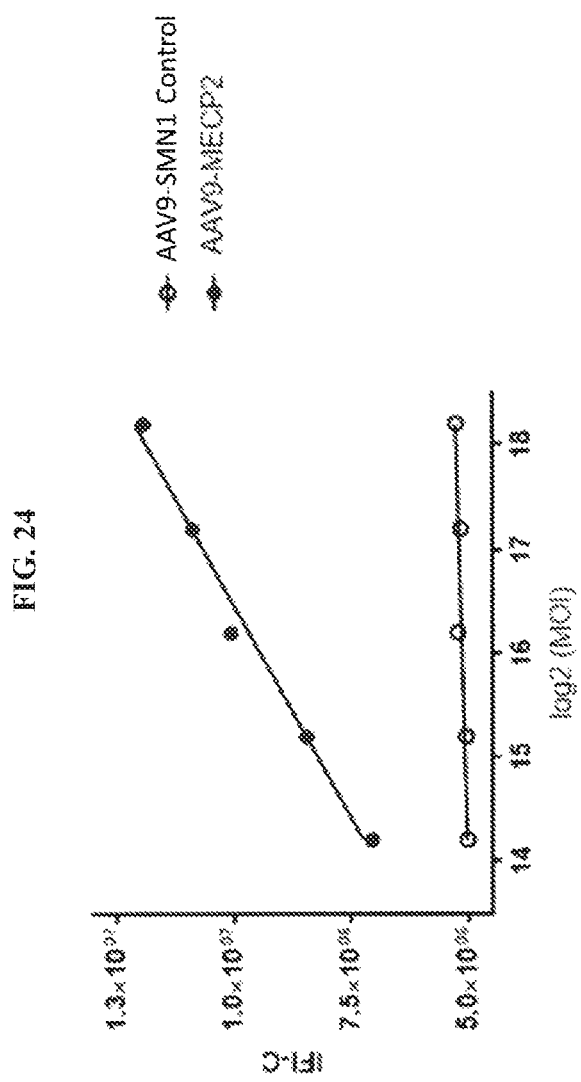
FIG. 24 is a plot illustrating a dose-dependent increase of IFI-C for AAV9-MECP2 transduction.

The data shown in FIG. 24 establishes dose-dependent and linear increase of MeCP2 staining in the cells transduced with AAV9-MECP2, demonstrating that anti-SMN1 antibody only specifically stained AAV9-SMN1 transduced cells. Therefore, the in vitro cell based potency assay for SMN1-encoding AAV9 vector, as described in Example 4, can be used for specifically determining relative potency of the AAV9-SMN1 vector drug product.

Example 9: The In-Vitro Relative Potency Cell-Based Assay for SMN1 Encoding AAV9 Vector Indicates Stability AAV9-SMN1 (GMPS Batch #600156) stress samples were tested for stability after being held at 20-25° C. for one and 1 and 3 months using the in vitro cell based potency assay methods described in Example 4.

All three samples (S1, DP Batch #600156; S2, held 1 month at 20-25° C. and S3, held 3 month at 20-25° C.) met acceptance criteria as shown by Table 46 below.

TABLE 46

System Suitability and Acceptance Criteria

|  | Intercept | Slope | $R^2$ | Assay dynamic window | Slope Pass/Fail? | $R^2$ Pass/Fail? | Signal to Noise Pass/Fail? | All RS Criteria |
|---|---|---|---|---|---|---|---|---|
| Reference Standard | −3.67E+06 | 3.35E+05 | 0.99 | 4.94 | Pass | Pass | Pass | Pass |

|  | $R^2$ | Slope Ratio (Sample/RS) | Relative Potency | $R^2$ Pass/Fail? | Slope Ratio Pass/Fail? | RP Pass/Fail? | All Sample Criteria |
|---|---|---|---|---|---|---|---|
| Assay Control | 1.00 | 0.95 | 93.9% | Pass | Pass | Pass | Pass |
| Sample 1 | 1.00 | 0.94 | 119.6% | Pass | Pass | NA | Pass |
| Sample 2 | 1.00 | 1.02 | 101.7% | Pass | Pass | NA | Pass |
| Sample 3 | 0.99 | 0.86 | 42.2% | Pass | Pass | NA | Pass |

TABLE 47

% RP of Tested Samples

| Sample ID | Sample Description | Measured % RP |
|---|---|---|
| S1 | DP Batch #600156 | 119.6% |
| S2 | T = 1 Month at 20-25° C. | 101.7% |
| S3 | T = 3 Months at 20-25° C. | 42.2% |

The relative potency of Sample 3 (Time=3 Month, at 20-25° C.) was reduced to less than 50%, while the relative potency of Sample 1 (Time=0, at 20-25° C.) and Sample 2 (Time=1 Month, at 20-25° C.) did not indicate any reduction. These data show that the in vitro relative potency assay can not only measure the relative potency of the recovery samples generated to asses linearity of the assay, but also that of the actual manufacturing samples. Moreover, the successful testing of the GMPS stress samples demonstrates that the AAV9-SMN1 in vitro potency assays is stability indicating, and is thus suitable for testing AAV9-SMN1 vector drug produces for their lot disposition.

Example 10: Generation of Pre-GMP Master Cell Bank for AAV9-SMN1 Manufacture Methods Thaw: A single cell vial (1×10⁶ cells) was thawed in a 37° C. water bath for about 1 minute and contents diluted in 5 mL of pre-warmed complete growth media. The cells were transferred into a T-25 cm² flask and grown in a 37° C. incubator for 4 days, with a replacement of culture media with pre-warmed complete growth media every day.

Figure 27:
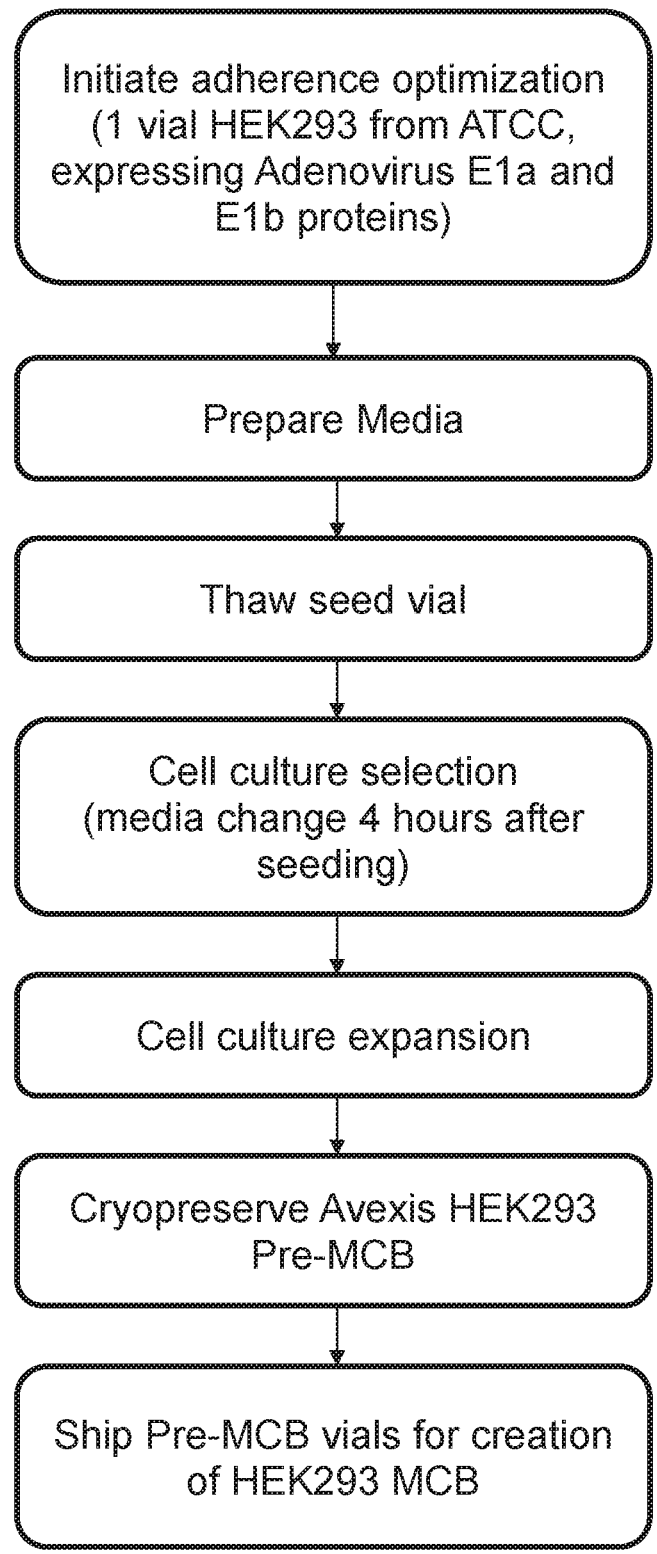
FIG. 27 shows a process flow chart for the selection of HEK293 cells for exceptional adherence and pre-master cell bank (MCB) banking.

Selection for Increased Adherence: The cells were cultured using the following technique to select for strongly adherent cells. Once the cells reached 95% confluency in the 25 cm² flask, the cells were subcultured. Cells were washed with 5 mL of PBS then dissociated with 0.5-1 mL of HyQTase for ~2 minutes at room temperature. Dissociation was stopped by adding 5 mL complete growth media and repeatedly pipetted to dissociate cell clumps. Cell suspension was then centrifuged for 4 minutes at 200×g. Supernatant was discarded and cell pellet was resuspended in 10 mL of complete growth media. Cells were transferred to a 75 cm² flask. after 4 hours of incubation in the 37° C. incubator, weakly adherent cells were washed away by aspirating cell culture media to remove weakly adherent and non-adherent cells. Culture media was replaced with 10 mL pre-warmed complete growth media. This process reduced cell mass by up to 35% of cell number, by visual inspection. The cells were incubated for an additional 2 days before being subcultured again. This selection process, consisting of the media change 4-hour post-seeding, was performed three times prior to expansion of the selected cell population (FIG. 27 and FIG. 28). In the final selection step, cells were seeded into 2×175 cm² flasks, with a final volume of 25 mL. It was noted that there was reduction in cell loss after the last 4-hour post-seeding media change.

Cell Expansion: Cells were subsequently expanded once the cells were confluent in the 2×175 cm² flasks. Cells were washed with 15 mL PBS then dissociated with 3 mL HyQTase and incubation for ~2 minutes at room temperature. Dissociation was stopped by adding 10 mL of complete growth media. Cell suspension was then centrifuged to produce 2 cell pellets once the supernatant was aspirated. Each pellet was resuspended in 8 mL of complete growth media and 2 mL of this concentrated cell suspension was added to 8×175 cm² flasks. The flasks were prepared by adding 20 mL of complete growth media, resulting in a total of 22 mL cell suspension and a splitting ratio of 1:4. The next expansion step used the same procedure with the following variations: 4×175 cm² flasks were expanded at a splitting ratio of 1:2 and 4×175 cm² flasks were expanded at a splitting ratio of 1:3. This resulted in a total of 20×175 cm² flasks.

Harvest: Cells were harvested from 20×175 cm² flasks. Cells were washed with 15 mL of PBS then dissociated with 3 mL HyQTase as previously described. Cell dissociation was stopped by adding 10 mL of complete growth media and collected into 50 mL tubes with cell suspension from 4×175 cm² flasks added to 1×50 mL tube. This resulted in 5×50 mL tubes with 40 mL of cell suspension in each. Tubes were centrifuged to create cell pellets, supernatants were aspirated, and cell were resuspended with 10 mL of complete growth media resulting in 50 mL of cell suspension.

The volume was split into 2×50 mL tubes, with a total of 25 mL of cell suspension in each tube. The samples diluted 1:2 were used to calculate viable cell counts per tube cells using a haemocytometer and Toludine (trypan) Blue. Tube 1 sample had a viable cell count of 1.99×10⁶ cells/mL yielding a cell concentration of 3.98×10⁶ cells/mL and Tube 2 sample had a viable cell count of 2.4×10⁶ cells/mL (total 1×10⁸ cells) yielding a cell concentration of 4.8×10⁶ cells/mL (total 1.2×10⁸ cells). Thus, a total of 2.2×10⁸ cells were harvested. Both tubes were centrifuged again (6 minutes, 200×g) and pellets were resuspended in 10 mL (Tube 1) and 12 mL (Tube 2) of freezing medium, respectively, to adjust the cell concentration to 1×10$^7$ cells/mL. The two cell suspensions were pooled and 1 mL aliquots (each containing 1×10$^7$ cells) were filled in 22 sterile cryovials (Table 48).

TABLE 48

Calculation of total harvested cells

| | Cell Concentration for a 1:2 sample | Cell Concentration for Harvest | Total cells for Harvest |
|---|---|---|---|
| Tube 1 | 1.99 × 10$^6$ cells/mL | 3.98 × 10$^6$ cells/mL | 1 × 10$^8$ cells |
| Tube 2 | 2.4 × 10$^6$ cells/mL | 4.8 × 10$^6$ cells/mL | 1.2 × 10$^8$ cells |
| Total | — | — | 2.2 × 10$^8$ cells |

Filled vials were then transferred to a freezing chamber with fresh isopropanol overnight in a −80° C. freezer for controlled rate freezing. The frozen vials were then transferred to vapor phase liquid nitrogen in a liquid nitrogen tank. Ten vials were transferred on dry ice to be banked in a GMP facility.

HEK293 cells from ATCC were thawed and successfully adapted for increased adherence in 3 passages prior to expansion and successful banking of a seed bank. The seed bank was tested for growth and presence of adventitious agents (*mycoplasma*, fungi and bacteria). Testing showed that the seed bank is suitable for Master Cell Banking in a GMP facility.

Example 11: Manufacturing Upstream Process

Figure 26A:
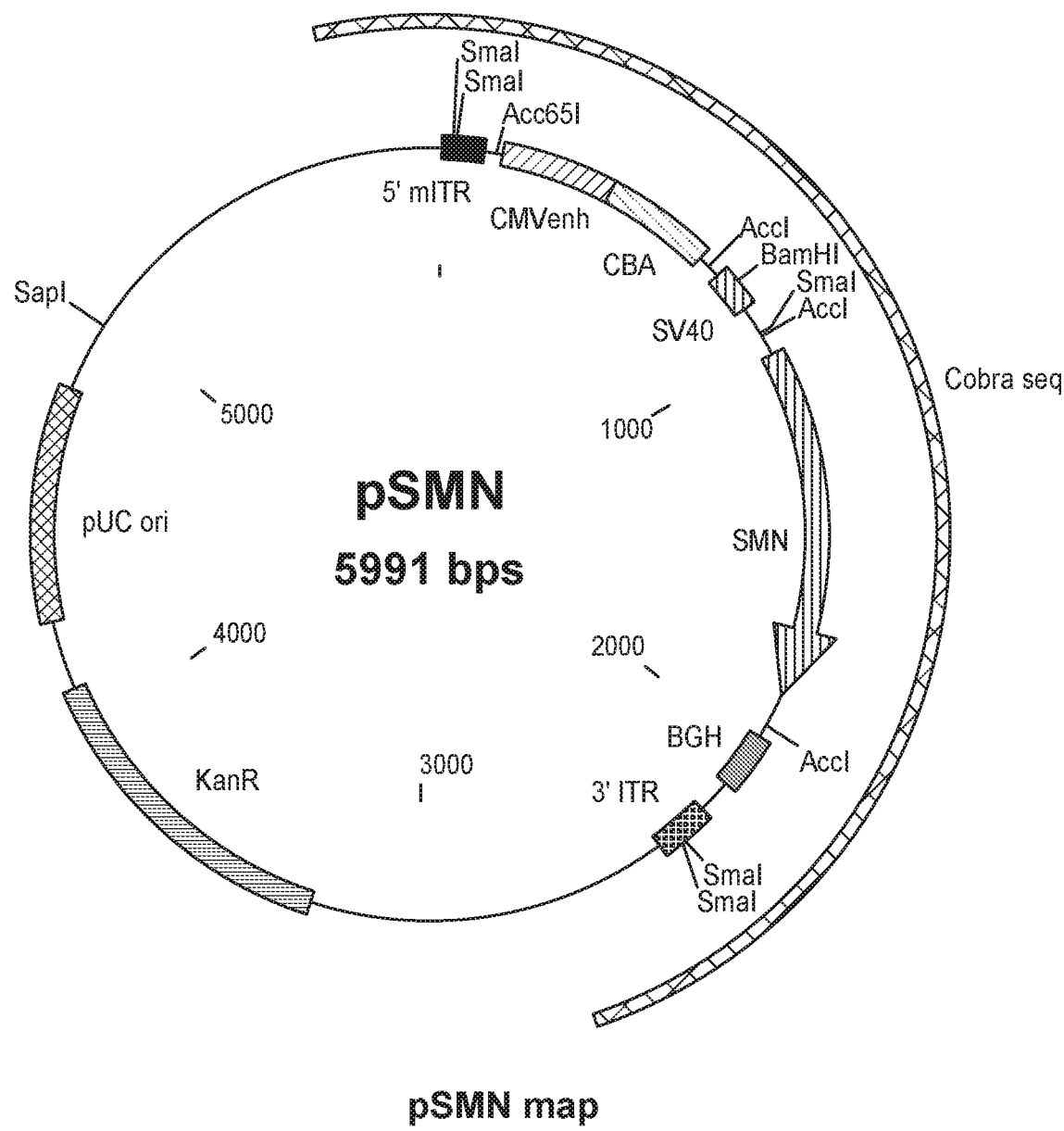
FIG. 26A shows the plasmid map of pSMN. pSMN is a plasmid that encodes the information for a recombinant self-complementary AAV DNA genome that expresses the human survival motor neuron (SMN) cDNA under the control of a chicken-beta-actin hybrid promoter with an immediate/early cytomegalovirus (CMV) enhancer element. The SMN cDNA encodes a full length, functional protein. The expression cassette contains a modified intron sequence derived from simian virus 40 (SV40) and a bovine growth hormone (BGH) polyadenylation signal. The expression cassette (CMV-CB-SV40-SMN-BGHpA) is flanked by AAV2 derived inverted terminal repeats (ITRs). The left ITR is modified to preferentially package self-complementary AAV genomes. Together, the regions between and including the ITRs are packaged into recombinant AAV9 capsids during the manufacture of the find drugs product. Key pSMN components that are not intended for packaging into recombinant AAV genomes include an open reading frame encoding resistance to kanamycin (KanR) and an origin of replication (ori) derived from pUC. The ori and KanR regions are useful for plasmid manufacture.
Figure 26B:
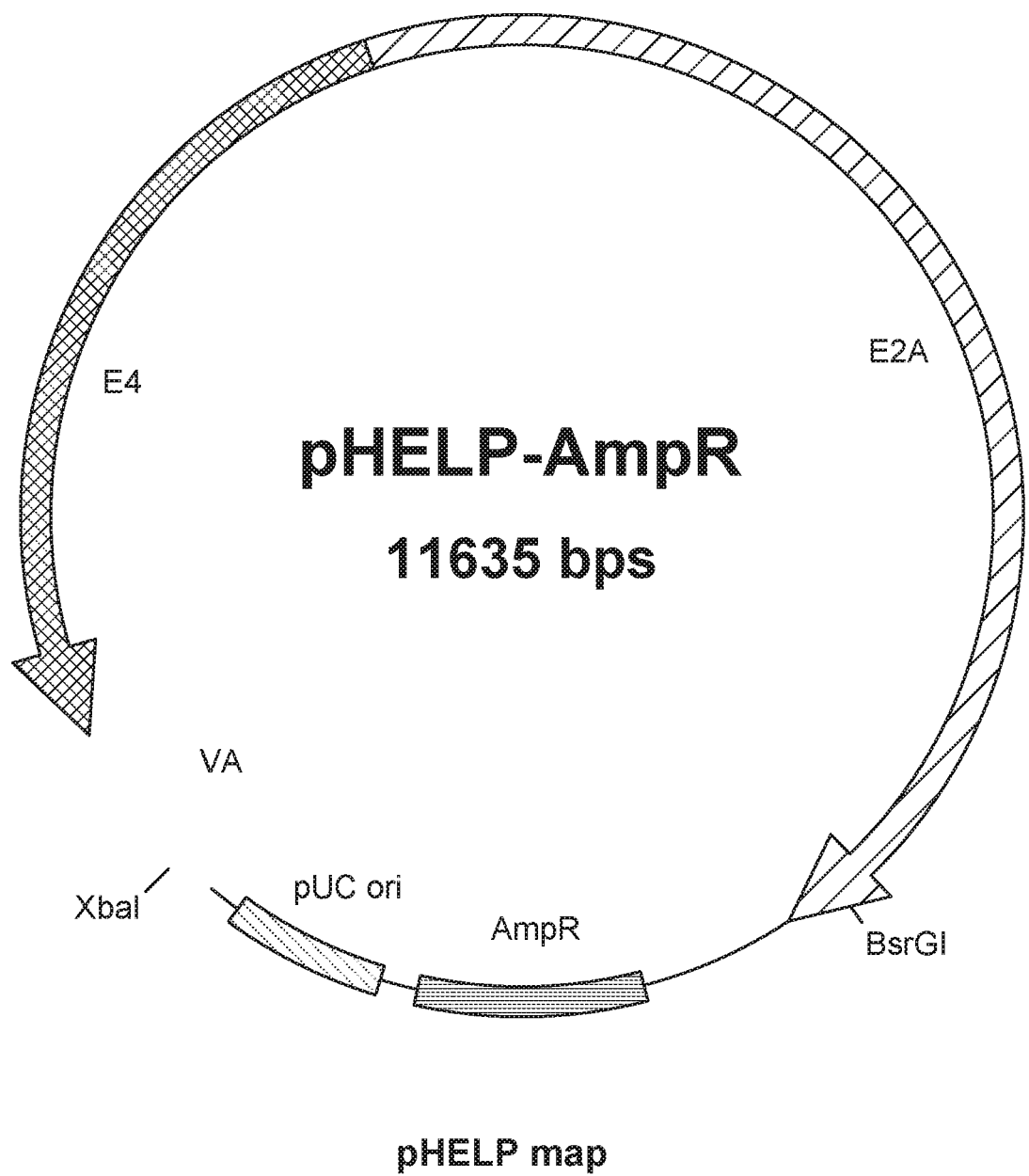
FIG. 26B shows the plasmid map of the pHELP plasmid. The pHELP plasmid contains the Trans-acting Adenoviral components necessary for recombinant adeno-associated virus production. The pHELP plasmid contains the regions of the adenovirus genome that provide factors that are important for AAV replication, namely E2A, E4, and VA RNA. The adenovirus E1 functions involved in rAAV replication are provided by the transfection host 293 cells. The pHELP plasmid does not, however, contain other adenovirus replication or structural genes. The adenovirus sequences present in this plasmid represent only ~28% (9,280/35,938) of the adenovirus genome and does not contain the cis elements critical for replication, such as the inverted terminal repeats. Therefore, no infectious adenovirus is expected to be generated from such a production system.
Figure 26C:
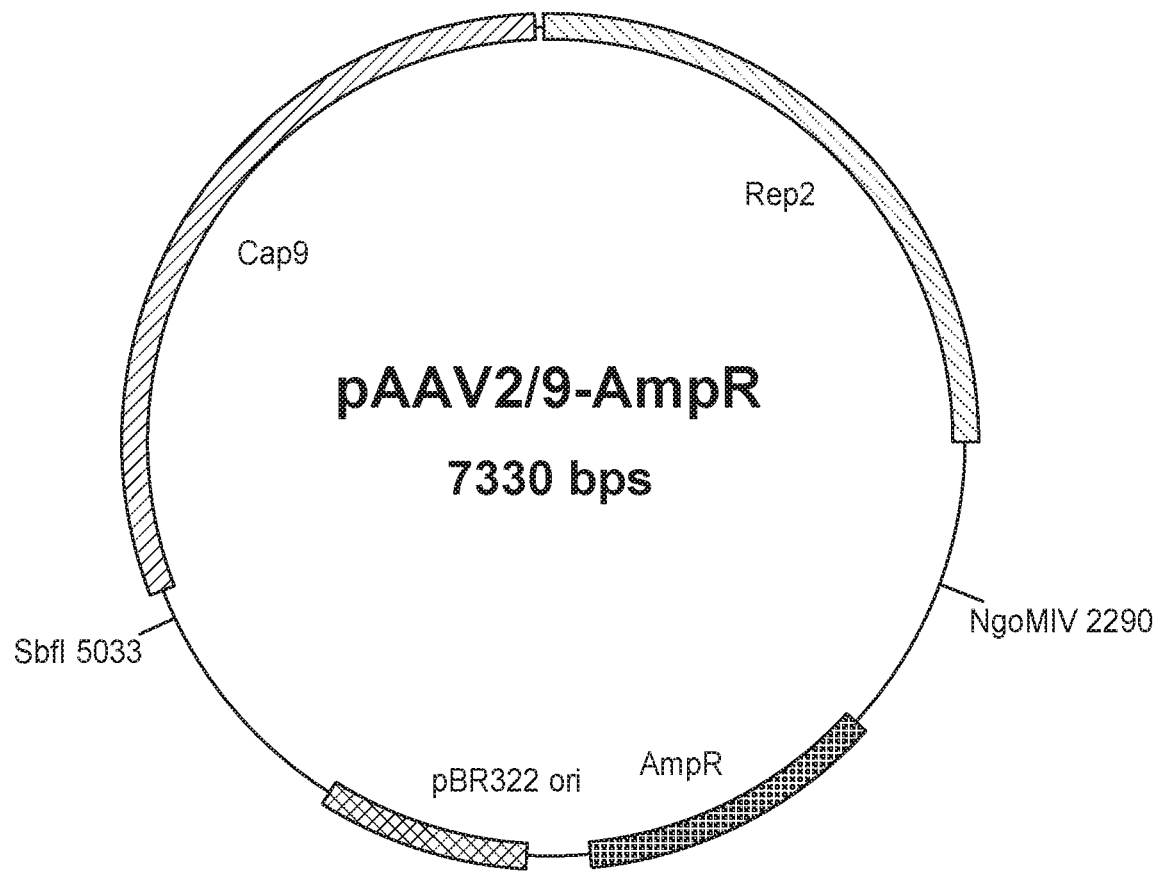
FIG. 26C shows the plasmid map of the AAV plasmid. The wild type AAV genome contains two non-coding structural elements called inverted terminal repeats that flank the rep and cap open reading frames. Rep and cap encode viral replication and capsid proteins respectively. In the production of recombinant adeno-associated viral vectors; the viral ITRs are the only elements used in cis while the viral open reading frames are supplied in trans. Using the transient transfection of adherent HEK293 cells method to make AAV addresses the cis/trans roles for the different genetic elements by dividing them to separate plasmids. The pAAV2/9 plasmid contains open reading frames for the AAV2 rep gene and the AAV9 cap gene.
Figure 29:
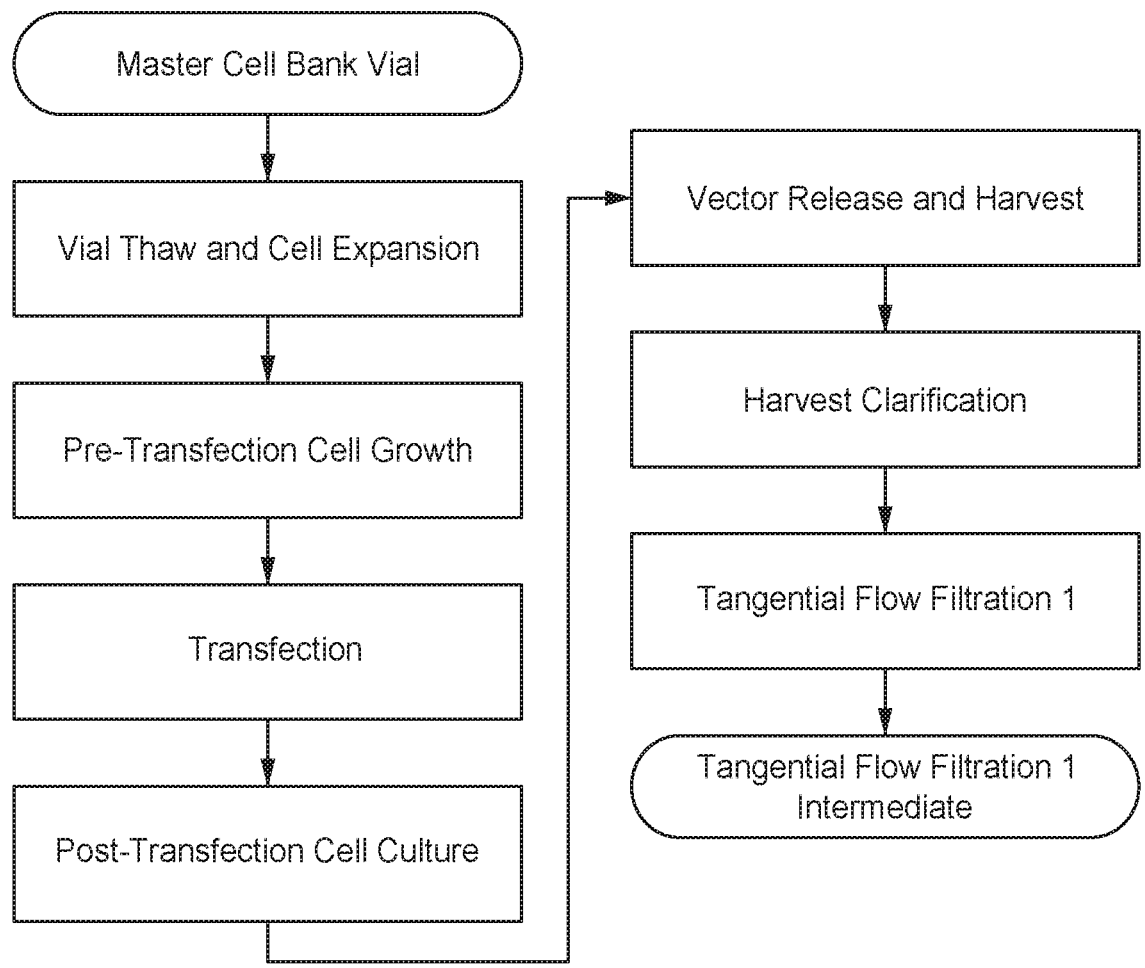
FIG. 29 describes the drug substance upstream process flow diagram.

An upstream process (see, e.g., FIG. 29) was used to produce an intermediate derived from a working cell bank, wherein the upstream process comprises the steps of (a) culturing adherent cells, (b) transfecting the cultured cells with three plasmids as shown in FIGS. 26A-26C (e.g., comprising AAV9-SMN1 described herein) to enable production of the AAV viral vector, (c) lysing the adherent cells to isolate the AAV viral vector, (d) purifying the viral particles via filtration to remove any intact cells or cellular debris, and (e) subjecting the purified product of (d) to tangential flow filtration, and (0 freezing the resultant intermediate preparation of purified viral particles.

(a) Culturing Adherent Cells

HEK293 cells were thawed and expanded through seven passages in disposable flasks with the use of CO$_2$ incubators. The thawed cells were washed with Cell Expansion Growth Media, centrifuged and resuspended with fresh Cell Expansion Growth Media. The resuspended cells were seeded into a flask containing Cell Expansion Growth Media and incubated.

When cells were confluent, they were washed with DPBS and removed from the flasks with TrypLE Select enzyme solution. Cell Expansion Growth Media was added to neutralize the enzyme solution, and the suspended cells were split and reseeded into new flasks containing Cell Expansion Growth Media. This expansion process was repeated for 7 times. In the last iteration, the suspended cells were not reseeded in flasks, but the cell slurry was instead inoculated in a bioreactor for further expansion.

An iCELLis 500/200 m$^2$ or an iCELLis 500/333 m$^2$ adherent cell bioreactor was prepared for inoculation in advance of inoculation. Preparation activities included unpacking of the disposable bioreactor, physical inspection, leak testing, tubing assembly attachment, and probe equilibration. Cell Expansion Growth Media was charged to equilibrate the bioreactor. Once the pH (pH 6.9 to 7.5), temperature (35° C. to 39° C.), and dissolved oxygen (40-125%) were verified to be within the defined ranges, the bioreactor was seeded at a target seeding density of 4800-7000 cells/cm$^2$ (for 200 m$^2$ reactor) or 5000-12000 cells/cm$^2$ (for 333 m$^2$ reactor). The cell slurry from the previous step was added to media in a recirculation media bag and circulated through the bioreactor.

(b) Transfecting Adherent Cells

On days 4, 5 or 6 from time of bioreactor inoculation, adherent HEK293 cells were transfected with a triple DNA plasmid PEI co-precipitation. The 3 plasmids utilized for this transfection are pSMN, pAAV2/9, and pHELP. The DMEM growth medium used for cell expansion is removed from the bioreactor and replaced with Transfection Media. The scAAV9.CB.SMN vector is produced using triple DNA plasmid transfection into Adherent Human Embryonic Kidney (HEK293) cells using a polyethylenimine ("PEI") co-precipitation in a large-scale adherent cell bioreactor. The vector plasmid pSMN contains the cDNA for the human survival motor neuron protein (SMN). The 3 plasmids utilized for this transfection are pSMN (222 mg), pAAV2/9 (333 mg), and pHELP (444 mg). The plasmids may be transfected at a ratio of 1:1:1 mole. The transfection medium was allowed to equilibrate in the bioreactor until the bioreactor temperature is ≥30° C. prior to the addition of the PEI-Plasmid co-precipitation. The PEI-Plasmid co-precipitation process involves the addition of the plasmids to Transfection Media and 0.2µ filtration into a reaction bag. The PEI was added to transfection medium and then to the reaction bag. The PEI-plasmid ratio is about 1:1 by weight. The PEI-Plasmid reaction was manually mixed to form a homogeneous suspension and the reaction occurs over a 15-30 minute period. At the end of the reaction time, the PEI-Plasmid co-precipitation was transferred from the reaction bag to the bioreactor. The PEI-Plasmid co-precipitation was allowed to mix in the bioreactor for 1-2 hours (alternative durations are described in Example 7) prior to restarting agitation. The Transfection Media was recirculated in the bioreactor for 18-24 hours before the next media change.

On bioreactor day 6, 18-24 hours post transfection, the bioreactor was drained and the Transfection Media recirculation media bag was replaced with Post-Transfection Media. The bioreactor was re-filled with Post-Transfection Media with recirculation in the bioreactor. On day 7, 18-24 hours post the media change on day 6, the Post-Transfection Media in the recirculation bag was replaced with a fresh bag of Post-Transfection Media. The bioreactor was not drained during this step. Recirculation of the media continues until harvest usually at day 9.

(c) Lysing the Transfected Adherent Cells

After 9 days in the bioreactor, the final pre-harvest samples were taken from the reactor and the total cell lysis process was initiated. Benzonase was added to the bioreactor to a final concentration of 100 U/mL. The Benzonase was allowed to mix in the reactor, and the Lysis Buffer was added to the reactor. The Lysis Buffer was mixed in the reactor at 15-25° C. for 2 hours before the contents of the bioreactor were transferred to the harvest bag. A Salt Sucrose Solution (SSS) which quenches the Benzonase reaction was added to the harvest bag and mixed for 15 minutes. The bioreactor was then rinsed with the Bioreactor Rinse Buffer for 15 minutes, and the rinse was then collected in the harvest collection bag, along with the quenched cell lysis solution. Once the rinse had been added to the collection bag, the contents were mixed for 15 minutes and the bulk harvest samples taken.

(d) Preparing the Viral Particles by Filtration and Tangential Flow Filtration

The mixed bulk harvest was filtered through a POD depth filter into a collection bag. Once all bulk harvest had been filtered, the depth filter was chased with TFF1 Buffer. The depth filter pool was mixed and sampled. The depth filter pool was then filtered through a 0.45 µm filter to further clarify the bulk harvest material. The 0.45 µm filter was then chased with TFF1 Buffer.

For the TFF1 step, 5.0 $m^2$ of 300 kDa MW cut off regenerated cellulose membrane cassettes were flushed, sanitized with NaOH solution and equilibrated with TFF1 buffer. The concentration phase of this operation was designed to reduce the volume of the clarified harvest by approximately 10×. Once the target retentate volume was reached, diafiltration operation are started. The retentate was diafiltered with 6 diavolumes of TFF1 buffer. Alternatively, the retentate may be diafiltered with more than 6 diavolumes of TFF1 buffer, e.g., 10 diavolumes, 12 diavolumes, or 15 diavolumes. Once 6 diavolumes of permeate total flow were achieved, the retentate was concentrated again and harvested into a collection bag. Two successive rinses of the membrane were executed to maximize the product recovery from the TFF system to produce an intermediate drug substance.

(e) Freezing Intermediate

The TFF1 intermediate was aliquoted into 1 or 2 liter sterile PETG bottles in a LFH hood and then frozen on dry ice or in a freezer and transferred to −60° C. storage.

pumped into a bag with a mixer. The pooled TFF 1 Intermediate was mixed, and a sample was taken to determine the titer. The pooled TFF1 Intermediate was immediately processed by the adding 11-14% of Tween 20. Tween 20 was used to promote flocculation of the bulk of host cell proteins and DNA under acidic pH conditions. The mixture was allowed to incubate for a 12-20 hours. The pH was then lowered by the addition of Acidification Buffer (1M glycine) to pH 3.3-3.7. The precipitate formed after the pH was lowered was then removed by filtering the solution through a 1.1 $m^2$ Clarisolve and a 2.2 $m^2$ Millistak+C0HC depth filters and 0.45 µm polishing filters. This process resulted in the Acidified and Clarified TFF Intermediate.

(b) Purification with Cation Exchange Chromatography

The cation exchange (CEX) chromatography step was used to separate the viral capsids from proteins, DNA, and other process impurities, e.g., host cell lipids, TWEEN 20. This step utilized a CIMmultus S03-8000 Advanced Composite Column (Sulfonyl) (0.2 µm pores) chromatography column (8.0 L) operated using an automated process chromatography system. Buffers and solutions are described in the following table:

TABLE 49

Buffers used in Upstream Process

| Name | Formulation | Process Step(s) Used |
|---|---|---|
| Cell Expansion Growth Media | DMEM with 10% FBS, 4.5 g/l glucose, 4 mM L-glutamine | Cell expansion, iCELLis Bioreactor pre-transfection |
| Transfection Media | DMEM with no FBS, no calcium, no L-glutamine and 4.5 g/L glucose | iCELLis Bioreactor transfection |
| Post Transfection Media | OptiMEM with 2.3 g/L glucose, 4 mM L-glutamine, and no FBS | iCELLis Bioreactor post transfection |
| Lysis Buffer | 500 mM HEPES, 10% Tween 20, 20 mM $MgCl_2$, pH 8.0 | iCELLis Bioreactor cell lysis |
| Salt Sucrose Solution (SSS) | 3700 mM NaCl, 10% Sucrose | Clarification |
| Bioreactor Rinse Buffer | 20 mM Tris, 1 mM $MgCl_2$, 500 mM NaCl, 1% Tween 20, 1% Sucrose | iCELLis bioreactor harvest |
| TFF1 Buffer | 20 mM Tris, 1 mM $MgCl_2$, 500 mM NaCl, 1% Sucrose | Clarification, TFF1 |
| TFF1 Sanitization Buffer | 0.5M NaOH | TFF1 membrane sanitization |

Example 12: Manufacturing Downstream Process

Figure 30:
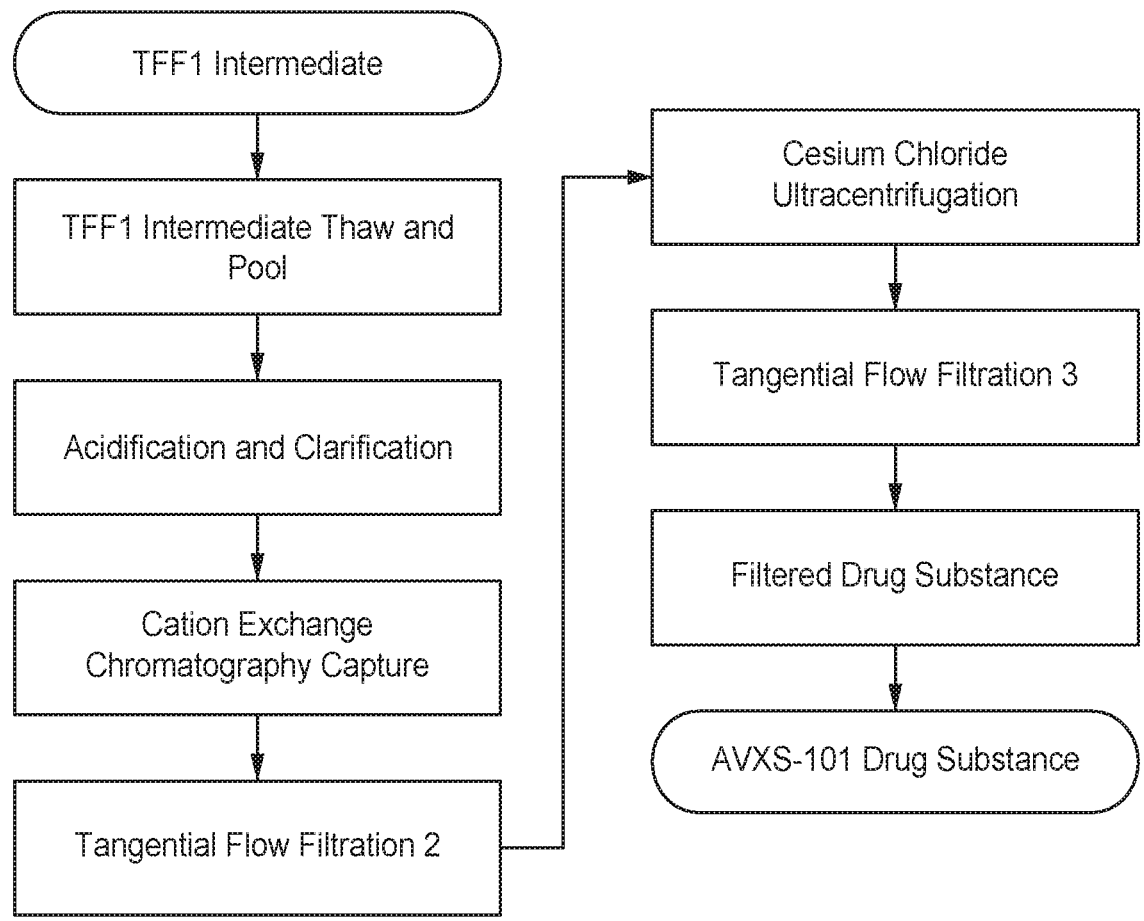
FIG. 30 describes the drug substance downstream process flow diagram.

A downstream process (see, e.g., FIG. 30) was used to process the TFF1 intermediate to a filtered drug substance. In some embodiments, the downstream process disclosed herein may be used to process an intermediate comprising an AAV9-SMN as described herein. The downstream process steps include: (a) acidifying and clarifying the intermediate (using filtration), (b) purifying using cation exchange chromatography, (c) filtering with tangential flow filtration ("TFF2"), (d) ultracentrifuging using CsCl buffer to separate filled and empty viral capsids, (e) collecting the AAV viral vectors, and (d) filtering the collected AAV viral vectors with a second tangential flow filtration ("TFF3") step.

(a) Acidification and Clarification

The TFF1 intermediate material from the upstream process (thawed to room temperature if previously frozen) was

TABLE 50

Buffers and solutions for one CEX cycle

| Solution name | Composition | Purpose | Volume (L) for one 8 L CEX Cycle |
|---|---|---|---|
| WFI | WFI | Column flushes | 200 L |
| CEX A-Buffer | 50 mM glycine, 500 mM NaCl, 1.0% sucrose, 0.20% poloxamer 188, pH 3.5 ± 0.1 at 20° C. | Equilibration, wash, elution | 256 L |
| CEX B-Buffer | 50 mM glycine, 2.0M NaCl, 1.0% sucrose, 0.20% poloxamer 188, pH 3.5 ± 0.1 at 20° C. | Column equilibration and elution | 40 L |

TABLE 50-continued

Buffers and solutions for one CEX cycle

| Solution name | Composition | Purpose | Volume (L) for one 8 L CEX Cycle |
|---|---|---|---|
| Monolith Cleaning Solution | 1M NaOH, 2M NaCl | Column Sanitization, CIP | 96 L |
| 1M ammonium acetate pH 9.0 Neutralization buffer | 1M ammonium acetate 1.0M Tris pH 9.1 ± 0.1 at 20° C. | Restore column pH pH adjustment of CEX product | 40 L 0.5 L |
| Storage solution | 20% Ethanol in WFI | Column storage | 40 L |

The Acidified and Clarified TFF Intermediate (i.e., CEX Load) was loaded onto a cleaned and equilibrated CEX column. The conditions were such that the viral vectors bind to the monolithic column. The unbound material was washed from the column with CEX A Buffer. The product was eluted from the resin with a gradient of CEX B Buffer in CEX A Buffer. Collection of Fraction 1 was initiated at the start of the elution gradient for 10 column volumes (CV) each defined volume of 2.3-2.7 CV. The chromatography column was discarded after each batch (i.e., the chromatography column was not re-used). The CEX product eluate (Fraction 2) was then neutralized using Neutralization Buffer to a pH of 7.7-8.3.

(c) Filtering with Tangential Flow Filtration (TFF2)

The TFF2 step concentrated the viral vector, removed protein impurities, and exchanged the buffer to an appropriate buffer for the CsCl ultracentrifugation step. The Neutralized CEX Eluate was processed using a TFF system fitted with 0.3 m² of 300 kDa MWCO regenerated cellulose membrane.

The volume of the Neutralized CEX Eluate was reduced to a target retentate volume. Once the target retentate volume was reached, diafiltration was started in discontinuous TFF mode (batch mode). The retentate was diluted 2-fold with TFF2 NaCl Diafiltration Buffer, and the retentate is concentrated to its initial volume. This was repeated until diafiltration with TFF2 NaCl Diafiltration Buffer was complete. The retentate was then diluted 2-fold with TFF2 CsCl Diafiltration Buffer and the retentate was concentrated to its initial volume. This was repeated until diafiltration with TFF2 NaCl Diafiltration Buffer was complete.

The retentate was further concentrated to a final mass based on the physical titer of the Neutralized CEX Eluate, the system hold-up volume, system flush volume, and retentate density to achieve the desired target vector concentration and recovered into a collection bag. One flush cycle of the system with TFF2 CsCl Diafiltration Buffer was followed by product blowdown to maximize the product recovery from the TFF system. A sample of the TFF2 Retentate, which contains the retentate and flush) was taken for physical titer measurement. The TFF2 membrane cassettes were discarded after each batch (i.e., TFF membranes were not reused).

TABLE 51

Buffers for TFF2

| Solution Name | Composition |
|---|---|
| TFF2 NaCl Diafiltration Buffer | 20 mM Tris, 2 mM MgCl$_2$, 150 mM NaCl, 0.2% Poloxamer 188, 1% Sucrose, pH 8.1 ± 0.1 at 20° C. |
| TFF2 CsCl Diafiltration Buffer | 20 mM Tris, 2 mM MgCl$_2$, 3M CsCl, 0.2% Poloxamer 188, pH 8.1 ± 0.1 at 20° C. |

(d) CsCl Ultracentrifugation

The purpose of the ultracentrifugation step was to remove empty capsids from full capsids by utilizing cesium chloride gradient ultracentrifugation. The TFF2 Retentate was added to ultracentrifugation tubes and the tubes were sealed. The tubes were placed in an ultracentrifuge, like an automated Optima XPN 100 Ultra Centrifuge system or equivalent system equipped with Type 50.2 Ti rotor or equivalent rotor. The filled tubes were centrifuged at 45,000 rpm for 22 hours at 20° C.

(e) Collecting AAV Viral Vectors

After completion of centrifugation step, tubes were removed from the ultracentrifuge and placed in a biosafety cabinet. Product containing tubes were mounted on ring stands above a waste container. A lamp was positioned directly under the tube to visualize the empty capsids band (Band A, highest band), the full capsid doublet bands (Band B and Band C, upper and lower bands of the doublet), and lowest band below the doublet (Band D). The tubes were punctured with a needle attached to a syringe to vent the tubes, and bands B, C, and D were removed by a needle. The collected material was transferred to a collection bag. The collected ultracentrifuged pool (UC Pool) was diluted with TFF2 Buffer to reach a consistent starting CsCl concentration in the TFF2 Load material. The diluted UC Pool is processed in the TFF3 step. The buffer for the CsCl ultracentrifugation step is listed in the table below:

TABLE 52

Buffer for CsCl Ultracentrifugation

| Solution Name | Composition |
|---|---|
| TFF2 CsCl Diafiltration Buffer | 20 mM Tris, 2 mM MgCl$_2$, 3M CsCl, 0.2% Poloxamer 188, pH 8.1 ± 0.10 |

(f) Filtering with Tangential Flow Filtration (TFF3)

The TFF3 step removed CsCl and concentrated the full vector using Final Formulation Buffer. A tangential flow filtration system was utilized in conjunction with 50 cm² of 300 kDa MWCO regenerated cellulose membranes. The viral vector was retained by the membranes.

The volume of the Diluted UC Pool was reduced to a target retentate volume. Once the target volume was reached, continuous diafiltration at a constant retentate volume was started. The retentate was diafiltered with TFF3 Buffer. A sample of the diafiltered retentate was taken for physical titer measurement. The retentate was further concentrated by targeting a permeate weight, which was calculated by 1) the volume of retentate in the TFF system at the end of diafiltration, 2) the Diluted UC Pool physical titer, 3) a target drug substance (DS) concentration, 4) the combined volume of system flushes and filter flushes, and 5) the density of the TFF3 Buffer. The TFF3 membrane cassettes were discarded after each batch (i.e., cassettes are not reused).

TABLE 53

Buffers for TFF3

| Solution Name | Composition |
|---|---|
| TFF3 Buffer option 1 | 20 mM Tris, 1 mM MgCl$_2$, 200 mM NaCl, 0.001% Poloxamer 188, pH 8.0 ± 0.1 at 20° C. |
| TFF3 Buffer option 2 | 20 mM Tris, 1 mM MgCl$_2$, 200 mM NaCl, 0.005% Poloxamer 188, pH 8.0 ± 0.1 at 20° C. |

Two successive 20 mL rinses of the TFF membranes with the TFF3 Buffer were performed to recover the vector from the TFF system. The rinses were recovered through a 0.2 mm Pall Supor® EKV Sterilizing-Grade Filter (Mini Kleenpak). A filter rinse was performed with TFF3 Buffer to recover any vector remaining in the filter and to adjust the final volume of the Filtered TFF3 Pool (i.e., Drug Substance DS). The DS was aliquoted into 125 or 250 mL PETG bottles and frozen at <−60° C.

Example 13: Formulating and Filling in the Manufacturing Process

The Drug Product (DP) was a single-dose, preservative-free, sterile, clear to slightly opaque, and colorless to faint white, intravenous infusion of non-replicating, self-complementary AAV9 vector at a target concentration of 2.0×10$^{13}$ vg/ml. The DP comprised 20 mM Tris, 1 mM MgCl$_2$, 200 mM NaCl, 0.005% w/v Poloxamer 188. The pH range of the solution was 7.7 to 8.3.

TABLE 54

Drug Product Unit Operation-Buffer Composition

| Solution Name | Composition |
|---|---|
| Drug Product (DP) Formulation Buffer option 1 | 20 mM Tris, 1 mM MgCl$_2$, 200 mM NaCl, 0.001% Poloxamer 188, pH 8.0 ± 0.1 |
| Drug Product (DP) Formulation Buffer option 2 | 20 mM Tris, 1 mM MgCl$_2$, 200 mM NaCl, 0.005% Poloxamer 188, pH 8.0 ± 0.1 |

The DP was filled into sterile, ready to use, 10 ml Crystal Zenith (CZ) vials, stoppered with sterile, ready to use, chlorobutyl elastomeric stoppers, and sealed with sterile, 20 mm flip-off aluminum seals. The vials were filled with a nominal fill volume of either 5.5 mL or 8.3 mL. The target overfill was 0.4 mL, and the vials were filled to 5.9±0.1 mL or 8.7±0.1 mL.

Example 14: In Vivo Potency Assay

The relative potency of the drug product was measured using a quantitative, in vivo assay. The assay used an established mouse model of SMA disease. Breeding pairs of the SMAΔ7 mouse strain (Jackson Laboratories, #005025) are phenotypically normal but ~25% of their offspring are homozygous for the targeted SMN gene mutation and display the SMA-like phenotype. By Day 5 they show signs of muscle weakness and in the following week, develop an abnormal gait and a tendency to fall over. Jackson Laboratories reports the mean survival for animals with the SMA-like phenotype as ~15±2 days. Pilot studies demonstrated a median survival time for untreated animals with SMA-like phenotype of 16.3 days (geometric mean; n=3 studies; 10 mice per study).

Biologically active drug product administered by intravenous (IV) infusion yields an increase in survival time that is a function of dose (vg/kg). Drug product potency was measured relative to the reference material (prior batch of vector). The titer of drug product and the reference material (vector genomes/mL; vg/mL) was determined by Droplet Digital polymerase chain reaction (ddPCR). Vector was diluted in saline to achieve each of three specified dose levels that will be administered to mice with the SMA-like phenotype.

An assay's results are considered to be acceptable if the assay passes suitability. Assay suitability consists of the following:
1. Acceptance limit for the Negative Control sample (15±2 days, Median Survival)
2. Acceptance limit for the Positive Control sample (>40 days, Median Survival)
3. Acceptance limits on the reference standard Median Survival dose-response curve A prior batch of vector (hereinafter, Prior Batch) was used in this study to determine the linear correlation between median survival (days) of SMAΔ7 mouse when dosed with drug product at five different dose levels including the 0 (zero) dose using 0.9% saline solution (untreated group).

The relative potency of drug product batch 816836 was established by comparing the linear regression curve of the Prior Batch reference standard to that of the drug product batch 816836 linear regression curve. This was accomplished by using the ratio of the y-intercept and slope of each linear regression line (i.e., Reference Standard and Test Article). The percent Relative Potency calculation is delineated in equation (1) below:

$$\% \text{ RP}=[(y\text{-Intercept/slope of Test Article})\div(y\text{-Intercept/slope of Reference Standard})]\times 100 \quad (1)$$

The NCH0613 batch used in the Phase-1 clinical trial was used as the Reference Standard batch and was assigned a potency of 100%.

The Δ7 mouse model was used to demonstrate efficacy of SMA therapeutics, including drug product. Untreated or saline-treated control animals provide a reliable baseline control from which product potency can be measured as an increase in median survival. Development work with drug product identified three (3) doses (excluding the vehicle treated dose) determined by Genomic Titer using Droplet Digital PCR (ddPCR) which affect survival in the mouse model with a linear correlation when administered dose (vg/kg) is log-transformed and plotted against the Median Survival (in days) of the treated SMAΔ7 neonatal mouse. See standard titers (vg/mL) in Table 56 for the low, mid, and high titer standards. In addition, the TFF Buffer (vehicle) solution is used for both the zero (0) calibration curve point as well as a Negative Control. A dose demonstrating ≥40 day survival (greater than the dose that demonstrates doubling of the median survival) was also included as a Positive Control.

TABLE 56

Target Doses

| Dose (vg/kg) | Median Survival (days) | Standards and Controls |
|---|---|---|
| Saline | 15 ± 2 | Negative Control (untreated) |

TABLE 56-continued

Target Doses

| Dose (vg/kg) | Median Survival (days) | Standards and Controls |
| --- | --- | --- |
| $1.50 \times 10^{14}$ | ≥40 days Median Survival | Positive Control |
| 0 (saline) | 15 ± 2 | Standard-1 |
| $1.2 \times 10^{13}$ | 22 ± 3 | Standard-2 |
| $7.5 \times 10^{13}$ | 31 ± 3 | Standard-3 |

Dose Solution Preparations (refer to Table 57 for the dilution scheme example). Negative Control—The 0.9% saline Solution was used as the Negative Control. Positive Control—The Test Article lot was prepared at a $1.5 \times 10^{14}$ vg/kg using saline. Reference Standard Solutions—The Reference Standard lot was prepared in three concentrations delineated in Table 56 using the saline Solution.

TABLE 57

Reference Standard and Test Article Dilution Scheme (Example)

| Dose (vg/kg) | Reference Standard/Test Article ddPCR Titer (vg/mL) | Conversion to vg/μL | Reference Standard/Test Article volume to use (μL) | Saline Solution (μL) | Total Dose Volume (μL) |
| --- | --- | --- | --- | --- | --- |
| $1.2 \times 10^{13}$ | $5.0 \times 10^{13}$ | $5.0 \times 10^{10}$ | 2.6 | 47.4 | 50.0 |

Test Article Preparation—The test article was diluted using the saline Solution. Dilutions were calculated to generate the test doses (vg/kg) delineated in Table 26 per mouse in a total final volume of 50 μl. Dilutions were made for 10 mice at the time with one extra volume as a Positive Control targeted to increase minimum lifespan of treated mice to ≥40 days of Median Survival (days).

Acceptance limits on control samples. Negative Control (untreated mice)—The assay acceptance limit for the Negative Control group was that the SMAΔ7 mice meet the median survival of 15±2 days. In addition, any mouse expiring in ≤10 days will be excluded from the analysis. If more than 7 mice are used in a group, a maximum of 2 mice may be excluded for expiring at <=10 days.

Positive Control (group treated at the target clinical dose)—The assay acceptance limit for the Positive Control group was that at a minimum lifespan of treated mice to be to ≥40 days Median Survival. In addition, any mouse expiring in ≤10 days will be excluded from the analysis. If more than 7 mice are used in a group, a maximum of 2 mice may be excluded for expiring at <=10 days.

Acceptance limits on the Reference Standard dose response curve. Assay suitability criteria will be determined for the reference standard Linear dose response curve plotting Median Survival (days) against the administered dose (vg/mL).

Y-Intercept/Slope Ratio—A linear regression curve of the Median Survival (days) versus the administered Dose (vg/kg) for the Reference Standard and the Test Article is determined. The ratio of y-Intercept to the slope for each linear regression is calculated.

Reporting Results

Qualitative Reporting of Relative Potency Results—The Assay Suitability criteria is evaluated for each assay prior to determination of a single point Median Survival (days) read at ≥40 days for the Positive Control material. If the Median Survival of the Positive Control group is ≥40 days, the Test Article may be dispositioned if the below criteria is met.

Quantitative Reporting of Relative Potency Results—The Assay Suitability criteria is evaluated for each assay prior to quantitative determination of Relative Potency for the Test Article. Relative potency for the Test Article may be reported once the Positive control reaches ≥40 days and the Median Survival of 31±3 days for the mouse group representing the upper standard dose of $7.5 \times 10^{13}$ vg/kg is reached. The Percent Relative Potency (% RP) for a Test Article will be calculated using the y-intercept and slope of the linear regression of the Median Survival (days) dose-response as follows:

% RP=100%*[(Test Article y-intercept/slope)÷(Reference Standard y-intercept/slope)].

Example 15: Surfactant Inactivation Study

To separate the influence of low pH and tween, a sample of drug substance TFF1 Intermediate that has a pH of 7.6 and 4-8% Tween-20 was used for the surfactant inactivation study. The Tween-20 concentration in TFF1 Intermediate is about 2.5-fold lower than in the full process when Tween-20 is added to TFF1 Intermediate prior to acidification. This lower Tween-20 concentration was considered a worst-case condition for surfactant driven inactivation in the drug substance process. The test article for the virus inactivation step by surfactant treatment was the TFF-1 Intermediate containing 4-8% Tween-20. To evaluate the capacity for virus inactivation by the surfactant treatment step, XMuLV and PRV were each used to spike the test article with virus in duplicate experiments. Virus was quantitated using a plaque-forming infectivity assay.

The TFF1 manufacturing step generates a surfactant concentration range of 4-8% Tween-20. The TFF1 Intermediate was pooled, and 12% more Tween-20 was added to the TFF1 Intermediate at an operating temperature of 16-20° C. with mixing for a duration of 12-20 hours. The viral clearance process was performed at a concentration of 4-8% Tween-20 and at a controlled temperature of 16.0° C.±0.1° C. The duration of the inactivation process was 120 minutes versus the typical process time of 16 hours.

For the inactivation process, the inactivation load was prepared by measuring the volume of the test article, equilibrating to the target temperature, and then spiking with virus. Samples of the spiked inactivation load were removed at six (6) time points to demonstrate the kinetics of inactivation over time: <1 minute, 15 minutes, 30 minutes, 60 minutes, 90 minutes, and 120 minutes. After collection, each sample was diluted in growth medium to cease virus inactivation, and was assayed for virus. To increase assay sensitivity at 90 minutes and 120 minutes, large volumes of these time point samples were also assayed for virus. Due to the presence of Tween-20 in the test article for this step, the titer of the inactivation load was calculated from the titer of the spiking virus and the volume of virus spiked.

Figure 31:
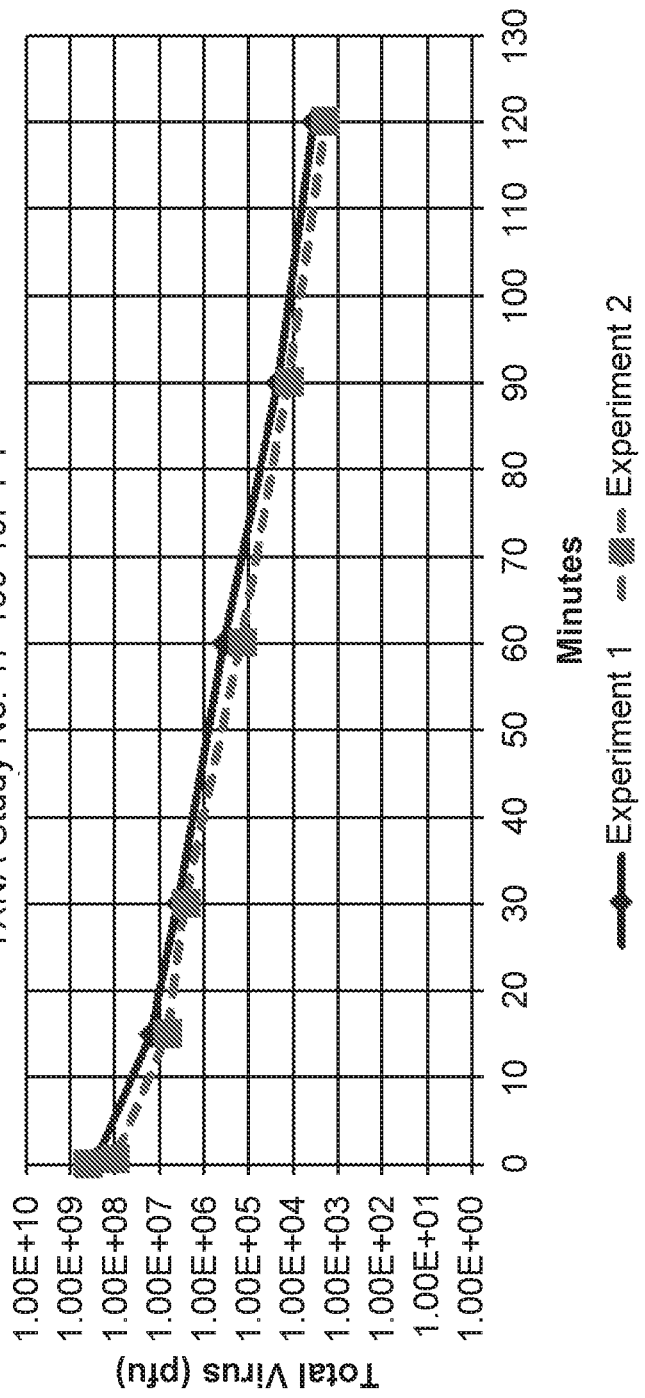
FIG. 31 shows the inactivation of XMuLV by Tween 20 added at up to 120 min.
Figure 32:
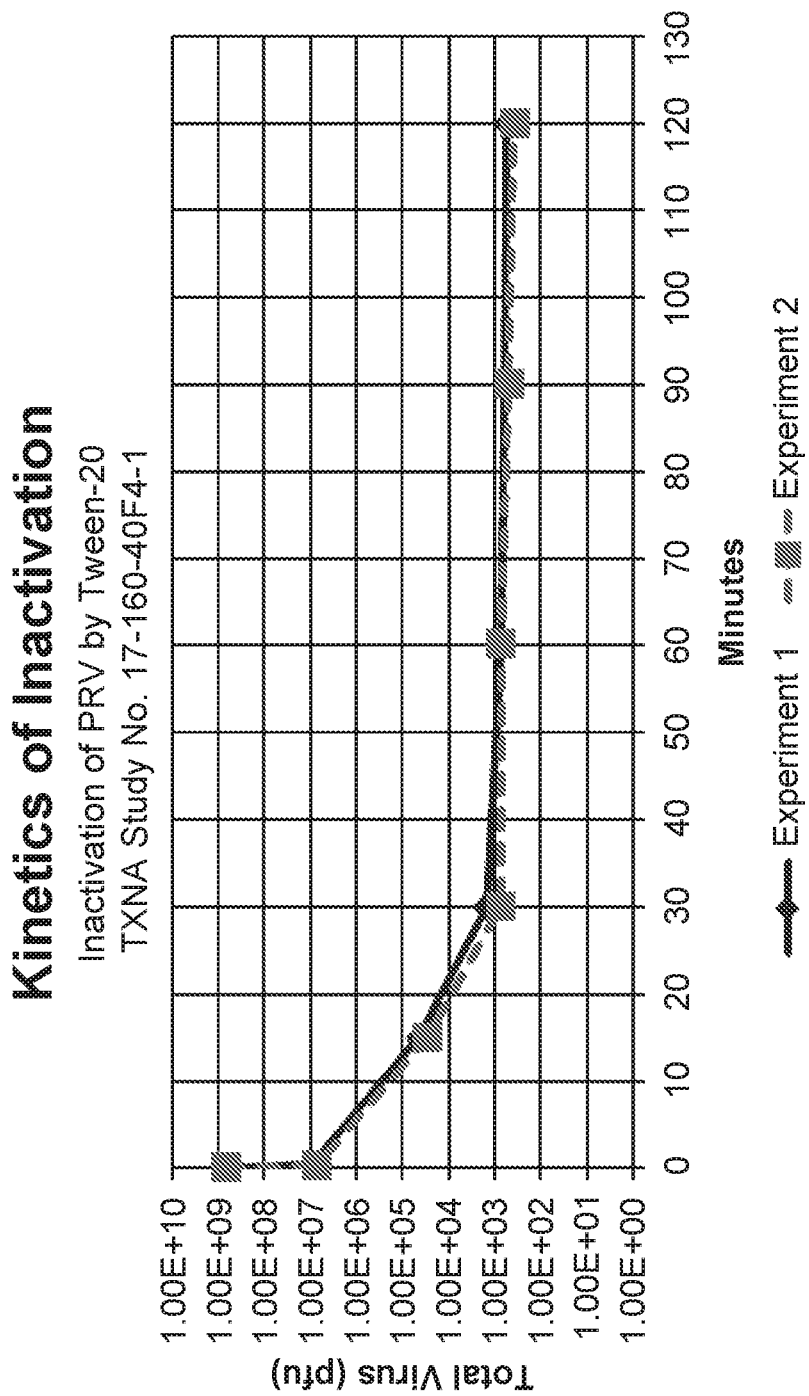
FIG. 32 shows the inactivation of PRV by Tween 20 added at up to 120 min.

The effectiveness of virus inactivation by surfactant treatment (Tween-20) was shown to be effective as evidenced by LRV values greater than 4 log 10 for both viruses at the 90-minute time point. The kinetics of inactivation by surfactant treatment are illustrated in FIG. 31 and FIG. 32 as graphs of the rate of virus inactivation over the course of 120 minutes during the Tween-20 surfactant treatment.

Example 16: Effect of Higher Seeding Density, Transfecting and Harvesting Earlier and DNA/PEI Mix Times on the Production of Drug Substance The effect of higher seeding density, transfecting and harvesting one day early and DNA/PEI mix times on the production of DS was evaluated. Each condition was evaluated in duplicate in a 1.6 m² bioreactor.

Materials and Methods

Cell Scale Up

Figure 33:
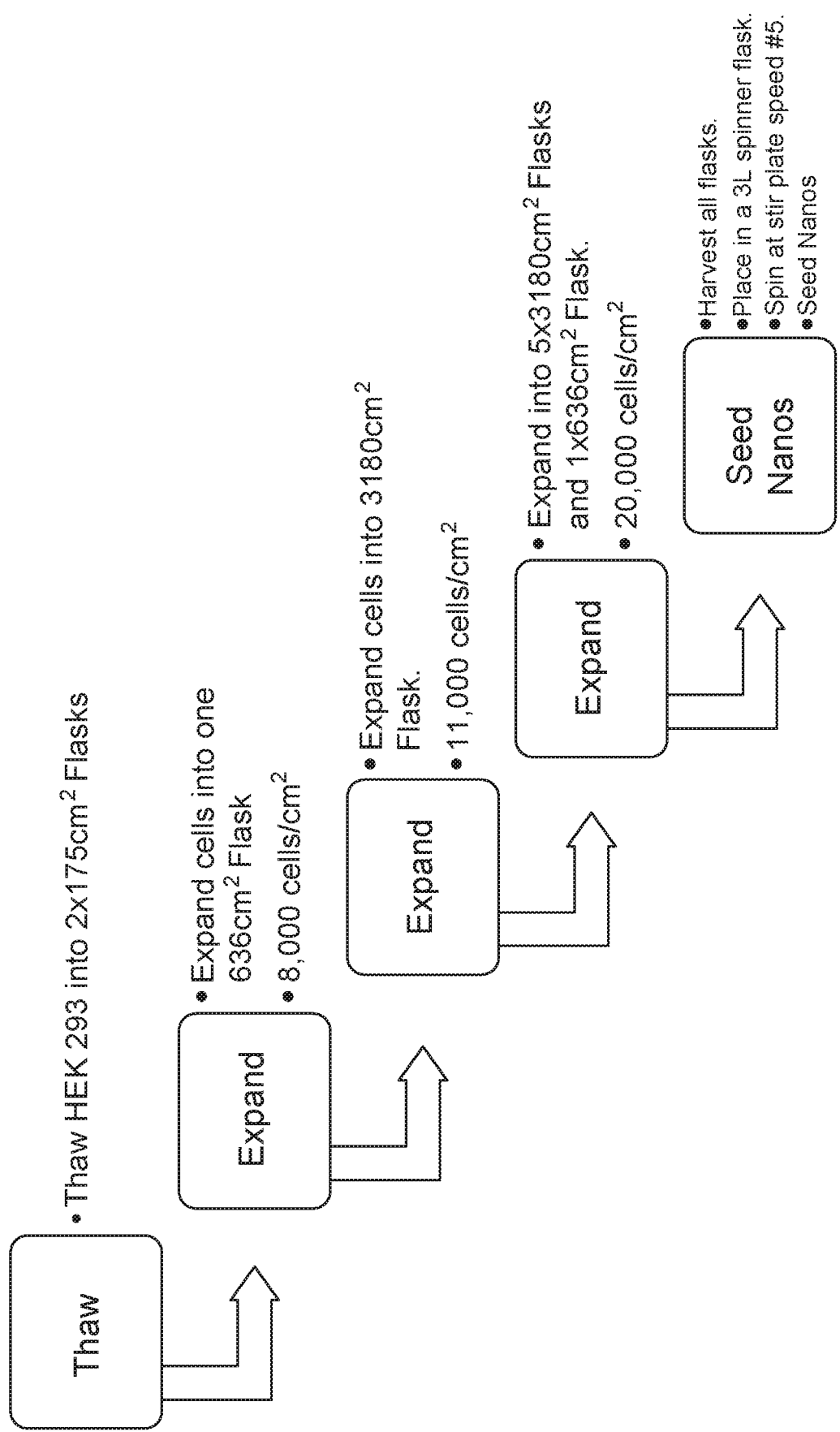
FIG. 33 describes the HEK 293 cell expansion process flow during cell seeding density experiments.
Figure 34A:
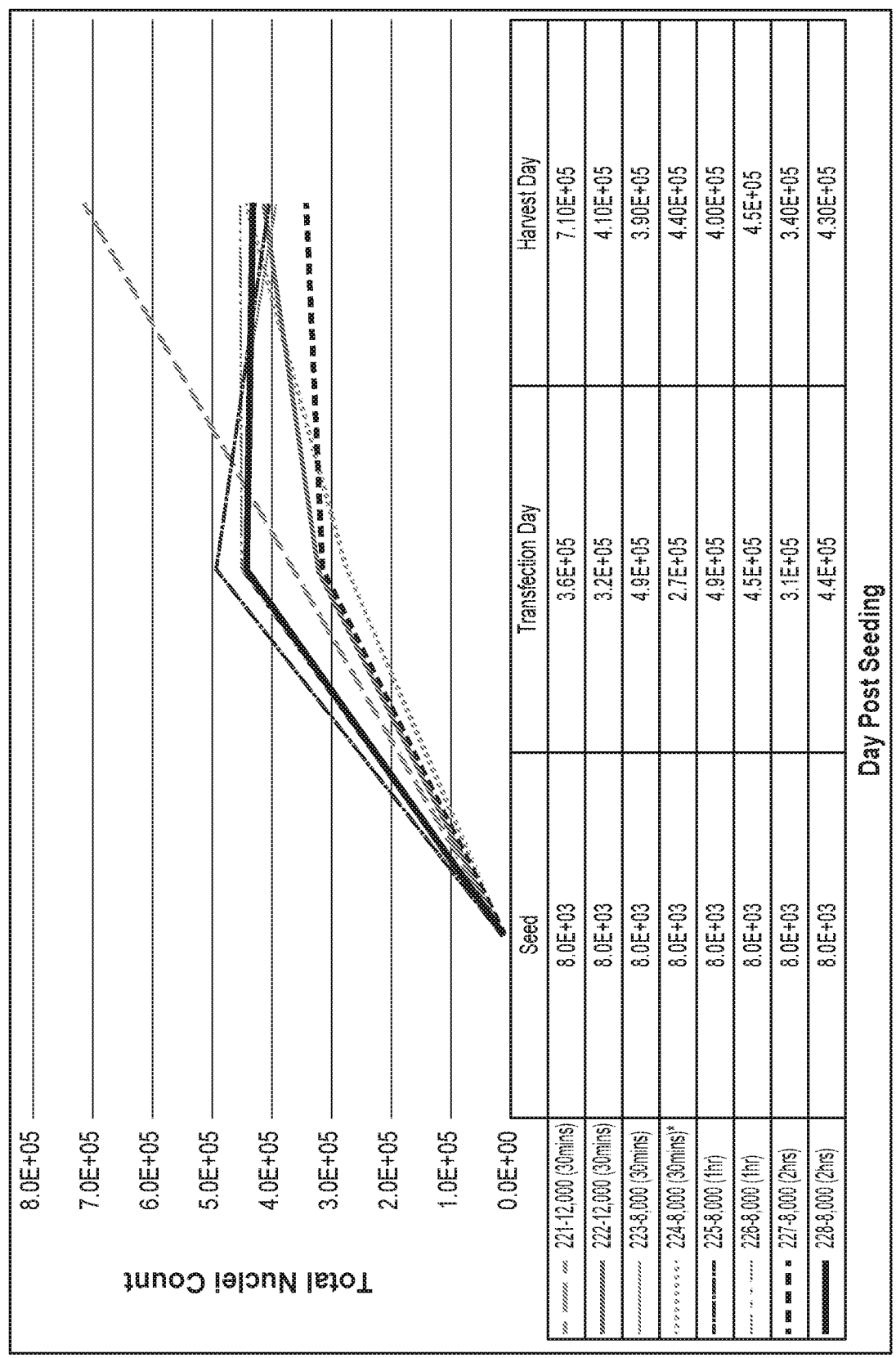
FIGS. 34A-34E show growth and metabolite profiles. HEK 293 cells were seeded in duplicate at 12,000 and 8,000 cells/cm$^2$ in bioreactors (pH 7.23, 37.0° C., 55% dissolved oxygen (DO)). Cells were transfected with DNA plasmids/PEI at four days (12,000 cells/cm$^2$) and five days (8,000 cells/cm$^2$) post-seeding. Bioreactors were harvested eight days (12,000 cells/cm$^2$) and nine days (8,000 cells/cm$^2$) post-seeding. pH and metabolite readings were read daily on Nova BioFlex.
Figure 34B:
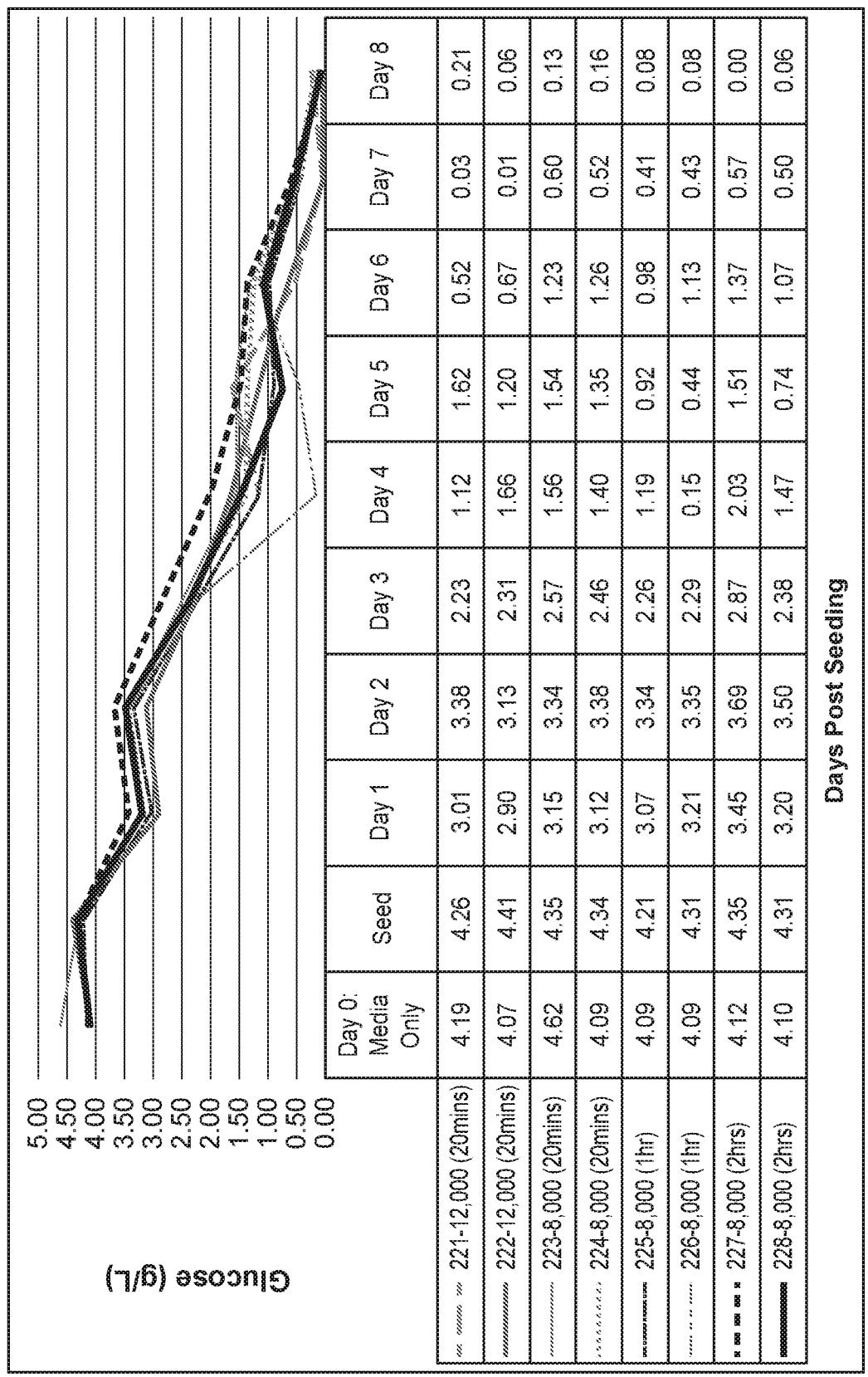
Figure 34C:
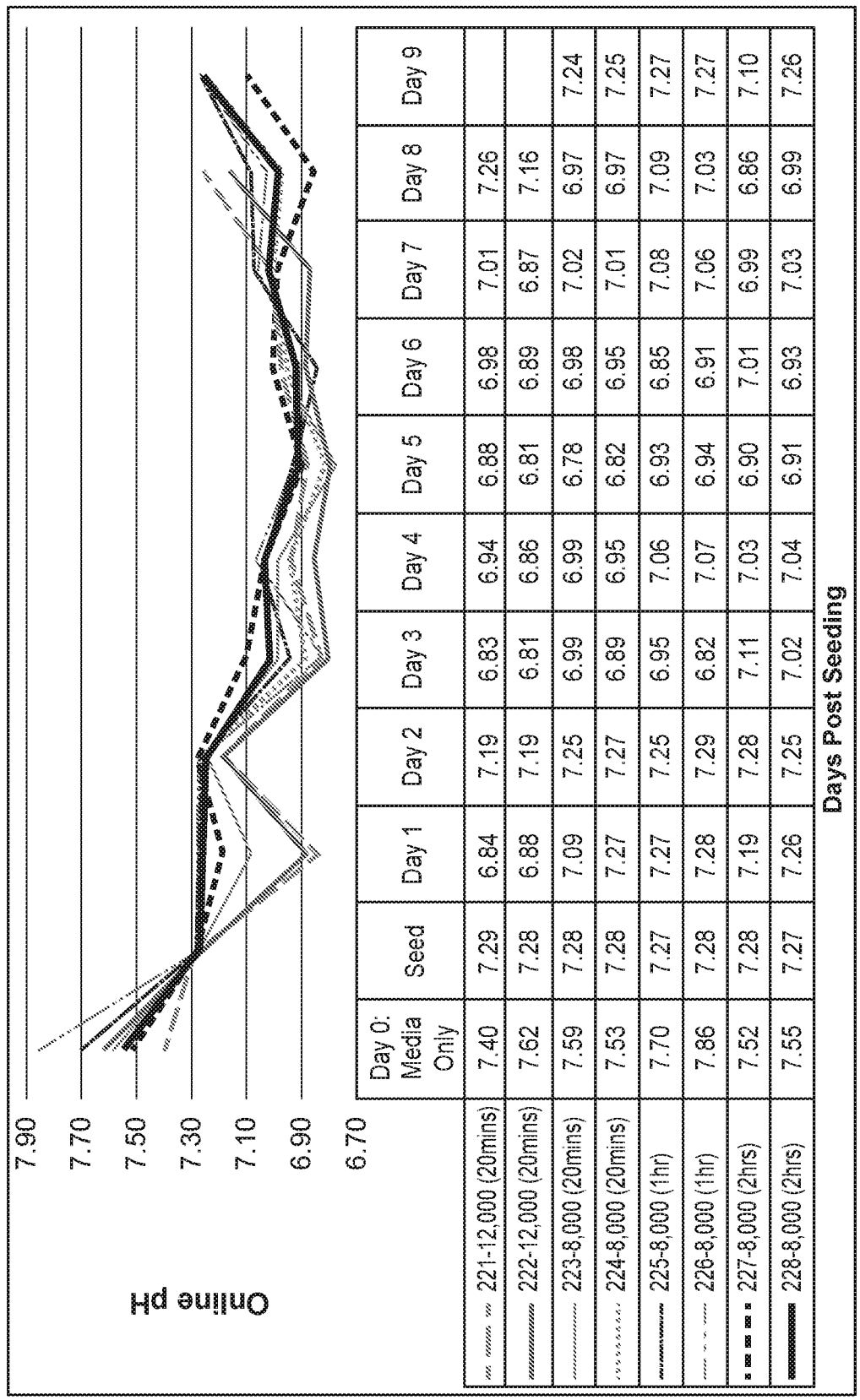
Figure 34D:
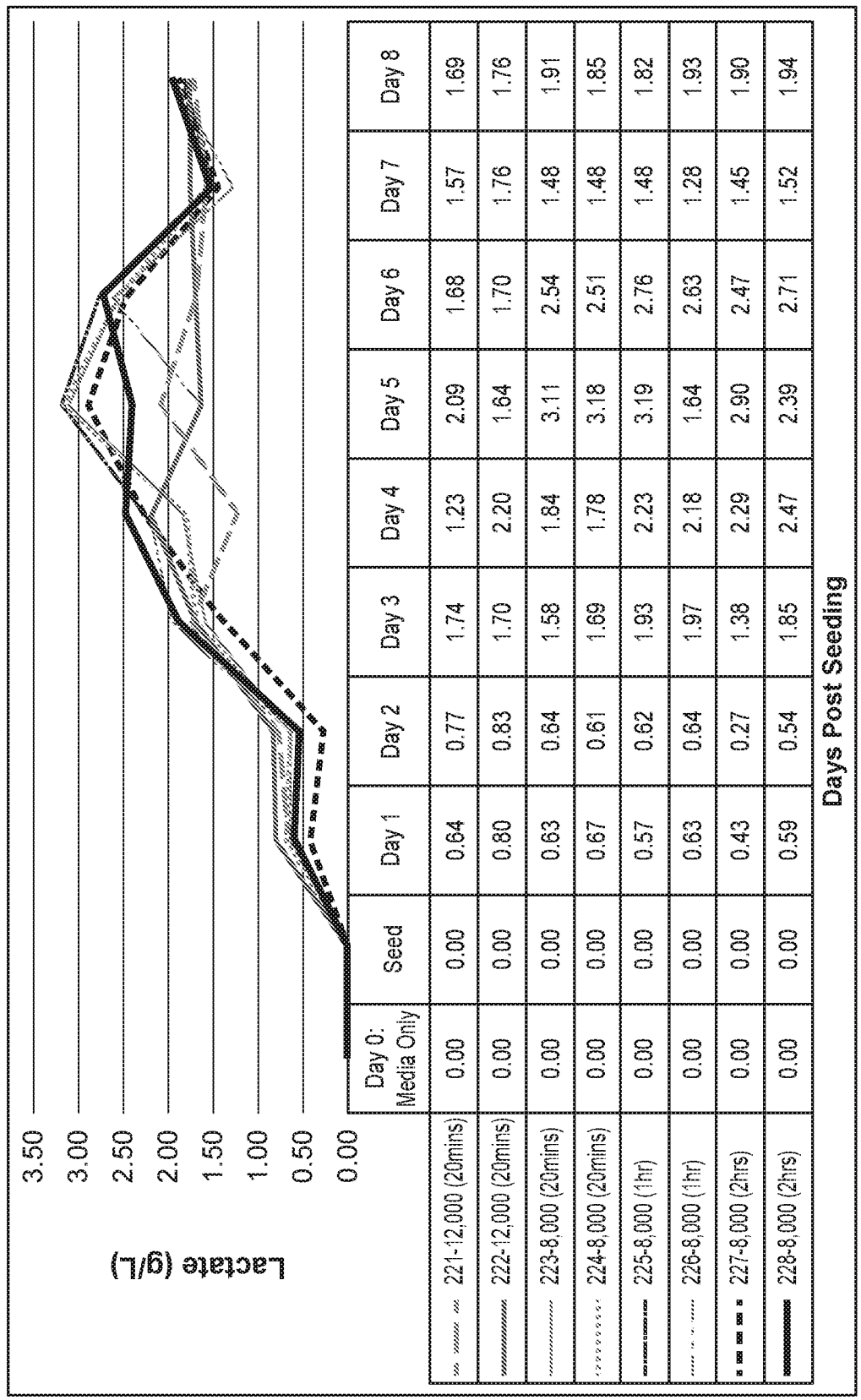
Figure 34E:
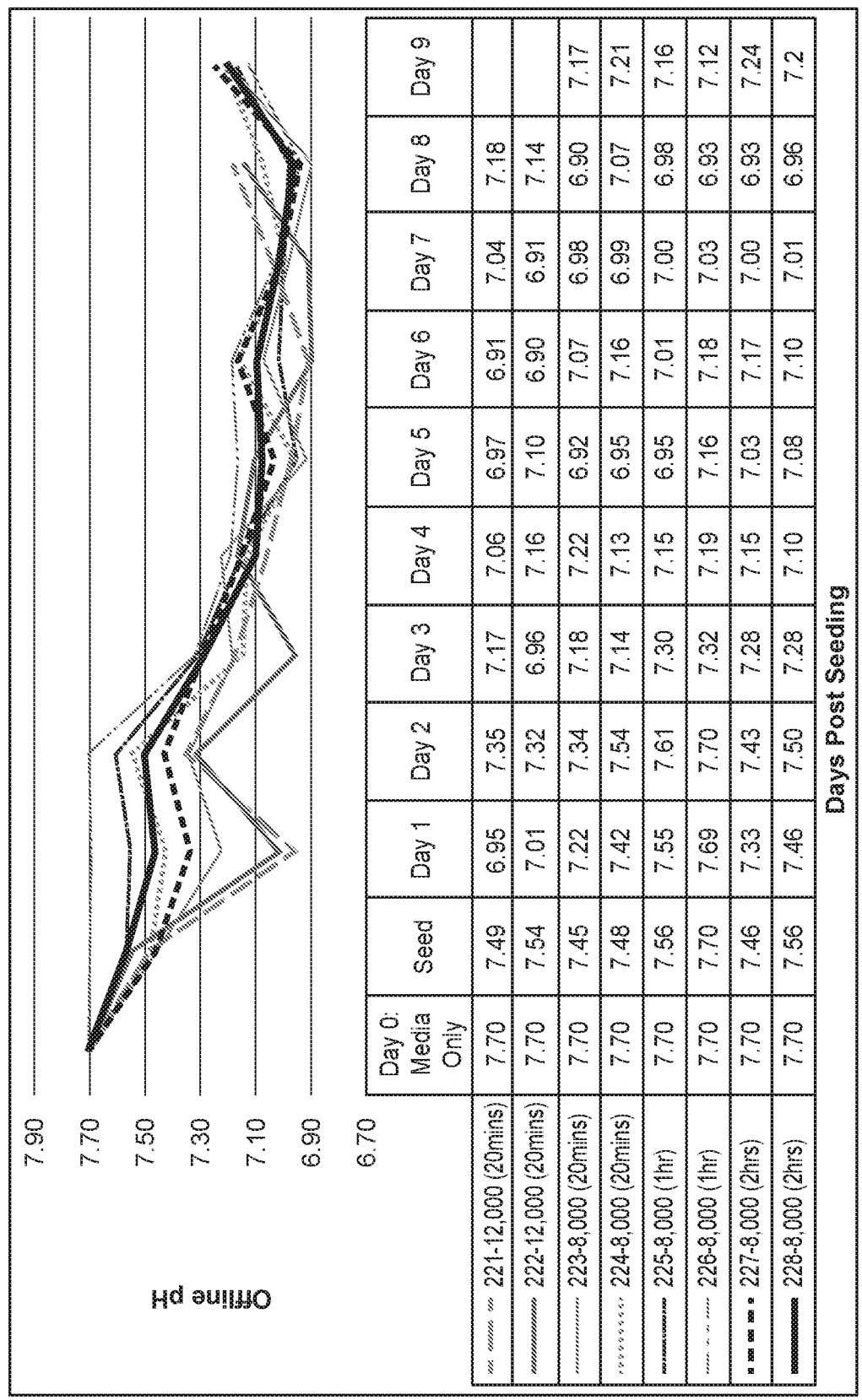

HEK 293 cells were thawed and resuspended in DMEM supplemented with 10% FBS. Cells were centrifuged at 209×g, 5 min, in room temperature, then supernatant was removed and fresh DMEM+10% FBS was added. Cells were counted for viable cell density and viability and were seeded in 2×T175 cm² flasks and incubated at 37.0° C., 5% $CO_2$ for three days until cultures reached ~90% confluency. For each cell passage, spent media was removed, flasks were washed with PBS (—$CaCl_2$), —MgCl2) at 0.08 mL/cm², and then flasks treated with TrypLE Select (0.0 µL mL/cm²) and incubated at 37.0° C., 5% $CO_2$ for 2-3 minutes. Trypsin was quenched with DMEM+10% FBS (0.0 µL mL/cm²). Cells were expanded and seeded per the diagram in FIG. 33.

Cell Inoculation and Monitoring

Bioreactors were inoculated in duplicate with HEK 293 cells at a target density of 8,000 cells/cm² and 12,000 cells/cm² in growth media (high glucose DMEM+10% Australian Origin FBS+1:100 Penicillin Streptomycin (Pen Strep) with agitation. Process parameters were set to pH 7.23, 37.0° C., 55% dissolved oxygen (DO) and linear speed of 2 cm/s. 24 hours' post seeding, recirculation with DMEM growth media (0.188 mL/cm²) was turned on to a recirculation speed (12.5 mL/min). Daily samples taken for offline pH, metabolites, and nutrients were read using a Nova BioFlex. On day four (12,000 cells/cm²), day five (8,000 cells/cm²) and day nine post seeding, three fibers were removed and lysed with 1:1:1 v/v PBS, A100 and B100 solution (ChemoMetec) and counted (NucleoCounter NC-200) for total nuclei to monitor culture growth.

Transfection

Day four (12,000 cells/cm²) and day five (8,000 cells/cm²) post cell inoculation, recirculation was stopped, and cells in each bioreactor were transfected with plasmid DNA and Polyethylenimine (PEI). DNA and PEI were mixed in a 1:1 mg/mg ratio. Plasmid DNAs were transfected in a 1:1.5:2 mass ratio with pSMN plasmid, pAAV2/9 plasmid and pHELP plasmid were added to DMEM−/− media; high glucose, —$CaCl_2$), -L-glutamine and 0.2 µM filtered and mixed by inversion. PEI was added to DMEM−/− media and mixed by inversion. PEI was then added to DNA, mixed by inversion and incubated at room temperature for 20 minutes for the 8,000 cells/cm² (control) and 12,000 cells/cm². DNA/PEI was incubated for 1 hr and 2 hr for the other two 8,000 cells/cm² conditions. This DNA/PEI complex mixture was used to transfect two bioreactors for each of the four conditions. DNA/PEI complex was added to each bioreactor and incubated at process parameters for two hours. Two hours post transfection recirculation loop was turned back on.

Post Transfection Media Exchange 24 hours post transfection, all media in bioreactors and recirculation loops were removed and replaced with OptiMEM+1:100 Pen Strep (0.132 mL/cm²) and recirculated for 24 hours at process parameters. 48 hours post transfection all media removed from recirculation only and replaced with OptiMEM+1:100 Pen Strep (12 mL/min) and recirculated at process parameters.

Harvest

Day eight (12,000 cells/cm²) and day nine (8,000 cells/cm²) post cell inoculation, Benzonase (100 U/mL) was added, chased with Lysis Buffer (50 mM HEPES, 1% Tween 20), and incubated for two hours at process parameters. Bioreactors were drained and Sucrose Salt Solution (500 mM NaCl, 1% w/v Sucrose) was added, and these were mixed by inversion. The bioreactors were washed with bioreactor rinse buffer (500 mM NaCl, 1% w/v Sucrose, 20 mM Tris Base, 1% v/v Tween 20, 1 mM $MgCl_2·6H_2O$) for about 15 minutes at process parameters. The bioreactors were drained and bioreactor rinse buffer was pooled with crude bulk harvest, mixed by inversion and sampled for ddPCR assay.

Depth Filtration and Tangential Flow Filtration

On day eight (12,000 cells/cm²) and day nine (control 8,000 cells/cm²), post cell inoculation bioreactors were harvested, sampled and crude lysate was pooled for each condition (n=2 bioreactors). Pooled lysate was then clarified through Millistak COHC Pod, 270 cm² filter and Millipak 40, 0.45 µm, Durapore, 200 cm² polish filter (EMD Millipore). Samples were taken post C0HC+0.45 and frozen at −80.0° C. Clarified lysate was then concentrated via tangential flow a Pellicon® 2 Ultrafiltration Module PLCMK C 0.1 m² filter (EMD Millipore). At least 6 diavolumes was used to diafiltrate the final product. Post TFF1 filtration samples were obtained and frozen at −80.0° C. All samples were submitted for AAV2/9 titer and host cell protein.

Plasmids were used to produce DS in bioreactors. Data represent each condition in duplicate, corresponding bioreactor number and condition shown in Table 59.

TABLE 59

Bioreactor numbers and corresponding conditions

| Bioreactor Number | Seeding Density cells/cm² | Transfection Day | PEI/DNA Incubation Time (mins) | Harvest Day |
|---|---|---|---|---|
| 221, 222 | 12,000 | 4 | 20 | 8 |
| 223, 224* | 8,000 | 5 | 20 | 9 |
| 225, 226 | 8,000 | 5 | 60 | 9 |
| 227, 228 | 8,000 | 5 | 120 | 9 |

Cell Growth: Cells were counted on the day of seeding (Day 0), and nuclei were counted at day 4 (12,000 cells/cm²), day 5 (8,000 cells/cm²) and day 9 post-seeding. Data indicates that cells in all reactors grew exponentially between day 0 and day 5. After transfection, day 9 nuclei count suggest that bioreactors 221 increased 2.0-fold in total nuclei from day 5 to day 9. All other reactors (222 through 228) did not exhibit significant growth between day 5 and day 9. The increase in growth in bioreactor 221 may be an artifact based on uneven distribution of cells on individual fibers used for total nuclei counts. It is possible that cells in all bioreactors grew similarly based on metabolite data shown in FIGS. 34A-34E.

pH, Nutrients and Metabolites: Glucose consumption trended the same in all bioreactor cultures, suggesting that despite the increase in bioreactor 221 growth curve, cells consumed glucose at similar rates. pH for bioreactors seeded at 12,000 cells/cm² averaged 7.06 and 8,000 cells/cm² averaged 7.18 for first three days. pH declined slightly with increased nutrient metabolism, and increased by day 9 concurrent with rise in ammonium ion levels. Lactate increased until day 5 (bioreactors 221, 223, 224, 225, 227) and day 6 (bioreactors 222, 226, 228) then leveled off toward the end of production, suggesting utilization of lactate as an energy source at this stage.

Production Titers

Figure 35:
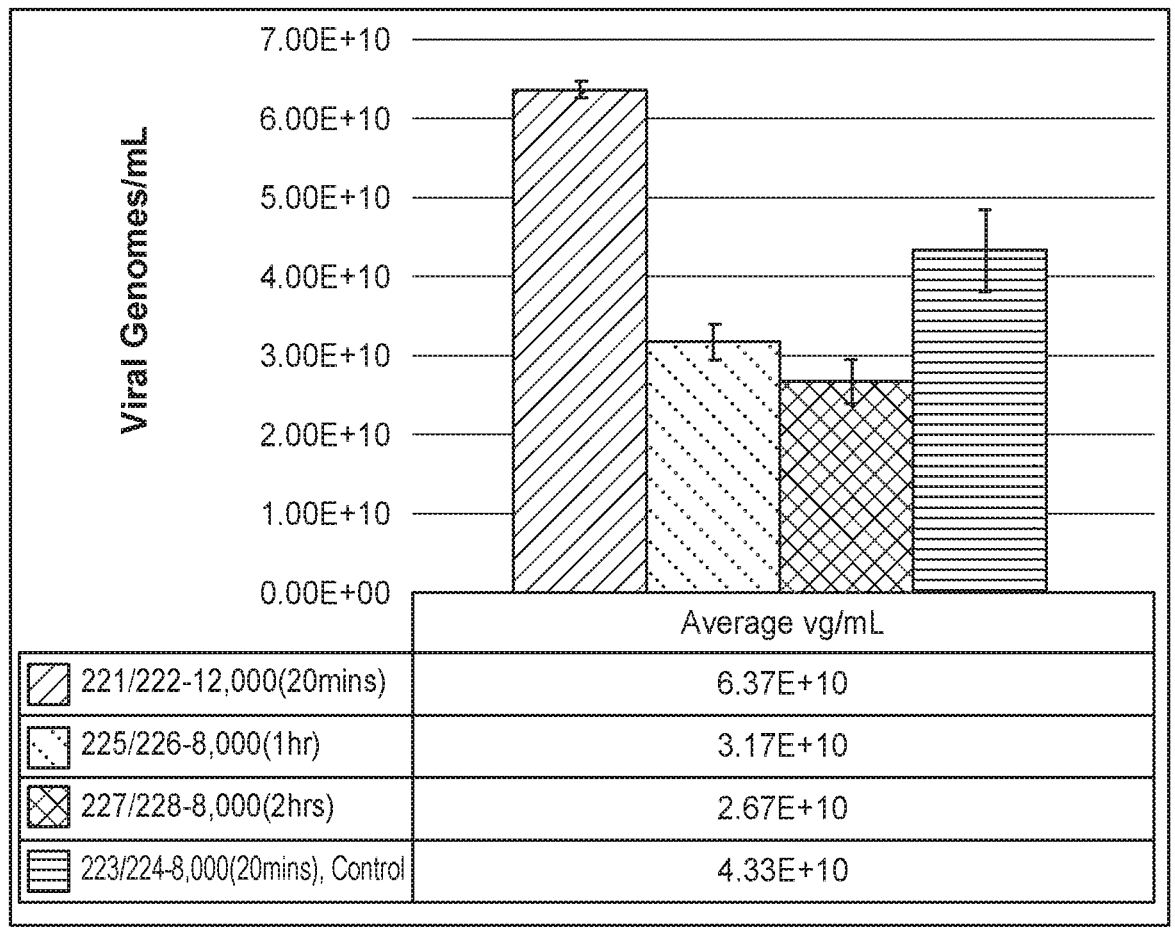
FIG. 35 shows viral genome production as a function of cell seeding density (8000 or 12000 cells/cm$^2$) and four different lengths of transfection time (20 min, 1 hour or 2 hours).

Viral genomes from harvest material were measured by digital droplet (ddPCR). Titers were about 1.5-fold higher in bioreactors seeded at 12,000 cells/cm² with an average titer measure of 6.37E+10 vg/mL (n=2) vs control bioreactors seeded at 8,000 cells/cm² with an average titer measure of 4.33E+10 vg/mL (n=2). Titer data suggests that seeding at a higher density, transfecting and harvesting one day early supports higher DS production yields. Titer yield for DNA/PEI incubated for one-hour exhibited a 1.4-fold decrease in average titer measured (3.17E10 vg/mL n=2) and for two-hour incubation average titer measured was 1.6-fold decrease (2.67E10 vg/mL n=2) compared to the control in which DNA/PEI incubated for 20 mins (4.33E10 vg/mL n=2). Data suggests that longer incubation time leads to decrease titer. This may be due to DNA and PEI forming large complexes that are unable to efficiently transfect HEK293 cells. Virus production per mL and surface area values are given in FIG. 35, as compared to production in a known process as a positive control.

Figure 36:
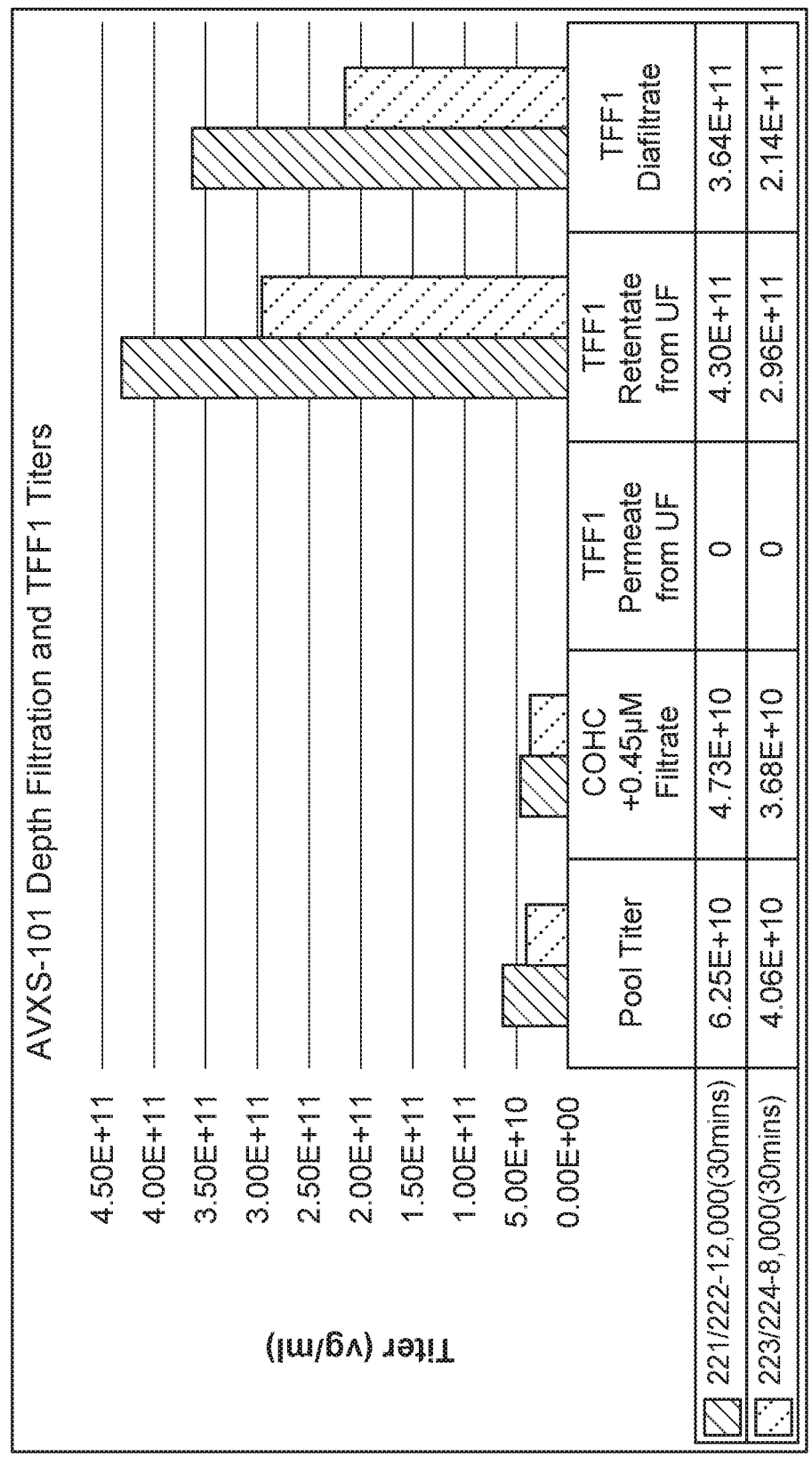
FIG. 36 shows viral titers from intermediates sampled at different filtration steps throughout the manufacturing process.

The viral titer measured at each step of the clarification and concentration steps are shown in FIG. 36. The residual host cell protein at each step during the TFF1 step is shown in FIGS. 37A-37B.

Example 17: Effect of Seeding Density on Production of Drug Substance

The effect of seeding density on production of DS was evaluated. Four seeding densities were evaluated and each seeding density were in duplicate in a bioreactor.

Cell Scale Up

Figure 38:
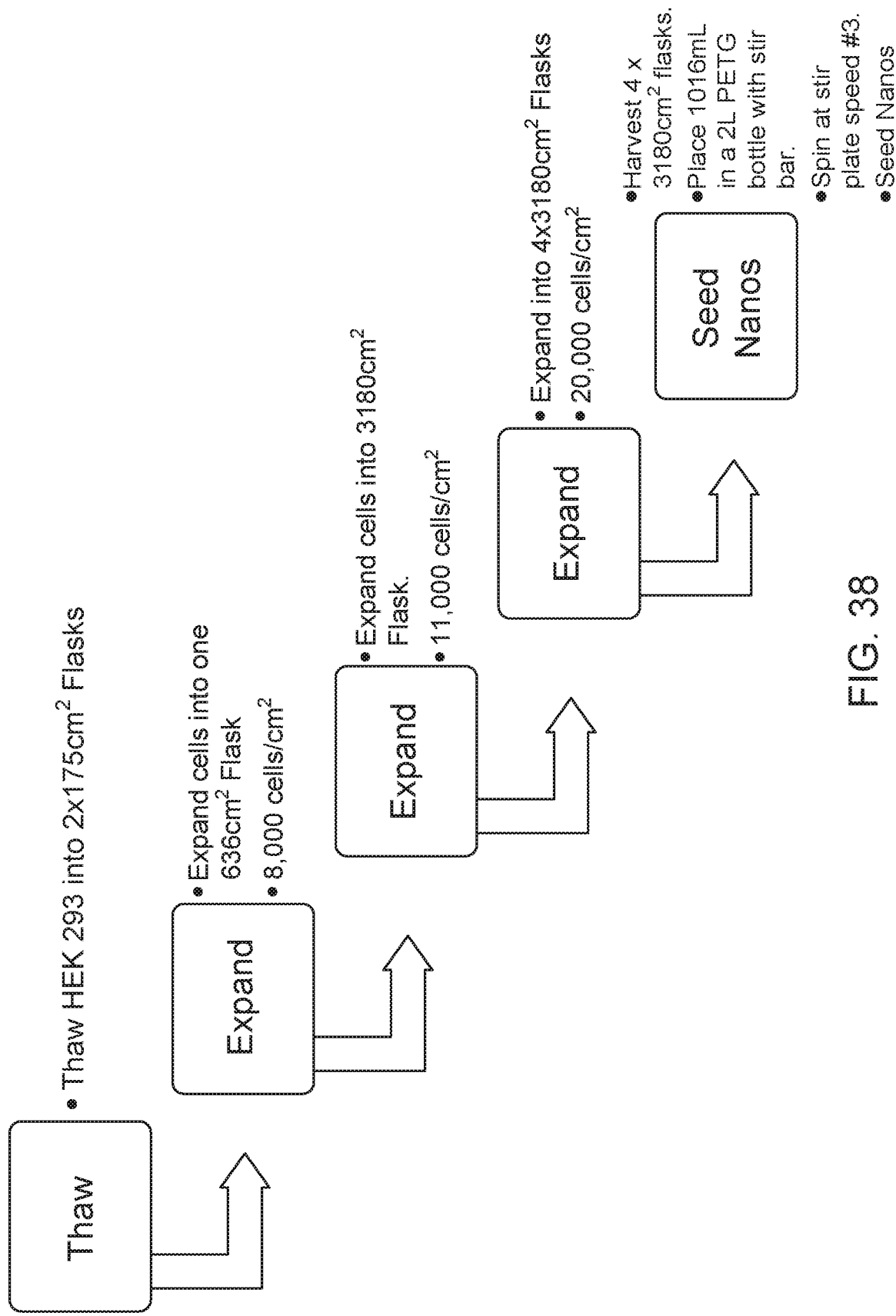
FIG. 38 describes the HEK 293 cell expansion process flow during cell seeding density experiments.

HEK 293 cells were thawed and resuspended in DMEM supplemented with 10% FBS. Cells were centrifuged at 209×g, 5 min, in room temperature, then supernatant was removed and fresh DMEM+10% FBS was added. Cells were counted for viable cell density and viability and were seeded in 2×T175 cm² flasks and incubated at 37.0° C., 5% $CO_2$ for four days until cultures reached ~90% confluency. For each cell passage, spent media was removed, flasks were washed with PBS (—$CaCl_2$), —$MgCl_2$) at 0.08 mL/cm², and then flasks treated with TrypLE Select (0.0 µL mL/cm²) and incubated at 37.0° C., 5% $CO_2$ for 2-3 mins. Trypsin was quenched with DMEM+10% FBS (0.0 µL mL/cm²). Cells were expanded and seeded per the diagram in FIG. 38.

Cell Inoculation and Monitoring

Bioreactors were inoculated with HEK 293 cells at four target densities, each in duplicate: 8,000 cells/cm², 9,350 cells/cm², 10,700 cells/cm² and 12,050 cells/cm² in 700 ml growth media (high glucose DMEM+10% Australian Origin FBS+1:100 Pen Strep) with agitation. Process parameters were set to pH 7.23, 37.0° C., 55% dissolved oxygen (DO) and linear speed of 2 cm/s. 24 hours post seeding, recirculation with DMEM growth media (total volume now 0.188 mL/cm2) was turned on to a recirculation speed (12.5 mL/min). Daily samples were taken for offline pH, metabolites, and nutrients were read using a Nova BioProfile 400. On day five and day nine post seeding, three fibers were removed and lysed with 1:1:1 v/v PBS, A100 and B100 solution (ChemoMetec) and counted (NucleoCounter NC-200) for total nuclei to monitor culture growth.

Transfection

Day five post cell inoculation, recirculation was stopped, and the media inside each bioreactor chamber (not recirculation bottle) was replaced with 600 ml DMEM−/− medium (high glucose, —$CaCl_2$), -Lglutamine). Each reactor was transfected with plasmid DNA and Polyethylenimine (PEIpro) in a 1:1 mass ratio. Plasmid DNAs were mixed in a 1:1.5:2 mass ratio (pSMN—3.56 mg, pAAV2/9-5.34 mg, and pHELP—7.1 mg), added to 300 mL DMEM−/− media, 0.2 µM filtered and mixed by inversion. PEI (16 mL) was added to 300 mL DMEM−/− media and mixed by inversion. The PEI and DNA mixtures were combined, mixed by inversion and incubated at room temperature for 20 minutes. Each 600 ml PEI/DNA complex mixture was used to transfect two Bioreactors, repeated for each corresponding seeding density. PEI/DNA complex was added to each bioreactor and incubated at process parameters for two hours. The recirculation loop was turned back on two hours post transfection (12.5 mL/min).

Post Transfection Media Exchange 24 hours post transfection, all media in bioreactors and recirculation loops was removed and replaced with OptiMEM (0.132 mL/cm²) and recirculated (12.5 mL/min) for 24 hours at process parameters. 48 hours post transfection media in the recirculation bottle was exchanged with fresh OptiMEM and recirculated at process parameters (12 mL/min). Harvest Day nine post cell inoculation, Benzonase (100 U/mL) was added, chased with Lysis Buffer (50 mM HEPES, 1% Tween 20), and incubated for two hours at process parameters. Bioreactors were drained and Sucrose Salt Solution (500 mM NaCl, 1% w/v Sucrose) added, mixed by inversion. Bioreactor washed with bioreactor rinse buffer (500 mM NaCl, 1% w/v Sucrose, 20 mM Tris Base, 1% v/v Tween 20, 1 mM $MgCl_2·6H2O$) for 15 mins at process parameters. Bioreactors drained and bioreactor rinse buffer pooled with crude bulk harvest, mixed by inversion and sampled for ddPCR assay.

Plasmids were used to produce Drug Substance in Bioreactors. Reactors were seeded at varying densities, and transfected and harvested on the same schedule (day 5, day 9 post seeding, respectively). Data represent duplicates of each seeding density, as shown in Table 60 below:

TABLE 60

| Starting Seeding Density | Bioreactor Number |
|---|---|
| 8,000 cells/cm² | 221, 222 |
| 9,350 cells/cm² | 223, 224 |
| 10,700 cells/cm² | 225, 226 |
| 12,050 cells/cm² | 227, 228 |

Figure 39A:
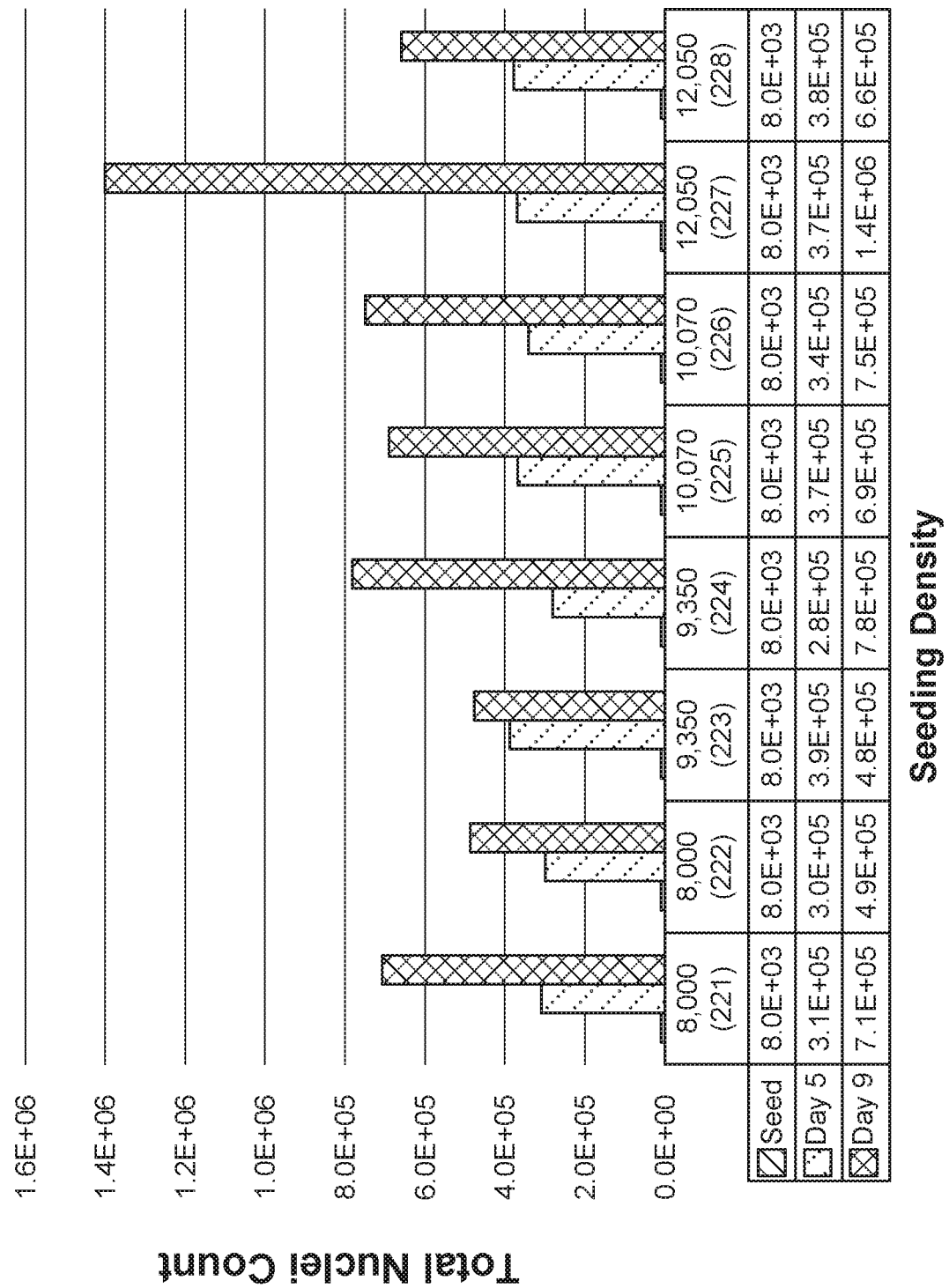
FIGS. 39A-39E show that HEK 293 cells were seeded in duplicate at 8,000 cells/cm$^2$, 9,350 cells/cm$^2$, 10,700 cells/cm$^2$, 12,050 cells/cm$^2$ in bioreactors (pH 7.23, 37.0° C., 55% DO). Cells were transfected with DNA plasmids/PEI (1:1 m/m) five days post-seeding. pH and metabolite analysis were performed using NOVA BioProfile 400.
Figure 39B:
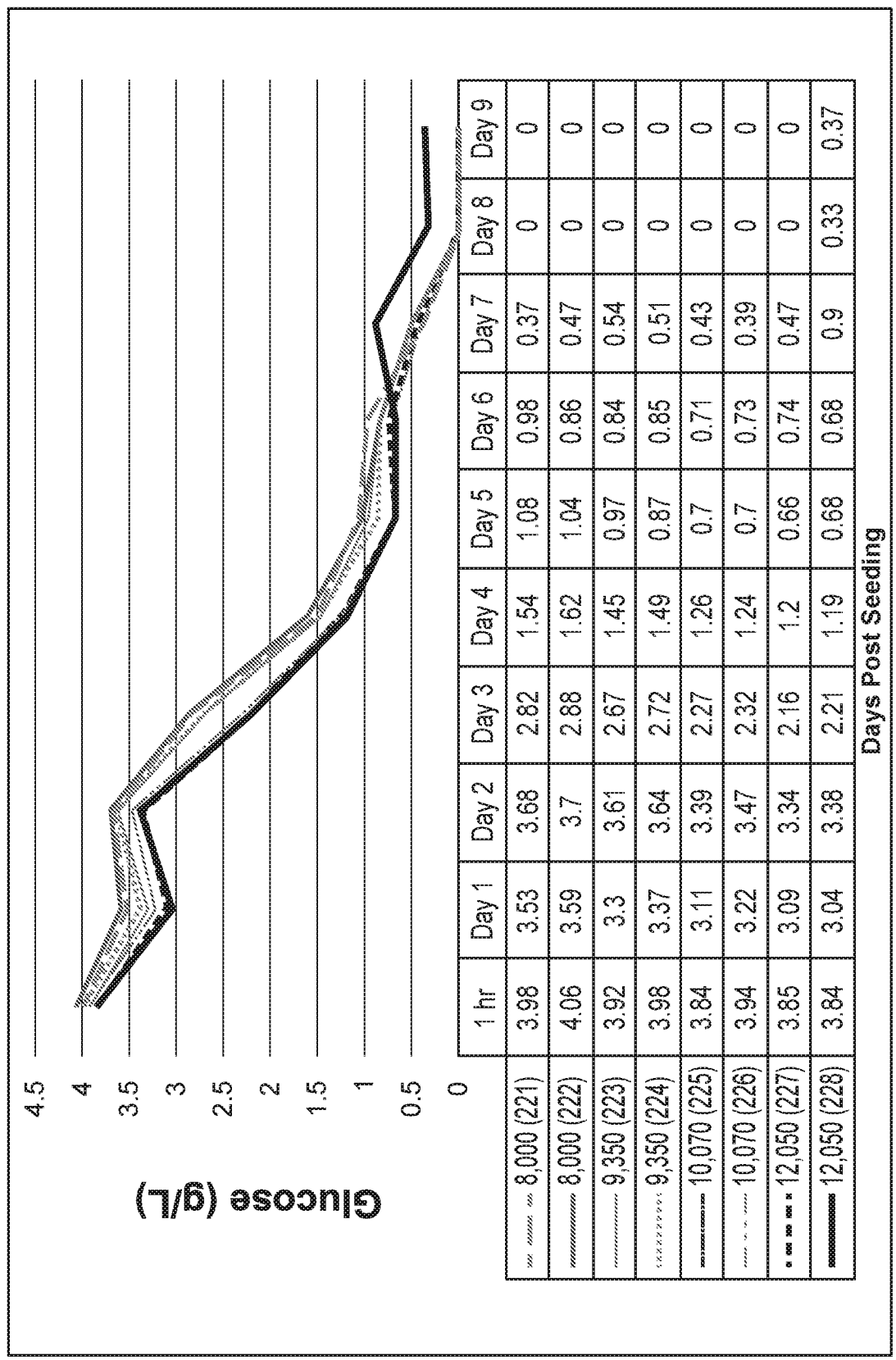
Figure 39C:
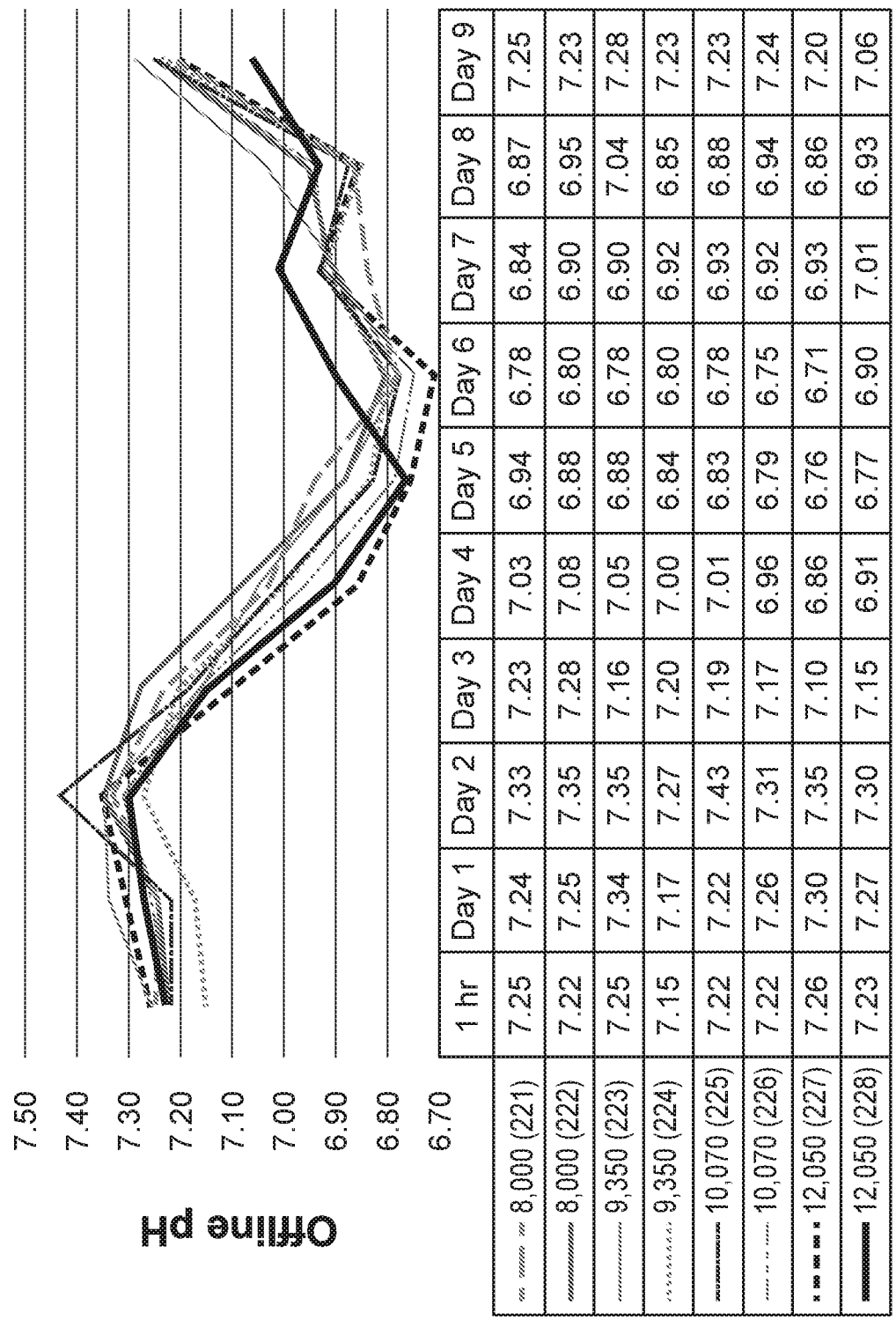
Figure 39D:
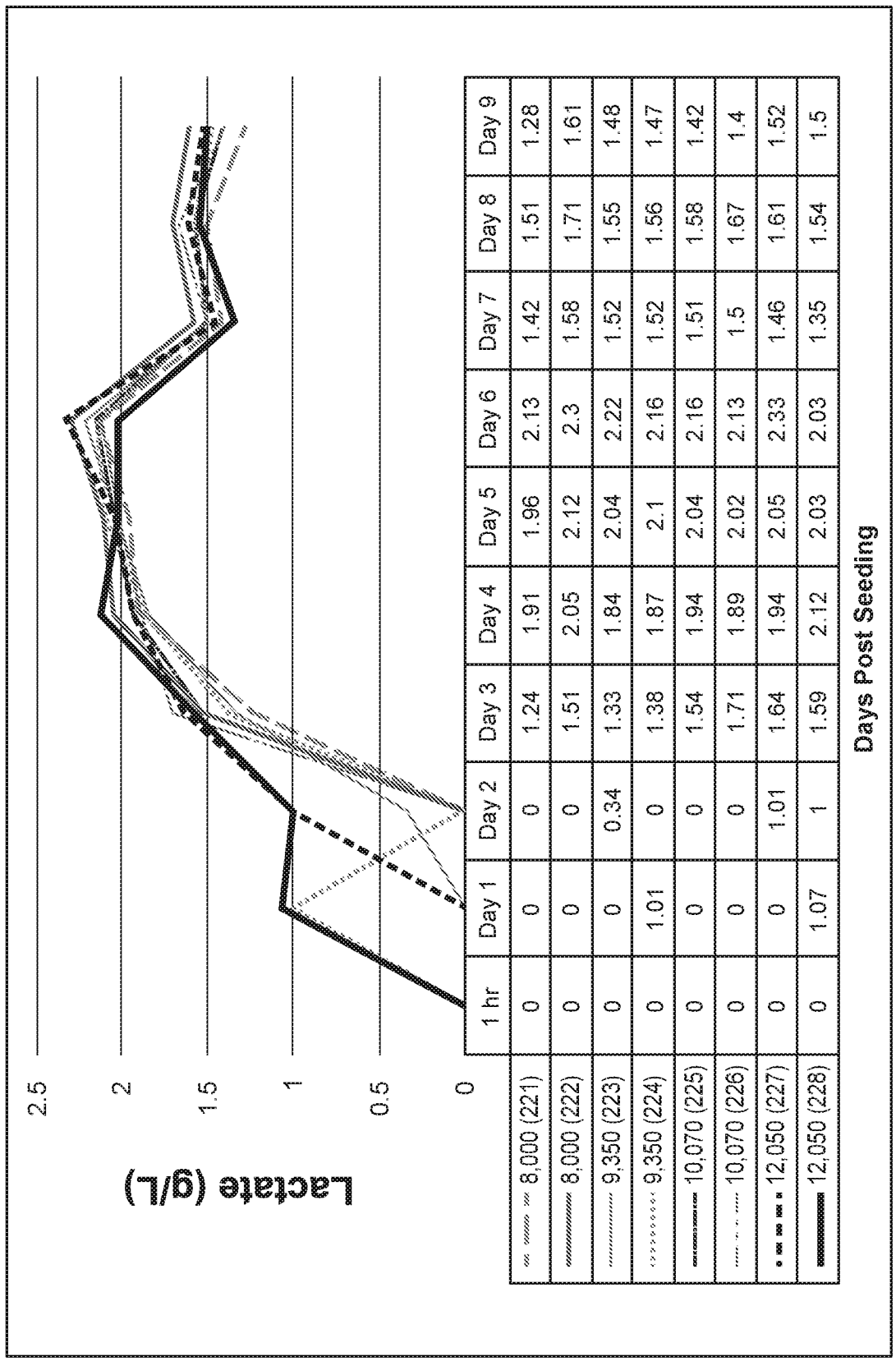
Figure 39E:
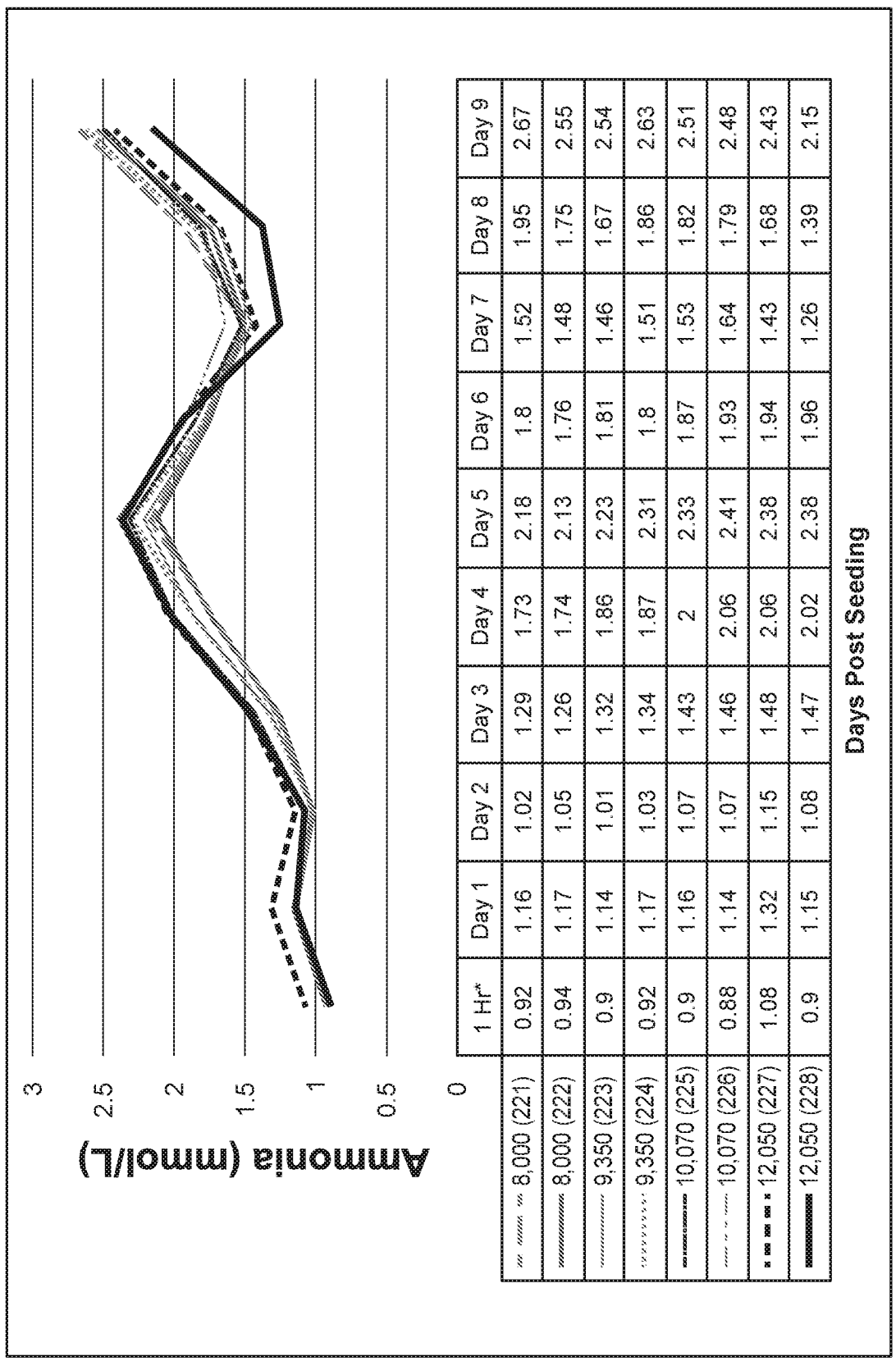

Cell Growth: Cells were counted on the day of seeding (Day 0), and nuclei were counted at day 5 and 9 post-seeding. Data indicate that cells in all reactors grew exponentially between day 0 and day 5. Despite differences in starting seeding densities, nuclei counts do not indicate major differences in cell numbers between groups at day 5. After transfection, day 9 nuclei count suggest that five of the reactors (221, 224, 225, 226, 228) doubled in total nuclei from day 5 to day 9. Two reactors (222, 223) increased 1.4-fold in total nuclei, as shown in FIG. 39A. Reactor 227 increased 3.8-fold in total nuclei from day 5 to day 9. This difference may be an artifact based on uneven distribution of cells between individual fibers used for counts. It is possible that cells in all reactors grew similarly based on metabolite data shown in FIG. 39B-E.

pH, Nutrients and Metabolites: Glucose consumption (FIG. 39B) trended the same in all bioreactor cultures, suggesting that despite the differences in starting seeding densities, cultures consumed glucose at similar rates. Offline pH (FIG. 39C) remained consistent (pH 7.25) for first three days in all cultures, declined with increased nutrient metabolism, and increased post day 8 concurrent with rise in ammonium ion levels (FIG. 39E). Lactate (FIG. 39D) increased until day 6 and then leveled off toward the end of production, suggesting utilization of lactate as an energy source at this stage. No significant difference in metabolite profiles were observed between reactors seeded at different starting densities. This could be because the difference in starting seeding densities is minimal, <1.2-fold difference.

Figure 40A:
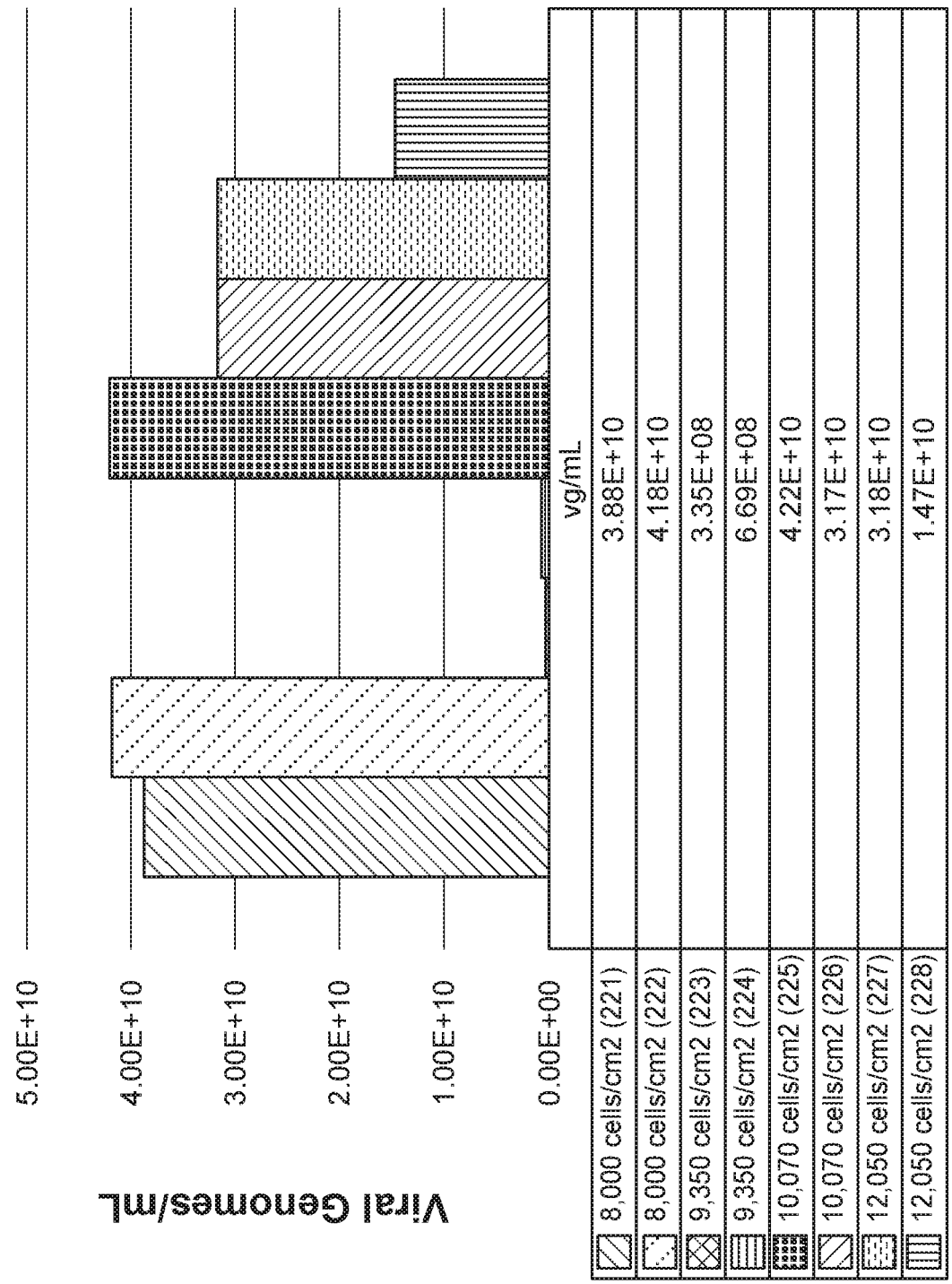
FIGS. 40A-40B show drug substance production from four starting seeding densities in bioreactors. Comparison of virus titer and vector genome harvested per unit surface area are shown.

Production Titers: Viral genomes from harvest material were measured by digital droplet (ddPCR). Titers were comparable between starting seeding densities of 8,000 cells/cm$^2$ and 10,070 cells/cm$^2$, averaging 3.99E+10±2.1E+09 vg/mL (n=2) and 3.70E+10±7.4E+09 vg/mL (n=2), respectively. For an unidentifiable reason, reactors seeded at 9,350 cells/cm2 exhibited an average titer measure of 5.02E+08 vg/mL (n=2), approximately 2 logs lower than average titers of reactors seeded at flanking densities. This difference is likely a result of an unidentified operational error during transfection or harvest rather than lack of productivity at this seeding density. Replicate reactors seeded at 12,050 cells/cm$^2$ demonstrated a twofold difference between each other, with one reactor in range observed for lower seeding densities, 3.2E+10 vg/ml, while the second produced a titer of only 1.4E+10 vg/ml. Virus production per mL and surface area values are given in FIG. 40A.

Figure 40B:
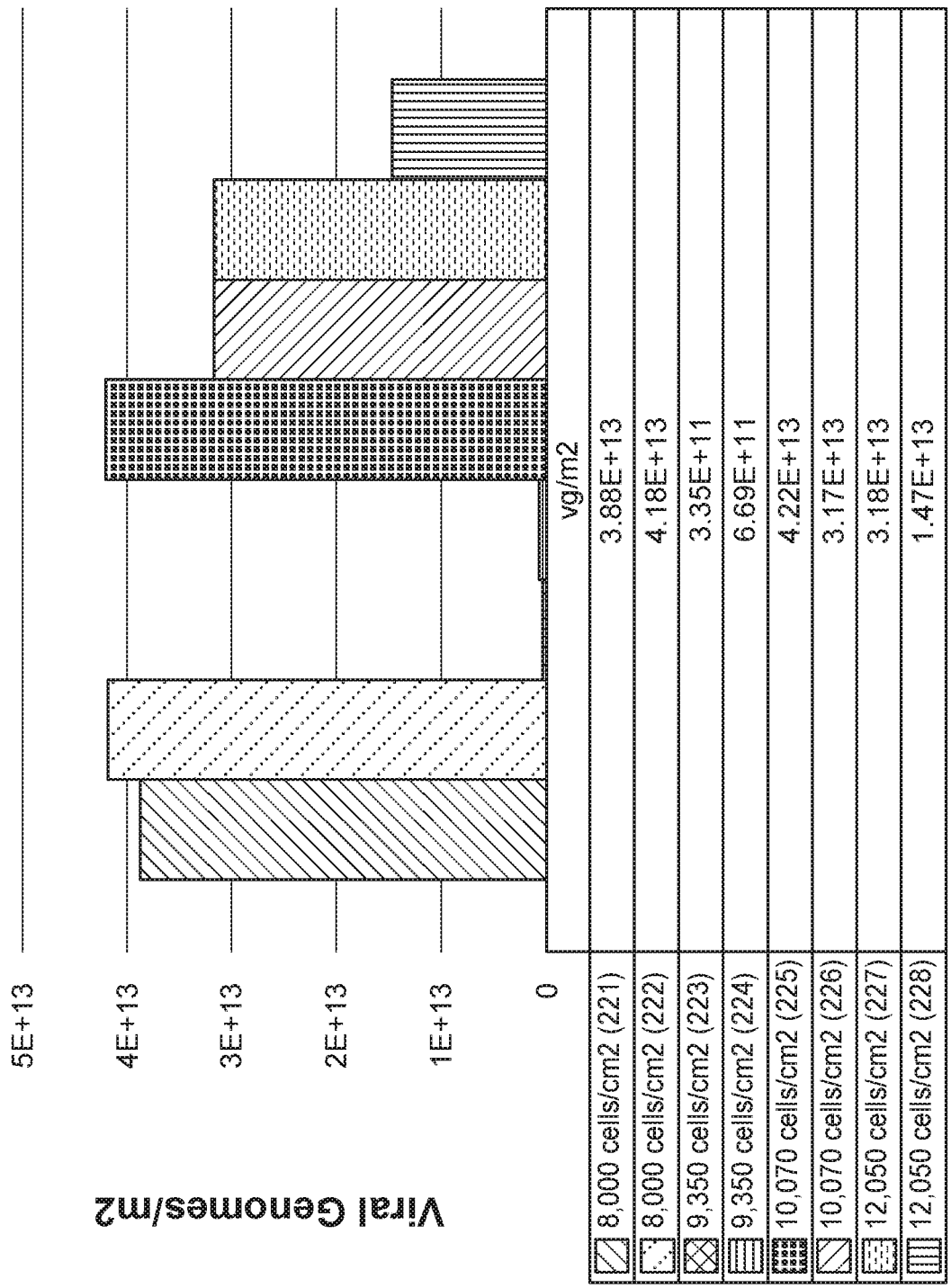

Seeding density and production of DS were evaluated, as shown in FIG. 40B. HEK 293 cells seeded in the range of 8E+03 to 10E+03 cells/cm$^2$ showed consistent growth profiles, pH, glucose consumption, lactate and ammonia generation. Additionally, comparable titers were produced suggesting slightly higher seeding density does not negatively impact production. In contrast, reactors seeded at the higher density of 12×10$^3$ cells/cm$^2$ exhibited more variability between duplicates, including lower average titer compared to other conditions, suggesting the approached used in this experiment may not be optimal for production. These results support seeding cells at a density ranging between 8×10$^3$ and 1×10$^4$ cells/cm$^2$ for bioreactor experiments.

Example 18: Comparability Assessment

Figure 41:
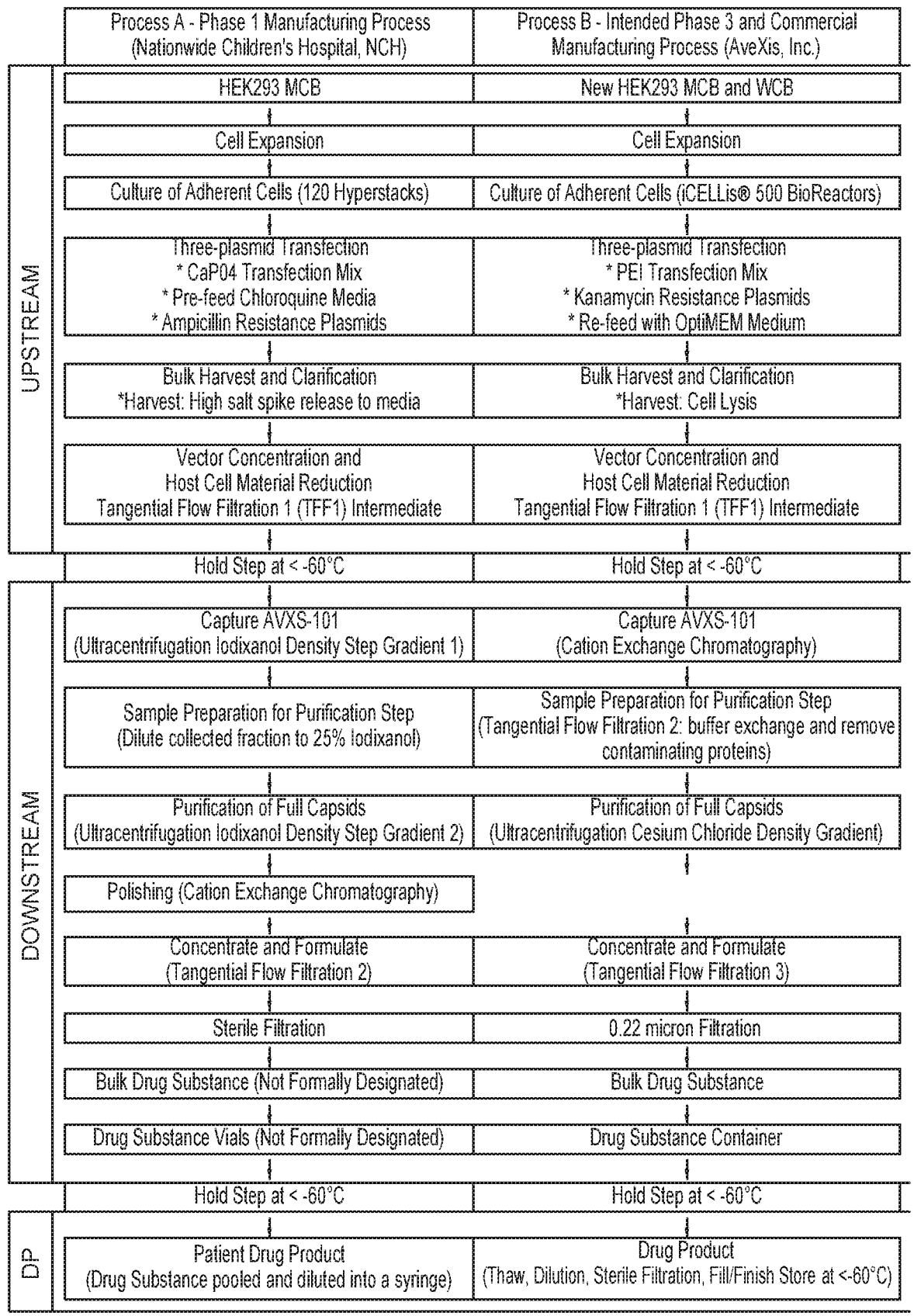
FIG. 41 shows Phase 1 (Process A) and Phase 3 Trial (Process B) Manufacturing Processes.

The comparability between AVXS-101 drug product used in Phase 1 clinical studies (Process A) and drug product used in pivotal clinical studies (Process B) was assessed as the primary objective with a secondary objective to assess manufacturing consistency using Process B by comparing drug product Lots 600156 and 600307. FIG. 41 represents the Phase 1 (Process A) and Phase 3 trial (Process B) manufacturing processes flows and the differences between them.

The comparability assessment was performed using Phase 1 clinical drug product Lot NCHAAV9SMN0613 manufactured at Nationwide Children's Hospital (NCH) and drug product Lot 600156 manufactured at AveXis.

Product

The following lots of material were evaluated, as summarized in Table 61. The assessment included a direct comparison of resulting quality attributes from the Phase 1 clinical drug product Lot NCHAAV9SMN0613 using Process A and AVXS-101 drug product Lot 600156 using Process B. In addition, the release testing results of Lot 600156 with Lot 600307 were evaluated holistically for scale-up process reproducibility and consistency.

TABLE 61

AVXS-101 Drug Product to be Evaluated for Comparability Between Process A (Phase 1) and Process B (Phase 3) and Manufacturing Consistency for Process B

| Use | Lot Number | MFG Date | MFG Date | Storage Condition |
|---|---|---|---|---|
| Phase 1 Study | NCHAAV9SMN0613 | 10 DEC. 2013 | Process A | ≤−60° C. |
| Phase 3 Study | AVXS-101 Lot 600156 | 7 NOV. 2017 | Process B | ≤−60° C. |
| | AVXS-101 Lot 600307 | 4 DEC. 2017 | Process B | ≤−60° C. |

Manufacturing Process Overview

FIGS. 42A-42B provides a summary of the comparability results.

Comparability and Manufacturing Consistency Assessment

Process A and Process B materials for assessed to be comparable and the Process B materials were assessed to be consistent. Process B materials were also determined to have additional benefits, e.g., for industrial scale production.

Test Methods pH pH analysis was performed on Lot NCHAAV9SMN0613 (Process A), Lot 600156 (Process B) and Lot 600307 (Process B). The results from both processes ranged from 7.9-8.0. This demonstrated that the pH of the Process A and Process B materials were comparable and that the Process B materials are consistent.

Appearance

Appearance by visual inspection was performed on Lot NCHAAV9SMN0613 (Process A), Lot 600156 (Process B) and Lot 600307 (Process B). The apparent differences in appearance results between Process A and Process B were due to different vector concentrations (genomic titer). Lot NCH AAV9SMN0613 had a lower vector concentration than the Process B lots. As a result, Lot NCH AAV9SMN0613 was more dilute leading to a more clear and colorless solution while the colorless to white and slightly opaque observations for Process B lots results from approximately 4 times concentration of viral particles in solution per mL.

Considering the concentration difference, the appearance of the Process A and Process B materials were assessed to be comparable and the Process B materials were assessed to be consistent.

Osmolality

Osmolality by freezing point depression was performed on Lot NCHAAV9SMN0613 (Process A), Lot 600156 (Process B) and Lot 600307 (Process B). The results from both processes ranged from 410-415 mOSm/kg. This demonstrated that the osmolality of the Process A and Process B materials were comparable and that the Process B materials were consistent.

Sub-Visible Particles

Sub-visible particles by light obscuration was performed on Lot NCHAAV9SMN0613 (Process A), Lot 600156 (Process B) and Lot 600307 (Process B). The results from both processes were well below the recommended limits in the USP monograph for injectable drug products. This demonstrated that the sub-visible particle counts for the Process A and Process B materials were comparable and that the Process B materials were consistent.

Genomic Titer

Genomic titer by ddPCR was performed on Lot NCHAAV9SMN0613 (Process A), Lot 600156 (Process B) and Lot 600307 (Process B). Genomic titer for AVXS-101 lots was expected to fluctuate based on target concentrations in manufacturing. Genomic titer produced by Process B ($3.7 \times 10^{13}$ vg/mL and $4.0 \times 10^{13}$ vg/ml) was at least 3 fold higher than that from Process A ($1.1 \times 10^{13}$ vg/mL), hence Process B was a better method for large-scale manufacture of AVXS-101 (AAV9-SMN1).

Infectious Titer

Infectious titer by TCID50 was performed on Lot NCHAAV9SMN0613 (Process A), Lot 600156 (Process B) and Lot 600307 (Process B). Process B ($1.3 \times 10^{10}$ IU/mL and $6.7 \times 10^{9}$ IU/ml) produced on average 66% higher infectious titer than Process A ($5.9 \times 10^{10}$ IU/mL), which may be advantageous, e.g., for large-scale manufacture of rAAV, e.g., AVXS-101.

Total Protein

Total Protein by micro BCA was performed on Lot NCHAAV9SMN0613 (Process A), Lot 600156 (Process B) and Lot 600307 (Process B). Normalized to $1.0 \times 10^{13}$ vg/mL, the results from both processes ranged from 167-179 µg/mL. The normalized total protein values demonstrated that the Process A and Process B materials were comparable and that the Process B materials were consistent.

Identity by Western Blot

Identity by Western Blot was performed on Lot NCHAAV9SMN0613 (Process A), Lot 600156 (Process B) and Lot 600307 (Process B). The blot profile and apparent molecular weight values for the main bands (VP1, VP2, and VP3) were assessed to be comparable for the Process A and Process B materials and it was also assessed that the Process B materials were consistent.

% Empty Capsid by AUC

% Empty Capsid by AUC was performed on Lot NCHAAV9SMN0613 (Process A), Lot 600156 (Process B) and Lot 600307 (Process B). The result for Lot NCHAAV9SMN0613 (Process A) was 7%. The results for Lots 600156 and 600307 (Process B) were 2% and 4% respectively. Process B (2% and 4%) produced about two-fold less empty capsids as measured by AUC than Process A (7%). Hence, Process B was able to produce an improved composition comprising a lower concentration of empty capsids.

Identity and Purity by SDS-PAGE

Identity and Purity by SDS-PAGE was performed on Lot NCHAAV9SMN0613 (Process A), Lot 600156 (Process B) and Lot 600307 (Process B). The % Total Purity from both processes were ≥98% and the banding patterns as well as the apparent molecular weight for each of the three capsid proteins were highly consistent. These results demonstrated that the Process A and Process B materials were comparable and that the Process B materials were consistent.

Residual Host Cell Protein

Residual Host Cell Protein by ELISA was performed on Lot NCHAAV9SMN0613 (Process A), Lot 600156 (Process B) and Lot 600307 (Process B). The results for all lots tested were <LOQ (8 ng/mL) for the assay. These results demonstrated that the Process A and Process B materials were comparable and that the Process B materials were consistent.

Residual Bovine Serum Albumin (BSA)

Residual BSA was performed on Lot NCHAAV9SMN0613 (Process A), Lot 600156 (Process B) and Lot 600307 (Process B). The results for all lots tested were <LOQ (0.50 ng/mL) for the assay. These results demonstrate that the Process A and Process B materials are comparable and that the Process B materials are consistent.

Residual Benzonase

Residual Benzonase by ELISA was performed on Lot NCHAAV9SMN0613 (Process A), Lot 600156 (Process B) and Lot 600307 (Process B). The results for all lots tested were <LOQ (0.20 ng/mL) for the assay. These results demonstrate that the Process A and Process B materials are comparable and that the Process B materials are consistent.

Residual Host Cell DNA

Residual Host Cell DNA by qPCR was performed on Lot NCHAAV9SMN0613 (Process A), Lot 600156 (Process B) and Lot 600307 (Process B). Normalized to $1.0 \times 10^{13}$ vg/mL, the result for Process A was $3.7 \times 10^{5}$ µg/mL while the results for Process B were $0.76 \times 10^{5}$ µg/mL and $0.68 \times 10^{5}$ µg/mL, respectively. Hence, Process B produced viral vectors with significantly lower residual hcDNA, which may be advantageous, e.g., for large-scale manufacture of rAAV, e.g., AVXS-101 (AAV9-SMN1).

Statistical Analysis

Statistical analysis was performed on the quantitative quality attributes. Comparisons were performed pair-wise between the Process A Lot (NCHAAV9SMN0613) and each Process B Lot (600156 and 600307) as listed below. These results are shown in FIGS. 43 and 44.

These studies show that Process B is a superior method of producing viral vectors. Process B consistently produced a larger quantity of viral vectors (as measured by genomic titer and infectious titer) with few impurities (lower residual hcDNA) with fewer empty capsids.

Next Generation Sequencing

Next Generation Sequencing (NGS) was also performed to establish the identity of (determine and/or confirm the genomic sequence) and assess if sequence variants (subpopulations) existed for the AVXS-101 drug product Phase 3 material from Process B. Alignment of the sequence dataset against the Sponsor provided reference sequence (pscSMN) revealed complete (100%) breadth and sufficient depth of coverage across the full length of the genome to enable variant detection. A total of four minor variant positions were noted, however these appear to represent sequencing errors within difficult to sequence regions (e.g., the inverted terminal repeats (ITRs) of AAVs which are notoriously difficult to sequence owing to their high GC content and palindromic sequences), rather than true variants. Refer to Table 62 for the sequencing results.

TABLE 62

DNA Sequencing Results of AVXS-101 Phase 3 Lot 600156 from Process B

| Total # of Reads Used for Mapping | Reference Sequence | Reference Length (Bases) | Total # of Mapped Reads | % of Population Mapped | Average Depth of Coverage | Consensus Length Generated by Mapping | % Reference Coverage | % Similarity to Reference | Total # of Unmapped or Low Quality Positions |
|---|---|---|---|---|---|---|---|---|---|
| 44,705,268 | AVXS-101 | 5,991 | 48,854,239 | 98.1 | 1,606,995.7 | 5,991 | 100 | 100 | 0 |

Phase 1 Lot NCHAAV9SMN0613 Stability Profile

Lot NCHAAV9SMN0613 was stored for 12 months at <−60° C. At each time point, the lot was analyzed. No unfavorable trends are noted. FIG. 45 shows the stability results to date.

A comparability study was completed for AVXS-101 used in Phase 1 clinical studies. The assessment was performed using Phase 1 clinical drug product Lot NCHAAV9SMN0613 manufactured at Nationwide Children's and AVXS-101 drug product Lot 600156 manufactured at AveXis. In addition, manufacturing consistency was evaluated using Process B Lots 600156 and 600307. For both the comparability assessment (Process A vs Process B) and manufacturing consistency (Process B Lots 600156 vs 600307), the study evaluated the identity, quality, purity, of AVXS-101 clinical trial material using the newly improved process and analytical methods to enable a robust assessment of comparability and manufacturing consistency.

Statistical analysis was performed on the quantitative quality attributes. Comparisons were performed pair-wise between the Process A Lot NCHAAV9SMN0613 and Process B Lot 600156. Process B was a better method that produced higher amounts of viral vectors at a higher purity than Process A. For example, as compared to Process A, viral vectors produced by Process B had a higher infectious titer, 8% higher genomic tier, 92% fewer subvisible particles more than 10 μm size, 50% fewer subvisible particles more than 25 μm size, 100% fewer empty capsids and 11% less residual hcDNA. All results were consistent relative to the Test Limit for each quality attribute.

Furthermore, to establish manufacturing consistency using Process B, pair-wise comparison was performed using Lots 600156 and 600307. The result from this initial pair-wise comparison between Process B Lot 600156 and 600307 exhibit consistency in manufacturing. All results were also consistent relative to the Test Limit for each quality attribute.

Based on the results evaluation, the resulting quality attributes from the Phase 1 clinical drug product Lot NCHAAV9SMN0613 using Process A and AVXS-101 drug product Lot 600156 using Process B demonstrated that Process B yields higher amounts of viral vector and improved purity, which may be advantageous, e.g., for large-scale manufacture of rAAV. Additionally, the two lots of material generated from Process B (Lots 600156 and 600307) were found to be reproducible further exhibiting manufacturing consistency.

Example 19: Analytical Ultracentrifugation (AUC) Analysis

Figure 46:
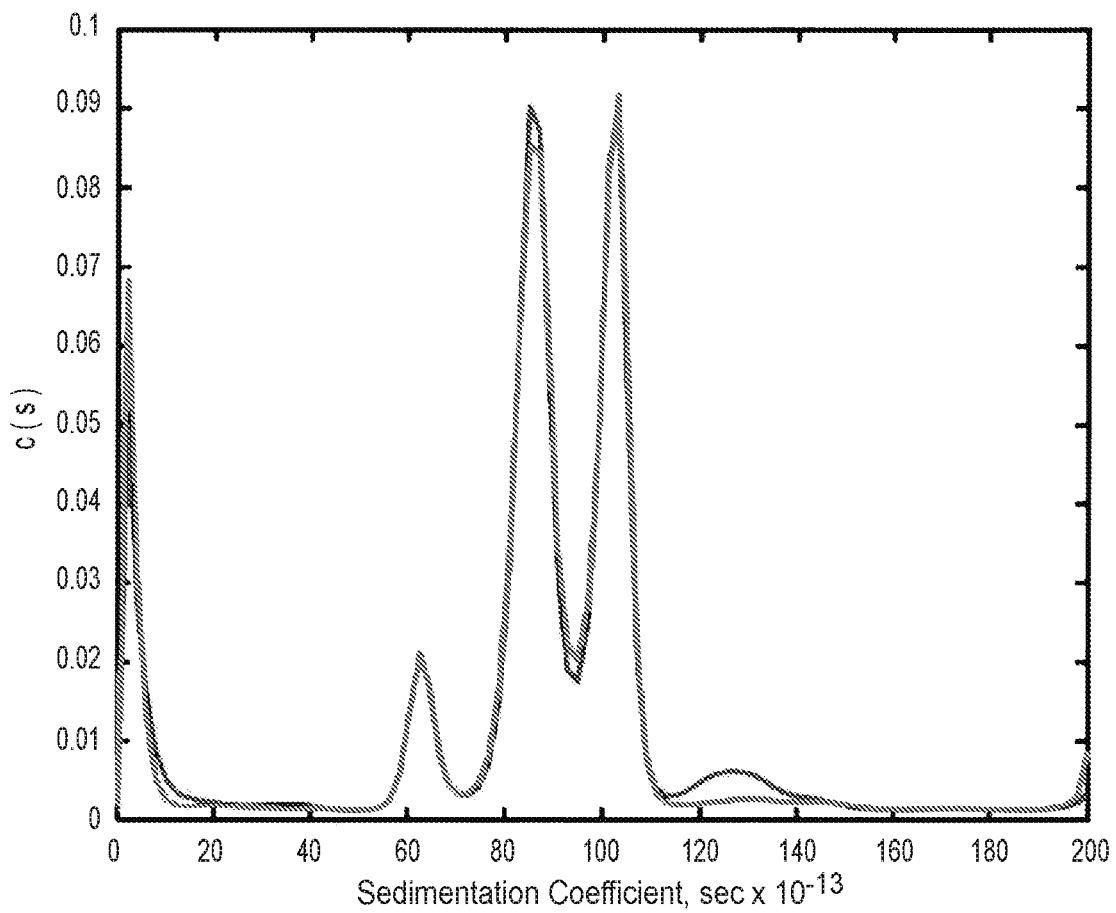
FIG. 46 shows sedimentation coefficients (sec×$10^{-13}$) for the Phase-1 material (NCHAAV9SMN0613) showing empty capsids (7%) with sedimentation coefficient of approximately 60×$10^{-13}$ sec, and the full capsids with sedimentation coefficient range of approximately 80-150×$10^{-13}$ sec.
Figure 47:
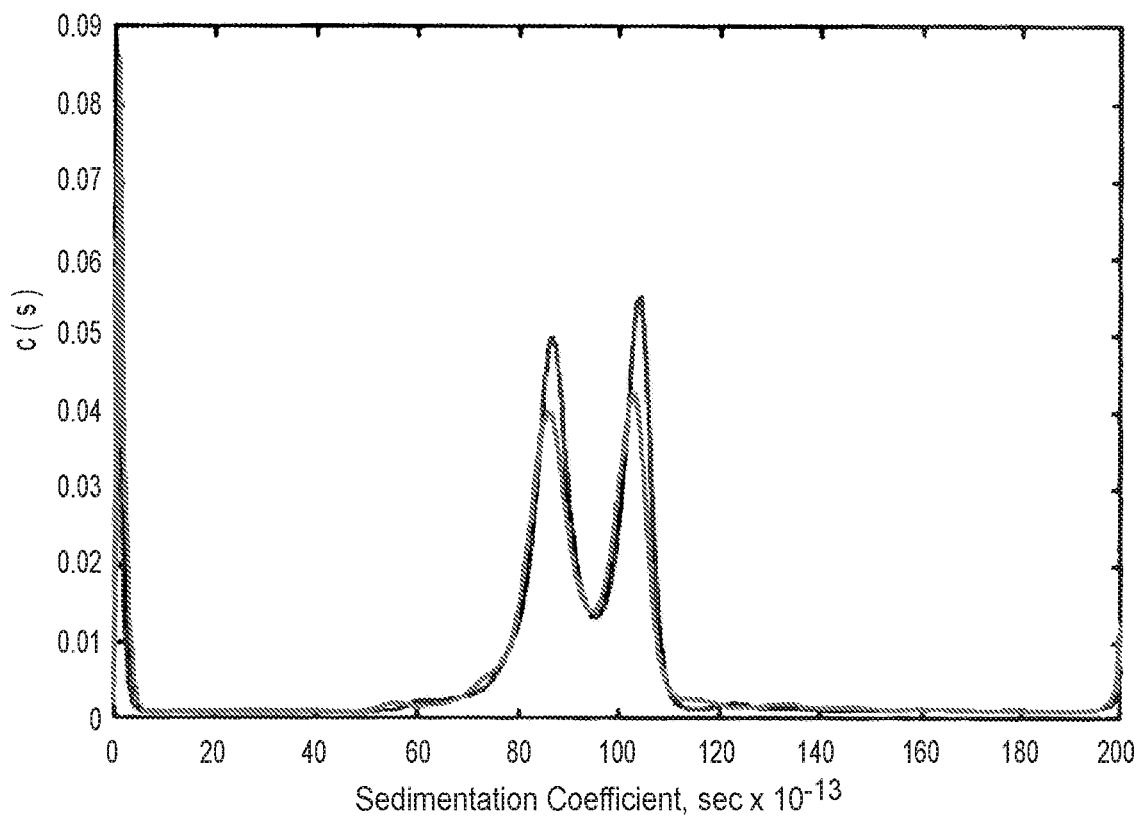
FIG. 47 shows sedimentation coefficients (sec×$10^{-13}$) for the Phase-3 material (600156) showing empty capsids (2%) with sedimentation coefficient of approximately 60×$10^{-13}$ sec, and the full capsids with sedimentation coefficient range of approximately 80-150×$10^{-13}$ sec.
Figure 48:
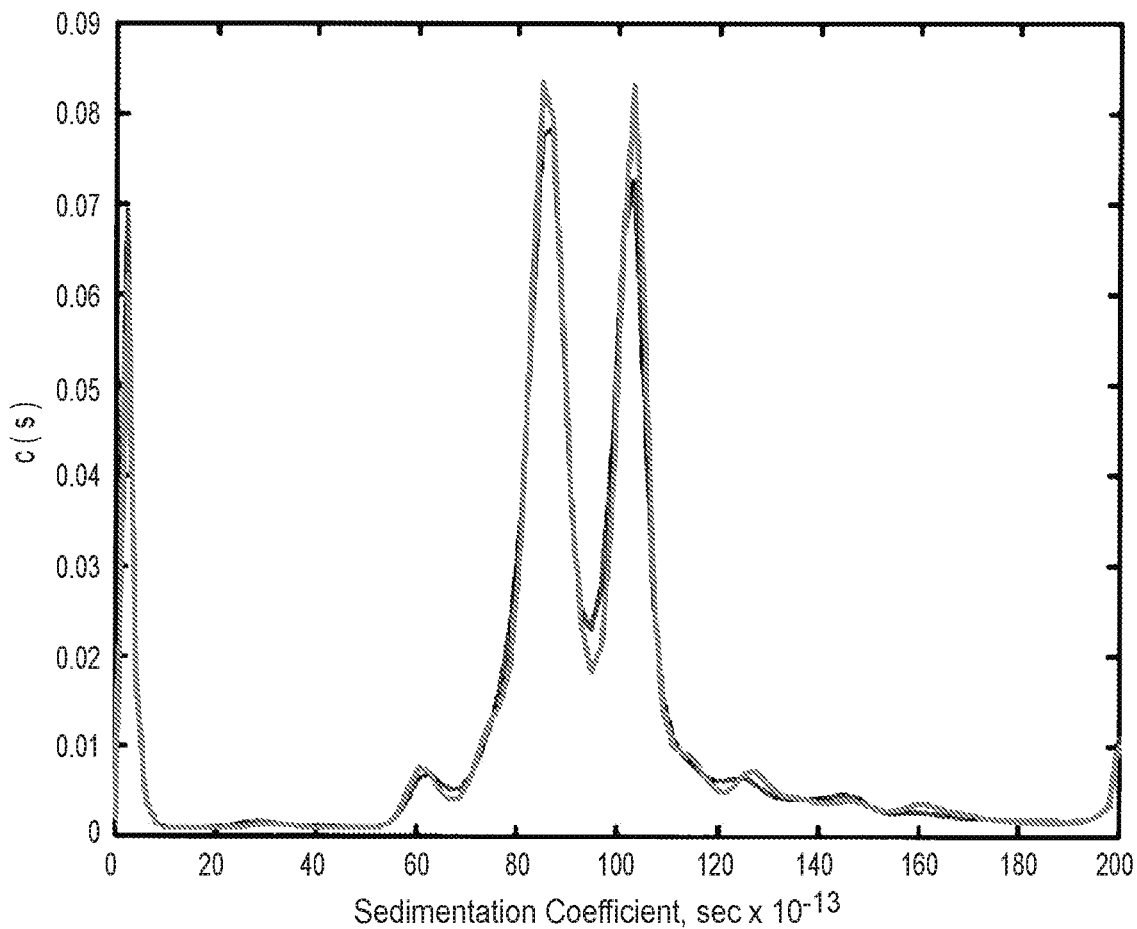
FIG. 48 shows sedimentation coefficients (sec×$10^{-13}$) for the Phase-3 material (600307) showing empty capsids (4%) with sedimentation coefficient of approximately 60×$10^{-13}$ sec, and the full capsids with sedimentation coefficient range of approximately 80-150×$10^{-13}$ sec.

The material from Phase-1 (Process A, Lot NCHAAV9SMN0613) and Phase-3 (Process B, Lots 600156 and 600307) were analyzed using the AUC method. The AUC Profiles (analyzed in duplicate) for the NCHAAV9SMN0613, 600156, and 600307 are shown in FIG. 46, FIG. 47, and FIG. 48, respectively.

The AUC analysis of each material exhibits similar sedimentation coefficients for the empty and the full capsids with the Phase-1 material (Process A, Lot NCHAAV9SMN0613) showing elevated empty capsid content (7%) when compared to the Phase-3 material (Process B, Lots 600156 and 600307) with empty capsid contents of 2% and 4% respectively. This is due to the ability of the CsCl gradient ultracentrifugation manufacturing step in Process B to more effectively separate the empty capsids from the full capsids with compared with the iodixanol gradient ultracentrifugation manufacturing step employed by Process A.

AVXS-101 production lots using the clinical and commercial presentation consistently exhibit three visible bands of capsids when subjected to the CsCl gradient purification process using ultracentrifugation, both in the Phase-1 clinical trial material produced at Nationwide Children's Hospital (NCHAAV9SMN0613) and in each subsequent production lots by AveXis. Based on the AUC profiles for the Phase 1 clinical drug product Lot NCHAAV9SMN0613 using Process A and AVXS-101 drug product Lot 600156 using Process B, these materials are considered to be comparable. Additionally, the AUC profiles for two lots of material generated from Process B (Lots 600156 and 600307) were assessed to be consistent.

Example 20: Manufacturing Upstream Process

An upstream process was used to produce intermediate derived from a working cell bank, wherein the upstream process comprises the steps of (a) culturing cells, (b) transfecting the cultured cells with three plasmids as shown in FIG. 26A-26C, (c) harvesting the expanded viral particles from the cells after a culture period, (d) purifying the viral particles via filtration to remove any intact cells or cellular debris, (e) subjecting the eluent from step (d) to tangential flow filtration, and (f) freezing the resultant intermediate preparation of purified viral particles.

Pre-transfection, cells were expanded for in suitable culture media, in flasks or a suitable bioreactor, or both. One culture media is DMEM with 10% FBS, 4.5 g/L glucose, 4 mM L-glutamine. In one embodiment, the adherent cells are grown in flasks initially and then transferred into an iCELLis bioreactor for further adherent cell expansion within the bioreactor.

After cell expansion, adherent HEK293 cells were transfected with a triple DNA plasmid PEI co-precipitation. The 3 plasmids utilized for this transfection are; pSMN, pAAV2/9, and pHELP. The DMEM growth medium used for cell expansion is replaced with a modified DMEM transfection media. The DMEM transfection media contained no FBS, no calcium, no L-glutamine and 4.5 g/L glucose. The scAAV9.CB.SMN vector was produced using triple DNA plasmid transfection into adherent HEK293 cells using a PEI co-precipitation in a large scale adherent cell bioreactor. The vector plasmid pSMN contains the cDNA for the human SMN. The 3 plasmids utilized for this transfection are; pSMN (222 mg), pAAV2/9 (333 mg), and pHELP (444 mg). The transfection medium was allowed to equilibrate in the bioreactor until the bioreactor temperature is >30° C. prior to the addition of the PEI-Plasmid co-precipitation. The PEI-Plasmid co-precipitation process involved the addition of the plasmids to the transfection media and 0.2μ filtration into a reaction bag. The PEI was added to transfection medium and then to the reaction bag. The PEI-Plasmid reaction was manually mixed to form a homogeneous suspension and the reaction occurs over a 15-30 minute period. At the end of the reaction time, the PEI-Plasmid co-precipitation was added to the bioreactor. The PEI-Plasmid co-precipitation was allowed to mix in the bioreactor for 1-2 hours prior to restarting the recirculation. The DMEM growth media was recirculated in the bioreactor for 18-24 hours before the next media change.

The rAAV SMN genome has in sequence an AAV2 ITR, the chicken β-actin promoter with a cytomegalovirus enhancer, an SV40 intron, the SMN coding DNA set out in (GenBank Accession Number NM_000344.2), a polyadenylation signal sequence from bovine growth hormone and another AAV2 ITR. Conservative nucleotide substitutions of SMN DNA are also contemplated (e.g., a guanine to adenine change at position 625 of GenBank Accession Number NM_000344.2). The genome lacks AAV rep and cap DNA, that is, there is no AAV rep or cap DNA between the ITRs of the genome. SMN polypeptides contemplated include, but are not limited to, the human SMN1 polypeptide set out in NCBI protein database number NP_000335.1.

On bioreactor day 6, 18-24 hours post transfection, the bioreactor was drained and the DMEM recirculation media bag was replaced with 200 liters of fresh OptiMEM post transfection media. The bioreactor was re-filled with 64 liters and recirculation in the bioreactor re-started. On day 7, 18-24 hours post the media change on day 6, the OptiMEM post transfection media in the recirculation bag (~135 liters) was replaced with a fresh bag of OptiMEM media. The bioreactor was not drained during this step. Recirculation of the media continued until harvest at day 9.

After 9 days in the bioreactor, the final pre-harvest samples were taken from the reactor and the cell lysis process was initiated. Benzonase was added to the bioreactor to a final concentration of 100 U/mL. After the Benzonase was allowed to mix in the reactor, 7.1 liters of lysis solution was added to the reactor. The lysis solution was mixed in the reactor for 2 hours prior to the first harvest step. At the end of the 2 hour lysis, the contents of the bioreactor were transferred to the harvest bag. 8.9 liters of salt sucrose solution (SSS) was added to the harvest bag and mixed for 15 minutes. The SSS solution quenched the Benzonase in the harvest media. The bioreactor was then rinsed with the bioreactor rinse buffer. For the bioreactor rinse, 64 liters of bioreactor rinse buffer was added to the bioreactor and mixed for 15 minutes. The rinse was then transferred to the common harvest collection bag. Once the rinse had been added to the collection bag, the contents were mixed for 15 minutes and the bulk harvest samples taken.

The mixed bulk harvest was filtered through the depth filter into a collection bag. Once all bulk harvest had been filtered, the depth filter was chased with 50 liters of TFF1 diafiltration buffer. The depth filter pool was mixed and sampled. The depth filter pool was then filtered through a 0.45 μm filter to further clarify the bulk harvest material. The 0.45 μm filter is then chased with 6 liters of TFF1 buffer.

For the TFF1 step, 5.0 m$^2$ of 300 kDaMW cut off regenerated cellulose membrane cassettes were flushed, sanitized with NaOH solution and equilibrated with TFF1 buffer. The concentration phase of this operation was designed to reduce the volume of the clarified harvest approximately 10×. Once the target retentate volume was reached, diafiltration operation are started. The retentate was diafiltered with 6 diavolumes of TFF1 buffer. Once 6 diavolumes of permeate total flow were achieved, the retentate was concentrated again and harvested into a collection bag. Two successive rinses of the membrane were executed to maximize the product recovery from the TFF system to produce an intermediate drug substance. The TFF1 intermediate was aliquoted into 1 or 2 liter sterile PETG bottles in a LFH hood and then frozen on dry ice or in a freezer and transferred to −60° C. storage.

TABLE 63

Buffers used in Upstream Process

| Name | Formulation | Process Step(s) Used |
|---|---|---|
| Cell Expansion Growth Media | DMEM with 10% FBS, 4.5 g/l glucose, 4 mM L-glutamine | Cell expansion, iCELLis Bioreactor pre-transfection |

TABLE 63-continued

Buffers used in Upstream Process

| Name | Formulation | Process Step(s) Used |
|---|---|---|
| Transfection Media | DMEM with no FBS, no calcium, no L-glutamine and 4.5 g/l glucose | iCELL is Bioreactor transfection |
| Post Transfection Media | OptiMEM with 2.3 g/l glucose, 4 mM L-glutamine, and no FBS | iCELLis Bioreactor post transfection |
| Lysis Buffer | 500 mM HEPES, 10% Tween 20, 20 mM MgCl$_2$, pH 8.0 | iCELLis Bioreactor cell lysis |
| Salt Sucrose Solution (SSS) | 3700 mM NaCl, 10% Sucrose | Clarification |
| Bioreactor Rinse Buffer | 20 mM Tris, 1 mM MgCl$_2$, 500 mM NaCl, 1% Tween 20, 1% Sucrose | iCELLis bioreactor harvest |
| TFF1 Buffer | 20 mM Tris, 1 mM MgCl$_2$, 500 mM NaCl, 1% Sucrose | Clarification, TFF1 |
| TFF1 Sanitization Buffer | 0.5M NaOH | TFF1 membrane sanitization |

Example 21: Manufacturing Downstream Process

A downstream process was used to process the intermediate to a filtered drug substance. The downstream process steps included an acidification and clarification step (using filtration), followed by cation exchange chromatography, tangential flow filtration ("TFF2"), CsCl ultracentrifugation and a further tangential flow filtration step ("TFF3") to produce a filtered drug substance where the purified AAV particles are suspended in a pharmaceutically acceptable carrier. Specifically, the downstream process contained the following manufacturing steps subsequent to production of the TFF1 intermediate: thaw and pool TFF1 intermediate, acidification and clarification, cation exchange chromatography (CEX), tangential flow filtration (TFF2), CsCl ultracentrifugation for Full/Empty Capsid Separation, tangential flow filtration (TFF3) for Concentration/Buffer Exchange, TFF 3 pool material filtration to generate drug substance, dilution and filtration of drug substance to produce drug product, storage of the drug product and filling of drug product into vials.

The TFF1 intermediate material was thawed and gently mixed. Tween 20 was used to promote flocculation of the bulk of host cell proteins and DNA under acidic pH. The pH of the TFF1 intermediate pool containing 15% Tween 20 was lowered for CEX chromatography (pH 3.5). The precipitate formed after the pH was lowered, was then removed by filtering the solution through a depth and 0.45 μm filters.

Tween 20 (36% Tween 20 solution in 20 mM Tris, 1 mM MgCl$_2$, 500 mM NaCl, 1% Sucrose m/v, pH 8.1) was slowly added to the TFF1 Intermediate solution over 4 hours to achieve a final concentration of 20% Tween 20. After overnight incubation at Room Temperature (RT) the pH of the Tween 20 containing TFF1 Intermediate was lowered by adding approximately 4 g of 1M glycine pH 2.5 per kg of TFF1 intermediate/Tween spike pool to achieve a target pH of 3.5±0.1. Once the pH was within the acceptable range, the solution was passed through the Clarisolve POD depth filter in line with a 0.45 μm Opticap XL10 Durapore filter or 0.8/0.45μ PES filter followed by a flush of the filters two times the hold-up volume of the POD filter plus one hold-up volume of the polishing filter with CEX Buffer A.

The cation exchange (CEX) capture chromatography step was used to separate the viral capsids from protein, DNA and other process impurities. This step utilized a CIMmultus S03-8000 Advanced Composite Column (Sulfonyl) (Pores 2 µm) chromatography column (8.0 L) operated using an automated process chromatography system. Buffers and solutions are described in the following table:

TABLE 64

Buffers and solutions for one CEX cycle

| Solution name | Composition | Purpose | Volume (L) for one 8 L CEX Cycle |
|---|---|---|---|
| WFI | WFI | Column flushes | 200 L |
| CEX A-Buffer | 50 mM glycine, 500 mM NaCl, 1.0% sucrose, 0.20% poloxamer 188, pH 3.5 ± 0.1 at 20° C. | Equilibration, wash, elution | 256 L |
| CEX B-Buffer | 50 mM glycine, 2.0M NaCl, 1.0 % sucrose, 0.20% poloxamer 188, pH 3.5 ± 0.1 at 20° C. | Column equilibration and elution | 40 L |
| Monolith Cleaning Solution | 1M NaOH, 2M NaCl | Column Sanitization, CIP | 96 L |
| 1M ammonium acetate pH 9.0 | 1M ammonium acetate | Restore column pH | 40 L |
| Neutralization buffer | 1.0M Tris pH 9.1 ± 0.1 at 20° C. | pH adjustment of CEX product | 0.5 L |
| Storage solution | 20% Ethanol in WFI | Column storage | 40 L |

The CEX column load was determined by the protein content of the clarified, acidified, TFF1 intermediate. The protein load for the CEX column was set at 70% of the maximum column capacity.

The elution peak was collected manually starting at a sharp rise in OD280. The OD280 rose when the conductivity was between 80-85 mS/cm. The approximate volume of CEX eluate (product) was ~20 liters or 2.5 CVs (column volumes). The CEX eluate was collected in two fractions. The first fraction started at the sharp rise in OD280 and was collected for 1.5 CVs. The second fraction started immediately after the first fraction and was collected for 1.0 CV. The two fractions were neutralized to pH 8.0±0.30 using pH 9.0 Neutralization Buffer.

The TFF2 step concentrated, removed protein impurities, and exchanged the buffer to an appropriate buffer for the CsCl ultracentrifugation step. A tangential flow filtration system was utilized in conjunction with 0.4 m² (two CEX cycles) or 0.2 m² (one CEX cycle) 300 k MWCO regenerated cellulose membranes.

The concentration phase of this operation reduced the volume of the CEX eluates. Once the target retentate volume was reached, diafiltration was started in discontinuous TFF mode (batch mode). The retentate was diluted 2× and diafiltered with 8 diavolumes of TFF2 NaCl diafiltration buffer and after that with 8 diavolumes of TFF2 CsCl diafiltration buffer in discontinuous TFF mode. Once CsCl diafiltration was complete, the retentate was concentrated to a prescribed volume that was dependent on the system hold-up volume. Two successive rinses of the membrane were executed to maximize the product recovery from the TFF2 system.

The retentate feed rate was set at 5 L/m²/min (500 mL/min per 0.1 m² cassette) with a 20% conversion rate to permeate (a permeate flow rate of 100 ml per 500 mL of retentate feed rate). The permeate flow rate was controlled by a clamp on the permeate tubing to maintain a permeate flow rate of 20% of retentate feed flow rate.

TABLE 65

Buffers for TFF2

| Solution Name | Composition |
|---|---|
| TFF2 NaCl Diafiltration Buffer | 20 mM Tris, 2 mM MgCl2, 150 mM NaCl, 0.2% Poloxamer 188, 1% Sucrose, pH 8.1 ± 0.1 at 20° C. |
| TFF2 CsCl Diafiltration Buffer | 20 mM Tris, 2 mM MgCl2, 3M CsCl, 0.2% Poloxamer 188, pH 8.1 ± 0.1 at 20° C. |

Ultracentrifugation may be used to remove empty capsids from full capsids by utilizing cesium chloride gradient ultracentrifugation. An automated Optima XPN 100 Ultra Centrifuge system or equivalent system equipped with Type 50.2 Ti rotor or equivalent rotor was used for CsCl ultracentrifugation step. TFF2 purified filtered material was slowly added in ultracentrifuge tubes along the inside of the tube wall without introducing bubbles into the solution. The filled tubes were sealed with handheld heat sealer and centrifuged at 302,000 g (50,000 rpm in 50.2 Ti rotor) for 17 hours at 20° C. After completion of centrifugation step, tubes were removed from the Ultra Centrifuge and placed in a biosafety cabinet. Product containing tubes were mounted on ring stands above a waste container. A Lamp was positioned directory under the tube and the empty capsids band (Band A is the highest band), the full capsid doublet bands (Bands B and C upper and lower bands of the doublet), and lowest band below the doublet was marked on the tubes. The bands B, C, and D were removed by an 18G needle attached to 30 mL syringe inserted just below band D to middle of tube. The collected material was transferred to a sterile 1 L PETG bottle. Material from all centrifuge tubes was pooled into a sterile 1 L PETG bottle to produce the Ultracentrifuge (UC) Pool. The Buffer for the CsCl ultracentrifugation step is listed in the table below:

TABLE 66

Buffer for CsCl Ultracentrifugation

| Solution Name | Composition |
|---|---|
| TFF2 CsCl Diafiltration Buffer | 20 mM Tris, 2 mM MgCl2, 3M CsCl, 0.2% Poloxamer 188, pH 8.1 ± 0.10 |

The TFF3 step removed CsCl and concentrated the full vector using Final Formulation Buffer. A tangential flow filtration system was utilized in conjunction with two 50 cm² 300 k MWCO regenerated cellulose membranes. The concentration phase of TFF3 operation was designed to reduce the concentration of residual CsCl and volume of the UC Pool. Once the target retentate volume was reached, diafiltration was started. The retentate was diafiltered with 10 diavolumes of TFF3 Buffer. Once diafiltration was complete, the concentrated retentate was transferred to a secondary conical tube through a 0.2 µm Pall Supor® EKV Sterilizing-Grade Filter (Mini Kleenpak) Filter.

A successive rinse of the membrane was executed to recover vector from the TFF3 system. TFF3 Buffer was added to the primary conical tube that previously held the TFF3 retentate. This material was recirculated through the cellulose membranes. After recirculation, the flush was transferred to the secondary conical tube through the 0.2 µm Pall Supor® EKV Sterilizing-Grade Filter (Mini Kleenpak) Filter. The TFF3 concentrate and partial pool was mixed to achieve a final vector concentration of ≥4.5×10$^{13}$ vg/mL of Drug Substance (pooled TFF3 retentate+two rinses).

A successive rinse of the membrane was executed to maximize the product recovery from the TFF3 system. TFF3 Buffer was added to the primary conical tube that previously held the TFF3 retentate and initial flush material. This material was recirculated through the cellulose membranes. The secondary flush is transferred to a secondary conical tube through the 0.2 µm Pall Supor® EKV Sterilizing-Grade Filter (Mini Kleenpak) Filter until the determined weight was achieved in the secondary conical tube. The final concentrated solution is referred to as Drug Substance (DS).

TABLE 67

Buffers for TFF3

| Solution Name | Composition |
| --- | --- |
| TFF3 Buffer | 20 mM Tris, 1 mM MgCl2, 200 mM NaCl, 0.001% Poloxamer 188, pH 8.0 ± 0.1 at 20° C. |

The DS was filtered with a Pall Supor® EKV Sterilizing-Grade Filter (Mini Kleenpak) into a sterile 1 L glass bottle using a sterilized single use assembly. Before filtration of the TFF3 pool, the filter was flushed by passing TFF3 Buffer through the filter using a peristaltic pump and discarding to a waste flush bag. The Drug Substance (DS) was then filtered through the flushed filter using a peristaltic pump and collected in the 1 L sterile glass bottle. Based on the targeted concentration of DS at 5×10$^{13}$ vg/mL, TFF3 Buffer was added to the secondary conical tube which held the DS and passed through the filter to prepare dilute drug product ("DP") to a target concentration of 3.5×10$^{13}$ vg/mL.

The TFF3 Buffer used in the filter flush and DS dilution to prepare the DP is comprised of the following formulation.

TABLE 68

Drug Product Unit Operation - Buffer Composition

| Solution Name | Composition |
| --- | --- |
| TFF3 Buffer | 20 mM Tris, 1 mM MgCl2, 200 mM NaCl, 0.001% Poloxamer 188, pH 8.0 ± 0.1 |

The DP was filled into 5 mL sterile, ready to use, Crystal Zenith (CZ) vials, stoppered with sterile, ready to use, stoppers, and sealed with sterile, ready to use, seals.

Example 22: Single-Dose Gene-Replacement Therapy for Spinal Muscular Atrophy: A Dose Study Spinal muscular atrophy (SMA) is a severe childhood monogenic disease resulting from loss or dysfunction of the gene encoding survival motor neuron 1 (SMN1). The incidence of this disease is approximately 1 in 10,000 live births, with a carrier frequency of 1 in 54. SMA is characterized by the degeneration and loss of lower motor neurons, which leads to muscle atrophy. The disease is divided into four subtypes (1 through 4) on the basis of the age at onset and milestone achievement. SMA type 1 (SMA1) is the most severe form and most common genetic cause of death among infants. There are two forms of SMN; SMN1 is the primary gene responsible for functional production of SMN protein. SMN2 preferentially excludes exon 7 during splicing and, as a result, produces only a small fraction of functional SMN protein as compared with SMN1. Therefore, the SMN2 copy number modifies the disease phenotype, and the presence of two copies of SMN2 is associated with SMA1.

Infants with SMN1 biallelic deletions and two copies of SMN2 have a 97% risk of SMA1.

Recent studies of the natural history of SMA1 (historical cohort) showed that the median age at symptom onset among infants with the disease was 1.2 months (range, 0 to 4 months), and the disease was characterized by hypotonia, severe weakness from early infancy, and failure to sit without support. In infants with SMA1 who have two copies of SMN2, the median age at death or the need for noninvasive ventilation for at least 16 hours per day for at least 14 consecutive days (considered equivalent to permanent ventilation) was 10.5 months. In one cohort of affected children, only 25% survived without permanent ventilatory support at 13.6 months, and 8% survived without this support by 20 months. Another prospective, multicenter historical study sponsored by the National Institutes of Health (NeuroNEXT) involving patients with two copies of SMN2 showed a median survival free of tracheostomy of 8 months (95% confidence interval, 6 to 17). All patients with SMA1 have a precipitous decline in respiratory and swallowing functions after birth and ultimately require mechanical nutritional support (through a nasogastric or gastrostomy tube) to maintain adequate nutrition and reduce the respiratory risks associated with aspiration. For patients with SMA1 in whom the onset of symptoms occurs by 3 months of age, most patients require feeding support by 12 months of age. Patients with SMA1 also do not achieve major milestones in motor function and have a decline in function, as measured on the CHOP INTEND (Children's Hospital of Philadelphia Infant Test of Neuromuscular Disorders) scale, which ranges from 0 to 64, with higher scores indicating better motor function, a tool that is sensitive to minor changes in motor function, such as antigravity movements of limbs. In a historical analysis of 34 patients with SMA1, all but 1 of the patients did not reach a score of at least 40 after 6 months of age. In the NeuroNEXT cohort, CHOP INTEND scores decreased by a mean of 10.7 points from 6 months to 12 months of age.

Therapeutic strategies to increase levels of SMN protein in motor neurons have focused on enhancing the effectiveness of SMN2. One approach has been central nervous system delivery of nusinersen (Ionis Pharmaceuticals/Biogen), an antisense oligonucleotide that was developed to inhibit exon 7 splicing in SMN2. This drug has been shown to improve weakness in the murine model of severe SMA and to increase the median life span of affected mice from 16 days to 25 days. In December 2016, nusinersen was approved by the Food and Drug Administration for the treatment of SMA. This drug is administered by means of repeated intrathecal injections after four loading doses within the first 2 months of life.

A potential alternative treatment for SMA1 is gene therapy, given as a one-time intravenous administration that delivers a copy of SMN in a self-complementary adeno-associated viral serotype 9 (scAAV9). (The coding region of this recombinant virus forms an intramolecular double-stranded DNA [or self-complementary] template.) This approach has induced SMN expression in motor neurons and peripheral tissues, which has countered the effects of SMA in a murine model and extended the average survival in this model from 15 days to 28.5 days with a low dose (6.7×10$^{13}$ vg per kilogram of body weight) and to more than 250 days with higher doses of the vector ($2.0\times10^{14}$ and $3.3\times10^{14}$ vg per kilogram).

In addition to crossing the blood-brain barrier and targeting central nervous system neurons at all regions of the spinal cord, the systemic administration of AAV9-mediated gene therapy may be advantageous, given that SMN protein is ubiquitously expressed and SMA1 affects multiple systems (e.g., autonomic and enteric nervous systems, cardiovascular system, and pancreas), along with many cell types (e.g., heart, pancreas, and skeletal muscle). The self-complementary feature of the vector combined with a hybrid cytomegalovirus enhancer-chicken beta actin promoter enables rapid and sustained expression of SMN. In April 2014, we initiated a study of gene-replacement therapy involving infants with SMA1 who received a one-time dose of scAAV9 with delivery of the human survival motor neuron gene (hSMN), under control of the chicken beta-actin promoter (scAAV9.CB.hSMIV) (AVXS-101).

Methods

Patient and Study Procedures: For the purposes of the study, all the patients had a genetically confirmed diagnosis of SMA1, homozygous SMN1 exon 7 deletions, and two copies of SMN2. Patients with the c.859G→C disease modifier in exon 7 of SMN2 were excluded. Patients who were selected had showed onset of disease from birth up to 6 months of age, characterized by hypotonia as determined by clinical evaluation accompanied by a delay in motor skills, poor head control, round shoulder posture and hypermobility of joints. Patients with active viral infections (including HIV or serology positive for hepatitis B or C) or concomitant illness that created unnecessary risks for gene transfer were excluded from the study. Patients that needed invasive ventilatory support (tracheotomy with positive pressure) or pulse oximetry <95% saturation at screening visit were also excluded.

Patients were enrolled in two cohorts, according to the dose of gene therapy that was administered. Patients in cohort 1 received a low dose ($6.7\times10$ vg per kilogram) and were enrolled over the course of five months; those in cohort 2 received a high dose ($2.0\times10^{14}$ vg per kilogram) and were enrolled over the course of one year. At day 30 post dosing, the IFN-γ ELISpot assay on Patient 1 in cohort 1 detected a T-cell response, and showed a sudden spike in spot forming cells (SFCs) per $10^6$ peripheral blood mononuclear cells (PBMCs) that was >50 directed against the AAV9 capsid (normal, <50 SFCs per $10^6$ PBMCs). Prednisolone was started at 2 mg/kg and was maintained for 35 days until T-cell response and serum transaminases were reduced. As a result, the experimental protocol was amended, and Patients 2 through 15 received oral prednisolone at a dose of 1 mg per kilogram per day for approximately 30 days, starting 24 hours before the administration of gene vector. Treatment was continued with prednisolone maintained until AST and ALT enzymes fell below the level of 120 IU/L and T-cell response fell below 100 SFCs per $10^6$ PBMCs, at which point the prednisolone would be tapered off based on clinical judgment.

The vector was delivered in normal saline (approximately 10 to 20 ml per kilogram) that was infused intravenously during a period of approximately 60 minutes. At the time of enrollment, some patients required enteral feeding by means of a gastrostomy or nasogastric tube, the choice of which was based on the preference of the parents or the primary physician. Once enrolled in the study, all the patients who required nutritional support underwent placement of a gastrostomy tube, and the tubes were not removed during the study.

Outcomes: The primary outcome was the determination of safety on the basis of any treatment-related adverse events of grade 3 or higher. The secondary outcome was the time until death or the need for permanent ventilatory assistance. The latter was defined as at least 16 hours of respiratory assistance per day continuously for at least 14 days in the absence of an acute, reversible illness or a perioperative state. Exploratory outcomes included motor-milestone achievements (particularly, sitting unassisted) and CHOP INTEND scores.

The maintenance of scores of more than 40 points has been considered to be clinically meaningful in SMA in the application of the CHOP INTEND scale. Sitting unassisted was evaluated and classified according to the following criteria: sitting unassisted for at least 5 seconds, according to item 22 of the Bayley Scales of Infant and Toddler Development gross motor subtest ("sitting unassisted"); sitting unassisted for at least 10 seconds, according to the World Health Organization (WHO) criteria ("sitting unassisted per WHO criteria"); and sitting unassisted for at least 30 seconds, according to item 26 of the Bayley Scales mentioned above ("independent functional sitting"). Major motor milestones were confirmed by means of an examination of video recordings of the patients by an independent reviewer by Ability Captured Through Interactive Video Evaluation-mini (ACTIVE-mini). Compound muscle action potentials (CMAP) were recorded from surface electrodes at baseline and every 6 months after infusion. Pathological status of muscles was quantified by Electrical Impedance Myography (EIM).

Statistical Analysis: Safety analyses were performed in all the patients, who were also included in the primary analysis of survival (as defined above and in the protocol) and in analyses of changes on the CHOP INTEND scale from baseline to 1 month and 3 months. Such changes from baseline to each study visit were analyzed with the use of a mixed-effects model for repeated measurements. The mixed model included the fixed effects of cohort and visit and a covariate of baseline score. Milestone achievements and nutritional and ventilatory support were analyzed in cohort 2. Statistical analyses were performed with the use of SAS software, version 9.4. All comparisons with historical cohorts were solely descriptive.

Results

Patients: Of the 16 patients who were screened, 1 was excluded because of persistently elevated anti-AAV9 antibody titers (>1:50). Of the 15 patients who were included in the study, 3 were enrolled in the low-dose cohort 1 and 12 were enrolled in the high-dose cohort 2. The mean age of patients at the time of treatment was 6.3 months (range, 5.9 to 7.2) in cohort 1 and 3.4 months (range, 0.9 to 7.9) in cohort 2 (Table 69).

TABLE 69

Demographic and Clinical Characteristics of the 15 Patients

| Characteristic | Cohort 1 (N = 3) | Cohort 2 (N = 12) |
|---|---|---|
| Mean age (range)-mo | 6.3 (5.9-7.2) | 3.4 (0.9-7.9) |
| Mean weight (range)-kg | 6.6 (6.0-7.1) | 5.7 (3.6-8.4) |
| Sex-no. (%) | | |
| Male | 1 (33) | 5 (42) |
| Female | 2 (67) | 7 (58) |
| Race-no. (%) | | |

TABLE 69-continued

Demographic and Clinical Characteristics of the 15 Patients

| Characteristic | Cohort 1 (N = 3) | Cohort 2 (N = 12) |
|---|---|---|
| White | 3 (100) | 5 (42) |
| Other | 0 | 1 (8) |
| Mean age at symptom onset (range)-mo | 1.7 (1.0-3.0) | 1.4 (0-3.0) |
| Mean age at genetic diagnosis (range)-days | 33 (4-85) | 60 (0-136) |
| Mean score on CHOP INTEND scale (range) | 16 (2-27) | 28 (12-50) |
| Patients with clinical support-no. (%) | | |
| Nutritional | 3 (100) | 5 (42) |
| Ventilatory | 3 (100) | 2 (17) | comparisons); 11 patients attained and sustained scores of more than 40 points. At the study cutoff on Aug. 7, 2017, patients in cohort 1 had a mean increase of 7.7 points from a mean baseline of 16.3 points, and those in cohort 2 had a mean increase of 24.6 points from a mean baseline of 28.2 points.

Motor Milestones in Cohort 2: A total of 11 of 12 patients in cohort 2 were able to sit unassisted for at least 5 seconds, 10 for at least 10 seconds, and 9 for at least 30 seconds (Table 70). A total of 11 achieved head control, 9 could roll over, and 2 were able to crawl, pull to stand, stand independently, and walk independently. Eleven patients attained the ability to speak. No patients in the historical cohorts had achieved any of these motor milestones and rarely had achieved the ability to speak.

TABLE 70

Event-free Survival and Motor and Other Milestones among the 12 Patients of Cohort 2.

| Variable | Age at Study Entry mo | Event-free Survival | Motor Milestones | | | | | Sits Unassisted | | | Other Achievements | | | |
|---|---|---|---|---|---|---|---|---|---|---|---|---|---|---|
| | | | Brings Hand to Mouth | Controls Head | Rolls Over | Sits with Assistance | | ≥5 sec | ≥10 sec | ≥30 sec | Speaks | Swallows | No NIV Use | No Nutritional Support |
| Patient no. | | | | | | | | | | | | | | |
| 4 | 5.6 | 31.1 | + | + | + | + | | + | | | + | + | | |
| 5 | 4.2 | 28.5 | + | + | + | + | | + | + | + | + | + | + | + |
| 6 | 1.9 | 26.1 | + | + | + | + | | + | + | + | + | + | + | + |
| 7 | 3.6 | 28.1 | + | + | + | + | | + | + | | + | + | + | |
| 8 | 7.9 | 32.4 | + | | | | | | | | | | | |
| 9 | 4.9 | 28.9 | + | + | + | + | | + | + | + | + | + | + | + |
| 10 | 0.9 | 25.3 | + | + | + | + | | + | + | + | + | + | + | + |
| 11 | 2.3 | 23.8 | + | + | + | + | | + | + | + | + | + | | |
| 12 | 2.6 | 23.9 | + | + | + | + | | + | + | + | + | + | + | + |
| 13 | 0.9 | 22.1 | + | + | | + | | + | + | + | + | + | | |
| 14 | 4.1 | 22.0 | + | + | + | + | | + | + | + | + | + | + | + |
| 15 | 2.1 | 20.6 | + | + | | + | | + | + | + | + | + | | |
| Patients with outcome (%) | | | | | | | | | | | | | | |
| This Study | 100 | 100 | 92 | 75 | 92 | 92 | | 83 | 75 | | 92 | 92 | 58 | 50 |
| Natural History Studies | 8 by 20 mo | NA | 0 | 0 | 0 | 0 | | 0 | 0 | | NA | NA | NA | 8 by 20 mo |

Survival and Permanent Ventilation: As of the end of the study, all the patients had reached an age of at least 20 months and did not require permanent mechanical ventilation; the median age at their last pulmonary assessment was 30.8 months in cohort 1 and 25.7 months in cohort 2. In contrast, only 8% of the patients in a historical cohort did not require permanent mechanical ventilation. At 29 months of age, one patient in cohort 1 required permanent ventilation because of hypersalivation. After salivary gland ligation, the requirement for the use of noninvasive ventilation was reduced by 25% to 15 hours per day.

Motor Function Assessments: All the patients in cohorts 1 and 2 had increased scores from baseline on the CHOP INTEND scale and maintained these changes during the study. Patients in cohort 2 had mean increases of 9.8 points at 1 month and 15.4 points at 3 months (P<0.001 for both Pulmonary and Nutritional Status in Cohort 2: Among the 12 patients in cohort 2, 10 did not require noninvasive ventilation at baseline as compared with 7 who were independent of ventilatory assistance at the last follow-up visit (Table 70). At baseline, 7 patients did not require enteral feeding, including 1 who later required placement of a gastrostomy tube after gene-replacement therapy, possibly in association with scoliosis surgery. Of the 5 patients who had received enteral feeding before gene-replacement therapy, at the last follow-up, 11 of the 12 patients had achieved or retained the ability to swallow independently and 4 were able to feed orally.

Safety: As of the end of the study, a total of 56 serious adverse events were observed in 13 patients in the two cohorts. Of these events, investigators determined that 2 events were treatment-related grade 4 events on the basis of laboratory values, according to Common Terminology Criteria for Adverse Events (Table 71). Patient 1 in cohort 1 had elevations in serum aminotransferase levels (31 times the upper limit of the normal range for alanine aminotransferase (ALT) and 14 times the upper limit for aspartate aminotransferase (AST)) without other liver-function abnormalities (i.e., total and indirect bilirubin and alkaline phosphatase) and without clinical manifestations. As described above, these elevations were attenuated by prednisolone treatment, which was subsequently administered in the remaining patients. One patient in cohort 2 required additional prednisolone to attenuate elevated serum ALT and AST levels (35 times the upper limit of the normal range for ALT and 37 times for AST). Of the 241 nonserious adverse events, 3 were deemed to be treatment related and consisted of asymptomatic elevations in serum aminotransferase levels in 2 patients (ALT and AST, both less than 10 times the upper limit of the normal range), which were resolved without additional prednisolone treatment (Table 71. There were no other abnormalities on liver-function testing. Of the 15 patients, 14 had respiratory illnesses, which in children with SMA1 frequently result in death or the need for tracheostomy.

TABLE 71

Adverse Events.

| Event | Cohort 1 (N = 3) Events no. | Cohort 1 (N = 3) Patients no. (%) | Cohort 2 (N = 12) Events no. | Cohort 2 (N = 12) Patients no. (%) | All Patients (N = 15) Events no. | All Patients (N = 15) Patients no. (%) |
|---|---|---|---|---|---|---|
| Any adverse event | 44 | 3 (100) | 253 | 12 (100) | 297 | 15 (100) |
| Any serious adverse event | 7 | 3 (100) | 49 | 10 (83) | 56 | 13 (87) |
| Adverse event associated with treatment | 1 | 1 (33) | 4 | 3 (25) | 5 | 4 (27) |
| *Common adverse event* | | | | | | |
| Upper respiratory tract infection | 3 | 1 (33) | 26 | 10 (83) | 29 | 11 (73) |
| Vomitting | 0 | 0 | 11 | 8 (67) | 11 | 8 (53) |
| Constipation | 4 | 4 (33) | 9 | 7 (58) | 10 | 8 (53) |
| Pyrexia | 1 | 1 (33) | 10 | 6 (50) | 11 | 7 (47) |
| Nasal congestion | 0 | 0 | 8 | 6 (50) | 8 | 6 (40) |
| Gastroesophageal reflux | 1 | 1 (33) | 6 | 5 (42) | 7 | 6 (40) |
| Enterovirus infection | 1 | 1 (33) | 7 | 4 (33) | 8 | 5 (33) |
| Pneumonia | 0 | 0 | 11 | 5 (42) | 9 | 5 (33) |
| Rhinovirus infection | 1 | 1 (33) | 10 | 4 (33) | 11 | 5 (33) |
| Cough | 0 | 0 | 9 | 5 (42) | 9 | 5 (33) |
| Otitis media | 6 | 2 (67) | 3 | 2 (17) | 9 | 4 (27) |
| Elevated aminotransferase level | 1 | 1 (33) | 3 | 3 (25) | 4 | 4 (27) |
| Respiratory failure | 1 | 1 (33) | 5 | 3 (25) | 6 | 4 (27) |
| Parainfluenza virus infection | 1 | 1 (33) | 4 | 3 (25) | 5 | 4 (27) |
| Rash | 0 | 0 | 5 | 4 (33) | 5 | 4 (27) |
| Atelectasis | 0 | 0 | 4 | 4 (33) | 4 | 4 (27) |
| Viral gastroenteritis | 0 | 0 | 4 | 4 (33) | 4 | 4 (27) |
| Rhinorrhea | 0 | 0 | 4 | 3 (25) | 4 | 3 (20) |
| Bronchiolitis | 0 | 0 | 3 | 3 (25) | 3 | 3 (20) |
| Diarrhea | 0 | 0 | 3 | 3 (25) | 3 | 3 (20) |
| Ear Infection | 1 | 1 (33) | 2 | 2 (17) | 3 | 3 (20) |
| Injury from fall | 0 | 0 | 3 | 3 (25) | 3 | 3 (20) |
| Human rhinovirus | 0 | 0 | 3 | 3 (25) | 3 | 3 (20) |
| Streptococcal pharyngitis | 1 | 1 (33) | 2 | 2 (17) | 3 | 3 (20) |
| *Respiratory syncytial virus* | | | | | | |
| Pneumonia | 1 | 1 (33) | 2 | 2 (17) | 3 | 3 (20) |
| Bronchiolitis | 1 | 1 (33) | 2 | 2 (17) | 3 | 3 (20) |
| Viral upper respiratory tract infection | 0 | 0 | 3 | 3 (25) | 3 | 3 (20) |

A single intravenous infusion of adeno-associated viral vector containing DNA coding for SMN in patients with SMA1 resulted in longer survival than in historical cohorts with this disease. All 15 patients surpassed the previously reported median age of survival without permanent ventilation of 10.5 months for patients with SMA1 with two SMN2 copies. All the patients also surpassed the benchmark of 20 months, at which time only 8% of the patients with this disease typically survive without permanent ventilation. 4 Of the 12 patients in cohort 2, all but 1 achieved motor-function milestones that have not been reported in historical cohorts. The attained motor function was clinically meaningful, as reflected by feeding (hand to mouth), sitting, and talking. The majority of the patients who did not require supportive care at enrollment were free of nutritional support (6 of 7 patients) and ventilatory support (7 of 10 patients) at the last follow-up visit. In the two cohorts, the patients had increases in the score on the CHOP INTEND scale from baseline. Within the first month in cohort 2, the mean increase was 9.8 points, in contrast to a decline of a mean of more than 10 points between 6 and 12 months of age in the historical cohort in the NeuroNEXT study.

Preclinical studies of SMN gene-replacement therapy in the SMN Δ 7 mouse model showed improvements in survival and motor function with early treatment, presumably at a time when motor neurons are still intact. The clinical findings in our study of early treatment reflected the direction of those in the preclinical studies. Two patients were able to crawl, stand, and walk without support after early treatment. Both of these patients had a family history of SMA, which probably contributed to the early diagnosis. Although all the patients in the two cohorts in our study have continued to have improvements in motor function, the preclinical and clinical data suggest a benefit for early treatment and newborn screening for SMA.

Serious adverse events caused by AAV gene replacement therapy were limited to elevated serum aminotransferase levels without other liver enzyme abnormalities approximately 3 weeks after treatment in two patients; two other patients had elevations that did not reach the cutoff for the definition of serious adverse events (i.e., >10 times the normal range). Elevations in liver enzymes were attenuated by prednisolone treatment. One patient did not pass screening owing to the presence of anti-AAV9 antibody, which is consistent with population studies that suggest a low rate of anti-AAV9 seropositivity among children and young adults and increasing rates of anti-AAV9 seropositivity among persons older than 40 years of age. However, the presence of antibodies to the virus may be a limitation of AAV gene-replacement therapy.

This study used a single-group design with a historical cohort as a control, which is one of a limited number of options when the natural history of a disease is well characterized and lethal. In order to enroll a homogeneous sample that was similar to those in published historical studies, we restricted enrollment to include only symptomatic patients with SMA1 who had biallelic SMN1 mutations and two SMN2 copies and did not enroll patients with the c.859G→C genetic modifier in exon 7 of SMN2, since this genetic modifier predicts a milder phenotype of the disease. However, this gene replacement therapy need not be limited to symptomatic patients, or patients with a specific genomic subtype.

In conclusion, a one-time intravenous infusion of a high dose of adeno-associated viral vector containing DNA coding for SMN in patients with SMA1 resulted in extended survival, improved motor function, and increased scores on the CHOP INTEND scale to levels that had not previously been observed in this disease. Such improvements resulted in a lower percentage of patients who needed supportive care than those in historical studies. In follow-ups of up to 2 years, no waning of effect or clinical regression in motor function had been reported. Several patients had transient and asymptomatic elevations in aminotransferase levels. Further studies are necessary to assess the long-term safety and durability of gene-replacement therapy in patients with SMA1.

Example 23: Pharmacokinetics of scAAV9.CB.hSMN

Conventional clinical pharmacokinetic studies are not applicable to gene replacement therapy products. However, scAAV9.CB.hSMN vector shedding studies, which assess the amount of vector eliminated from the body through fluids and waste, are a measure that may be used in lieu of conventional pharmacokinetic studies for gene replacement therapies.

Vector shedding after infusion with scAAV9.CB.hSMN was investigated at multiple time points during the clinical study. Samples of saliva, urine and stool were collected weekly through day 30 and then monthly through Month 12 and every 3 months thereafter. Samples from 5 patients were used for scAAV9.CB.hSMN vector shedding analysis by droplet digital polymerase chain reaction through the Month 18 visit. All 5 patients analyzed for scAAV9.CB.hSMN vector shedding were dosed with the therapeutic dose of $1.1 \times 10^{14}$ vg/kg. scAAV9.CB.hSMN was detectable in shed samples post-infusion.

scAAV9.CB.hSMN concentrations in urine and saliva were 0.1% to 0.01% of initial concentration in the body at day 1 post-infusion, after which concentrations fell below the limit of quantitation. In stool, levels 10% to 30% of the initial concentration in the body were detectable at day 1 post-infusion. One patient showed a peak concentration in stool at day 14 post-infusion of 280% of initial concentration in body. In contrast, 3 patients for whom data were available showed a concentration of <1% of initial concentration in the body at day 14 post-infusion, with concentrations declining approximately 4 logs (10,000-fold) over 30 days post-infusion. Overall, scAAV9.CB.hSMN was primarily cleared from the body in stool and by day 60 post-infusion was below the limit of quantitation in stool.

Example 24: Non-Clinical Toxicology Tests

Animal Pharmacology: Following infusion of scAAV9.CB.hSMN vector in a delta 7 SMA mouse model of disease (SMN Δ7 mice), body weight increased, righting behavior improved, survival was significantly extended in a dose-dependent manner and SMA-related cardiac deficits returned toward normal compared to untreated SMN Δ7 mice.

Animal Toxicology: Following intravenous infusion in the mouse, vector and transgene were widely distributed with the highest expression generally observed in heart and liver, and substantial expression in the brain and spinal cord. In pivotal Good Laboratory Practice (GLP) compliant 3-month mouse toxicology studies, the main target organs of toxicity were the heart and liver. scAAV9.CB.hSMN vector-related findings in the ventricles of the heart were comprised of dose-related inflammation, edema and fibrosis, and in the atrium, inflammation and thrombosis. Liver findings were comprised on hepatocellular hypertrophy, Kupffer cell activation, and scattered hepatocellular necrosis. A No Adverse Effect Level (NoAEL) was not identified for scAAV9.CB.hSMN vector-related heart and liver findings in the mouse, and the Maximum Tolerated Dose was defined as $1.5 \times 10^{14}$ vg/kg, providing a safety margin of approximately 1.4-fold relative to the recommended therapeutic dose of $1.1 \times 10^{14}$ vg/kg. The translatability of the observed findings in mice to primates is not known at this time.

Example 25: Spinal Muscular Atrophy in Pediatric Patients

This trial was a Phase 1 study evaluating safety and efficacy of scAAV9.CB.hSMN vector in SMA Type 1 patients genetically tested to confirm bi-allelic SMN1 deletions, 2 copies of survival motor neuron 2 (SMN2), negative findings for the c.859G>C modification in exon 7 and with the onset of clinical symptoms before 6 months of age. scAAV9.CB.hSMN vector was delivered intravenously during a single-dose infusion in patients 0.9 to 7.9 months of age. Two cohorts were dosed: Cohort 1 (n=3) received the low dose used in this study and Cohort 2 (n=12) received the high dose (therapeutic dose: $1.1 \times 10^{14}$ vg/kg) used in this study. The reported study outcomes reflect Cohort 2 and includes follow-up of all patients out to 24 months following scAAV9.CB.hSMN vector infusion.

Mortality and Event-Free Survival

Survival and time-to-event analyses support the efficacy of scAAV9.CB.hSMN vector. In Cohort 2, all 12 patients (100%) were over 24 months of age and event-free, as opposed to only 8% of patients in a natural history study. This indicates a significant and clinically meaningful increase in overall survival for patients infused with scAAV9.CB.hSMN vector when compared to untreated patients. At 2 years following infusion, no patient deaths were reported.

Development Motor Milestones

Development motor milestones were examined; assessments for all 15 patients were video-recorded to allow confirmation of the achievement of developmental motor milestones. Patients in Cohort 2 consistently achieved and maintained key developmental motor milestones. At 24 months of follow-up post-dose, 11 patients (91.7%) were able to hold their head erect for ≥3 seconds and sit without support for ≥5 seconds, 10 patients (83.3%) were able to sit without support for ≥10 seconds, 9 patients (75.0%) were able to sit without support for ≥30 seconds and 2 patients each (16.7%) were able to stand alone, walk with assistance and walk alone. Cohort 2 patients who are currently enrolled in an ongoing observational long-term follow-up of this study have maintained their developmental motor milestones, with some achieving additional motor milestones.

TABLE 72

Patients Who Developed Significant Motor Function Milestones Based on Independent Central Review at 24 Months of Follow-up Post-Dose (Full Analysis Set)

| | scAAV9.CB.hSMN vector Cohort 2 (N = 12) n (%) |
|---|---|
| Rolling (back to side from both sides) | 9 (75.0) |
| Hold head erect ≥3 seconds, unsupported | 11 (91.7) |
| Sits with support, non-independent sitting | 11 (91.7) |
| Sits without support ≥5 seconds | 11 (91.7) |
| Sits without support ≥10 seconds | 10 (83.3) |
| Sits without support ≥30 seconds | 9 (75.0) |
| Stands with assistance | 2 (16.7) |
| Stands alone | 2 (16.7) |
| Walks with assistance | 2 (16.7) |
| Walks alone | 2 (16.7) |

Pulmonary

Of the 10 patients in Cohort 2 that were not using non-invasive ventilation (NIV) at baseline, 7 were free of daily NIV use at 24 months of follow-up. Nearly all patients experienced common childhood respiratory illnesses that, in children with SMA Type 1, typically result in tracheostomy or death. All patients survived respiratory hospitalizations without tracheostomy or the need for permanent ventilation.

Nutritional

Nutritional gains were also observed. In Cohort 2, seven patients did not receive enteral feeding prior to gene replacement therapy. One (1) of these 7 patients had nutritional support to assist wound healing following a difficult recovery from scoliosis surgery but was also feeding orally. Four (4) of the 5 patients in Cohort 2 who received enteral feeding prior to gene replacement therapy were able to feed orally at end of study; thus, a total of 11 of the 12 patients in Cohort 2 were able to feed orally, 6 exclusively.

Motor Function (CHOP-INTEND)

Patients receiving the therapeutic dose achieved statistically significant motor function improvements by Month 1 and Month 3; Children's Hospital of Philadelphia Infant Test of Neuromuscular Disorders (CHOP-INTEND) mean increases from baseline were 9.8 points (n=12, P<0.001) and 15.4 points (n=12, P<0.001), respectively.

Motor function improvements were sustained over time in patients infused with scAAV9.CB.hSMN vector. Eleven of twelve (91.7%) Cohort 2 patients achieved a ≥50 CHOP-INTEND score at 24 months. Early intervention and dose appear to positively affect the response. In general clinical practice, untreated SMA Type 1 children 6 months of age or older do not surpass a score of 40 points on the CHOP-INTEND. Furthermore, an average decline of 10.7 points between the ages of 6 and 12 months were reported amongst untreated infants followed as part of a prospective natural history.

Example 26: Measurement of Residual Host Cell DNA in AAV9 Viral Vectors Using qPCR Method This method was used for quantification of residual he DNA in AAV drug substance, e.g., AVXS-101, and in-process samples by qPCR. Up to six samples were tested per plate. A qPCR assay was performed using a TaqMan probe. The TaqMan probe has a fluorogenic reporter dye bound to the 5'-end and a non-fluorescent quencher bound to the 3'-end. While the probe is intact, the proximity of the quencher to the reporter dye greatly reduces the fluorescence emitted by the reporter dye. Cleavage of the probe separates the reporter dye and quencher, increasing the reporter fluorescence.

Flanking forward and reverse primers, designed to bind to a repetitive sequence within the human genome, were added to the reaction mixture and annealed to the target sequence present in the sample and standards. The TaqMan fluorogenic probe annealed between primer sites. Successive cycles of template denaturation, primer annealing and product extension amplified the target sequence. During the extension step of the amplification cycle, the exonuclease activity of Taq DNA polymerase released the reporter dye from the probe, freeing the dye from the quencher, resulting in a fluorescence emission proportional to the amount of template.

The fluorescence of each well of a 96-well plate was measured by a qPCR instrument. Through additional PCR cycles, increasing amounts of the target sequence were made, and the result is that more reporter dye was released from the probe and higher fluorescence in each successive PCR cycle. The number of amplification cycles required for the fluorescent signal to reach a pre-determined threshold value is measured. This cycle is referred to as the threshold cycle or CT value. The greater the starting concentration of DNA in the sample or standard well, the fewer the number of PCR cycles required to reach the threshold fluorescence level, and the lower the CT value. The standard curve is determined by plotting log₁₀ (DNA concentration) versus the CT value measured for each standard point. The CT value is used to determine the amount of DNA present in the sample by using the individual CT value for the sample and solving for the DNA value.

Samples were first prepared using a Wako DNA Extractor Kit (Wako, 295-50201). Briefly, the samples for testing were mixed well and diluted 1000-fold. The diluted samples were split into four tubes (500 μL each) and 50 μL of water was added to two of the tubes (unspiked replicates) while 504 of 30,000 μg/mL DNA standard was added to the other two tubes (spiked control). Protein solubilization was performed by adding 20 μL of Sodium N-Lauroyl Sarcosinate solution to each tube, vortexing for 5 seconds then centrifuging briefly. NaI solution containing glycogen and Pellet Paint (Novagen, 70748) was prepared such that they were in a ratio of 2000:5:4 of NaI:Glycogen:Pellet Paint. 500 μL of the NaI mixture was added to each tube and incubated at 53° C.±1° C. for 15 minutes. The tubes were removed from heat, mixed with 900 μL of isopropanol and incubated at room temperature for 15 minutes. The tubes were then centrifuged at 10,000 g for 15 min at 18° C. and the supernatant decanted. The remaining pellet was washed with 800 μL of Wash Solution A, spun and repelleted two times. Finally, the pellet was washed with 1500 μL of chilled Isopropanol Wash Solution containing glycogen, spun and repelleted. The final pelleted was resuspended in 500 μL nuclease-free water.

The qPCR was performed using a resDNA SEQ Human Quantitative Kit (Applied Biosystems, A26366). A Reaction Mix was prepared by combining 2× Environmental Master Mix, 10× Human DNA Assay Mix and Negative control as instructed in the kit. 20 μL Reaction Mix was mixed with 10 μL of prepared sample and added to each well on the PCR plate. Each sample was plated in triplicate. The plate was sealed with optical adhesive film. During thermocycling, a melt was first performed at 95° C. for 10 min, and then the samples were cycled between 95° C. for 15 sec and 60° C. for 1 min for 40 cycles.

A standard curve was generated by plotting the CT value vs. quantity of DNA in log([pg/mL]). The data was fit to a straight line given by the following equation:

$$CT\ value = m \times \log 10(x) + b$$

where x=concentration of standard in μg/mL, m is the slope and b is the y-intercept. The concentration of host cell DNA was back-calculated from the CT value of the well using the above equation, then corrected by the dilution factor.

Results

The residual host cell DNA measured by qPCR was $3.7 \times 10^5$ μg/mL for prior batch of vector, $0.76 \times 10^5$ μg/mL for AVXS-101 Lot 600156, $0.68 \times 10^5$ μg/mL for AVXS1-101 Lot 600307 and $1.3 \times 10^5$ μg/mL for AVXS-201 DS.

Example 27: Measurement of Residual Host Cell Protein (HCP) in AAV9 Viral Vectors by ELISA Method The host cell protein (HCP) concentration in AVXS-101 samples was measured using a commercial enzyme-linked immunosorbent assay (ELISA) kit. The Cygnus Technologies Human Embryonic Kidney 293 HCP ELISA Kit is a solid phase two-site enzyme immunoassay. It is based on a direct sandwich technique in which two polyclonal antibodies are directed against separate antigenic determinants of HCP. During incubation, the HCP in the sample bound with anti-HCP antibodies bound to a microplate well and with peroxidase-conjugated anti-HCP antibodies in solution.

After the incubation period, the wells were washed to remove any unbound enzyme-conjugated antibody. A 3,3', 5, 5'-tetramethylbenzidine (TMB) substrate solution was then added to the wells. The bound peroxidase conjugate catalyzed a color change reaction in the substrate. The reaction was stopped by the addition of acid, which gave a colorimetric endpoint that could be read spectrophotmetrically at 450 nm. The amount of hydrolyzed substrate was directly proportional to the concentration of HCP present.

The samples to be tested were diluted to meet the range of the method, from 4 ng/mL to 200 ng/mL. Each sample was then diluted 2-fold in SDB (1104 sample and 1104 SDB) and mixed. Spiked controls were also made to check for consistency. In the spiked controls, 110 μL of each sample was mixed with 27.5 μL of 200 ng/mL HCP standard and 82.5 μL of SDB. Finally, 50 μL of each standard, control or test sample was added to a well on the 96-well plate and mixed with 100 μL of anti-HEK 293-HRP conjugate. All conditions were plated in triplicates. The plate was sealed with a sealing tape and shaken at 400-600 rpm for 2 hours at room temperature. After the incubation, the solutions in the wells were removed by flicking the plate upside down and blotting with an absorbent towel. The wells were washed with a wash bottle, blotted quickly and tapped without letting the wash solution soak in the wells. The wash was repeated 4 times and allowed to rest upside down for about 20 sec to drain after the last wash. Finally, 100 μL of TMB Substrate was added to each well of the plate and incubated for 20-30 min at room temperature with no agitation. The reaction was stopped by adding 100 μL of Stop Solution to each well. The plate was loaded onto a plate reader within 45 min of adding the Stop Solution and the plate was read at 450 nm and 650 nm.

The mean absorbance of the standards were plotted against the theoretical HCP concentration of the standards in a semi-logarithmic graph to generate a four-parameter logistic (4PL) fit curve based on the following equation:

$$Y = [(A-D)/(1+(X/C)^B)] + D$$

where A is the bottom asymptote, B is the Hill-slope, C is the concentration corresponding to the midpoint absorbance values between the two asymptotes (ng/mL), D is the top asymptote, X is the sample concentration (ng/mL) and Y is the absorbance. The standard curve was then used to determine the HCP concentration in the spiked sample control and the unspiked test samples using SoftMax Pro Software. The test was only accepted if the $r^2$ of the standard curve was ≥0.98, the mean corrected absorbance of the 200 ng/mL standard was ≥1.0 OD, the mean corrected absorbance of the 0 ng/mL standard was ≤0.2 OD, and the coefficient of variation of the corrected absorbance over 3 well replicates was ≤15%. The HCP final concentration for each sample was calculated using the equation:

$$HCP\ Concentration_{sample}\ (ng/mL) = Dilution\ factor \times Mean\ measured\ HCP\ concentration\ (ng/mL).$$

Results

The residual host cell protein measured by ELISA was below the limit of quantification (8 ng/mL) for prior batch of vector, AVXS-101 Lot 600156, AVXS1-101 Lot 600307 and AVXS-201 DS.

Example 28: Measurement of Residual Benzonase in AAV9 Viral Vectors by ELISA Method The residual benzonase concentration in the AAV product, e.g., AVXS-101, was measured using a commercial enzyme-linked immunosorbent assay (ELISA) kit. The Merck Benzonase Endonuclease ELISA Kit II is a solid phase two-site enzyme immunoassay. It is based on a direct sandwich technique in which two polyclonal antibodies are directed against separate antigenic determinants of Benzonase. During incubation, the Benzonase in the sample bound with anti-Benzonase antibodies bound to a microplate well and with peroxidase-conjugated anti-Benzonase antibodies in solution.

After the incubation period, the wells were washed to remove any unbound enzyme-conjugated antibody. A 3,3', 5,5'-tetramethylbenzidine (TMB) substrate solution was then added to the wells. The bound peroxidase conjugate catalyzed a color change reaction in the substrate. The reaction was stopped by the addition of acid, which gave a colorimetric endpoint that could be read spectrophotometrically at 450 nm. The amount of hydrolyzed substrate is directly proportional to the concentration of Benzonase present.

Briefly, samples were diluted 2-fold by combining 175 µL of sample with 175 µL of PBST. In parallel, a benzonase spiked sample control was also prepared by combining 175 µL of sample with 35 µL of 10 ng/mL Benzonase standard and 140 µL of PBST. Pre-coated ELISA strips from the kit were mounted in a strip support and 100 µL of each test mix was loaded per well. For blanks, 100 µL of PBST was loaded instead of sample. Each condition was loaded in triplicate. The plate was sealed and incubated at room temperature for 2 hours±5 minutes with agitation on a plate shaker (450 rpm). After incubation, the contents were discarded and the plate was washed by adding ~350 µL of PBST using an immunowasher and incubated for 1 minute, then inverted and tapped onto an absorbent towel. A total of 3 washes were performed before 100 µL of diluted HRP-Conjugated Antibody was added to each well. The plate was sealed and incubated at room temperature for 1 hour±5 minutes with agitation on a plate shaker (450 rpm). After incubation, the contents were discarded and the plate was washed by adding ~350 µL of PBST using an immunowasher and incubated for 1 minute, then inverted and tapped onto an absorbent towel. A total of 3 washes were performed before 100 µL of TMB substrate was added to each well. The plate was sealed and the contents incubated for 15-40 minutes at room temperature without agitation in the dark. The reaction was stopped by adding 100 µL of 0.2N $H_2SO_4$ Stop Solution to each well. The absorbance of the plate was measured using a spectrophotometer at 450 nm within 45 minutes of the addition of the Stop Solution.

The mean absorbance of the standards was plotted against the theoretical Benzonase concentration of the standards in a semi-logarithmic graph to generate a four-parameter logistic (4PL) fit curve based on the following equation:

$$Y=[(A-D)/(1+(X/C)^{-B})]+D$$

where A is the bottom asymptote, B is the Hill-slope, C is the concentration corresponding to the midpoint absorbance values between the two asymptotes (ng/mL), D is the top asymptote, X is the sample concentration (ng/mL) and Y is the absorbance. The standard curve was then used to determine the HCP concentration in the spiked sample control and the unspiked test samples using SoftMax Pro Software. The test was only accepted if the $r^2$ of the standard curve was ≥0.98, the mean corrected absorbance of the 2.5 ng/mL standard was ≥1.0 OD, the mean corrected absorbance of the 0.10 ng/mL standard was greater than the mean OD of the PBST blank, and the coefficient of variation of the corrected absorbance over 3 well replicates was ≤15%. The HCP final concentration for each sample was calculated using the equation:

Benzonase Concentration$_{sample}$ (ng/mL)=Dilution factor×Mean measured Benzonase concentration (ng/mL).

Results

The residual benzonase concentration measured by ELISA was below the limit of quantification (0.2 ng/mL) for prior batch of vector, AVXS-101 Lot 600156 and AVXS1-101 Lot 600307.

Example 29: Measurement of Protein Concentration in AAV9 Viral Vectors by Micro BCA Assay Method The amount of proteins in in-process, drug substance and drug product samples, e.g., of AVXS-101, were measured by micro BCA plate assay, using a 2 mg/mL Bovine Serum Albumin (Thermo Fisher Scientific, 23209) reference protein standard and a Micro BCA Protein Assay Kit (Thermo Fisher Scientific, 23235). The assay is based on a detergent-compatible bicinchoninic acid (BCA) formulation for colorimetric detection and quantitation of total protein. The BCA detects $Cu^{1+}$ which is formed when $Cu^{2+}$ is reduced by protein in an alkaline environment. A purple-colored reaction product is formed by the chelation of two molecules of BCA with one cuprous ion ($Cu^{1+}$), which exhibits a strong absorbance at 562 nm that is linear with increasing protein concentrations.

Briefly, standards were prepared by performing serial dilutions of 2 mg/mL BSA in Diluent (20-fold dilution of the Formulation Buffer, 200 mM NaCl, 20 mM Tris, 1 mM MgCl2, 0.001% w/v Pluronic F-68, pH 8.0). The test samples of AVXS-101 were also diluted 20-fold in water and serial dilutions made in Diluent. The target concentration is about 7.5 µg/mL. The Working Reagent (WR) was prepared by mixing 25 parts Micro BCA Reagent A, 24 parts Reagent B and 1 part of Reagent C from the kit. 150 µL of each standard and test sample was loaded in triplicate into a 96-well plate, and mixed with 150 µL of WR. The plate was sealed and shaken at 300 rpm on a plate shaker for 30 seconds. The plate was then incubated without shaking at 37° C.±2° C. for 2 hours. After incubation, the plate was centrifuge at 1000 rpm for 2 minutes to collect the condensation, and the plate was cooled for 15-60 min after incubation. The plate was read in a plate reader at 562 nm and the data was analyzed with SoftMax Pro.

The mean absorbance of the standards vs. the theoretical protein concentration of the standards was plotted in a semi-logarithmic plot and a quadratic fit was generated. The quadratic fit is based on the equation:

$$Y=A+Bx+Cx^2$$

where A, B, C are curve fit parameters, x is the sample concentration in µg/mL and Y is the absorbance in OD. The test was only accepted if the $r^2$ of the standard curve was ≥0.98, the mean absorbance of the blank was less than that of the lowest standard (1 µg/mL), and the coefficient of variation of the absorbance over 3 well replicates of each standard was ≤10%. The standard curve was then used to determine the protein concentration in the test samples. The final protein concentration was calculated using the equation:

Total Protein Concentration (µg/mL)=Dilution Factor×Mean measured protein concentration (µg/mL).

Results

The total protein concentration measured by Micro BCA was 167 µg/mL per $1.0 \times 10^{13}$ vg/mL for prior batch of vector, 179 µg/mL per $1.0 \times 10^{13}$ vg/mL for AVXS-101 Lot 600156, and 176 µg/mL per $1.0 \times 10^{13}$ vg/mL for AVXS1-101 Lot 600307.

Example 30: Purity and Release Specifications of AVXS-101 (AAV9-SMN1)

AVXS-101 Drug Substance and AVXS-101 Drug Product from Examples 1 to 4 were tested for purity. Table 78 and 79 shows the specification and release criteria for these products.

TABLE 73

Release specification for AVXS-101 Drug Substance

| Process-Related Impurity | Origin | Acceptance Criteria |
|---|---|---|
| Host Cell Protein (HCP) | Cell Substrate | ≤4 ng per 1.0E13 vg |
| Host cell DNA | Cell Substrate | ≤1.15E5 pg per 1.0E13 vg |
| Bovine Serum Albumin (BSA) | Cell Culture | ≤0.22 ng per 1.0E13 vg |
| Plasmid DNA (pDNA) | Cell Culture | ≤6.8E5 pg per 1.0E13 vg |
| Polyethyleimine (PEI) | Cell Culture | Not tested at Release |
| Benzonase | Downstream Processing | ≤0.09 ng per 1.0E13 vg |
| Tween 20 | Downstream Processing | Not tested at Release |
| Poloxamer 188 | Downstream Processing | 20-80 ppm |
| Cesium (Cs) | Downstream Processing | ≤30 µg/g (ppm) |
| Ethanol | Downstream Processing | Not tested at Release |

TABLE 74

Release specifications for AVXS-101 Drug Product

| Category | Attribute | Acceptance Criterion |
|---|---|---|
| General | Appearance | Clear to slightly opaque, colorless to faint white solution, free of visible particulates |
|  | pH | 7.7-8.3 |
|  | Psmolality | 390-430 mOsm/kg |
|  | Sub-visible particles | ≤600 particles ≥25 µm per container ≤6000 particles ≥10 µm per container |
| Quantity | Genomic Titer by ddPCR | 1.7E13-2.3E13 vg/mL |
|  | Infectious Titer by TaqMan $TCID_{50}$ | 3.9E8-8.4E10 IU per 1.0E13 vg |
|  | Total Protein by Micro BCA | 100-300 µg per 1.0E13 vg |
|  | Pluronic F-68 Content by HPLC-ELSD | 20-80 ppm |
| Potency | In vivo Functionality Test by A7SMA Mouse Model | Median Survival representing the 7.5E13 vg/kg dose is ≥24 days |
|  | In vitro Relative Potency by Cell-based Assay | 70-130% |
| Identity | Vector Genome Identity by ddPCR | Confirms |
|  | Identity (Protein) by SDS-PAGE | Main Bands of VP1, VP2, VP3 co-migrate with the AVXS-101 Reference Standard |
|  | Identity (Protein) by Western Blot | Positive for AAV capsid protein |
| Purity | % Capsid Distribution by SV-AUC | % Empty ≤5% % Peak 1 + Peak 2 ≥91.9% % Full (Peak 1) 37.4-70.3% % Full (Peak 2) 24.9-60.1% % Total Other Peaks ≤5% |
|  | % Total Purity by SDS-PAGE | % Total Purity (VP1, VP2, VP3) ≥95.0% |
|  | % Total Impurities by SDS-PAGE | % Total Impurities ≤5% No single un-named related impurity >2.0% Named related impurities: Report value % to 0.1% (down to LOQ) Imp 1A (~71-73 kDa) Imp 1 (~61-67 kDa) Imp 2 (~56-64 kDa) Imp 3 (~48-58 kDa) Imp 4 (~33-38 kDa) Imp 5 (~30-34 kDa) |
| Safety | Endotoxin | ≤0.75 EU/mL |
|  | Sterility | No growth |
|  | Container Closure Integrity Vacuum Decay | Pass |

Having described embodiments of the invention with reference to the accompanying drawings, it is to be understood that the invention is not limited to the precise embodiments, and that various changes and modifications may be effected therein by those skilled in the art without departing from the scope or spirit of the invention as defined in the appended claims.

What is claimed is:

1. An in vitro method for measuring transgene expression, comprising:

a) providing a first plurality of terminally differentiated neural progenitor cells (NPCs) comprising a homozygous Survival Motor Neuron (SMN1)-/- mutation;

b) transducing the first plurality of terminally differentiated NPCs with a test sample comprising an AAV9 viral vector comprising a sequence encoding a Survival Motor Neuron (SMN1) protein;

c) incubating the transduced first plurality of terminally differentiated NPCs under conditions sufficient to express the SMN1 protein;

d) contacting the first plurality of terminally differentiated NPCs from (c) with a molecule specific for the SMN1 protein;

e) imaging the first plurality of terminally differentiated NPCs to obtain an integrated fluorescent intensity per cell (IFI-C) assay readout; and f) determining the expression of the SMN1 protein based on the IFI-C readout, wherein said first plurality of terminally differentiated NPCs is produced by terminally differentiating neural progenitor cells isolated from the cortex of an SMN1-/- mouse embryo, and wherein the SMN1-/- mutation comprises a deletion of SMN1 exon 7 (Δ7).

2. The method of claim 1, wherein the incubating step c) is followed by fixing and permeabilizing the first plurality of terminally differentiated NPCs.

3. The method of claim 1, further comprising:

g) providing a second plurality of terminally differentiated NPCs comprising a homozygous Survival Motor Neuron (SMN1)-/- mutation;

h) transducing the second plurality of terminally differentiated NPCs with a reference standard comprising the AAV9 viral vector;
i) incubating the transduced second plurality of terminally differentiated NPCs under conditions sufficient to express the SMN1 protein;
j) contacting the second plurality of terminally differentiated NPCs from (i) with a molecule specific for the SMN1 protein;
k) imaging the second plurality of terminally differentiated NPCs to obtain an integrated fluorescent intensity per cell (IFI-C) assay readout; and
l) comparing the IFI-C of the first plurality of terminally differentiated NPCs with the IFI-C of the second plurality of terminally differentiated NPCs,
thereby determining the relative potency of the AAV9 viral vector of the test sample relative to the reference standard,
wherein said second plurality of terminally differentiated NPCs is produced by terminally differentiating neural progenitor cells isolated from the cortex of an SMN1−/− mouse embryo, and wherein the SMN1−/− mutation comprises a deletion of SMN1 exon 7 (Δ7).

4. The method of claim 3, wherein the incubating step (i) is followed by fixing and permeabilizing the second plurality of terminally differentiated NPCs.

5. The method of claim 3, wherein the first and second pluralities of terminally differentiated neural progenitor cells (NPCs) are terminally differentiated by:
 a. culturing the NPCs in serum free culture media containing Epidermal Growth Factor (EGF) and Fibroblast Growth Factor-basic (bFGF) to form neurospheres;
 b. dissociating said neurospheres to produce dissociated NPCs; and
 C. culturing the dissociated NPCs in serum-enriched media without growth factors,
thereby producing terminally differentiated NPCs.

6. The method of claim 3, wherein said first and second pluralities of NPCs are transduced by the test sample and the reference standard at at least two different multiplicities of infection (MOI) of the AAV9 viral vector.

7. The method of claim 5, wherein the first and second pluralities of NPCs are transduced by the test sample and the reference sample at 5 MOIs comprising 300,000, 150,000, 75,000, 37,500, and 18,750 viral particles per cell.

8. The method of claim 3, wherein the comparing step (l) comprises plotting a standard curve of MOI versus IFI-C for each of the test sample and the reference standard.

9. The method of claim 3, wherein the comparing step (l) comprises calculating a linear regression of log MOI versus IFI-C for each of the test sample and the reference standard, thereby deriving a test sample slope and a reference standard slope.

10. The method of claim 5, wherein determining the relative potency of the viral vector is performed by parallel line analysis (PLA), and wherein the PLA comprises measuring a slope ratio of the test sample slope against the reference standard slope.

11. The method of claim 10, wherein the reference standard slope is greater than or equal to 1.02E+05, and wherein the slope ratio is between 0.69-1.45.

12. The method of claim 10, further comprising calculating an assay dynamic window of the reference standard, wherein the assay dynamic window is greater than or equal to 2.69.

13. The method of claim 1, wherein the AAV9 viral vector comprises AAV serotype 2 inverted terminal repeats (ITRs).

14. The method of claim 1, wherein the AAV9 viral vector comprises a sequence encoding cytomegalovirus (CMV) enhancer/chicken-β-actin-hybrid promoter (CB) operably linked to the sequence encoding the SMN1 protein.

15. The method of claim 1, wherein the viral vector comprises a sequence of SEQ ID NO: 1.

16. The method of claim 1, wherein the IFI-C readout reflects a measurement of protein expression.

17. The method of claim 1, wherein the molecule that is specific for the SMN1 protein comprises an antibody, an antibody fragment, or an aptamer.

18. The method of claim 17, wherein the antibody is provided at a concentration of about 4 μg/mL.

19. The method of claim 1, wherein the molecule comprises a detectable label.

20. The method of claim 1, further comprising contacting the terminally differentiated NPCs with a second molecule that specifically recognizes the molecule specific for the SMN1 protein.

21. The method of claim 20, wherein the second molecule comprises a detectable label.

22. The method of claim 20, wherein the second molecule comprises an antibody, an antibody fragment or an aptamer.

23. The method of claim 2, wherein the first plurality of terminally differentiated NPCs are contacted with an anti-nuclear detectable label following the fixing and permeabilizing step.

24. The method of claim 1, wherein the terminally differentiated NPCs are on a solid surface.

* * * * *